US009441250B2

(12) United States Patent
Bhalla et al.

(10) Patent No.: US 9,441,250 B2
(45) Date of Patent: Sep. 13, 2016

(54) GLYCEROL 3- PHOSPHATE DEHYDROGENASE FOR BUTANOL PRODUCTION

(71) Applicant: BUTAMAX ADVANCED BIOFUELS LLC, Wilmington, DE (US)

(72) Inventors: Ritu Bhalla, Tirmulgherry (IN); Gopal K Chotani, Palo Alto, CA (US); Michael Dauner, Wilmington, DE (US); Mark J Nelson, Newark, DE (US); Daniel P O'Keefe, Ridley Park, PA (US); Caroline M Peres, Palo Alto, CA (US); Jahnavi Chandra Prasad, Wilmington, DE (US); Jean-Francois Tomb, Wilmington, DE (US)

(73) Assignee: Butamax Advanced Biofuels LLC, Wilmington, DE (US)

( * ) Notice: Subject to any disclaimer, the term of this patent is extended or adjusted under 35 U.S.C. 154(b) by 0 days.

(21) Appl. No.: 14/208,474

(22) Filed: Mar. 13, 2014

(65) Prior Publication Data

US 2014/0273129 A1 Sep. 18, 2014

Related U.S. Application Data

(60) Provisional application No. 61/782,651, filed on Mar. 14, 2013, provisional application No. 61/934,096, filed on Jan. 31, 2014.

(51) Int. Cl.

| | |
|---|---|
| ***C12P 7/16*** | (2006.01) |
| ***C12N 9/04*** | (2006.01) |
| ***C12N 1/20*** | (2006.01) |
| ***C12N 1/00*** | (2006.01) |
| ***C12N 15/52*** | (2006.01) |

(52) U.S. Cl.

CPC ............... *C12P 7/16* (2013.01); *C12N 9/0006* (2013.01); *C12N 15/52* (2013.01); *C12Y 101/01008* (2013.01); *C12Y 101/01094* (2013.01); *C12Y 101/05003* (2013.01); *Y02E 50/10* (2013.01); *Y02P 20/52* (2015.11)

(58) Field of Classification Search

CPC ............. C12P 7/16; C12Y 101/01094; C12Y 101/01008; C12Y 101/05003; Y02E 50/10; C12N 15/52; C12N 9/0006; Y02P 20/52

USPC ........... 435/160, 190, 252.3, 252.31, 252.32, 435/252.33, 252.34, 254.11, 254.2, 254.21, 435/254.22

See application file for complete search history.

(56) References Cited

U.S. PATENT DOCUMENTS

| | | | |
|---|---|---|---|
| 4,683,202 | A | 7/1987 | Mullis et al. |
| 5,514,583 | A | 5/1996 | Picataggio et al. |
| 5,686,276 | A | 11/1997 | Laffend et al. |
| 5,712,133 | A | 1/1998 | Picataggio et al. |
| 6,432,688 | B1 | 8/2002 | Ito et al. |
| 7,223,575 | B2 | 5/2007 | Zhang et al. |
| 7,541,173 | B2 | 6/2009 | Bramucci et al. |
| 7,574,601 | B2 | 8/2009 | Jahromi et al. |
| 7,659,104 | B2 | 2/2010 | Bramucci et al. |
| 7,741,119 | B2 | 6/2010 | Viitanen et al. |
| 7,851,188 | B2 | 12/2010 | Donaldson et al. |
| 7,910,342 | B2 | 3/2011 | Liao et al. |
| 7,993,889 | B1 | 8/2011 | Donaldson et al. |
| 8,017,364 | B2 | 9/2011 | Bramucci et al. |
| 8,129,162 | B2 | 3/2012 | Li et al. |
| 8,178,328 | B2 | 5/2012 | Donaldson et al. |
| 8,188,250 | B2 | 5/2012 | Bramucci et al. |
| 8,206,970 | B2 | 6/2012 | Eliot et al. |
| 8,222,017 | B2 | 7/2012 | Li et al. |
| 8,241,878 | B2 | 8/2012 | Anthony et al. |
| 8,247,208 | B2 | 8/2012 | Caimi et al. |
| 8,273,558 | B2 | 9/2012 | Donaldson et al. |
| 8,283,144 | B2 | 10/2012 | Donaldson et al. |
| 8,372,612 | B2 | 2/2013 | Larossa et al. |
| 8,389,252 | B2 | 3/2013 | Larossa |
| 8,455,224 | B2 | 6/2013 | Paul |
| 8,455,225 | B2 | 6/2013 | Bramucci et al. |

(Continued)

FOREIGN PATENT DOCUMENTS

| | | |
|---|---|---|
| WO | 2009009142 | 1/2009 |
| WO | 2011149353 | 12/2011 |

(Continued)

OTHER PUBLICATIONS

Broun et al., Catalytic plasticity of fatty acid modification enzymes underlying chemical diversity of plant lipids. Science, 1998, vol. 282: 1315-1317.*

Devos et al., Practical limits of function prediction. Proteins: Structure, Function, and Genetics. 2000, vol. 41: 98-107.*

Kisselev L., Polypeptide release factors in prokaryotes and eukaryotes: same function, different structure. Structure, 2002, vol. 10: 8-9.*

Seffernick et al., Melamine deaminase and Atrazine chlorohydrolase: 98 percent identical but functionally different. J. Bacteriol., 2001, vol. 183 (8): 2405-2410.*

(Continued)

*Primary Examiner* — Ganapathirama Raghu

(57) ABSTRACT

Provided herein are glycerol-3-phosphate dehydrogenase (GPD) enzymes with increased $K_M$ for NADH and GPD enzymes with substantially the same affinity for NADH and NADPH and/or are feedback inhibited by glycerol-3-phosphate. Also provided herein are recombinant microorganisms comprising a heterologous gene encoding GPD and a deletion or disruption in an endogenous gene encoding GPD. Also provided are recombinant microorganisms comprising a heterologous gene encoding GPD and a butanol biosynthetic pathway. Further provided are methods of producing butanol comprising providing the recombinant microorganisms described herein and contacting the recombinant microorganism with at least one fermentable carbon substrate under conditions wherein butanol is produced.

8 Claims, 9 Drawing Sheets

(56) References Cited

U.S. PATENT DOCUMENTS 8,455,239 B2 * 6/2013 Feldman ............. C12N 9/0006 435/157
8,465,964 B2 6/2013 Anthony et al.
8,518,678 B2 8/2013 Flint et al.
8,557,562 B2 10/2013 Bramucci et al.
8,614,085 B2 12/2013 Van Dyk et al.
8,637,281 B2 1/2014 Paul et al.
8,637,289 B2 1/2014 Anthony et al.
8,652,823 B2 2/2014 Flint et al.
8,669,094 B2 3/2014 Anthony et al.
8,691,540 B2 4/2014 Bramucci et al.
8,735,114 B2 5/2014 Donaldson et al.
8,765,433 B2 7/2014 Gude et al.
8,785,166 B2 7/2014 Anthony et al.
8,795,992 B2 8/2014 Bramucci et al.
8,828,694 B2 9/2014 Anthony et al.
8,828,704 B2 9/2014 Donaldson et al.
8,871,488 B2 10/2014 Dauner et al.
8,889,385 B2 11/2014 Donaldson et al.
8,895,307 B2 11/2014 Li et al.
8,906,666 B2 12/2014 Alsaker et al.
8,911,981 B2 12/2014 Li et al.
8,940,511 B2 1/2015 Larossa
8,945,859 B2 2/2015 Donaldson et al.
8,945,899 B2 2/2015 Li et al.
8,951,774 B2 2/2015 Donaldson et al.
8,951,937 B2 2/2015 Flint et al.
8,956,850 B2 2/2015 Anthony et al.
8,962,298 B2 2/2015 Donaldson et al.
8,969,065 B2 3/2015 Anthony et al.
8,980,612 B2 3/2015 Donaldson et al.
2007/0031918 A1 2/2007 Dunson et al.
2008/0182308 A1 7/2008 Donaldson et al.
2009/0155870 A1 6/2009 Donaldson et al.
2009/0203099 A1 8/2009 Caimi et al.
2009/0246846 A1 10/2009 Viitanen et al.
2009/0305370 A1 12/2009 Grady et al.
2010/0081154 A1 4/2010 Flint et al.
2010/0081179 A1 4/2010 Anthony et al.
2010/0081182 A1 4/2010 Paul et al.
2010/0093020 A1 4/2010 Bramucci et al.
2010/0120105 A1 5/2010 Anthony et al.
2011/0020889 A1 1/2011 Feldman et al.
2011/0097773 A1 4/2011 Grady et al.
2011/0124060 A1 5/2011 Anthony et al.
2011/0136192 A1 6/2011 Paul et al.
2011/0195505 A1 8/2011 Euler et al.
2011/0244536 A1 10/2011 Nagarajan et al.
2011/0250610 A1 10/2011 Bramucci et al.
2011/0275130 A1 11/2011 Pronk et al.
2012/0058541 A1 3/2012 Alsaker et al.
2012/0064561 A1 3/2012 Flint et al.
2012/0149080 A1 6/2012 Bramucci et al.
2012/0196341 A1 8/2012 Donaldson et al.
2012/0237988 A1 9/2012 Anthony et al.
2012/0258873 A1 10/2012 Gibson et al.
2012/0295319 A1 11/2012 Nevoigt et al.
2013/0035515 A1 2/2013 Dobson et al.
2013/0071898 A1 3/2013 Anthony et al.
2013/0171706 A1 7/2013 Donaldson et al.
2013/0203138 A1 8/2013 McElvain et al.
2013/0252296 A1 9/2013 Maggio-Hall et al.
2013/0316414 A1 11/2013 Paul et al.
2014/0004526 A1 1/2014 Dauner et al.
2014/0030782 A1 1/2014 Anthony et al.
2014/0030783 A1 1/2014 Anthony et al.
2014/0038263 A1 2/2014 Flint et al. (Butamax)
2014/0038268 A1 2/2014 Flint et al. (Butamax)
2014/0051133 A1 2/2014 Govindarajan et al.
2014/0051137 A1 2/2014 Flint et al.
2014/0057329 A1 2/2014 Li et al.
2014/0093930 A1 4/2014 Li et al.
2014/0096439 A1 4/2014 Bramucci et al.
2014/0141479 A1 5/2014 Anthony et al.
2014/0170732 A1 6/2014 Bramucci et al.
2014/0186910 A1 7/2014 Rothman et al.
2014/0186911 A1 7/2014 Anthony et al.
2014/0273116 A1 9/2014 Kelly et al.
2014/0273129 A1 9/2014 Bhalla et al.
2014/0308735 A1 10/2014 Anthony et al.
2014/0335582 A1 11/2014 Donaldson et al.
2014/0349349 A1 11/2014 Dauner et al.
2014/0377824 A1 12/2014 Satagopan et al.
2015/0037855 A1 2/2015 Bhadra et al.
2015/0111269 A1 4/2015 Li et al.
2015/0119608 A1 4/2015 Donaldson et al.
2015/0125920 A1 5/2015 Anthony et al.

FOREIGN PATENT DOCUMENTS

WO 2012138942 10/2012
WO 2013141905 9/2013
WO 2014081803 5/2014

OTHER PUBLICATIONS

Whisstock et al., Prediction of protein function from protein sequence. Q. Rev. Biophysics., 2003, vol. 36 (3): 307-340.*

Witkowski et al., Conversion of b-ketoacyl synthase to a Malonyl Decarboxylase by replacement of the active cysteine with glutamine. Biochemistry, 1999, vol. 38: 11643-11650.*

Albertyn et al., "Purification and characterization of glycerol-3-phosphate dehydrogenase of *Saccharomyces cerevisiae*," FEBS Lett 308:130-132 (1992).

Bell, "Mutants of *Escherichia coli* defective in membrane phospholipid synthesis: macromolecular synthesis in an sn-glycerol 3-phosphate acyltransferase Km mutant," J. Bact. 117:1065-76 (1974).

Carmon and MacIntyre, "The alpha-glycerophosphate cycle in *Drosophila melanogaster* VI. Structure and evolution of enzyme paralogs in the genus Drosphila," Journal of Heredity 101:225-234 (2010).

Database UniProtKB (Online), "Glycerol-3-phosphate dehydrogenase", XP002726310, Database accession No. B3LGS7 (Sep. 2, 2008).

Dickinson et al., "," J. Biol. Chem. 273:25752-25756 (1998).

Edgar and Bell, "Biosyntheiss in *Escherichia coli* of sn-glycerol-3-phosphate, a precursor of phospholipid," J Biol Chem 255: 3492-97 (1980).

Edgar and Bell, "Biosynthesis in *Escherichia coli* of sn-glycerol 3-hopshate, a precursor of phospholipid," JBC 253:6354-63 (1978).

Feldmann et al., "Pentose metabolism in Zymomonas mobilis wild-type and recombinant strains," Appl. Microbiol. Biotechnol. 38:354-61 (1992).

Frohlich et al, "*Rickettsia prowazekii* uses an sn-glycerol-3-phosphate dehydrogenase and a novel dihydroxyacetone phosphate transport system to supply triose phosphate for phospholipit biosynthesis," J Bacteriol 192: 4281-4288 (2010).

Hahnai et al., "Engineered synthetic pathway for isopropanol production in *Escherichia coli*," Appl. Environ. 73:7814-8 (2007).

Jain et al., "Effect of alternative NAD+-regenerating pathways on the formation of primary and secondary aroma compounds in a *Saccharomyces cerevisiae* glycerol-defective mutant", Applied Microbiol Biotechnol 93:131-141 (2012).

Niesel et al., "sn-Glycerol-3-phosphate dehydrogenase (soluble) from *Drosophila melanogaster*," Methods Enzymol. 89:296-301 (1982).

Norbeck, "Purification and characterization of two isoenzymes of DL-glycerol-3-phosphatase from *Saccharomyces cerevisiae*," JBC 271:13875-81 (1996).

Ohta et al., "Genetic improvement of *Escherichia coli* for ethanol production: chromosomal integration of Zymomonas mobilis genes encoding pyruvate decarboxylase and alcohol dehydrogenase II," Appl. Environ. Microbiol. 57:893-900 (1991).

Ou et al, "Crystal structures of human glycerol-3-phosphate dehydrogenase 1 (GPD1)," J.Mol.Biol. 357: 858-869 (2005).

Ruijter et al, "Polyol accumulation by Aspergillus oryzae at low water activity in solid-state fermentation," Microbiology 150: 1095-101 (2004).

(56) References Cited

OTHER PUBLICATIONS

Sakasegawa et al, "Structural and functional analysis of the gpsA gene product of Archaeoglobus fulgidus: a glycerol-3-phopaste dehydrogenase with an unusual NADP+ preference," Protein Science 13: 3161-71 (2004).
Shen and Liao, "Metabolic engineering of *Escherichia coli* for 1-butanol and 1-propanol production via the keto-acid pathways," Metab. Eng. 10:312-20 (2008).
Underwood et al., "Flux through citrate synthase limits the growth of ethanologenic *Escherichia coli* KO11 during xylose fermentation," Appl. Envrion. Microbiol. 68:1071-81 (2002).
Valadi et al, "Distinct intracellular localization of GPD1p and GPD2p, the two yeast isoforms of NAD+ dependent glycerol-3-phosphate dehydrogenase, explains their different contributions to redox-driven glycerol production," J. Biol Chem 279: 39677-39685 (2004).
Watanabe et al, "Expression of glycerol 3-phosphate dehydrogenase gene (CvGPD1) in salt-tolerant yeast Candida versatilis is stimulated by high concentrations of NaCI," Yeast 25:107-116 (2008).
Zhang et al., "Metabolic engineering of a pentose metabolism pathway in ethanologenic Zymomonas mobilis," Science 267:240-3 (1995).
International Search Report and Written Opinion, mailed on Jul. 11, 2014, in International Patent Application No. PCT/US2014/025714, filed on Mar. 13, 2014.
Alarcon et al., "Structure of glycerol-3-phosphate dehydrogenase (GPD1) from *Saccharomyces cerevisiae* at 2.45A resolution," Acta Crystallographica F68:1279-83 (2012).

* cited by examiner

```
                                  F41                                                                                F97
                                   ↓                                                                                  ↓
Human-Truncated          (35)RVTMWVFEEDIGGKKLTEIINTQHENVKYLPGHKLPPNVVAVPDVVQAAEDADILIFVVPHQFIGK
Saccharomyces GPD1       (67)IVQMWVFEEEINGEKLTEIINTRHQNVKYLPGITLPDNLVANPDLIDSVKDVDIIVFNIPHQFLPR
Rickettsia               (29)NVTLFLRDEII-----LKEILYKKTNAQYLGDIELPTNLQATTNLS-VIKDFELIIIAVPSYAFDD
Beggiatoa                (29)PIYLWGKDPAH-----VHTLQIQRCNQRFLPNAVFPDNLYAITDFVTLMPIVEDIIIVVPSHGFRE
Kangiella                (29)SVQLWARNSQH-----VVEMQQAKQNTKYLPDVAFPDNLSVTDQIDVALKHHPIILVAVPSHAFRD
```

FIG. 2

GLYCEROL 3- PHOSPHATE DEHYDROGENASE FOR BUTANOL PRODUCTION

CROSS REFERENCE TO RELATED APPLICATIONS

This application claims benefit of priority from U.S. Provisional Application No. 61/782,651, filed Mar. 14, 2013, and U.S. Provisional Application No. 61/934,096, filed Jan. 31, 2014, each of which is hereby incorporated by reference in its entirety.

FIELD OF THE INVENTION

The invention relates to the field of industrial microbiology and the fermentative production of butanol and isomers thereof. More specifically, the invention relates to glycerol-3-phosphate dehydrogenase (GPD) enzymes with a high $K_M$ for NADH, substantially the same affinity for NADH and NADPH and/or GPD enzymes that are feedback inhibited, recombinant microorganisms comprising such enzymes, and methods of using such enzymes to produce butanol.

REFERENCE TO SEQUENCE LISTING SUBMITTED ELECTRONICALLY

The content of the electronically submitted sequence listing in ASCII text file (Name: 20140314_CL5707USNP_Sequence Listing; Size: 401,408 bytes, and Date of Creation: Mar. 12, 2014) filed with the application is incorporated herein by reference in its entirety.

BACKGROUND

Butanol is an important industrial chemical, useful as a fuel additive, as a feedstock chemical in the plastics industry, and as a food grade extractant in the food and flavor industry. Each year 10 to 12 billion pounds of butanol are produced by petrochemical means and the need for this commodity chemical will likely increase in the future.

Methods for the chemical synthesis of isobutanol are known, such as oxo synthesis, catalytic hydrogenation of carbon monoxide (Ullmann's Encyclopedia of Industrial Chemistry, 6th edition, 2003, Wiley-VCH Verlag GmbH and Co., Weinheim, Germany, Vol. 5, pp. 716-719) and Guerbet condensation of methanol with n-propanol (Carlini et al., *J. Molec. Catal. A. Chem.* 220:215-220, 2004). These processes use starting materials derived from petrochemicals, are generally expensive, and are not environmentally friendly. The production of isobutanol from plant-derived raw materials would minimize greenhouse gas emissions and would represent an advance in the art.

Isobutanol is produced biologically as a by-product of yeast fermentation or by recombinantly engineered microorganisms modified to express a butanol biosynthetic pathway for producing butanol. See e.g., U.S. Pat. No. 7,851,188, which is incorporated herein by reference in its entirety. As a component of "fusel oil" that forms as a result of the incomplete metabolism of amino acids by fungi, isobutanol is specifically produced from catabolism of L-valine. After the amine group of L-valine is harvested as a nitrogen source, the resulting α-keto acid is decarboxylated and reduced to isobutanol by enzymes of the so-called Ehrlich pathway (Dickinson et al., *J. Biol. Chem.* 273:25752-25756, 1998).

One of the key yield loss mechanisms in yeast butanol production is the loss of carbon and reducing equivalents that are diverted from glycolysis by the conversion of dihydroxyacetone phosphate to glycerol. The first step in this conversion is catalyzed by an enzyme called glycerol-3-phosphate dehydrogenase (GPD). Eliminating GPD, and therefore glycerol production, in butanol-producing yeast, has been proposed previously. However, glycerol is required for growth and is an osmoprotectant.

Accordingly, methods of increasing butanol yield and decreasing glycerol production represent an advance in the art.

BRIEF SUMMARY OF THE INVENTION

Provided herein are GPD enzymes, recombinant microorganisms, and methods for production of butanol.

Provided herein are recombinant microorganisms comprising (a) an engineered butanol biosynthetic pathway comprising at least one polypeptide that is heterologous to the recombinant microorganism; (b) a heterologous glycerol-3-phosphate dehydrogenase (GPD), wherein the heterologous GPD has a higher $K_M$ for NADH as compared to the $K_M$ of the endogenous GPD of the microorganism; and (c) a deletion or disruption in an endogenous gene encoding GPD. In some embodiments, the recombinant microorganism has improved or increased production of butanol as compared to a control recombinant microorganism that lacks the heterologous GPD. In some embodiments, the recombinant microorganism has reduced or decreased production of glycerol as compared to a control recombinant microorganism that lacks the heterologous GPD. In some embodiments, the recombinant microorganism has an increased butanol to glycerol molar ratio as compared to a control recombinant microorganism that lacks the heterologous GPD. In some embodiments, the recombinant microorganism has an increased effective yield as compared to a control recombinant microorganism that lacks the heterologous GPD.

Also provided herein are recombinant microorganisms comprising (a) an engineered butanol biosynthetic pathway comprising at least one polypeptide that is heterologous to the recombinant microorganism; (b) a heterologous glycerol-3-phosphate dehydrogenase (GPD), wherein the heterologous GPD has substantially the same affinity for NADH and NADPH and/or is feedback inhibited; and (c) a deletion or disruption in an endogenous gene encoding GPD. In some embodiments, the recombinant microorganism has improved production of butanol as compared to a control recombinant microorganism that lacks the heterologous GPD. Optionally, the heterologous GPD is feedback inhibited by glycerol-3-phosphate. In some embodiments, the recombinant microorganism has reduced or decreased production of glycerol as compared to a control recombinant microorganism that lacks the heterologous GPD. In some embodiments, the recombinant microorganism has an increased butanol to glycerol molar ratio as compared to a control recombinant microorganism that lacks the heterologous GPD. In some embodiments, the recombinant microorganism has an increased effective yield as compared to a control recombinant microorganism that lacks the heterologous GPD.

In certain embodiments, the heterologous GPD is a naturally occurring GPD. In certain embodiments, the naturally occurring GPD is selected from EC number 1.1.1.8, 1.1.5.3, or 1.1.1.94. The naturally occurring GPD can be a GPD from an organism selected from the group consisting of *Leish-*

*mania mexicana, Dunaliella viridis, Jaculus orientalis, Archeoglobus fulgidus, Rickettsia prowazekii, Beggiatoa alba, Kangiella koreenis Aspergillus oryzae, Candida versatilis, Escherichia coli*, and *Oryctolagus cuniculu*.

In certain embodiments, the heterologous GPD is an engineered GPD. The engineered GPD can comprise at least one substitution corresponding to position 42, 44, 45, 71, 73, 75, 95, 124, 126, 129, 151, 152, 183, 184, 185, 246, 310, 336, 337, or 339 of SEQ ID NO: 195. In certain embodiments the engineered GPD comprises at least one substitution at a residue corresponding to position 73 of SEQ ID NO:195. In certain embodiments the engineered GPD comprises at least one substitution at a residue corresponding to position 129 of SEQ ID NO:195. In certain embodiments the engineered GPD comprises at least one substitution at a residue corresponding to position 73 of SEQ ID NO:195 and a substitution at a residue corresponding to position 129 of SEQ ID NO:195.

Also provided are engineered glycerol-3-phosphate dehydrogenase (GPD) enzymes. In certain embodiments, the engineered GPD enzyme has at least 85% identity to SEQ ID NO:195. In certain embodiments, the engineered GPD enzyme comprises at least one substitution at a residue corresponding to position 42, 44, 45, 71, 73, 75, 95, 124, 126, 129, 151, 152, 183, 184, 185, 246, 310, 336, 337, or 339 of SEQ ID NO: 195. In certain embodiments, the engineered GPD enzyme comprises at least one substitution corresponding to position 73 of SEQ ID NO:195. In certain embodiments, the engineered GPD enzyme comprises at least one substitution corresponding to position 129 of SEQ ID NO:195. In certain embodiments, the engineered GPD enzyme comprises at least one substitution corresponding to position 73 of SEQ ID NO:195 and a substitution corresponding to position 129 of SEQ ID NO:129. In certain embodiments, the engineered GPD enzyme has a $K_M$ for NADH from about 0.01 mM to 1 mM.

Also provided are recombinant microorganisms comprising any of the engineered GPD enzymes disclosed herein. Optionally, the recombinant microorganism can comprise an engineered butanol biosynthetic pathway that comprises at least one gene that is heterologous to the recombinant microorganism. The recombinant microorganism can, for example, comprise a deletion or disruption of an endogenous gene encoding GPD. In certain embodiments, the recombinant microorganism has improved or increased production of butanol compared to a microorganism that lacks the engineered GPD enzyme. In some embodiments, the recombinant microorganism has reduced or decreased production of glycerol as compared to a control recombinant microorganism that lacks the engineered GPD. In some embodiments, the recombinant microorganism has an increased butanol to glycerol molar ratio as compared to a control recombinant microorganism that lacks the engineered GPD. In some embodiments, the recombinant microorganism has an increased effective yield as compared to a control recombinant microorganism that lacks the engineered GPD.

Also provided are methods for the production of butanol. The methods comprise providing a recombinant microorganism comprising (i) an engineered butanol biosynthetic pathway, (ii) a deletion or disruption in an endogenous gene encoding GPD, and; (iii) at least one of (a) an engineered GPD enzyme; (b) a heterologous glycerol-3-phosphate dehydrogenase (GPD), wherein the heterologous GPD has a higher $K_M$ for NADH as compared to the $K_M$ of the microorganism's endogenous GPD; or (c) a heterologous GPD, wherein the heterologous GPD has substantially the same affinity for NADH and NADPH and/or is feedback inhibited; and contacting the recombinant microorganism with at least one fermentable carbon substrate under conditions wherein butanol is produced. Optionally, the heterologous GPD is feedback inhibited by glycerol-3-phosphate. In certain embodiments, the recombinant microorganism is grown under anaerobic conditions.

The recombinant microorganism can comprise an engineered butanol biosynthetic pathway selected from the group consisting of (a) a 1-butanol biosynthetic pathway; (b) a 2-butanol biosynthetic pathway; and (c) an isobutanol biosynthetic pathway.

Optionally, the 1-butanol biosynthetic pathway comprises at least one polypeptide that performs one of the following substrate to product conversions: (a) acetyl-CoA to acetoacetyl-CoA, as catalyzed by acetyl-CoA acetyltransferase; (b) acetoacetyl-CoA to 3-hydroxybutyryl-CoA, as catalyzed by 3-hydroxybutyryl-CoA dehydrogenase; (c) 3-hydroxybutyryl-CoA to crotonyl-CoA, as catalyzed by crotonase; (d) crotonyl-CoA to butyryl-CoA, as catalyzed by butyryl-CoA dehydrogenase; (e) butyryl-CoA to butyraldehyde, as catalyzed by butyraldehyde dehydrogenase; and (f) butyraldehyde to 1-butanol, as catalyzed by 1-butanol dehydrogenase.

Optionally, the 2-butanol biosynthetic pathway comprises at least one polypeptide that performs one of the following substrate to product conversions: (a) pyruvate to alpha-acetolactate, as catalyzed by acetolactate synthase; (b) alpha-acetolactate to acetoin, as catalyzed by acetolactate decarboxylase; (c) acetoin to 2,3-butanediol, as catalyzed by butanediol dehydrogenase; (d) 2,3-butanediol to 2-butanone, as catalyzed by butanediol dehydratase; and (e) 2-butanone to 2-butanol, as catalyzed by 2-butanol dehydrogenase.

Optionally, the isobutanol biosynthetic pathway comprises at least one polypeptide that performs one of the following substrate to product conversions: (a) pyruvate to acetolactate, as catalyzed by acetolactate synthase; (b) acetolactate to 2,3-dihydroxyisovalerate, as catalyzed by ketol-acid reductoisomerase; (c) 2,3-dihydroxyisovalerate to α-ketoisovalerate, as catalyzed by dihydroxyacid dehydratase; (d) α-ketoisovalerate to isobutyraldehyde, as catalyzed by a branched chain keto acid decarboxylase; and (e) isobutyraldehyde to isobutanol, as catalyzed by branched-chain alcohol dehydrogenase.

In certain embodiments, the recombinant microorganism is from a genus selected from the group consisting of *Clostridium, Zymomonas, Escherichia, Salmonella, Serratia, Erwinia, Klebsiella, Shigella, Rhodococcus, Pseudomonas, Bacillus, Lactobacillus, Enterococcus, Alcaligenes, Paenibacillus, Arthrobacter, Corynebacterium, Brevibacterium, Schizosaccharomyces, Kluveromyces, Yarrowia, Pichia, Zygosaccharomyces, Debaryomyces, Candida, Brettanomyces, Pachysolen, Hansenula, Issatchenkia, Trichosporon, Yamadazyma*, and *Saccharomyces*.

Also provided are recombinant microorganisms comprising (a) a heterologous glycerol-3-phosphate dehydrogenase (GPD), wherein the heterologous GPD has a higher $K_M$ for NADH as compared to the $K_M$ of the endogenous GPD of the microorganism; and (b) a deletion or disruption in an endogenous gene encoding GPD. In some embodiments the microorganism has decreased production of glycerol as compared to a control recombinant microorganism that lacks the heterologous GPD.

Also provided are recombinant microorganisms comprising (a) a heterologous glycerol-3-phosphate dehydrogenase (GPD), wherein the heterologous GPD has substantially the same affinity for NADH and NADPH and/or is feedback inhibited; and (b) a deletion or disruption in an endogenous gene encoding GPD. Optionally, the heterologous GPD is feedback inhibited by glycerol-3-phosphate. In some embodiments the microorganism has decreased production of glycerol as compared to a control recombinant microorganism that lacks the heterologous GPD.

Also provided are recombinant microorganisms comprising a heterologous GPD, wherein the heterologous GPD has substantially the same affinity for NADH and NADPH and/or is feedback inhibited, and wherein the recombinant microorganism has decreased production of glycerol as compared to a control recombinant microorganism that lacks the heterologous GPD. Optionally, the heterologous GPD is feedback inhibited by glycerol-3-phosphate.

BRIEF DESCRIPTION OF THE DRAWINGS/FIGURES

FIG. 2 shows a partial alignment of the GPD sequences of human truncated (SEQ ID NO:190), *Saccharomyces cerevisiae* (GPD1) (SEQ ID NO:191), *Rickettsia prowazekii* (SEQ ID NO:192), *Beggiatoa alba* (SEQ ID NO:193), and *Kangiella koreensis* (SEQ ID NO:194) Asterisk (*) indicates the positions of the phe41 and phe97 in the human truncated sequence.

Figure 1:
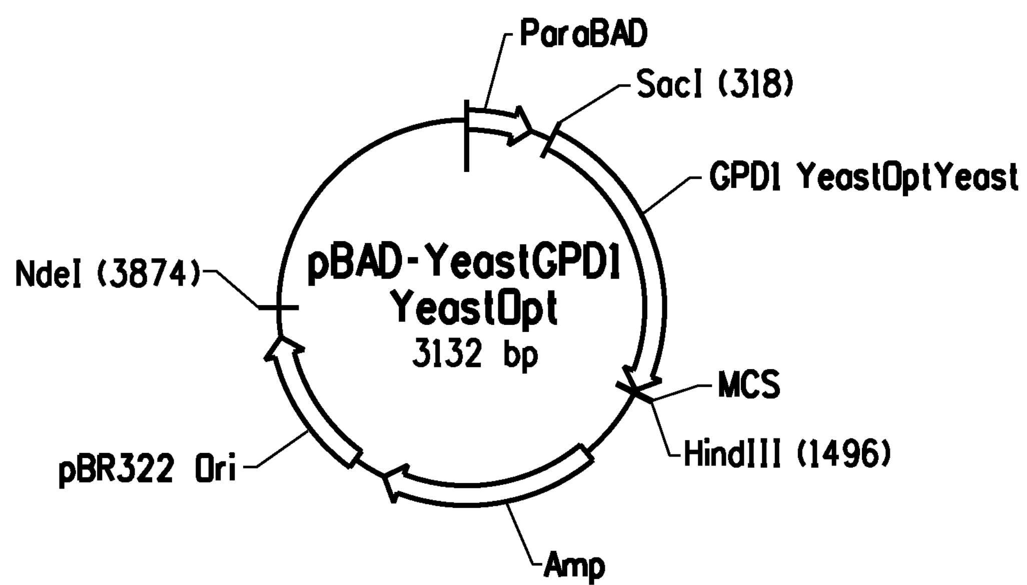
FIG. 1 shows a map of the plasmid used to express variant GPD proteins in *E. coli*.
Figure 3:
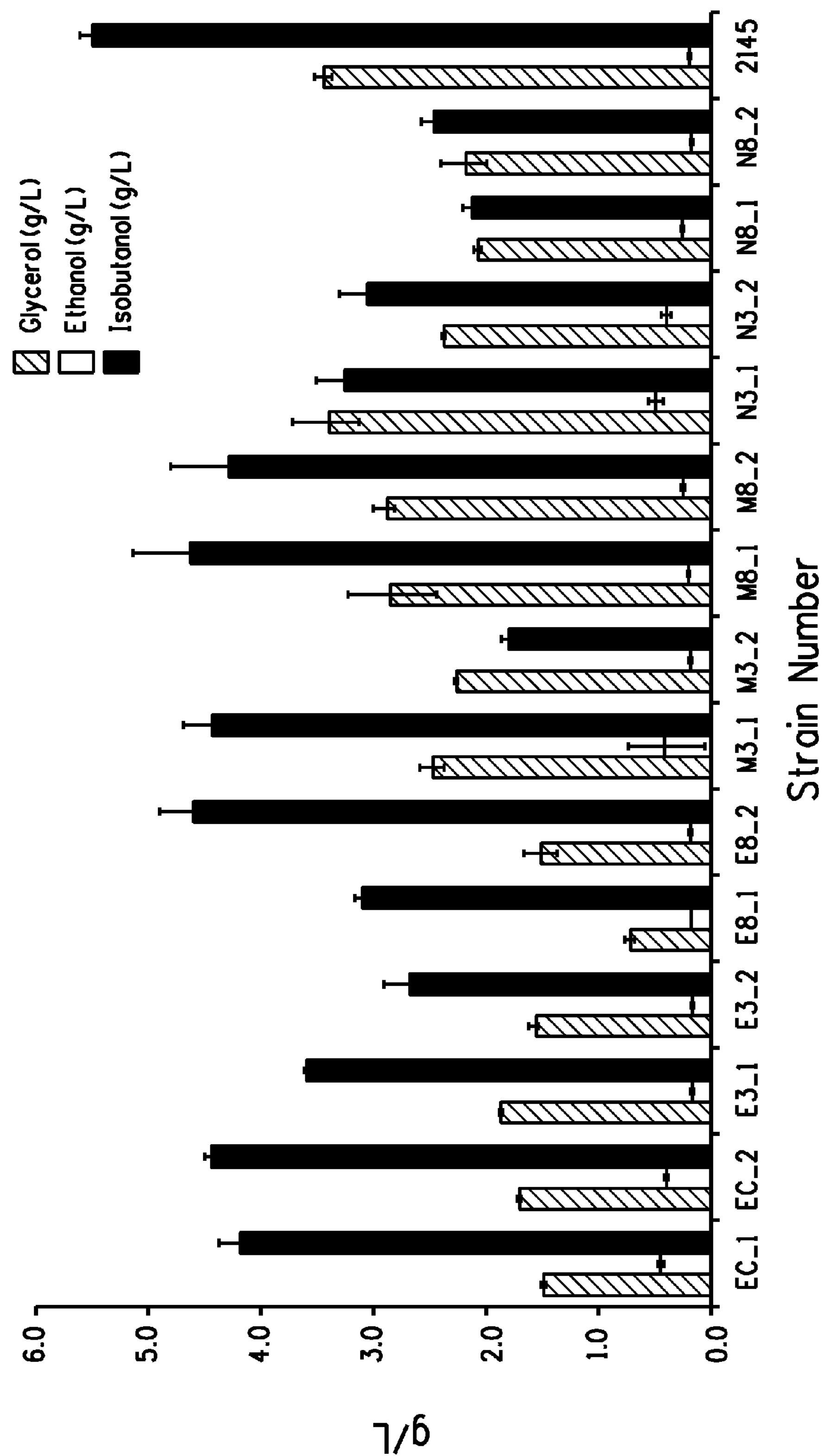

FIG. 3 shows a graph demonstrating 20 hour production data for the indicated GPD1 variant and control cell cultures. Two clones for each variant were tested in duplicate. 2145: isobutanologen control strain with WT GPD which is PNY2145 transformed with pLMH11-JM44; EC_1 and EC_2: *E. coli* optimized GPD; E3 and E8: *E. coli* optimized GPD1 variants; N3 and N8: yeast native codon-usage GPD variants; M3 and M8: Yeast codon optimized GPD variants. Variants E3, N3, and M3 has F73A substitution and variants E8, N8, and M8 have F73G/F129G substitutions.

Figure 4:
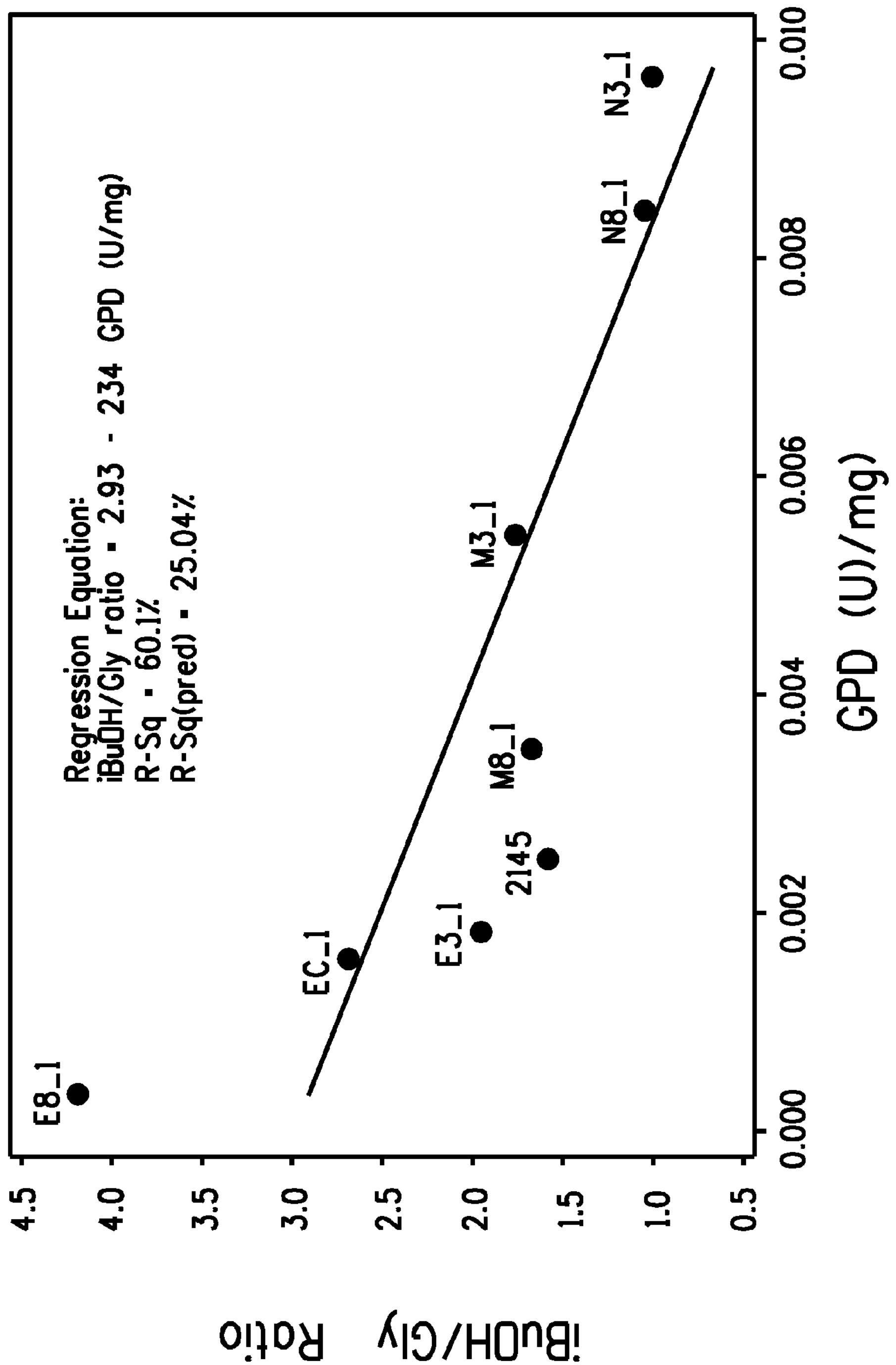

FIG. 4 shows a graph demonstrating a comparison of isobutanol (iBuOH)/glycerol (Gly) ratio with measured GPD activity (U/mg). The regression equation for the iBuOH/Gly ratio equals 2.93-234GPD (U/mg) (R-Sq=60.1%; $R\text{-}Sq_{(pred)}$=25.04%).

Figure 5:
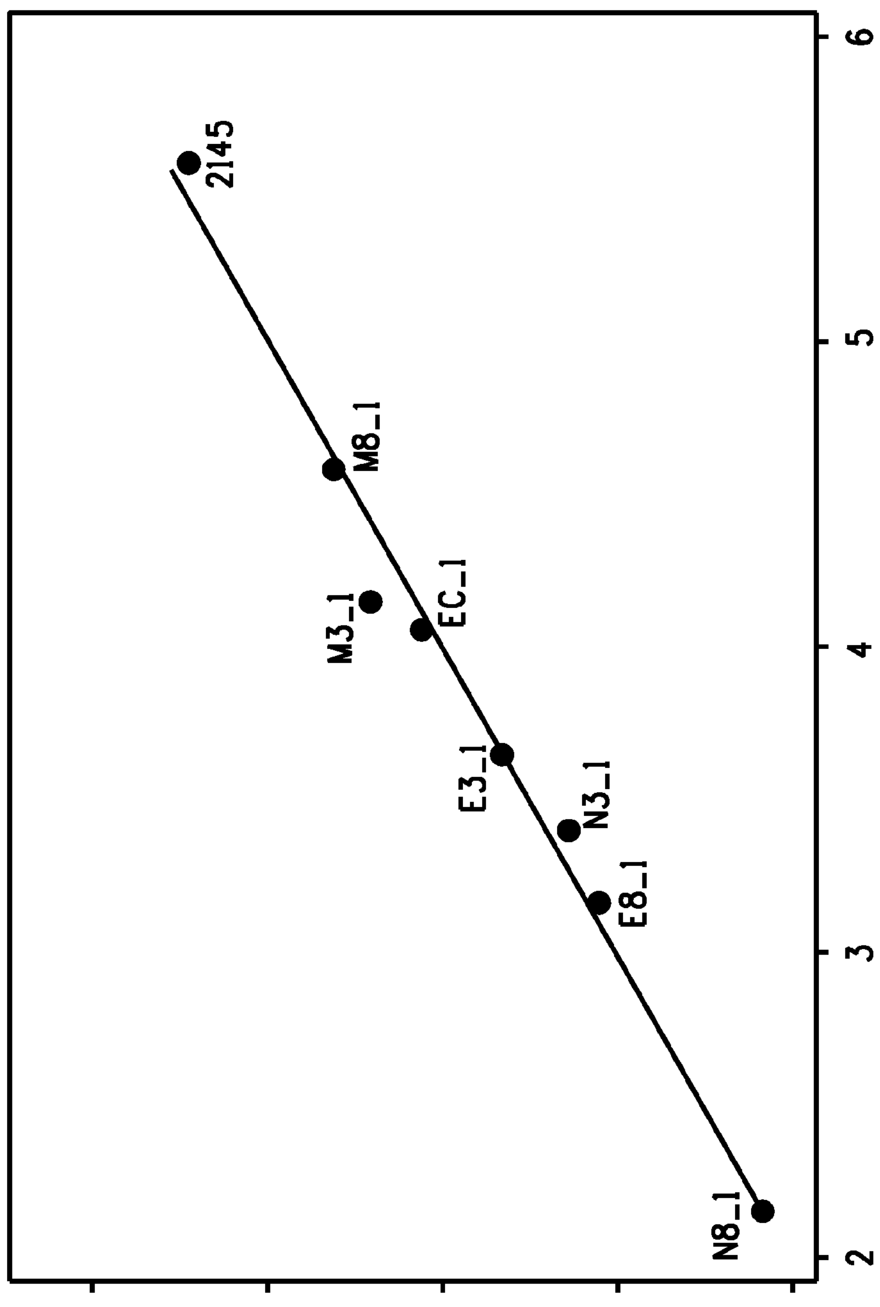

FIG. 5 shows a graph demonstrating a comparison of measured isobutanol titer to values calculated by the linear regression equation (FIT 2) (S=0.159277; R-Sq=98.6%; $R\text{-}Sq_{(adj)}$=97.6%; PRESS=0.415575; $R\text{-}Sq_{(pred)}$=94.32%). The constant and coefficients for the regression equation are provided in Table 12.

Figure 6:
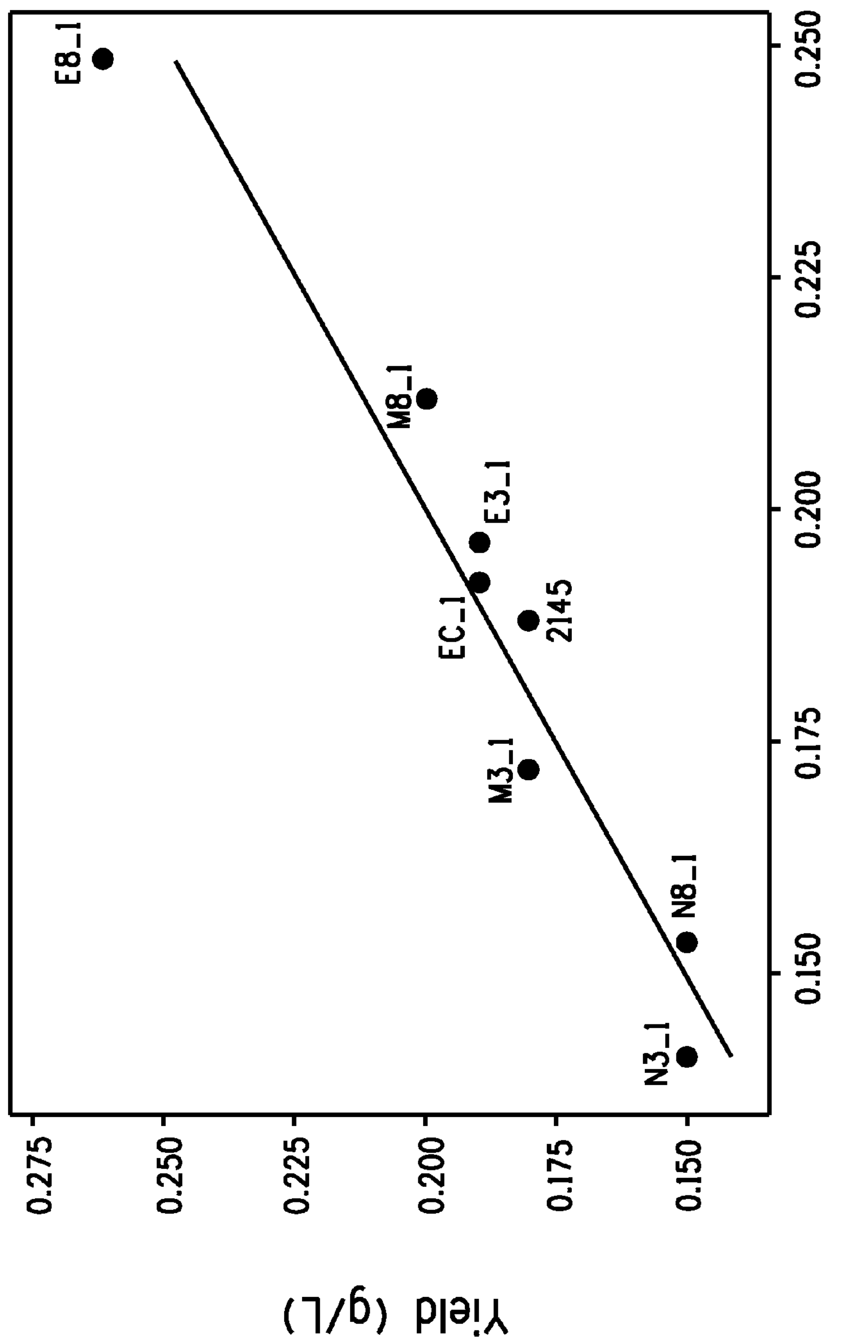

FIG. 6 shows a graph demonstrating a comparison of isobutanol yield (grams isobutanol/gram glucose consumed) to values calculated by the linear regression equation (FIT_4) (S=0.0101071; R-Sq=93.9%; R-Sq(adj)=91.4%; PRESS=0.00197878; R-Sq(pred)=76.30%). The constant and coefficients for the regression equation are provided in Table 13.

Figure 7:
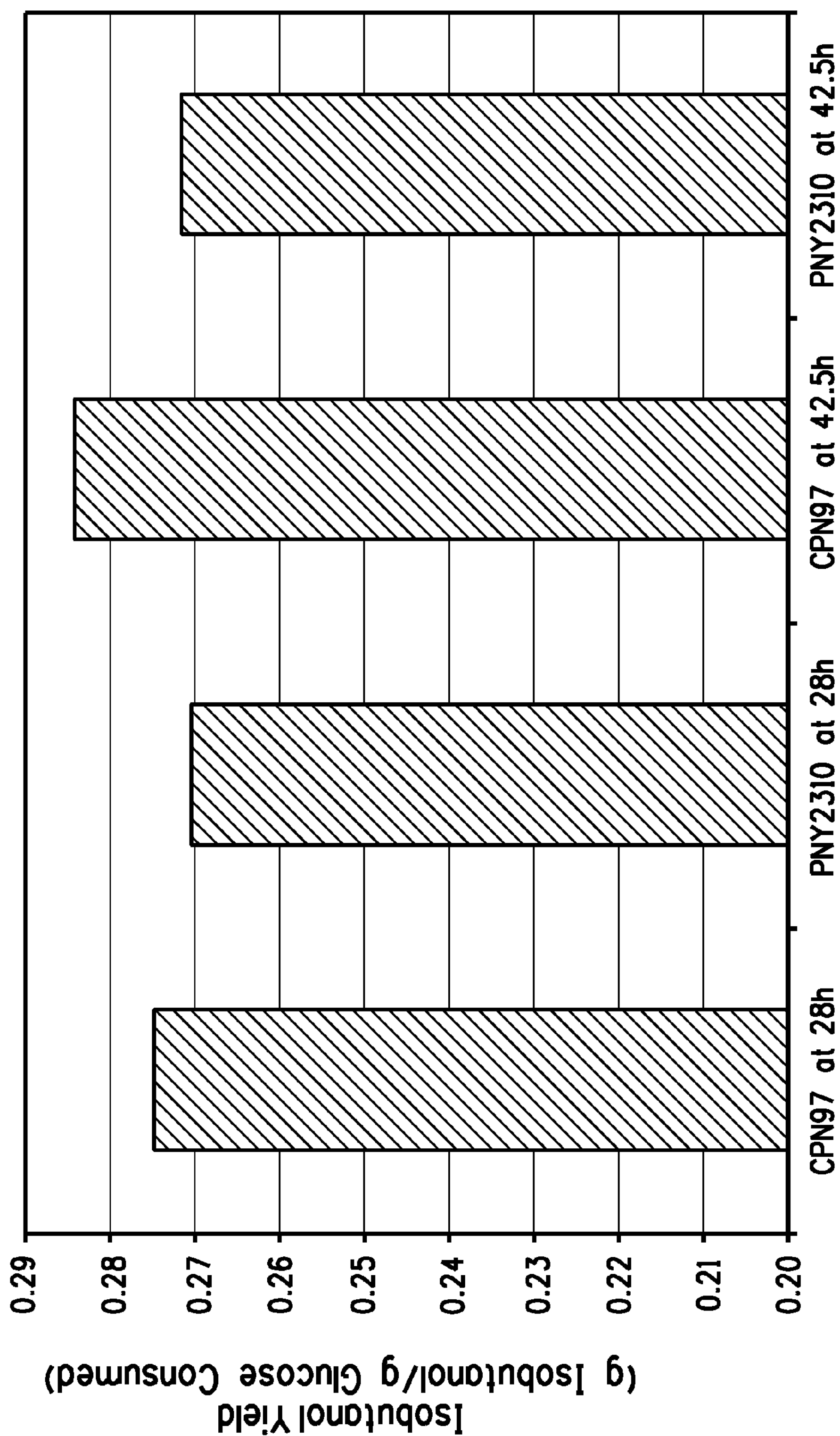

FIG. 7 shows a graph of the isobutanol yield (grams of isobutanol produced per gram of glucose consumed) at 28 and 42 hours for CPN97 and PNY2310 isobutanologen strains.

Figure 8:
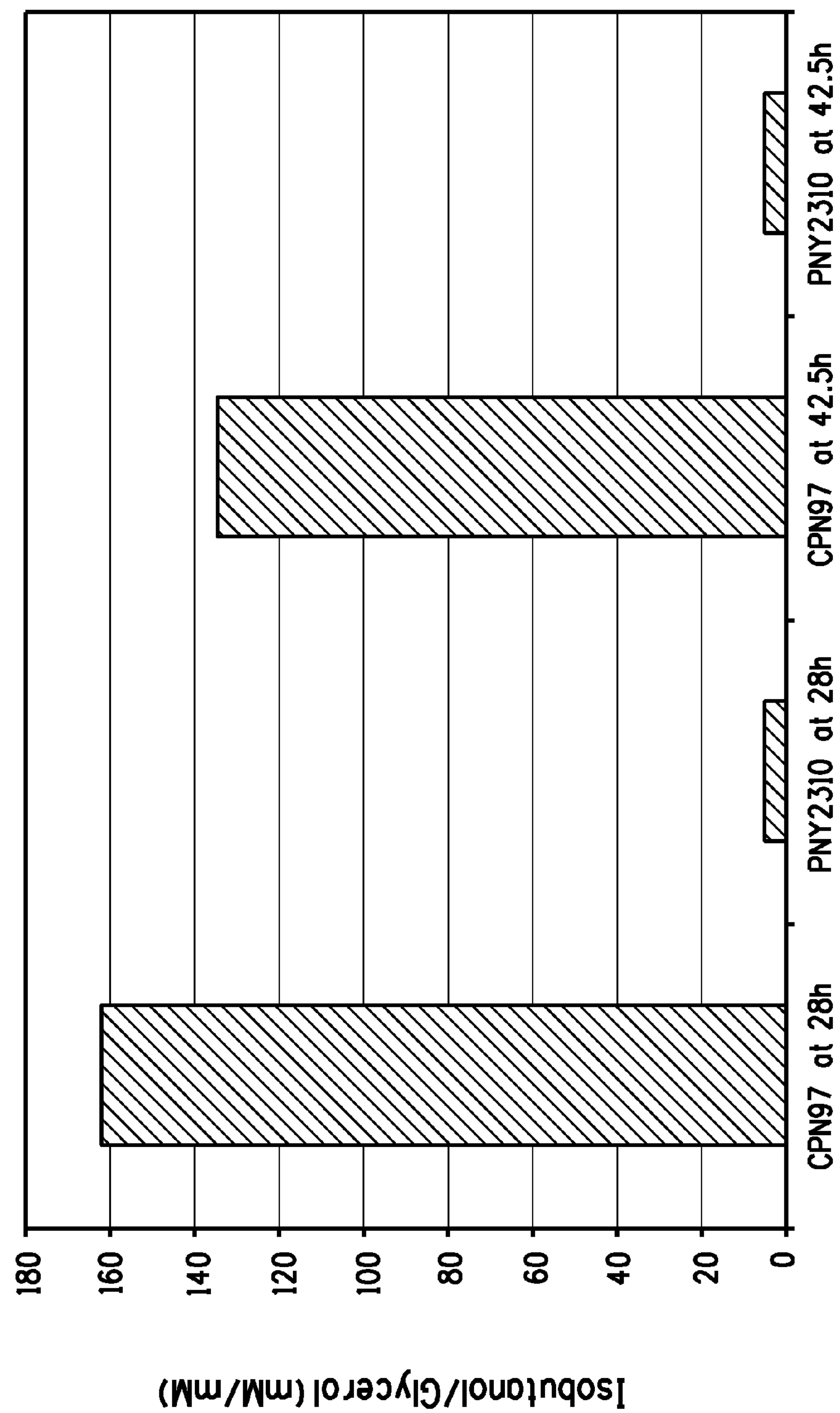

FIG. 8 shows a graph of the isobutanol/glycerol ratio at 28 and 42 hours for CPN97 and PNY2310 isobutanologen strains.

Figure 9:
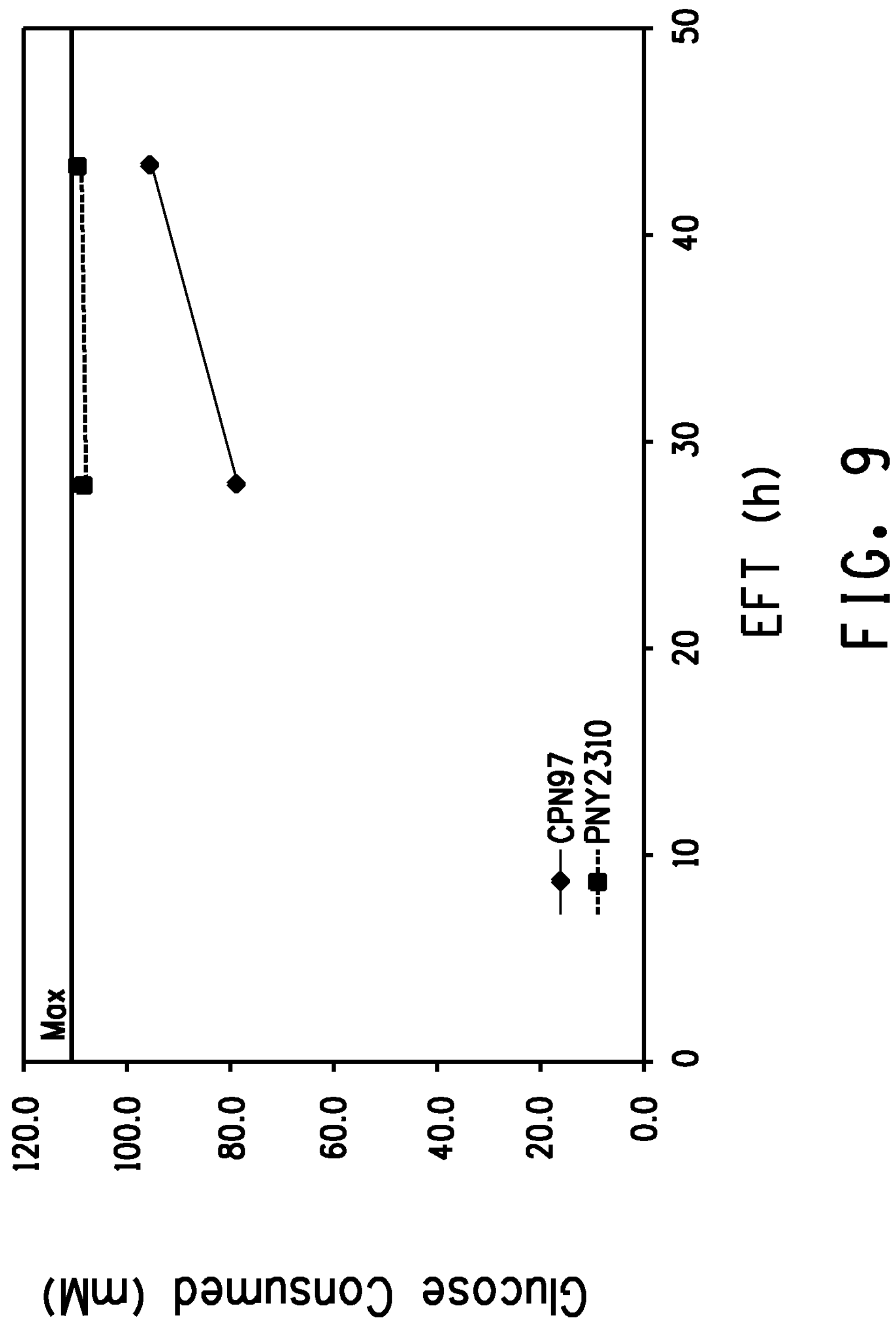

FIG. 9 shows a graph of glucose consumed as a function of time for CPN97 and PNY2310 isobutanologen strains.

DETAILED DESCRIPTION OF THE INVENTION

Unless defined otherwise, all technical and scientific terms used herein have the same meaning as commonly understood by one of ordinary skill in the art to which this invention belongs. In case of conflict, the present application including the definitions will control. Also, unless otherwise required by context, singular terms shall include pluralities and plural terms shall include the singular. All publications, patents and other references mentioned herein are incorporated by reference in their entireties for all purposes as if each individual publication or patent application were specifically and individually indicated to be incorporated by reference, unless only specific sections of patents or patent publications are indicated to be incorporated by reference.

In order to further define this invention, the following terms, abbreviations and definitions are provided.

It will be understood that "derived from" with reference to polypeptides disclosed herein encompasses sequences synthesized based on the amino acid sequences of the GPDs, or other enzymes, present in the indicated organisms as well as those cloned directly from the genetic material of the organism.

As used herein, the terms "comprises," "comprising," "includes," "including," "has," "having," "contains" or "containing," or any other variation thereof, will be understood to imply the inclusion of a stated integer or group of integers but not the exclusion of any other integer or group of integers and are intended to be non-exclusive or open-ended. For example, a composition, a mixture, a process, a method, an article, or an apparatus that comprises a list of elements is not necessarily limited to only those elements but can include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

As used herein, the term "consists of," or variations such as "consist of" or "consisting of," as used throughout the specification and claims, indicate the inclusion of any recited integer or group of integers, but that no additional integer or group of integers can be added to the specified method, structure, or composition.

As used herein, the term "consists essentially of," or variations such as "consist essentially of" or "consisting essentially of," as used throughout the specification and claims, indicate the inclusion of any recited integer or group of integers, and the optional inclusion of any recited integer or group of integers that do not materially change the basic or novel properties of the specified method, structure or composition. See M.P.E.P. §2111.03.

Also, the indefinite articles "a" and "an" preceding an element or component of the invention are intended to be nonrestrictive regarding the number of instances, i.e., occurrences of the element or component. Therefore "a" or "an" should be read to include one or at least one, and the singular word form of the element or component also includes the plural unless the number is obviously meant to be singular.

The term "invention" or "present invention" as used herein is a non-limiting term and is not intended to refer to any single embodiment of the particular invention but encompasses all possible embodiments as described in the claims as presented or as later amended and supplemented, or in the specification.

As used herein, the term "about" modifying the quantity of an ingredient or reactant of the invention employed refers to variation in the numerical quantity that can occur, for example, through typical measuring and liquid handling procedures used for making concentrates or solutions in the real world; through inadvertent error in these procedures; through differences in the manufacture, source, or purity of the ingredients employed to make the compositions or to carry out the methods; and the like. The term "about" also encompasses amounts that differ due to different equilibrium conditions for a composition resulting from a particular initial mixture. Whether or not modified by the term "about", the claims include equivalents to the quantities. In one embodiment, the term "about" means within 10% of the reported numerical value, or within 5% of the reported numerical value.

The term "butanol biosynthetic pathway" as used herein refers to the enzymatic pathway to produce 1-butanol, 2-butanol, or isobutanol.

The term "1-butanol biosynthetic pathway" refers to an enzymatic pathway to produce 1-butanol. A "1-butanol biosynthetic pathway" can refer to an enzyme pathway to produce 1-butanol from acetyl-coenzyme A (acetyl-CoA). For example, 1-butanol biosynthetic pathways are disclosed in U.S. Patent Application Publication No. 2008/0182308 and International Publication No. WO 2007/041269, which are herein incorporated by reference in their entireties.

The term "2-butanol biosynthetic pathway" refers to an enzymatic pathway to produce 2-butanol. A "2-butnaol biosynthetic pathway" can refer to an enzyme pathway to produce 2-butanol from pyruvate. For example, 2-butanol biosynthetic pathways are disclosed in U.S. Pat. No. 8,206, 970, U.S. Patent Application Publication No. 2007/0292927, International Publication Nos. WO 2007/130518 and WO 2007/130521, which are herein incorporated by reference in their entireties.

The term "isobutanol biosynthetic pathway" refers to an enzymatic pathway to produce isobutanol. An "isobutanol biosynthetic pathway" can refer to an enzyme pathway to produce isobutanol from pyruvate. For example, isobutanol biosynthetic pathways are disclosed in U.S. Pat. No. 7,851, 188, U.S. Application Publication No. 2007/0092957, and International Publication No. WO 2007/050671, which are herein incorporated by reference in their entireties. From time to time "isobutanol biosynthetic pathway" is used synonymously with "isobutanol production pathway."

The term "butanol" as used herein refers to the butanol isomers 1-butanol (1-BuOH), 2-butanol (2-BuOH), tert-butanol (t-BuOH), and/or isobutanol (iBuOH or i-BuOH, also known as 2-methyl-1-propanol), either individually or as mixtures thereof. From time to time, as used herein the terms "biobutanol" and "bio-produced butanol" may be used synonymously with "butanol."

Uses for butanol can include, but are not limited to, fuels (e.g., biofuels), a fuel additive, an alcohol used for the production of esters that can be used as diesel or biodiesel fuel, as a chemical in the plastics industry, an ingredient in formulated products such as cosmetics, and a chemical intermediate. Butanol may also be used as a solvent for paints, coatings, varnishes, resins, gums, dyes, fats, waxes, resins, shellac, rubbers, and alkaloids.

As used herein, the term "bio-produced" means that the molecule (e.g., butanol) is produced from a renewable source (e.g., the molecule can be produced during a fermentation process from a renewable feedstock). Thus, for example, bio-produced isobutanol can be isobutanol produced by a fermentation process from a renewable feedstock. Molecules produced from a renewable source can further be defined by the $^{14}C/^{12}C$ isotope ratio. A $^{14}C/^{12}C$ isotope ratio in range of from 1:0 to greater than 0:1 indicates a bio-produced molecule, whereas a ratio of 0:1 indicates that the molecule is fossil derived.

A recombinant host cell comprising an "engineered alcohol production pathway" (such as an engineered butanol or isobutanol production pathway) refers to a host cell containing a modified pathway that produces alcohol in a manner different than that normally present in the host cell. Such differences include production of an alcohol not typically produced by the host cell, or increased or more efficient production.

The term "heterologous biosynthetic pathway" as used herein refers to an enzyme pathway to produce a product in which at least one of the enzymes is not endogenous to the host cell containing the biosynthetic pathway.

The term "extractant" as used herein refers to one or more organic solvents which can be used to extract alcohol (e.g., butanol) from a fermentation broth.

The term "effective isobutanol productivity" as used herein refers to the total amount in grams of isobutanol produced per gram of cells.

The term "effective titer" as used herein, refers to the total amount of a particular alcohol (e.g., butanol) produced by fermentation per liter of fermentation medium. The total amount of butanol includes: (i) the amount of butanol in the fermentation medium; (ii) the amount of butanol recovered from the organic extractant; and (iii) the amount of butanol recovered from the gas phase, if gas stripping is used.

The term "effective rate" as used herein, refers to the total amount of alcohol (e.g., butanol) produced by fermentation per liter of fermentation medium per hour of fermentation.

The term "effective yield" as used herein, refers to the amount of alcohol (e.g., butanol) produced per unit of fermentable carbon substrate consumed by the biocatalyst.

The term "separation" as used herein is synonymous with "recovery" and refers to removing a chemical compound from an initial mixture to obtain the compound in greater purity or at a higher concentration than the purity or concentration of the compound in the initial mixture.

The term "aqueous phase," as used herein, refers to the aqueous phase of a biphasic mixture obtained by contacting a fermentation broth with a water-immiscible organic extractant. In an embodiment of a process described herein that includes fermentative extraction, the term "fermentation broth" then specifically refers to the aqueous phase in biphasic fermentative extraction.

The term "organic phase," as used herein, refers to the non-aqueous phase of a biphasic mixture obtained by contacting a fermentation broth with a water-immiscible organic extractant.

The term "carbon substrate" or "fermentable carbon substrate" refers to a carbon source capable of being metabolized by host organisms of the present invention and particularly carbon sources selected from the group consisting of monosaccharides, oligosaccharides, polysaccharides, and one-carbon substrates or mixtures thereof. Non-limiting examples of carbon substrates are provided herein and include, but are not limited to, monosaccharides, disaccharides, oligosaccharides, polysaccharides, ethanol, lactate, succinate, glycerol, carbon dioxide, methanol, glucose, fructose, lactose, sucrose, xylose, arabinose, dextrose, cellulose, methane, amino acids, or mixtures thereof.

"Fermentation broth" as used herein means the mixture of water, sugars (fermentable carbon sources), dissolved solids (if present), microorganisms producing alcohol, product alcohol and all other constituents of the material in which product alcohol is being made by the reaction of sugars to alcohol, water and carbon dioxide ($CO_2$) by the microorganisms present. From time to time, as used herein the term "fermentation medium" and "fermented mixture" can be used synonymously with "fermentation broth."

As used herein a "fermentor" refers to any container, containers, or apparatus that are used to ferment a substrate. A fermentor can contain a fermentation medium and microorganism capable of fermentation. The term "fermentation vessel" refers to the vessel in which the fermentation reaction is carried out whereby alcohol such as butanol is made. "Fermentor" can be used herein interchangeably with "fermentation vessel."

The term "fermentation product" includes any desired product of interest, including, but not limited to 1-butanol, 2-butanol, isobutanol, etc.

"Biomass" as used herein refers to a natural product containing a hydrolysable starch that provides a fermentable sugar, including any cellulosic or lignocellulosic material and materials comprising cellulose, and optionally further comprising hemicellulose, lignin, starch, oligosaccharides, disaccharides, and/or monosaccharides. Biomass can also comprise additional components, such as protein and/or lipids. Biomass can be derived from a single source, or biomass can comprise a mixture derived from more than one source. For example, biomass can comprise a mixture of corn cobs and corn stover, or a mixture of grass and leaves. Biomass includes, but is not limited to, bioenergy crops, agricultural residues, municipal solid waste, industrial solid waste, sludge from paper manufacture, yard waste, wood, and forestry waste. Examples of biomass include, but are not limited to, corn grain, corn cobs, crop residues such as corn husks, corn stover, grasses, wheat, rye, wheat straw, barley, barley straw, hay, rice straw, switchgrass, waste paper, sugar cane bagasse, sorghum, soy, components obtained from milling of grains, trees, branches, roots, leaves, wood chips, sawdust, shrubs and bushes, vegetables, fruits, flowers, animal manure, and mixtures thereof.

"Feedstock" as used herein means a product containing a fermentable carbon source. Suitable feedstock include, but are not limited to, rye, wheat, corn, corn mash, cane, cane mash, sugar cane, barley, cellulosic material, lignocellulosic material, and mixtures thereof.

The term "biomass" as used herein, in some instances, refers to the mass of the culture, e.g., the amount of recombinant microorganisms, typically provided in units of grams per liter (g/l) dry cell weight (dcw).

The term "aerobic conditions" as used herein means growth conditions in the presence of oxygen.

The term "microaerobic conditions" as used herein means growth conditions with low levels of oxygen (i.e., below normal atmospheric oxygen levels).

The term "anaerobic conditions" as used herein means growth conditions in the absence of oxygen.

The term "polynucleotide" is intended to encompass a singular nucleic acid as well as plural nucleic acids, and refers to a nucleic acid molecule or construct, e.g., messenger RNA (mRNA) or plasmid DNA (pDNA). A polynucleotide can contain the nucleotide sequence of the full-length cDNA sequence, or a fragment thereof, including the untranslated 5' and 3' sequences and the coding sequences. The polynucleotide can be composed of any polyribonucleotide or polydeoxyribonucleotide, which can be unmodified RNA or DNA or modified RNA or DNA. For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that can be single-stranded or, more typically, double-stranded or a mixture of single- and double-stranded regions. "Polynucleotide" embraces chemically, enzymatically, or metabolically modified forms.

A polynucleotide sequence can be referred to as "isolated," in which it has been removed from its native environment. For example, a heterologous polynucleotide encoding a polypeptide or polypeptide fragment having ALS activity contained in a vector is considered isolated for the purposes of the present invention. Further examples of an isolated polynucleotide include recombinant polynucleotides maintained in heterologous host cells or purified (partially or substantially) polynucleotides in solution. Isolated polynucleotides or nucleic acids according to the present invention further include such molecules produced synthetically. An isolated polynucleotide fragment in the form of a polymer of DNA can be comprised of one or more segments of cDNA, genomic DNA or synthetic DNA."

As used herein, "reduced activity" refers to any measurable decrease in a known biological activity of a polypeptide when compared to the same biological activity of the polypeptide prior to the change resulting in the reduced activity. Such a change can include a modification of a polypeptide or a polynucleotide encoding a polypeptide as described herein. A reduced activity of a polypeptide disclosed herein can be determined by methods well known in the art and disclosed herein. Reduced activity of an enzyme refers to down-regulation, whether partial or total, of the activity of the enzyme as compared to the activity of the wildtype enzyme. Down-regulation may occur when a native gene has a "disruption" or "modification," referring to an insertion, deletion, or targeted mutation within a portion of that gene, that results in e.g., a complete gene knockout such that the gene is deleted from the genome and no protein is translated or a translated subunit protein having an insertion, deletion, amino acid substitution or other targeted mutation. The location of the modification in the protein may be, for example, within the N-terminal portion of the protein or within the C-terminal portion of the protein. The modified protein will have impaired activity with respect to the protein that was not disrupted, and can be non-functional. Reduced activity in an enzyme could also result via manipulating the upstream regulatory domains or by use of sense, antisense or RNAi technology, etc. Another mechanism of reducing activity of an enzyme is introduction of a mutation that alters kinetic properties of the enzyme (e.g., reducing the affinity for a substrate, lowering the $k_{cat}$, etc.).

As used herein, "eliminated activity" refers to the complete abolishment of a known biological activity of a polypeptide when compared to the same biological activity of the polypeptide prior to the change resulting in the eliminated activity. Such a change can include a modification of a polypeptide or a polynucleotide encoding a polypeptide as described herein. An eliminated activity includes a biological activity of a polypeptide that is not measurable when compared to the same biological activity of the polypeptide prior to the change resulting in the eliminated activity. An eliminated activity of a polypeptide disclosed herein can be determined by methods well known in the art and disclosed herein.

The terms "PDC-," "PDC knockout," or "PDC-KO" as used herein refer to a cell that has a genetic modification to inactivate or reduce expression of a gene encoding pyruvate decarboxylase (PDC) so that the cell substantially or completely lacks pyruvate decarboxylase enzyme activity. If the cell has more than one expressed (active) PDC gene, then each of the active PDC genes can be inactivated or have minimal expression thereby producing a PDC− cell.

The term "specific activity" as used herein is defined as the units of activity in a given amount of protein. Thus, the specific activity is not directly measured but is calculated by dividing 1) the activity in units/ml of the enzyme sample by 2) the concentration of protein in that sample, so the specific activity is expressed as units/mg, where an enzyme unit is defined as moles of product formed/minute. The specific activity of a sample of pure, fully active enzyme is a characteristic of that enzyme. The specific activity of a sample of a mixture of proteins is a measure of the relative fraction of protein in that sample that is composed of the active enzyme of interest.

The terms "$k_{cat}$" and "$K_M$" are known to those skilled in the art and are described in Enzyme Structure and Mechanism, $2^{nd}$ ed. (Ferst; W.H. Freeman Press, NY, 1985; pp 98-120). $K_M$, the Michaelis constant, is the concentration of substrate that leads to half-maximal velocity. The term "$k_{cat}$", often called the "turnover number", is defined as the maximum number of substrate molecules converted to products per active site per unit time, or the number of times the enzyme turns over per unit time. $k_{cat}=V_{max}/[E]$, where [E] is the enzyme concentration (Ferst, supra). The terms "total turnover" and "total turnover number" are used herein to refer to the amount of product formed by the reaction of an enzyme with substrate.

The term "catalytic efficiency" is defined as the $k_{cat}/K_M$ of an enzyme. Catalytic efficiency is used to quantify the specificity of an enzyme for a substrate.

The term "isolated nucleic acid molecule", "isolated nucleic acid fragment" and "genetic construct" are used interchangeably and mean a polymer of RNA or DNA that is single or double-stranded, optionally containing synthetic, non natural or altered nucleotide bases. An isolated nucleic acid fragment in the form of a polymer of DNA can be comprised of one or more segments of cDNA, genomic DNA or synthetic DNA.

The term "amino acid" refers to the basic chemical structural unit of a protein or polypeptide. The abbreviations in Table 1 are used herein to identify specific amino acids.

TABLE 1

Amino acids and abbreviations thereof.

| Amino Acid | Three-Letter Abbreviation | One-Letter Abbreviation |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

The term "gene" refers to a nucleic acid fragment that is capable of being expressed as a specific protein, optionally including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene can comprise regulatory sequences and coding sequences that are derived from different sources, or regulatory sequences and coding sequences derived from the same source, but arranged in a manner different than that found in nature. "Endogenous gene" refers to a native gene in its natural location in the genome of a microorganism. A "foreign" gene refers to a gene not normally found in the host microorganism, but that is introduced into the host microorganism by gene transfer. Foreign genes can comprise native genes inserted into a non-native microorganism, or chimeric genes. A "transgene" is a gene that has been introduced into the genome by a transformation procedure.

As used herein, "native" refers to the form of a polynucleotide, gene, or polypeptide as found in nature with its own regulatory sequences, if present.

As used herein the term "coding sequence" or "coding region" refers to a DNA sequence that encodes for a specific amino acid sequence.

As used herein, "endogenous" refers to the native form of a polynucleotide, gene or polypeptide in its natural location in the organism or in the genome of an organism. "Endogenous polynucleotide" includes a native polynucleotide in its natural location in the genome of an organism. "Endogenous gene" includes a native gene in its natural location in the genome of an organism. "Endogenous polypeptide" includes a native polypeptide in its natural location in the organism transcribed and translated from a native polynucleotide or gene in its natural location in the genome of an organism.

The term "heterologous" when used in reference to a polynucleotide, a gene, or a polypeptide refers to a polynucleotide, gene, or polypeptide not normally found in the host organism. "Heterologous" also includes a native coding region, or portion thereof, that is reintroduced into the source organism in a form that is different from the corresponding native gene, e.g., not in its natural location in the organism"s genome. The heterologous polynucleotide or gene can be introduced into the host organism by, e.g., gene transfer. A heterologous gene can include a native coding region with non-native regulatory regions that is reintroduced into the native host. For example, a heterologous gene can include a native coding region that is a portion of a chimeric gene including non-native regulatory regions that is reintroduced into the native host. "Heterologous polypeptide" includes a native polypeptide that is reintroduced into the source organism in a form that is different from the corresponding native polypeptide. A "heterologous" polypeptide or polynucleotide can also include an engineered polypeptide or polynucleotide that comprises a difference from the "native" polypeptide or polynucleotide, e.g., a point mutation within the endogenous polynucleotide can result in the production of a "heterologous" polypeptide. As used herein a "chimeric gene," a "foreign gene," and a "transgene," can all be examples of "heterologous" genes.

A "transgene" is a gene that has been introduced into the genome by a transformation procedure.

As used herein, the term "modification" refers to a change in a polynucleotide disclosed herein that results in reduced or eliminated activity of a polypeptide encoded by the polynucleotide, as well as a change in a polypeptide disclosed herein that results in reduced or eliminated activity of the polypeptide. Such changes can be made by methods well known in the art, including, but not limited to, deleting, mutating (e.g., spontaneous mutagenesis, random mutagenesis, mutagenesis caused by mutator genes, or transposon mutagenesis), substituting, inserting, down-regulating, altering the cellular location, altering the state of the polynucleotide or polypeptide (e.g., methylation, phosphorylation or ubiquitination), removing a cofactor, introduction of an antisense RNA/DNA, introduction of an interfering RNA/DNA, chemical modification, covalent modification, irradiation with UV or X-rays, homologous recombination, mitotic recombination, promoter replacement methods, and/or combinations thereof. Guidance in determining which nucleotides or amino acid residues can be modified can be found by comparing the sequence of the particular polynucleotide or polypeptide with that of homologous polynucleotides or polypeptides, e.g., yeast or bacterial, and maximizing the number of modifications made in regions of high homology (conserved regions) or consensus sequences.

The term "recombinant genetic expression element" refers to a nucleic acid fragment that expresses one or more specific proteins, including regulatory sequences preceding (5' non-coding sequences) and following (3' termination sequences) coding sequences for the proteins. A chimeric gene is a recombinant genetic expression element. The coding regions of an operon can form a recombinant genetic expression element, along with an operably linked promoter and termination region.

"Regulatory sequences" refers to nucleotide sequences located upstream (5' non-coding sequences), within, or downstream (3' non-coding sequences) of a coding sequence, and which influence the transcription, RNA processing or stability, or translation of the associated coding sequence. Regulatory sequences can include promoters, enhancers, operators, repressors, transcription termination signals, translation leader sequences, introns, polyadenylation recognition sequences, RNA processing site, effector binding site and stem-loop structure.

The term "promoter" refers to a nucleic acid sequence capable of controlling the expression of a coding sequence or functional RNA. In general, a coding sequence is located 3' to a promoter sequence. Promoters can be derived in their entirety from a native gene, or be composed of different elements derived from different promoters found in nature, or even comprise synthetic nucleic acid segments. It is understood by those skilled in the art that different promoters can direct the expression of a gene in different tissues or cell types, or at different stages of development, or in response to different environmental or physiological conditions. Promoters which cause a gene to be expressed in most cell types at most times are commonly referred to as "constitutive promoters". "Inducible promoters," on the other hand, cause a gene to be expressed when the promoter is induced or turned on by a promoter-specific signal or molecule. It is further recognized that since in most cases the exact boundaries of regulatory sequences have not been completely defined, DNA fragments of different lengths can have identical promoter activity. For example, it will be understood that "FBA1 promoter" can be used to refer to a fragment derived from the promoter region of the FBA1 gene.

The term "terminator" as used herein refers to DNA sequences located downstream of a coding sequence. This includes polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The 3' region can influence the transcription, RNA processing or stability, or translation of the associated coding sequence. It is recognized that since in most cases the exact boundaries of regulatory sequences have not been completely defined, DNA fragments of different lengths can have identical terminator activity. For example, it will be understood that "CYC1 terminator" can be used to refer to a fragment derived from the terminator region of the CYC1 gene.

The term "operably linked" refers to the association of nucleic acid sequences on a single nucleic acid fragment so that the function of one is affected by the other. For example, a promoter is operably linked with a coding sequence when it is capable of effecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression can also refer to translation of mRNA into a polypeptide.

The term "overexpression," as used herein, refers to expression that is higher than endogenous expression of the same or related gene. A heterologous gene is overexpressed if its expression is higher than that of a comparable endogenous gene.

The term overexpression refers to an increase in the level of nucleic acid or protein in a host cell. Thus, overexpression can result from increasing the level of transcription or translation of an endogenous sequence in a host cell or can result from the introduction of a heterologous sequence into a host cell. Overexpression can also result from increasing the stability of a nucleic acid or protein sequence.

As used herein the term "transformation" refers to the transfer of a nucleic acid fragment into the genome of a host microorganism, resulting in genetically stable inheritance. Host microorganisms containing the transformed nucleic acid fragments are referred to as "transgenic" or "recombinant" or "transformed" microorganisms.

The terms "plasmid", "vector" and "cassette" refer to an extra chromosomal element often carrying genes which are not part of the central metabolism of the cell, and usually in the form of circular double-stranded DNA fragments. Such elements can be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitates transformation of a particular host cell. "Expression cassette" refers to a specific vector containing a foreign gene and having elements in addition to the foreign gene that allow for enhanced expression of that gene in a foreign host.

As used herein the term "codon degeneracy" refers to the nature in the genetic code permitting variation of the nucleotide sequence without affecting the amino acid sequence of an encoded polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

The term "codon-optimized" as it refers to genes or coding regions of nucleic acid molecules for transformation of various hosts, refers to the alteration of codons in the gene or coding regions of the nucleic acid molecules to reflect the typical codon usage of the host organism without altering the polypeptide encoded by the DNA. Such optimization includes replacing at least one, or more than one, or a significant number, of codons with one or more codons that are more frequently used in the genes of that organism.

Deviations in the nucleotide sequence that comprise the codons encoding the amino acids of any polypeptide chain allow for variations in the sequence coding for the gene. Since each codon consists of three nucleotides, and the nucleotides comprising DNA are restricted to four specific bases, there are 64 possible combinations of nucleotides, 61 of which encode amino acids (the remaining three codons encode signals ending translation). The "genetic code" which shows which codons encode which amino acids is reproduced herein as Table 2A. As a result, many amino acids are designated by more than one codon. For example, the amino acids alanine and proline are coded for by four triplets, serine and arginine by six, whereas tryptophan and methionine are coded by just one triplet. This degeneracy allows for DNA base composition to vary over a wide range without altering the amino acid sequence of the proteins encoded by the DNA.

TABLE 2A

The Standard Genetic Code

| | T | C | A | G |
|---|---|---|---|---|
| T | TTT Phe (F) | TCT Ser (S) | TAT Tyr (Y) | TGT Cys (C) |
| | TTC Phe (F) | TCC Ser (S) | TAC Tyr (Y) | TGC |
| | TTA Leu (L) | TCA Ser (S) | TAA Stop | TGA Stop |
| | TTG Leu (L) | TCG Ser (S) | TAG Stop | TGG Trp (W) |
| C | CTT Leu (L) | CCT Pro (P) | CAT His (H) | CGT Arg (R) |
| | CTC Leu (L) | CCC Pro (P) | CAC His (H) | CGC Arg (R) |
| | CTA Leu (L) | CCA Pro (P) | CAA Gln (Q) | CGA Arg (R) |
| | CTG Leu (L) | CCG Pro (P) | CAG Gln (Q) | CGG Arg (R) |
| A | ATT Ile (I) | ACT Thr (T) | AAT Asn (N) | AGT Ser (S) |
| | ATC Ile (I) | ACC Thr (T) | AAC Asn (N) | AGC Ser (S) |
| | ATA Ile (I) | ACA Thr (T) | AAA Lys (K) | AGA Arg (R) |
| | ATG Met (M) | ACG Thr (T) | AAG Lys (K) | AGG Arg (R) |
| G | GTT Val (V) | GCT Ala (A) | GAT Asp (D) | GGT Gly (G) |
| | GTC Val (V) | GCC Ala (A) | GAC Asp (D) | GGC Gly (G) |
| | GTA Val (V) | GCA Ala (A) | GAA Glu (E) | GGA Gly (G) |
| | GTG Val (V) | GCG Ala (A) | GAG Glu (E) | GGG Gly (G) |

Many organisms display a bias for use of particular codons to code for insertion of a particular amino acid in a growing peptide chain. Codon preference, or codon bias, differences in codon usage between organisms, is afforded by degeneracy of the genetic code, and is well documented among many organisms. Codon bias often correlates with the efficiency of translation of messenger RNA (mRNA), which is in turn believed to be dependent on, inter alia, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization.

Given the large number of gene sequences available for a wide variety of animal, plant and microbial species, it is possible to calculate the relative frequencies of codon usage. Codon usage tables are readily available, for example, at the "Codon Usage Database" available at the Kazusa DNA Research Institute, Japan, and these tables can be adapted in a number of ways. See Nakamura, Y., et al. *Nucl. Acids Res.* 28:292 (2000). Codon usage tables for yeast, calculated from GenBank Release 128.0 [15 Feb. 2002], are reproduced below as Table 2B. This table uses mRNA nomenclature, and so instead of thymine (T) which is found in DNA, the tables use uracil (U) which is found in RNA. The Table has been adapted so that frequencies are calculated for each amino acid, rather than for all 64 codons.

TABLE 2B

Codon Usage Table for *Saccharomyces cerevisiae*.

| Amino Acid | Codon | Number | Frequency per thousand |
|---|---|---|---|
| Phe | UUU | 170666 | 26.1 |
| Phe | UUC | 120510 | 18.4 |
| Leu | UUA | 170884 | 26.2 |
| Leu | UUG | 177573 | 27.2 |
| Leu | CUU | 80076 | 12.3 |
| Leu | CUC | 35545 | 5.4 |
| Leu | CUA | 87619 | 13.4 |
| Leu | CUG | 68494 | 10.5 |
| Ile | AUU | 196893 | 30.1 |
| Ile | AUC | 112176 | 17.2 |
| Ile | AUA | 116254 | 17.8 |
| Met | AUG | 136805 | 20.9 |
| Val | GUU | 144243 | 22.1 |
| Val | GUC | 76947 | 11.8 |
| Val | GUA | 76927 | 11.8 |
| Val | GUG | 70337 | 10.8 |
| Ser | UCU | 153557 | 23.5 |
| Ser | UCC | 92923 | 14.2 |
| Ser | UCA | 122028 | 18.7 |
| Ser | UCG | 55951 | 8.6 |
| Ser | AGU | 92466 | 14.2 |
| Ser | AGC | 63726 | 9.8 |
| Pro | CCU | 88263 | 13.5 |
| Pro | CCC | 44309 | 6.8 |
| Pro | CCA | 119641 | 18.3 |
| Pro | CCG | 34597 | 5.3 |
| Thr | ACU | 132522 | 20.3 |
| Thr | ACC | 83207 | 12.7 |
| Thr | ACA | 116084 | 17.8 |
| Thr | ACG | 52045 | 8.0 |
| Ala | GCU | 138358 | 21.2 |
| Ala | GCC | 82357 | 12.6 |
| Ala | GCA | 105910 | 16.2 |
| Ala | GCG | 40358 | 6.2 |
| Tyr | UAU | 122728 | 18.8 |
| Tyr | UAC | 96596 | 14.8 |
| His | CAU | 89007 | 13.6 |
| His | CAC | 50785 | 7.8 |
| Gln | CAA | 178251 | 27.3 |
| Gln | CAG | 79121 | 12.1 |
| Asn | AAU | 233124 | 35.7 |
| Asn | AAC | 162199 | 24.8 |
| Lys | AAA | 273618 | 41.9 |
| Lys | AAG | 201361 | 30.8 |
| Asp | GAU | 245641 | 37.6 |
| Asp | GAC | 132048 | 20.2 |
| Glu | GAA | 297944 | 45.6 |
| Glu | GAG | 125717 | 19.2 |
| Cys | UGU | 52903 | 8.1 |
| Cys | UGC | 31095 | 4.8 |
| Trp | UGG | 67789 | 10.4 |
| Arg | CGU | 41791 | 6.4 |
| Arg | CGC | 16993 | 2.6 |
| Arg | CGA | 19562 | 3.0 |
| Arg | CGG | 11351 | 1.7 |
| Arg | AGA | 139081 | 21.3 |

TABLE 2B-continued

| Codon Usage Table for *Saccharomyces cerevisiae*. | | | |
|---|---|---|---|
| Amino Acid | Codon | Number | Frequency per thousand |
| Arg | AGG | 60289 | 9.2 |
| Gly | GGU | 156109 | 23.9 |
| Gly | GGC | 63903 | 9.8 |
| Gly | GGA | 71216 | 10.9 |
| Gly | GGG | 39359 | 6.0 |
| Stop | UAA | 6913 | 1.1 |
| Stop | UAG | 3312 | 0.5 |
| Stop | UGA | 4447 | 0.7 |

By utilizing this or similar tables, one of ordinary skill in the art can apply the frequencies to any given polypeptide sequence, and produce a nucleic acid fragment of a codon-optimized coding region which encodes the polypeptide, but which uses codons optimal for a given species.

Randomly assigning codons at an optimized frequency to encode a given polypeptide sequence, can be done manually by calculating codon frequencies for each amino acid, and then assigning the codons to the polypeptide sequence randomly. Additionally, various algorithms and computer software programs are readily available to those of ordinary skill in the art. For example, the "EditSeq" function in the Lasergene Package, available from DNAstar, Inc., Madison, Wis., the backtranslation function in the VectorNTI Suite, available from InforMax, Inc., Bethesda, Md., and the "backtranslate" function in the GCG-Wisconsin Package, available from Accelrys, Inc., San Diego, Calif. In addition, various resources are publicly available to codon-optimize coding region sequences, e.g., the "backtranslation" function (Entelechon GmbH, Regensburg, Germany) and the "backtranseq" function (NRC Saskatoon Bioinformatics, Saskatoon, Saskatchewan, Canada). Constructing a rudimentary algorithm to assign codons based on a given frequency can also easily be accomplished with basic mathematical functions by one of ordinary skill in the art.

Codon-optimized coding regions can be designed by various methods known to those skilled in the art including software packages such as "synthetic gene designer" (University of Maryland, Baltimore, Md.).

A polynucleotide or nucleic acid fragment is "hybridizable" to another nucleic acid fragment, such as a cDNA, genomic DNA, or RNA molecule, when a single-stranded form of the nucleic acid fragment can anneal to the other nucleic acid fragment under the appropriate conditions of temperature and solution ionic strength. Hybridization and washing conditions are well known and exemplified in Sambrook, J., Fritsch, E. F. and Maniatis, T. Molecular Cloning: A Laboratory Manual, 2nd ed., Cold Spring Harbor Laboratory: Cold Spring Harbor, N.Y. (1989), particularly Chapter 11 and Table 11.1 therein (entirely incorporated herein by reference). The conditions of temperature and ionic strength determine the "stringency" of the hybridization. Stringency conditions can be adjusted to screen for moderately similar fragments (such as homologous sequences from distantly related organisms), to highly similar fragments (such as genes that duplicate functional enzymes from closely related organisms). Post hybridization washes determine stringency conditions. One set of conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. Another set of stringent conditions uses higher temperatures in which the washes are identical to those above except for the temperature of the final two 30 min washes in 0.2×SSC, 0.5% SDS was increased to 60° C. Another set of highly stringent conditions uses two final washes in 0.1×SSC, 0.1% SDS at 65° C. An additional set of stringent conditions include hybridization at 0.1×SSC, 0.1% SDS, 65° C. and washes with 2×SSC, 0.1% SDS followed by 0.1×SSC, 0.1% SDS, for example.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50 9.51). For hybridizations with shorter nucleic acids, i.e., oligonucleotides, the position of mismatches becomes more important, and the length of the oligonucleotide determines its specificity (see Sambrook et al., supra, 11.7 11.8). In one embodiment the length for a hybridizable nucleic acid is at least about 10 nucleotides. In one embodiment, a minimum length for a hybridizable nucleic acid is at least about 15 nucleotides; at least about 20 nucleotides; or the length is at least about 30 nucleotides. Furthermore, the skilled artisan will recognize that the temperature and wash solution salt concentration can be adjusted as necessary according to factors such as length of the probe.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" can be used instead of, or interchangeably with any of these terms. A polypeptide can be derived from a natural biological source or produced by recombinant technology, but is not necessarily translated from a designated nucleic acid sequence. It can be generated in any manner, including by chemical synthesis.

By an "isolated" polypeptide or a fragment, variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated for purposed of the invention, as are native or recombinant polypeptides which have been separated, fractionated, or partially or substantially purified by any suitable technique.

As used herein, the terms "variant" and "mutant" are synonymous and refer to a polypeptide differing from a specifically recited polypeptide by one or more amino acid insertions, deletions, mutations, and substitutions, created using, e.g., recombinant DNA techniques, such as mutagenesis. Guidance in determining which amino acid residues can be replaced, added, or deleted without abolishing activities of interest, can be found by comparing the sequence of the particular polypeptide with that of homologous polypeptides, e.g., yeast or bacterial, and minimizing the number of amino acid sequence changes made in regions of high homology (conserved regions) or by replacing amino acids with consensus sequences.

"Engineered polypeptide" as used herein refers to a polypeptide that is synthetic, i.e., differing in some manner from a polypeptide found in nature.

Alternatively, recombinant polynucleotide variants encoding these same or similar polypeptides can be synthesized or selected by making use of the "redundancy" in the genetic code. Various codon substitutions, such as silent changes which produce various restriction sites, can be introduced to optimize cloning into a plasmid or viral vector for expression. Mutations in the polynucleotide sequence can be reflected in the polypeptide or domains of other peptides added to the polypeptide to modify the properties of any part of the polypeptide. For example, mutations can be used to reduce or eliminate expression of a target protein and include, but are not limited to, deletion of the entire gene or a portion of the gene, inserting a DNA fragment into the gene (in either the promoter or coding region) so that the protein is not expressed or expressed at lower levels, introducing a mutation into the coding region which adds a stop codon or frame shift such that a functional protein is not expressed, and introducing one or more mutations into the coding region to alter amino acids so that a non-functional or a less enzymatically active protein is expressed.

Amino acid "substitutions" can be the result of replacing one amino acid with another amino acid having similar structural and/or chemical properties, i.e., conservative amino acid replacements, or they can be the result of replacing one amino acid with an amino acid having different structural and/or chemical properties, i.e., non-conservative amino acid replacements. "Conservative" amino acid substitutions can be made on the basis of similarity in polarity, charge, solubility, hydrophobicity, hydrophilicity, or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. Alternatively, "non-conservative" amino acid substitutions can be made by selecting the differences in polarity, charge, solubility, hydrophobicity, hydrophilicity, or the amphipathic nature of any of these amino acids. "Insertions" or "deletions" can be within the range of variation as structurally or functionally tolerated by the recombinant proteins. The variation allowed can be experimentally determined by systematically making insertions, deletions, or substitutions of amino acids in a polypeptide molecule using recombinant DNA techniques and assaying the resulting recombinant variants for activity.

A "substantial portion" of an amino acid or nucleotide sequence is that portion comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Altschul, S. F., et al., *J. Mol. Biol.,* 215:403-410 (1993)). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20-30 contiguous nucleotides can be used in sequence-dependent methods of gene identification (e.g., Southern hybridization) and isolation (e.g., in situ hybridization of bacterial colonies or bacteriophage plaques). In addition, short oligonucleotides of 12-15 bases can be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence. The instant specification teaches the complete amino acid and nucleotide sequence encoding particular proteins. The skilled artisan, having the benefit of the sequences as reported herein, can now use all or a substantial portion of the disclosed sequences for purposes known to those skilled in this art. Accordingly, the instant invention comprises the complete sequences as reported in the accompanying Sequence Listing, as well as substantial portions of those sequences as defined above.

The term "complementary" is used to describe the relationship between nucleotide bases that are capable of hybridizing to one another. For example, with respect to DNA, adenine is complementary to thymine and cytosine is complementary to guanine, and with respect to RNA, adenine is complementary to uracil and cytosine is complementary to guanine.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: 1.) *Computational Molecular Biology* (Lesk, A. M., Ed.) Oxford University: NY (1988); 2.) *Biocomputing: Informatics and Genome Projects* (Smith, D. W., Ed.) Academic: NY (1993); 3.) *Computer Analysis of Sequence Data, Part I* (Griffin, A. M., and Griffin, H. G., Eds.) Humania: NJ (1994); 4.) *Sequence Analysis in Molecular Biology* (von Heinje, G., Ed.) Academic (1987); and 5.) *Sequence Analysis Primer* (Gribskov, M. and Devereux, J., Eds.) Stockton: NY (1991).

Methods to determine identity are designed to give the best match between the sequences tested. Methods to determine identity and similarity are codified in publicly available computer programs. Sequence alignments and percent identity calculations can be performed using the MegAlign™ program of the LASERGENE bioinformatics computing suite (DNASTAR Inc., Madison, Wis.). Multiple alignments of the sequences are performed using the "Clustal method of alignment" which encompasses several varieties of the algorithm including the "Clustal V method of alignment" corresponding to the alignment method labeled Clustal V (described by Higgins and Sharp, *CABIOS.* 5:151-153 (1989); Higgins, D. G. et al., *Comput. Appl. Biosci.,* 8:189-191 (1992)) and found in the MegAlign™ program of the LASERGENE bioinformatics computing suite (DNASTAR Inc.). For multiple alignments, the default values correspond to GAP PENALTY=10 and GAP LENGTH PENALTY=10. Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences using the Clustal V program, it is possible to obtain a "percent identity" by viewing the "sequence distances" table in the same program. Additionally the "Clustal W method of alignment" is available and corresponds to the alignment method labeled Clustal W (described by Higgins and Sharp, *CABIOS*. 5:151-153 (1989); Higgins, D. G. et al., *Comput. Appl. Biosci.* 8:189-191 (1992)) and found in the MegAlign™ v6.1 program of the LASERGENE bioinformatics computing suite (DNASTAR Inc.). Default parameters for multiple alignment (GAP PENALTY=10, GAP LENGTH PENALTY=0.2, Delay Divergen Seqs(%)=30, DNA Transition Weight=0.5, Protein Weight Matrix=Gonnet Series, DNA Weight Matrix=IUB). After alignment of the sequences using the Clustal W program, it is possible to obtain a "percent identity" by viewing the "sequence distances" table in the same program.

It is well understood by one skilled in the art that many levels of sequence identity are useful in identifying polypeptides, such as from other species, wherein such polypeptides have the same or similar function or activity, or in describing the corresponding polynucleotides. Useful examples of percent identities include, but are not limited to: 55%, 60%, 65%, 70%, 75%, 80%, 85%, 90%, or 95%, or any integer percentage from 55% to 100% can be useful in describing the present invention, such as 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%. Suitable polynucleotide fragments not only have the above homologies but typically comprise a polynucleotide having at least 50 nucleotides, at least 100 nucleotides, at least 150 nucleotides, at least 200 nucleotides, or at least 250 nucleotides. Further, suitable polynucleotide fragments having the above homologies encode a polypeptide having at least 50 amino acids, at least 100 amino acids, at least 150 amino acids, at least 200 amino acids, or at least 250 amino acids.

The term "sequence analysis software" refers to any computer algorithm or software program that is useful for the analysis of nucleotide or amino acid sequences. "Sequence analysis software" can be commercially available or independently developed. Typical sequence analysis software will include, but is not limited to: 1.) the GCG suite of programs (Wisconsin Package Version 9.0, Genetics Computer Group (GCG), Madison, Wis.); 2.) BLASTP, BLASTN, BLASTX (Altschul et al., *J. Mol. Biol.,* 215:403-410 (1990)); 3.) DNASTAR (DNASTAR, Inc. Madison, Wis.); 4.) Sequencher (Gene Codes Corporation, Ann Arbor, Mich.); and 5.) the FASTA program incorporating the Smith-Waterman algorithm (W. R. Pearson, *Comput. Methods Genome Res*., [Proc. Int. Symp.] (1994), Meeting Date 1992, 111-20. Editor(s): Suhai, Sandor. Plenum: New York, N.Y.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

Standard recombinant DNA and molecular cloning techniques are well known in the art and are described by Sambrook, J., Fritsch, E. F. and Maniatis, T., *Molecular Cloning: A Laboratory Manual*, Second Edition, Cold Spring Harbor Laboratory Press, Cold Spring Harbor, N.Y. (1989) (hereinafter "Maniatis"); and by Silhavy, T. J., Bennan, M. L. and Enquist, L. W., *Experiments with Gene Fusions*, Cold Spring Harbor Laboratory Press, Cold Spring Harbor, N.Y. (1984); and by Ausubel, F. M. et al., *Current Protocols in Molecular Biology*, published by Greene Publishing Assoc. and Wiley-Interscience (1987). Additional methods used here are in *Methods in Enzymology*, Volume 194, *Guide to Yeast Genetics and Molecular and Cell Biology* (Part A, 2004, Christine Guthrie and Gerald R. Fink (Eds.), Elsevier Academic Press, San Diego, Calif.). Other molecular tools and techniques are known in the art and include splicing by overlapping extension polymerase chain reaction (PCR) (Yu, et al. (2004) *Fungal Genet. Biol.* 41:973-981), positive selection for mutations at the URA3 locus of *Saccharomyces cerevisiae* (Boeke, J. D. et al. (1984) *Mol. Gen. Genet.* 197, 345-346; M A Romanos, et al. *Nucleic Acids Res.* 1991 Jan. 11; 19(1): 187), the cre-lox site-specific recombination system as well as mutant lox sites and FLP substrate mutations (Sauer, B. (1987) *Mol Cell Biol* 7: 2087-2096; Senecoff, et al. (1988) *Journal of Molecular Biology*, Volume 201, Issue 2, Pages 405-421; Albert, et al. (1995) *The Plant Journal*. Volume 7, Issue 4, pages 649-659), "seamless" gene deletion (Akada, et al. (2006) *Yeast;* 23(5):399-405), and gap repair methodology (Ma et al., *Genetics* 58:201-216; 1981).

Polypeptides with GPD Activity

Endogenous NAD-dependent "glycerol-3-phosphate dehydrogenase" or "GPD" is a key enzyme in glycerol synthesis, converting dihydroxyacetone phosphate (DHAP) to glycerol-3-phosphate. The terms "glycerol-3-phosphate dehydrogenase" and "GPD" refer to any polypeptide (or polypeptides) having the biological function of GPD. Such polypeptides include polypeptides having an enzyme activity that catalyzes the conversion of dihydroxyacetone phosphate to glycerol-3-phosphate. GPDs are widespread in nature and can fall into three categories. In the first category, EC 1.1.1.8, a GPD is a soluble cytoplasmic enzyme where the redox cofactor is the NAD/NADH couple, GPDs in the EC 1.1.1.8 category are described as NADH specific, but this does not preclude that some of the GPDs may have measurable activity with NADPH. *Saccharomyces cerevisiae* GPD1 is an example of this type of GPD (Albertyn et. Al, 1992, FEBS Lett 308: 130-132; Valadi, et al, 2004, J. Biol Chem 279: 39677-39685). Another example is the human GPD1, for which there are multiple 3-dimensional structural studies (Ou et al, 2005, J. Mol. Biol. 357: 858-869). Assays for enzymes in this category can utilize the spectrophotometric measurement of NADH oxidation in the presence of DHAP and the GPD enzyme (Niesel et al. 1982 Methods Enzymol 89: 296-301). The second category, EC 1.1.5.3, GPD enzymes are intrinsic membrane proteins of the mitochondrial inner membrane, and contain a flavin cofactor, and reducing equivalents are transferred to the quinone/quinol couple in the mitochondrion. There is a third minor category of GPDs, EC 1.1.1.94 which utilize either NADH or NADPH with substantially the same affinity. GPDs of the third minor category can also be feedback inhibited by glycerol-3-phosphate.

Recombinant microorganisms such as yeast can have one or more endogenous genes encoding glycerol-3-phosphate dehydrogenase (GPD). In some yeasts, such as *S. cerevisiae, S. pombe*, and *P. stipitis*, GPD1 and GPD2 are functional homologs. Any of the genes encoding GPD enzymes of yeast may be disrupted to reduce GPD activity in a yeast cell.

One of the key yield loss mechanisms in yeast butanol production is the loss of carbon and reducing equivalents that are diverted from glycolysis by the conversion of dihydroxyacetone phosphate to glycerol. Since GPD catalyzes the first step in this conversion of dihydroxyacetone phosphate to glycerol, the activity of GPD can contribute to the production of glycerol and the loss of butanol yield. As a result, some have considered eliminating the function of GPD (for example, by knocking out the gene encoding GPD protein) in butanol-producing yeast. However, glycerol is required for growth and is an important osmoprotectant. Thus, retaining the ability to make some glycerol offers certain advantages.

One way to retain the ability to make glycerol, but also improve the production of product alcohol is to alter the cofactor specificity of GPD. *Saccharomyces cerevisiae* GPD1 generally favors the cofactor nicotinamide adenine dinucleotide ("NADH") in catalyzing the first step in the conversion of dihydroxyacetone phosphate to glycerol in a yeast cell. However, as demonstrated herein, GPD enzymes can also use the cofactor nicotinamide adenine dinucleotide phosphate ("NADPH").

The use of GPD enzymes with preference for NADPH as compared to NADH can allow host cells to retain the ability to produce glycerol under different metabolic conditions when compared with enzymes with a preference for NADH. However, this glycerol production can advantageously be limited under anaerobic conditions when NADPH production is limited.

At the same time, decreasing the preference for NADH by GPD can increase the availability of NADH in a host cell. NADH is also used by other enzymes in a product alcohol production pathway, for example, in the isobutanol production pathway the available NADH can be utilized by KARI and alcohol dehydrogenase. Thus, decreasing the affinity of GPD for NADH can increase product alcohol (e.g., isobutanol) production. Accordingly, in some embodiments, a heterologous and/or engineered GPD is expressed in a recombinant microorganism that also expresses an NADH-utilizing enzyme, for example, an NADH-utilizing enzyme that acts in the isobutanol production pathway such as KARI and alcohol dehydrogenase.

An additional way to improve the production of a product alcohol (e.g., butanol) is to alter the GPD to decrease the $K_M$ for NADPH. Decreasing the $K_M$ for NADPH by altering GPD can increase the rate of NADPH oxidation catalyzed by GPD, thus allowing an increase in the availability of NADH in the host cell. The available NADH can be used by other enzymes in the product alcohol production pathway, for example, in the isobutanol production pathway the available NADH can be utilized by KARI and alcohol dehydrogenase. Thus, increasing the affinity of GPD for NADPH can increase product alcohol (e.g., isobutanol) production. Accordingly, in some embodiments, a heterologous and/or engineered GPD is expressed in recombinant microorganism that also expresses other NADH-utilizing enzymes, for example, an NADH-utilizing enzyme that acts in the isobutanol production pathway such as KARI and alcohol dehydrogenase.

Another way to retain the ability to make some glycerol and also improve the production of product alcohol is to use heterologous GPD enzymes that can reduce the amount of glycerol produced as compared to the amount produced by the endogenous GPD enzymes. An example heterologous enzyme is *E. coli* gpsA. Two mechanistic features of *E. coli* gpsA that may contribute to its ability to produce less glycerol include (1) gpsA is product inhibited by glycerol-3-phosphate, and (2) gpsA utilizes the cofactors NADH and NADPH with substantially the same affinity (Edgar and Bell, JBC 255:3492-7 (1980)) and under certain conditions this can also allow for the production of glycerol using NADPH, thus allowing for the availability of NADH in the host cell. Product inhibition by glycerol-3-phosphate in *Saccharomyces* may result in reduced glycerol production, especially if the glycerol-3-phosphate phosphatase enzymatic reaction is slower than the GPD enzymatic reaction. The published Michaelis constants for the *Saccharomyces* phosphatases GPP1 and GPP2 are 3.1 and 3.9, respectively (Norbeck, JBC 271:13875-81 (1996), which is nearly 1000-fold higher than the inhibition constant ($K_i$) of glycerol-3-phosphate on *E. coli* gpsA (Edgar and Bell, JBC 253:6345-63 (1978)). Most conditions are conducive to product inhibition by glycerol-3-phosphate.

GPD enzymes that can utilize NADH or NADPH and/or are feedback inhibited by glycerol-3-phosphate can include both naturally occurring proteins and engineered proteins. For instance, NADH-utilizing or NADPH-utilizing GPD enzymes are described by EC 1.1.1.94 and have been found in *Aspergillus oryzae, Candida versatilis, Escherichia coli*, and *Oryctolagus cuniculus*.

In some embodiments, the heterologous GPD used herein is a *Leishmania mexicana, Dunaliella viridis, Jaculus orientalis, Archeoglobus fulgidus, Rickettsia prowazekii, Beggiatoa alba, Kangiella koreenis Aspergillus oryzae, Candida versatilis, Escherichia coli*, or *Oryctolagus cuniculu* GPD.

In certain embodiments, the sequences of other GPD enzymes that can utilize either NADH or NADPH and/or are feedback inhibited by glycerol-3-phosphate can be identified in the literature and candidates can be identified in bioinformatics databases well known to the skilled person using sequences disclosed herein and available in the art. For example, such sequences can be identified through BLAST searching of publicly available databases with known GPD encoding polynucleotide or polypeptide sequences. In such a method, identities can be based on the Clustal W method of alignment using the default parameters of GAP PENALTY=10, GAP LENGTH PENALTY=0.1, and Gonnet 250 series of protein weight matrix.

Additionally, GPD polynucleotide or polypeptide sequences disclosed herein or known in the art can be used to identify other candidate GPD homologs in nature. For example, the GPD encoding nucleic acid sequences disclosed herein or known in the art can be used to isolate genes encoding homologous proteins. Isolation of homologous genes using sequence-dependent protocols include, but are not limited to (1) methods of nucleic acid hybridization; (2) methods of DNA and RNA amplification, as exemplified by various uses of nucleic acid amplification technologies (e.g., polymerase chain reaction (PCR), Mullis et al., U.S. Pat. No. 4,683,202; ligase chain reaction (LCR), Tabor, S. et al., *PNAS USA* 82:1074 (1985); or strand displacement amplification (SDA), Walker et al., *PNAS USA* 89:392 (1992)]; and (3) methods of library construction and screening by complementation.

Another way to improve the production of a product alcohol is to alter the GPD to increase the $K_M$ for NADH. Increasing the $K_M$ for NADH by altering GPD can decrease the rate of NADH oxidation catalyzed by GPD, thus allowing an increase in the availability of NADH in a host cell. The available NADH can be used by other enzymes in the product alcohol production pathway, for example, in the isobutanol production pathway the available NADH can be utilized by KARI and alcohol dehydrogenase. Thus, decreasing the affinity of GPD for NADH can increase product alcohol (e.g., isobutanol) production. Accordingly, in some embodiments, a heterologous and/or engineered GPD is expressed in recombinant microorganism that also expresses other NADH-utilizing enzymes, for example, an NADH-utilizing enzyme that acts in the isobutanol production pathway such as KARI and alcohol dehydrogenase.

GPD enzymes with an increased $K_M$ for NADH can also be produced by means of protein engineering. In some embodiments, the GPD has at least 50%, 55%, 60%, 65%, 70%, 75%, 80%, 85%, 90% or 95% identity to *Saccharomyces cerevisiae* GPD 1 (SEQ ID NO: 195), but is not 100% identical to SEQ ID NO:195. In some embodiments, the GPD comprises at least one substitution at a residue corresponding to position 42, 44, 45, 71, 73, 75, 95, 124, 126, 129, 151, 152, 183, 184, 185, 246, 310, 336, 337, or 339 of *Saccharomyces cerevisiae* GPD 1 (SEQ ID NO: 195).

For example, in some embodiments, the GPD comprises a substitution of the residue corresponding to position 44 of SEQ ID NO:195 (Asn in SEQ ID NO:195) to an amino acid selected from the group consisting of A, C, G, I, L, M, S, and V.

In some embodiments, the GPD comprises a substitution of the residue corresponding to position 45 of SEQ ID NO:195 (Trp in SEQ ID NO:195) to an amino acid selected from the group consisting of A, C, G, H, I, K, L, M, N, Q, R, S, T, and V.

In some embodiments, the GPD comprises a substitution of the residue corresponding to position 73 of SEQ ID NO:195 (Phe in SEQ ID NO:195) to an amino acid selected from the group consisting of G, A, R, and K.

In some embodiments, the GPD comprises a substitution of the residue corresponding to position 129 of SEQ ID NO:195 (Phe in SEQ ID NO:195) to an amino acid selected from the group consisting of G, A, R, and K.

In some embodiments, the GPD comprises a substitution of the residue corresponding to position 337 of SEQ ID NO:195 (Ser in SEQ ID NO:195) to an amino acid selected from the group consisting of A, C, D, E, G, I, L, M, N, Q, and V.

In some embodiments, the GPD comprises a substitution of the residue corresponding to position 339 of SEQ ID NO:195 (Gln in SEQ ID NO:195) to an amino acid selected from the group consisting of A, C, G, I, L, M, S, and V.

In some embodiments, the GPD comprises a substitution of the residue corresponding to position 42, 71, 75, 95, 124, 126, 151, 152, 183, 184, 185, 246, 310, and/or 336 of SEQ ID NO:195 (Ser, Trp, Glu, Tyr, Gln, Pro, Leu, Lys, Asn, Ile, Ala, Asn, Arg, Gln of SEQ ID NO: 195, respectively) to any other amino acid selected from the 19 naturally occurring amino acids.

In some embodiments, the GPD has a $K_M$ for NADH that is about 0.01 mM to about 1 mM. In some embodiments, the GPD has a $K_M$ for NADH that is about 0.05 mM to about 1 mM. In some embodiments, the GPD has a $K_M$ for NADH that is about 0. 10 mM to about 1 mM. In some embodiments, the GPD has a $K_M$ for NADH that is about 0.15 mM to about 1 mM. In some embodiments, the GPD has a $K_M$ for NADH that is about 0.20 mM to about 1 mM. In some embodiments, the GPD has a $K_M$ for NADH that is about 0.30 mM to about 1 mM. In some embodiments, the GPD has a $K_M$ for NADH that is about 0.40 mM to about 1 mM. In some embodiments, the GPD has a $K_M$ for NADH that is about 0.50 mM to about 1 mM. Assays for measuring the $K_M$ for NADH of GPD are disclosed in Example 1 below and are known in the art, see, e.g., Niesel et al., Methods Enzymol. 89:296-301 (1982). Certain assays can be referred to as "NADH consumption assays," which refer to an enzyme assay for the determination of the specific activity of the GPD enzyme, involving measuring the disappearance of the GPD cofactor, NADH, from the enzyme reaction.

In some embodiments, the GPD has a $K_M$ for NADPH that is about 0.01 mM to about 1 mM. In some embodiments, the GPD has a $K_M$ for NADPH that is about 0.05 mM to about 1 mM. In some embodiments, the GPD has a $K_M$ for NADPH that is about 0. 10 mM to about 1 mM. In some embodiments, the GPD has a $K_M$ for NADPH that is about 0.15 mM to about 1 mM. In some embodiments, the GPD has a $K_M$ for NADPH that is about 0.20 mM to about 1 mM. In some embodiments, the GPD has a $K_M$ for NADPH that is about 0.30 mM to about 1 mM. In some embodiments, the GPD has a $K_M$ for NADPH that is about 0.40 mM to about 1 mM. In some embodiments, the GPD has a $K_M$ for NADPH that is about 0.50 mM to about 1 mM. The NADH assays disclosed below in Example 1 can be adapted to measure the $K_M$ for NADPH of GPD by replacing NADH with NADPH. Additional assays for measuring the $K_M$ for NADPH of GPD are known in the art, see, e.g., Niesel et al., Methods Enzymol. 89:296-301 (1982). Certain assays can be referred to as "NADPH consumption assays," which refer to an enzyme assay for the determination of the specific activity of the GPD enzyme, involving measuring the disappearance of the GPD cofactor, NADH, from the enzyme reaction.

In some embodiments, the heterologous and/or engineered GPD can increase the growth of a recombinant microorganism comprising the heterologous and/or engineered GPD as compared to a recombinant microorganism that does not contain the heterologous and/or engineered GPD.

In some embodiments, the heterologous and/or engineered GPD can increase the product alcohol (e.g., isobutanol) production of a recombinant microorganism comprising the heterologous and/or engineered GPD as compared to a recombinant microorganism that does not contain the heterologous and/or engineered GPD.

In some embodiments, the heterologous and/or engineered GPD can decrease the glycerol production of a recombinant microorganism comprising the GPD as compared to a recombinant microorganism that does not contain the heterologous and/or engineered GPD.

In some embodiments, the heterologous and/or engineered GPD can increase the ratio of product alcohol (e.g., isobutanol) to glycerol produced by a recombinant microorganism comprising the heterologous and/or engineered GPD as compared to a recombinant microorganism that does not contain the heterologous and/or engineered GPD.

In some embodiments, the heterologous and/or engineered GPD can increase the yield (e.g., gram of isobutanol produced per gram of substrate consumed) of a recombinant microorganism comprising the heterologous and/or engineered GPD as compared to a recombinant microorganism that does not contain the heterologous and/or engineered GPD.

Thus in a recombinant microorganism comprising a butanol biosynthetic pathway, a heterologous and/or engineered GPD that has a higher $K_M$ for NADH than the microorganism's endogenous GPD, and a deletion or disruption of an endogenous gene encoding GPD, "improved production of butanol" can refer to increased production of butanol, a decreased production of glycerol, or both, as compared to a microorganism that lacks the heterologous and/or engineered GPD.

In a recombinant microorganisms comprising a heterologous and/or engineered GPD that has a higher $K_M$ for NADH than the microorganism's endogenous GPD, and a deletion or disruption in an endogenous gene encoding GPD, "improved production of alcohol" can refer to an increased production of alcohol, a decreased production of glycerol, or both, as compared to a microorganism that lacks the heterologous and/or engineered GPD.

Thus, in a recombinant microorganism comprising a butanol biosynthetic pathway, a heterologous GPD that has substantially the same affinity for NADH and NADPH and/or is feedback inhibited by glycerol-3-phosphate, and a deletion or disruption of an endogenous gene encoding GPD, "improved production of butanol" can refer to increased production of butanol, a decreased production of glycerol, or both, as compared to a microorganism that lacks the heterologous GPD.

In a recombinant microorganisms comprising a heterologous GPD that has substantially the same affinity for NADH and NAPDH and/or is feedback inhibited by glycerol-3-phosphate, and a deletion or disruption in an endogenous gene encoding GPD, "improved production of alcohol" can refer to an increased production of alcohol, a decreased production of glycerol, or both, as compared to a microorganism that lacks the heterologous GPD.

Recombinant Microorganisms

While not wishing to be bound by theory, it is believed that the processes described herein are useful in conjunction with any alcohol producing microorganism, particularly recombinant microorganisms which produce alcohol.

Recombinant microorganisms which produce alcohol are also known in the art (e.g., Ohta et al., *Appl. Environ. Microbiol.* 57:893-900 (1991); Underwood et al., *Appl. Envrion. Microbiol.* 68:1071-81 (2002); Shen and Liao, *Metab. Eng.* 10:312-20 (2008); Hahnai et al., *Appl. Environ.* 73:7814-8 (2007); U.S. Pat. Nos. 5,514,583; 5,712,133; International Publication No. WO 1995/028476; Feldmann et al., *Appl. Microbiol. Biotechnol.* 38:354-61 (1992); Zhang et al., *Science* 267:240-3 (1995); U.S. Patent Publication No. 2007/0031918A1; U.S. Pat. Nos. 7,223,575; 7,741,119; U.S. Patent Publication No. 2009/0203099A1; U.S. Patent Publication No. 2009/0246846A1; and International Publication No. WO 2010/075241, which are herein incorporated by reference).

For example, the metabolic pathways of microorganisms may be genetically modified to produce butanol. These pathways may also be modified to reduce or eliminate undesired metabolites, and thereby improve yield of the product alcohol. The production of butanol by a microorganism is disclosed, for example, in U.S. Pat. Nos. 7,851,188; 7,993,889; 8,178,328, 8,206,970; U.S. Patent Application Publication Nos. 2007/0292927; 2008/0182308; 2008/0274525; 2009/0305363; 2009/0305370; 2011/0250610; 2011/0313206; 2011/0111472; 2012/0258873; and 2013/0071898, the entire contents of each are herein incorporated by reference. In certain embodiments, the microorganism is genetically modified to comprise a butanol biosynthetic pathway or a biosynthetic pathway for a butanol isomer, such as 1-butanol, 2-butanol, or isobutanol. In certain embodiments, at least one, at least two, at least three, at least four, or at least five polypeptides catalyzing substrate to product conversions in the butanol biosynthetic pathway are encoded by heterologous polynucleotides in the microorganism. In certain embodiments, all the polypeptides catalyzing substrate to product conversions of the butanol biosynthetic pathway are encoded by heterologous polynucleotides in the microorganism. In will be appreciated that microorganisms comprising a butanol biosynthetic pathway may further comprise one or more additional genetic modifications as disclosed in U.S. Patent Application Publication No. 2013/0071898, which is herein incorporated by reference in its entirety.

In some embodiments, the microorganism may be bacteria, cyanobacteria, filamentous fungi, or yeasts. Suitable microorganisms capable of producing product alcohol (e.g., butanol) via a biosynthetic pathway include a member of the genera *Clostridium, Zymomonas, Escherichia, Salmonella, Serratia, Erwinia, Klebsiella, Shigella, Rhodococcus, Pseudomonas, Bacillus, Lactobacillus, Enterococcus, Alcaligenes, Paenibacillus, Arthrobacter, Corynebacterium, Brevibacterium, Schizosaccharomyces, Kluveromyces, Yarrowia, Pichia, Zygosaccharomyces, Debaryomyces, Candida, Brettanomyces, Pachysolen, Hansenula, Issatchenkia, Trichosporon, Yamadazyma*, or *Saccharomyces*. In one embodiment, recombinant microorganisms may be selected from the group consisting of *Escherichia coli, Alcaligenes eutrophus, Bacillus licheniformis, Paenibacillus macerans, Rhodocuccus erythropolis, Pseudomonas putida, Lactobacillus plantarum, Enterococcus faecium, Enterococcus gallinarium, Enterococcus faecalis, Bacillus subtilis, Candida sonorensis, Candida methanosorbosa, Kluyveromyces lactis, Kluyveromyces marxianus, Kluveromyces thermotolerans, Issatchenkia orientalis, Debaryomyces hansenii*, and *Saccharomyces cerevisiae*. In one embodiment, the genetically modified microorganism is yeast. In one embodiment, the genetically modified microorganism is a crabtree-positive yeast selected from *Saccharomyces, Zygosaccharomyces, Schizosaccharomyces, Dekkera, Torulopsis, Brettanomyces*, and some species of *Candida*. Species of crabtree-positive yeast include, but are not limited to, *Saccharomyces cerevisiae, Saccharomyces kluyveri, Schizosaccharomyces pombe, Saccharomyces bayanus, Saccharomyces mikitae, Saccharomyces paradoxus, Saccharomyces uvarum, Saccharomyces castelli, Zygosaccharomyces rouxii, Zygosaccharomyces bailli*, and *Candida glabrata*.

In some embodiments, the host cell is *Saccharomyces cerevisiae. Saccharomyces cerevisiae* are known in the art and are available from a variety of sources including, but not limited to, American Type Culture Collection (Rockville, Md.), Centraalbureau voor Schimmelcultures (CBS) Fungal Biodiversity Centre, LeSaffre, Gert Strand AB, Ferm Solutions, North American Bioproducts, Martrex, and Lallemand. *S. cerevisiae* include, but are not limited to, BY4741, CEN.PK 113-7D, Ethanol Red® yeast, Ferm Pro™ yeast, Bio-Ferm® XR yeast, Gert Strand Prestige Batch Turbo alcohol yeast, Gert Strand Pot Distillers yeast, Gert Strand Distillers Turbo yeast, FerMax™ Green yeast, FerMax™ Gold yeast, Thermosacc® yeast, BG-1, PE-2, CAT-1, CBS7959, CBS7960, and CBS7961.

In some embodiments, the microorganism may be immobilized or encapsulated. For example, the microorganism may be immobilized or encapsulated using alginate, calcium alginate, or polyacrylamide gels, or through the induction of biofilm formation onto a variety of high surface area support matrices such as diatomite, celite, diatomaceous earth, silica gels, plastics, or resins. In some embodiments, ISPR may be used in combination with immobilized or encapsulated microorganisms. This combination may improve productivity such as specific volumetric productivity, metabolic rate, product alcohol yields, tolerance to product alcohol. In addition, immobilization and encapsulation may minimize the effects of the process conditions such as shearing on the microorganisms.

Biosynthetic pathways for the production of isobutanol that may be used include those as described by Donaldson et al. in U.S. Pat. Nos. 7,851,188; 7,993,388; and International Publication No. WO 2007/050671, which are incorporated herein by reference. In one embodiment, the isobutanol biosynthetic pathway comprises the following substrate to product conversions:

a) pyruvate to acetolactate, which may be catalyzed, for example, by acetolactate synthase;
b) the acetolactate from step a) to 2,3-dihydroxyisovalerate, which may be catalyzed, for example, by ketol-acid reductoisomerase;
c) the 2,3-dihydroxyisovalerate from step b) to α-ketoisovalerate, which may be catalyzed, for example, by dihydroxyacid dehydratase;
d) the α-ketoisovalerate from step c) to isobutyraldehyde, which may be catalyzed, for example, by a branched-chain α-keto acid decarboxylase; and,
e) the isobutyraldehyde from step d) to isobutanol, which may be catalyzed, for example, by a branched-chain alcohol dehydrogenase.

In another embodiment, the isobutanol biosynthetic pathway comprises the following substrate to product conversions:

a) pyruvate to acetolactate, which may be catalyzed, for example, by acetolactate synthase;
b) the acetolactate from step a) to 2,3-dihydroxyisovalerate, which may be catalyzed, for example, by ketol-acid reductoisomerase;
c) the 2,3-dihydroxyisovalerate from step b) to α-ketoisovalerate, which may be catalyzed, for example, by dihydroxyacid dehydratase;
d) the α-ketoisovalerate from step c) to valine, which may be catalyzed, for example, by transaminase or valine dehydrogenase;
e) the valine from step d) to isobutylamine, which may be catalyzed, for example, by valine decarboxylase;
f) the isobutylamine from step e) to isobutyraldehyde, which may be catalyzed by, for example, omega transaminase; and,
g) the isobutyraldehyde from step f) to isobutanol, which may be catalyzed, for example, by a branched-chain alcohol dehydrogenase.

In another embodiment, the isobutanol biosynthetic pathway comprises the following substrate to product conversions:

a) pyruvate to acetolactate, which may be catalyzed, for example, by acetolactate synthase;
b) the acetolactate from step a) to 2,3-dihydroxyisovalerate, which may be catalyzed, for example, by ketol-acid reductoisomerase;
c) the 2,3-dihydroxyisovalerate from step b) to α-ketoisovalerate, which may be catalyzed, for example, by dihydroxyacid dehydratase;
d) the α-ketoisovalerate from step c) to isobutyryl-CoA, which may be catalyzed, for example, by branched-chain keto acid dehydrogenase;
e) the isobutyryl-CoA from step d) to isobutyraldehyde, which may be catalyzed, for example, by acylating aldehyde dehydrogenase; and,
f) the isobutyraldehyde from step e) to isobutanol, which may be catalyzed, for example, by a branched-chain alcohol dehydrogenase.

Biosynthetic pathways for the production of 1-butanol that may be used include those described in U.S. Patent Application Publication No. 2008/0182308 and WO2007/041269, which are incorporated herein by reference. In one embodiment, the 1-butanol biosynthetic pathway comprises the following substrate to product conversions:

a) acetyl-CoA to acetoacetyl-CoA, which may be catalyzed, for example, by acetyl-CoA acetyltransferase;
b) the acetoacetyl-CoA from step a) to 3-hydroxybutyryl-CoA, which may be catalyzed, for example, by 3-hydroxybutyryl-CoA dehydrogenase;
c) the 3-hydroxybutyryl-CoA from step b) to crotonyl-CoA, which may be catalyzed, for example, by crotonase;
d) the crotonyl-CoA from step c) to butyryl-CoA, which may be catalyzed, for example, by butyryl-CoA dehydrogenase;
e) the butyryl-CoA from step d) to butyraldehyde, which may be catalyzed, for example, by butyraldehyde dehydrogenase; and,
f) the butyraldehyde from step e) to 1-butanol, which may be catalyzed, for example, by butanol dehydrogenase.

Biosynthetic pathways for the production of 2-butanol that may be used include those described by Donaldson et al. in U.S. Pat. No. 8,206,970; U.S. Patent Application Publication Nos. 2007/0292927 and 2009/0155870; International Publication Nos. WO 2007/130518 and WO 2007/130521, all of which are incorporated herein by reference. In one embodiment, the 2-butanol biosynthetic pathway comprises the following substrate to product conversions:

a) pyruvate to alpha-acetolactate, which may be catalyzed, for example, by acetolactate synthase;
b) the alpha-acetolactate from step a) to acetoin, which may be catalyzed, for example, by acetolactate decarboxylase;
c) the acetoin from step b) to 3-amino-2-butanol, which may be catalyzed, for example, acetoin aminase;
d) the 3-amino-2-butanol from step c) to 3-amino-2-butanol phosphate, which may be catalyzed, for example, by aminobutanol kinase;
e) the 3-amino-2-butanol phosphate from step d) to 2-butanone, which may be catalyzed, for example, by aminobutanol phosphate phosphorylase; and,
f) the 2-butanone from step e) to 2-butanol, which may be catalyzed, for example, by butanol dehydrogenase.

In another embodiment, the 2-butanol biosynthetic pathway comprises the following substrate to product conversions:

a) pyruvate to alpha-acetolactate, which may be catalyzed, for example, by acetolactate synthase;
b) the alpha-acetolactate from step a) to acetoin, which may be catalyzed, for example, by acetolactate decarboxylase;
c) the acetoin to 2,3-butanediol from step b), which may be catalyzed, for example, by butanediol dehydrogenase;
d) the 2,3-butanediol from step c) to 2-butanone, which may be catalyzed, for example, by diol dehydratase; and,
e) the 2-butanone from step d) to 2-butanol, which may be catalyzed, for example, by butanol dehydrogenase.

Biosynthetic pathways for the production of 2-butanone that may be used include those described in U.S. Pat. No. 8,206,970 and U.S. Patent Application Publication Nos. 2007/0292927 and 2009/0155870, which are incorporated herein by reference. In one embodiment, the 2-butanone biosynthetic pathway comprises the following substrate to product conversions:

a) pyruvate to alpha-acetolactate, which may be catalyzed, for example, by acetolactate synthase;
b) the alpha-acetolactate from step a) to acetoin, which may be catalyzed, for example, by acetolactate decarboxylase;

c) the acetoin from step b) to 3-amino-2-butanol, which may be catalyzed, for example, acetoin aminase;

d) the 3-amino-2-butanol from step c) to 3-amino-2-butanol phosphate, which may be catalyzed, for example, by aminobutanol kinase; and, e) the 3-amino-2-butanol phosphate from step d) to 2-butanone, which may be catalyzed, for example, by aminobutanol phosphate phosphorylase.

In another embodiment, the 2-butanone biosynthetic pathway comprises the following substrate to product conversions:

a) pyruvate to alpha-acetolactate, which may be catalyzed, for example, by acetolactate synthase;

b) the alpha-acetolactate from step a) to acetoin which may be catalyzed, for example, by acetolactate decarboxylase;

c) the acetoin from step b) to 2,3-butanediol, which may be catalyzed, for example, by butanediol dehydrogenase;

d) the 2,3-butanediol from step c) to 2-butanone, which may be catalyzed, for example, by diol dehydratase.

The terms "acetohydroxyacid synthase," "acetolactate synthase," and "acetolactate synthetase" (abbreviated "ALS") are used interchangeably herein to refer to an enzyme that catalyzes the conversion of pyruvate to acetolactate and $CO_2$. Example acetolactate synthases are known by the EC number 2.2.1.6 (Enzyme Nomenclature 1992, Academic Press, San Diego). These enzymes are available from a number of sources, including, but not limited to, *Bacillus subtilis* (GenBank Nos: CAB07802.1, Z99122, NCBI (National Center for Biotechnology Information) amino acid sequence, NCBI nucleotide sequence, respectively), CAB 15618, *Klebsiella pneumoniae* (GenBank Nos: AAA25079, M73842), and *Lactococcus lactis* (GenBank Nos: AAA25161, L16975).

The term "ketol-acid reductoisomerase" ("KARI"), "acetohydroxy acid isomeroreductase," and "acetohydroxy acid reductoisomerase" will be used interchangeably and refer to enzymes capable of catalyzing the reaction of (S)-acetolactate to 2,3-dihydroxyisovalerate. Example KARI enzymes may be classified as EC number EC 1.1.1.86 (Enzyme Nomenclature 1992, Academic Press, San Diego), and are available from a vast array of microorganisms, including, but not limited to, *Escherichia coli* (GenBank Nos: NP_418222, NC_000913), *Saccharomyces cerevisiae* (GenBank Nos: NP_013459, NC_001144), *Methanococcus maripaludis* (GenBank Nos: CAF30210, BX957220), and *Bacillus subtilis* (GenBank Nos: CAB 14789, Z99118). KARIs include *Anaerostipes caccae* KARI variants "K9G9" (SEQ ID NO:85), "K9D3" (SEQ ID NO:86), and "K9JB4P" (SEQ ID NO:87). Ketol-acid reductoisomerase (KARI) enzymes are described in U.S. Pat. Nos. 7,910,342 and 8,129,162; U.S. Patent Application Publication Nos. 2008/0261230, 2009/0163376, 2010/0197519, PCT Application Publication No. WO/2011/041415, PCT Application Publication No. WO2012/129555; and U.S. patent application Ser. No. 14/038,455, filed on Sep. 26, 2013, all of which are incorporated herein by reference. Examples of KARIs disclosed therein are those from *Lactococcus lactis, Vibrio cholera, Pseudomonas aeruginosa* PAO1, and *Pseudomonas fluorescens* PF5 mutants. In some embodiments, the KARI utilizes NADH. In some embodiments, the KARI utilizes NADPH. In some embodiments, the KARI utilizes NADH or NADPH.

The term "acetohydroxy acid dehydratase" and "dihydroxyacid dehydratase" ("DHAD") refers to an enzyme that catalyzes the conversion of 2,3-dihydroxyisovalerate to α-ketoisovalerate. Example acetohydroxy acid dehydratases are known by the EC number 4.2.1.9. Such enzymes are available from a vast array of microorganisms, including, but not limited to, *E. coli* (GenBank Nos: YP_026248, NC000913), *Saccharomyces cerevisiae* (GenBank Nos: NP_012550, NC_001142), *M. maripaludis* (GenBank Nos: CAF29874, BX957219), *B. subtilis* (GenBank Nos: CAB14105, Z99115), *L. lactis* (SEQ ID NO:88), and *N. crassa*. U.S. Patent Application Publication No. 2010/0081154, U.S. Pat. Nos. 7,851,188, and 8,241,878, which are incorporated herein by reference in their entireties, describe dihydroxyacid dehydratases (DHADs), including a DHAD from *Streptococcus mutans* (SEQ ID NO:89) and variants thereof.

The term "branched-chain α-keto acid decarboxylase," "α-ketoacid decarboxylase," "α-ketoisovalerate decarboxylase," or "2-ketoisovalerate decarboxylase" ("KIVD") refers to an enzyme that catalyzes the conversion of α-ketoisovalerate to isobutyraldehyde and $CO_2$. Example branched-chain α-keto acid decarboxylases are known by the EC number 4.1.1.72 and are available from a number of sources, including, but not limited to, *Lactococcus lactis* (GenBank Nos: AAS49166, AY548760; CAG34226, AJ746364), *Salmonella typhimurium* (GenBank Nos: NP_461346, NC_003197), *Clostridium acetobutylicum* (GenBank Nos: NP_149189, NC_001988), *M. caseolyticus*, and *L. grayi*. Suitable branched-chain α-keto acid decarboxylases can comprise SEQ ID NO:90 from *Lactococcus lactis* and SEQ ID NO:91 from *Listeria grayi*.

The term "branched-chain alcohol dehydrogenase" ("ADH") refers to an enzyme that catalyzes the conversion of isobutyraldehyde to isobutanol. Example branched-chain alcohol dehydrogenases are known by the EC number 1.1.1.265, but may also be classified under other alcohol dehydrogenases (specifically, EC 1.1.1.1 or 1.1.1.2). Alcohol dehydrogenases may be NADPH dependent or NADH dependent. Such enzymes are available from a number of sources, including, but not limited to, *S. cerevisiae* (GenBank Nos: NP_010656, NC_001136, NP_014051, NC_001145), *E. coli* (GenBank Nos: NP_417484, NC_000913), *C. acetobutylicum* (GenBank Nos: NP_349892, NC_003030; NP_349891, NC_003030). U.S. Patent Application Publication No. 2009/0269823 describes SadB, an alcohol dehydrogenase (ADH) from *Achromobacter xylosoxidans* (SEQ ID NO:92). Alcohol dehydrogenases also include horse liver ADH (SEQ ID NO:93) and *Beijerinkia indica* ADH (SEQ ID NO:94) (as described by U.S. Patent Application Publication No. 2011/0269199, which is incorporated herein by reference).

The term "butanol dehydrogenase" refers to a polypeptide (or polypeptides) having an enzyme activity that catalyzes the conversion of isobutyraldehyde to isobutanol or the conversion of 2-butanone and 2-butanol. Butanol dehydrogenases are a subset of a broad family of alcohol dehydrogenases. Butanol dehydrogenase may be NAD- or NADP-dependent. The NAD-dependent enzymes are known as EC 1.1.1.1 and are available, for example, from *Rhodococcus ruber* (GenBank Nos: CAD36475, AJ491307). The NADP dependent enzymes are known as EC 1.1.1.2 and are available, for example, from *Pyrococcus furiosus* (GenBank Nos: AAC25556, AF013169). Additionally, a butanol dehydrogenase is available from *Escherichia coli* (GenBank Nos: NP_417484, NC_000913) and a cyclohexanol dehydrogenase is available from *Acinetobacter* sp. (GenBank Nos: AAG10026, AF282240). The term "butanol dehydrogenase" also refers to an enzyme that catalyzes the conversion of butyraldehyde to 1-butanol, using either NADH or NADPH as cofactor. Butanol dehydrogenases are available from, for example, *C. acetobutylicum* (GenBank NOs: NP_149325, NC_001988; note: this enzyme possesses both aldehyde and alcohol dehydrogenase activity); NP_349891, NC_003030; and NP_349892, NC_003030) and *E. coli* (GenBank NOs: NP_417-484, NC_000913).

The term "branched-chain keto acid dehydrogenase" refers to an enzyme that catalyzes the conversion of α-ketoisovalerate to isobutyryl-CoA (isobutyryl-coenzyme A), typically using $NAD^+$ (nicotinamide adenine dinucleotide) as an electron acceptor. Example branched-chain keto acid dehydrogenases are known by the EC number 1.2.4.4. Such branched-chain keto acid dehydrogenases are comprised of four subunits and sequences from all subunits are available from a vast array of microorganisms, including, but not limited to, *B. subtilis* (GenBank Nos: CAB14336, Z99116; CAB14335, Z99116; CAB14334, Z99116; and CAB14337, Z99116) and *Pseudomonas putida* (GenBank Nos: AAA65614, M57613; AAA65615, M57613; AAA65617, M57613; and AAA65618, M57613).

The term "acylating aldehyde dehydrogenase" refers to an enzyme that catalyzes the conversion of isobutyryl-CoA to isobutyraldehyde, typically using either NADH or NADPH as an electron donor. Example acylating aldehyde dehydrogenases are known by the EC numbers 1.2.1.10 and 1.2.1.57. Such enzymes are available from multiple sources, including, but not limited to, *Clostridium beijerinckii* (GenBank Nos: AAD31841, AF157306), *C. acetobutylicum* (GenBank Nos: NP_149325, NC_001988; NP_149199, NC_001988), *P. putida* (GenBank Nos: AAA89106, U13232), and *Thermus thermophilus* (GenBank Nos: YP_145486, NC_006461).

The term "transaminase" refers to an enzyme that catalyzes the conversion of α-ketoisovalerate to L-valine, using either alanine or glutamate as an amine donor. Example transaminases are known by the EC numbers 2.6.1.42 and 2.6.1.66. Such enzymes are available from a number of sources. Examples of sources for alanine-dependent enzymes include, but are not limited to, *E. coli* (GenBank Nos: YP_026231, NC_000913) and *Bacillus licheniformis* (GenBank Nos: YP_093743, NC_006322). Examples of sources for glutamate-dependent enzymes include, but are not limited to, *E. coli* (GenBank Nos: YP_026247, NC_000913), *Saccharomyces cerevisiae* (GenBank Nos: NP_012682, NC_001142) and *Methanobacterium thermoautotrophicum* (GenBank Nos: NP_276546, NC_000916).

The term "valine dehydrogenase" refers to an enzyme that catalyzes the conversion of α-ketoisovalerate to L-valine, typically using NAD(P)H as an electron donor and ammonia as an amine donor. Example valine dehydrogenases are known by the EC numbers 1.4.1.8 and 1.4.1.9 and such enzymes are available from a number of sources, including, but not limited to, *Streptomyces coelicolor* (GenBank Nos: NP_628270, NC_003888) and *B. subtilis* (GenBank Nos: CAB14339, Z99116).

The term "valine decarboxylase" refers to an enzyme that catalyzes the conversion of L-valine to isobutylamine and $CO_2$. Example valine decarboxylases are known by the EC number 4.1.1.14. Such enzymes are found in *Streptomyces*, such as for example, *Streptomyces viridifaciens* (GenBank Nos: AAN10242, AY116644).

The term "omega transaminase" refers to an enzyme that catalyzes the conversion of isobutylamine to isobutyraldehyde using a suitable amino acid as an amine donor. Example omega transaminases are known by the EC number 2.6.1.18 and are available from a number of sources, including, but not limited to, *Alcaligenes denitrificans* (AAP92672, AY330220), *Ralstonia eutropha* (GenBank Nos: YP_294474, NC_007347), *Shewanella oneidensis* (GenBank Nos: NP_719046, NC_004347), and *P. putida* (GenBank Nos: AAN66223, AE016776).

The term "acetyl-CoA acetyltransferase" refers to an enzyme that catalyzes the conversion of two molecules of acetyl-CoA to acetoacetyl-CoA and coenzyme A (CoA). Example acetyl-CoA acetyltransferases are acetyl-CoA acetyltransferases with substrate preferences (reaction in the forward direction) for a short chain acyl-CoA and acetyl-CoA and are classified as E.C. 2.3.1.9 [Enzyme Nomenclature 1992, Academic Press, San Diego]; although, enzymes with a broader substrate range (E.C. 2.3.1.16) will be functional as well. Acetyl-CoA acetyltransferases are available from a number of sources, for example, *Escherichia coli* (GenBank Nos: NP_416728, NC_000913; NCBI (National Center for Biotechnology Information) amino acid sequence, NCBI nucleotide sequence), *Clostridium acetobutylicum* (GenBank Nos: NP_349476.1, NC_003030; NP_149242, NC_001988, *Bacillus subtilis* (GenBank Nos: NP_390297, NC_000964), and *Saccharomyces cerevisiae* (GenBank Nos: NP_015297, NC_001148).

The term "3-hydroxybutyryl-CoA dehydrogenase" refers to an enzyme that catalyzes the conversion of acetoacetyl-CoA to 3-hydroxybutyryl-CoA. 3-Example hydroxybutyryl-CoA dehydrogenases may be reduced nicotinamide adenine dinucleotide (NADH)-dependent, with a substrate preference for (S)-3-hydroxybutyryl-CoA or (R)-3-hydroxybutyryl-CoA. Examples may be classified as E.C. 1.1.1.35 and E.C. 1.1.1.30, respectively. Additionally, 3-hydroxybutyryl-CoA dehydrogenases may be reduced nicotinamide adenine dinucleotide phosphate (NADPH)-dependent, with a substrate preference for (S)-3-hydroxybutyryl-CoA or (R)-3-hydroxybutyryl-CoA and are classified as E.C. 1.1.1.157 and E.C. 1.1.1.36, respectively. 3-Hydroxybutyryl-CoA dehydrogenases are available from a number of sources, for example, *C. acetobutylicum* (GenBank NOs: NP_349314, NC_003030), *B. subtilis* (GenBank NOs: AAB09614, U29084), *Ralstonia eutropha* (GenBank NOs: YP_294481, NC_007347), and *Alcaligenes eutrophus* (GenBank NOs: AAA21973, J04987).

The term "crotonase" refers to an enzyme that catalyzes the conversion of 3-hydroxybutyryl-CoA to crotonyl-CoA and $H_2O$. Example crotonases may have a substrate preference for (S)-3-hydroxybutyryl-CoA or (R)-3-hydroxybutyryl-CoA and may be classified as E.C. 4.2.1.17 and E.C. 4.2.1.55, respectively. Crotonases are available from a number of sources, for example, *E. coli* (GenBank NOs: NP_415911, NC_000913), *C. acetobutylicum* (GenBank NOs: NP_349318, NC_003030), *B. subtilis* (GenBank NOs: CAB13705, Z99113), and *Aeromonas caviae* (GenBank NOs: BAA21816, D88825).

The term "butyryl-CoA dehydrogenase" refers to an enzyme that catalyzes the conversion of crotonyl-CoA to butyryl-CoA. Example butyryl-CoA dehydrogenases may be NADH-dependent, NADPH-dependent, or flavin-dependent and may be classified as E.C. 1.3.1.44, E.C. 1.3.1.38, and E.C. 1.3.99.2, respectively. Butyryl-CoA dehydrogenases are available from a number of sources, for example, *C. acetobutylicum* (GenBank NOs: NP_347102, NC_003030), *Euglena gracilis* (GenBank NOs: Q5EU90, AY741582), *Streptomyces collinus* (GenBank NOs: AAA92890, U37135), and *Streptomyces coelicolor* (GenBank NOs: CAA22721, AL939127).

The term "butyraldehyde dehydrogenase" refers to an enzyme that catalyzes the conversion of butyryl-CoA to butyraldehyde, using NADH or NADPH as cofactor. Butyraldehyde dehydrogenases with a preference for NADH are known as E.C. 1.2.1.57 and are available from, for example, *Clostridium beijerinckii* (GenBank NOs: AAD31841, AF157306) and *C. acetobutylicum* (GenBank NOs: NP_149325, NC_001988).

The term "isobutyryl-CoA mutase" refers to an enzyme that catalyzes the conversion of butyryl-CoA to isobutyryl-CoA. This enzyme uses coenzyme $B_{12}$ as cofactor. Example isobutyryl-CoA mutases are known by the EC number 5.4.99.13. These enzymes are found in a number of *Streptomyces*, including, but not limited to, *Streptomyces cinnamonensis* (GenBank Nos: AAC08713, U67612; CAB59633, AJ246005), *S. coelicolor* (GenBank Nos: CAB70645, AL939123; CAB92663, AL939121), and *Streptomyces avermitilis* (GenBank Nos: NP_824008, NC_003155; NP_824637, NC_003155).

The term "acetolactate decarboxylase" refers to a polypeptide (or polypeptides) having an enzyme activity that catalyzes the conversion of alpha-acetolactate to acetoin. Example acetolactate decarboxylases are known as EC 4.1.1.5 and are available, for example, from *Bacillus subtilis* (GenBank Nos: AAA22223, L04470), *Klebsiella terrigena* (GenBank Nos: AAA25054, L04507) and *Klebsiella pneumoniae* (GenBank Nos: AAU43774, AY722056).

The term "acetoin aminase" or "acetoin transaminase" refers to a polypeptide (or polypeptides) having an enzyme activity that catalyzes the conversion of acetoin to 3-amino-2-butanol. Acetoin aminase may utilize the cofactor pyridoxal 5'-phosphate or NADH (reduced nicotinamide adenine dinucleotide) or NADPH (reduced nicotinamide adenine dinucleotide phosphate). The resulting product may have (R) or (S) stereochemistry at the 3-position. The pyridoxal phosphate-dependent enzyme may use an amino acid such as alanine or glutamate as the amino donor. The NADH- and NADPH-dependent enzymes may use ammonia as a second substrate. A suitable example of an NADH dependent acetoin aminase, also known as amino alcohol dehydrogenase, is described by Ito, et al. (U.S. Pat. No. 6,432,688). An example of a pyridoxal-dependent acetoin aminase is the amine:pyruvate aminotransferase (also called amine:pyruvate transaminase) described by Shin and Kim (*J. Org. Chem.* 67:2848-2853, 2002).

The term "acetoin kinase" refers to a polypeptide (or polypeptides) having an enzyme activity that catalyzes the conversion of acetoin to phosphoacetoin. Acetoin kinase may utilize ATP (adenosine triphosphate) or phosphoenolpyruvate as the phosphate donor in the reaction. Enzymes that catalyze the analogous reaction on the similar substrate dihydroxyacetone, for example, include enzymes known as EC 2.7.1.29 (Garcia-Alles, et al., *Biochemistry* 43:13037-13046, 2004).

The term "acetoin phosphate aminase" refers to a polypeptide (or polypeptides) having an enzyme activity that catalyzes the conversion of phosphoacetoin to 3-amino-2-butanol O-phosphate. Acetoin phosphate aminase may use the cofactor pyridoxal 5'-phosphate, NADH or NADPH. The resulting product may have (R) or (S) stereochemistry at the 3-position. The pyridoxal phosphate-dependent enzyme may use an amino acid such as alanine or glutamate. The NADH and NADPH-dependent enzymes may use ammonia as a second substrate. Although there are no reports of enzymes catalyzing this reaction on phosphoacetoin, there is a pyridoxal phosphate-dependent enzyme that is proposed to carry out the analogous reaction on the similar substrate serinol phosphate (Yasuta, et al., *Appl. Environ. Microbial.* 67:4999-5009, 2001).

The term "aminobutanol phosphate phospholyase," also called "amino alcohol O-phosphate lyase," refers to a polypeptide (or polypeptides) having an enzyme activity that catalyzes the conversion of 3-amino-2-butanol O-phosphate to 2-butanone. Amino butanol phosphate phospho-lyase may utilize the cofactor pyridoxal 5'-phosphate. There are reports of enzymes that catalyze the analogous reaction on the similar substrate 1-amino-2-propanol phosphate (Jones, et al., *Biochem J.* 134:167-182, 1973). U.S. Patent Application Publication No. 2007/0259410 describes an aminobutanol phosphate phospho-lyase from the organism *Erwinia carotovora.*

The term "aminobutanol kinase" refers to a polypeptide (or polypeptides) having an enzyme activity that catalyzes the conversion of 3-amino-2-butanol to 3-amino-2-butanol O-phosphate. Amino butanol kinase may utilize ATP as the phosphate donor. Although there are no reports of enzymes catalyzing this reaction on 3-amino-2-butanol, there are reports of enzymes that catalyze the analogous reaction on the similar substrates ethanolamine and 1-amino-2-propanol (Jones, et al., supra). U.S. Patent Application Publication No. 2009/0155870 describes, in Example 14, an amino alcohol kinase of *Erwinia carotovora* subsp. *Atroseptica.*

The term "butanediol dehydrogenase" also known as "acetoin reductase" refers to a polypeptide (or polypeptides) having an enzyme activity that catalyzes the conversion of acetoin to 2,3-butanediol. Butanedial dehydrogenases are a subset of the broad family of alcohol dehydrogenases. Butanediol dehydrogenase enzymes may have specificity for production of (R)- or (S)-stereochemistry in the alcohol product. (S)-specific butanediol dehydrogenases are known as EC 1.1.1.76 and are available, for example, from *Klebsiella pneumoniae* (GenBank Nos: BBA13085, D86412). (R)-specific butanediol dehydrogenases are known as EC 1.1.1.4 and are available, for example, from *Bacillus cereus* (GenBank Nos. NP 830481, NC_004722; AAP07682, AE017000), and *Lactococcus lactis* (GenBank Nos. AAK04995, AE006323).

The term "butanediol dehydratase," also known as "dial dehydratase" or "propanediol dehydratase" refers to a polypeptide (or polypeptides) having an enzyme activity that catalyzes the conversion of 2,3-butanediol to 2-butanone. Butanediol dehydratase may utilize the cofactor adenosyl cobalamin (also known as coenzyme Bw or vitamin $B_{12}$; although vitamin B12 may refer also to other forms of cobalamin that are not coenzyme B12). Adenosyl cobalamin-dependent enzymes are known as EC 4.2.1.28 and are available, for example, from *Klebsiella oxytoca* (GenBank Nos: AA08099 (alpha subunit), D45071; BAA08100 (beta subunit), D45071; and BBA08101 (gamma subunit), D45071 (Note all three subunits are required for activity), and *Klebsiella pneumonia* (GenBank Nos: AAC98384 (alpha subunit), AF102064; GenBank Nos: AAC98385 (beta subunit), AF102064, GenBank Nos: AAC98386 (gamma subunit), AF102064). Other suitable dial dehydratases include, but are not limited to, B12-dependent dial dehydratases available from *Salmonella typhimurium* (GenBank Nos: AAB84102 (large subunit), AF026270; GenBank Nos: AAB84103 (medium subunit), AF026270; GenBank Nos: AAB84104 (small subunit), AF026270); and *Lactobacillus collinoides* (GenBank Nos: CAC82541 (large subunit), AJ297723; GenBank Nos: CAC82542 (medium subunit); AJ297723; GenBank Nos: CAD01091 (small subunit), AJ297723); and enzymes from *Lactobacillus* brevis (particularly strains CNRZ 734 and CNRZ 735, Speranza, et al., *J. Agric. Food Chem.* 45:3476-3480, 1997), and nucleotide sequences that encode the corresponding enzymes. Methods of diol dehydratase gene isolation are well known in the art (e.g., U.S. Pat. No. 5,686,276).

The term "pyruvate decarboxylase" refers to an enzyme that catalyzes the decarboxylation of pyruvic acid to acetaldehyde and carbon dioxide. Pyruvate decarboxylases are known by the EC number 4.1.1.1. These enzymes are found in a number of yeast, including *Saccharomyces cerevisiae* (GenBank Nos: CAA97575, CAA97705, CAA97091).

It will be appreciated that host cells comprising an isobutanol biosynthetic pathway as provided herein may further comprise one or more additional modifications. U.S. Patent Application Publication No. 2009/0305363 (incorporated by reference) discloses increased conversion of pyruvate to acetolactate by engineering yeast for expression of a cytosol-localized acetolactate synthase and substantial elimination of pyruvate decarboxylase activity. In some embodiments, the host cells comprise modifications to reduce glycerol-3-phosphate dehydrogenase activity and/or disruption in at least one gene encoding a polypeptide having pyruvate decarboxylase activity or a disruption in at least one gene encoding a regulatory element controlling pyruvate decarboxylase gene expression as described in U.S. Patent Application Publication No. 2009/0305363 (incorporated herein by reference), modifications to a host cell that provide for increased carbon flux through an Entner-Doudoroff Pathway or reducing equivalents balance as described in U.S. Patent Application Publication No. 2010/0120105 (incorporated herein by reference). Other modifications include integration of at least one polynucleotide encoding a polypeptide that catalyzes a step in a pyruvate-utilizing biosynthetic pathway.

Other modifications include at least one deletion, mutation, and/or substitution in an endogenous polynucleotide encoding a polypeptide having acetolactate reductase activity. As used herein, "acetolactate reductase activity" refers to the activity of any polypeptide having the ability to catalyze the conversion of acetolactate to DHMB. Such polypeptides can be determined by methods well known in the art and disclosed herein. As used herein, "DHMB" refers to 2,3-dihydroxy-2-methyl butyrate. DHMB includes "fast DHMB," which has the 2S, 3S configuration, and "slow DHMB," which has the 2S, 3R configurate. See Kaneko et al., *Phytochemistry* 39: 115-120 (1995), which is herein incorporated by reference in its entirety and refers to fast DHMB as anglyceric acid and slow DHMB as tiglyceric acid. In embodiments, the polypeptide having acetolactate reductase activity is YMR226C of *Saccharomyces cerevisiae* or a homolog thereof.

Additional modifications include a deletion, mutation, and/or substitution in an endogenous polynucleotide encoding a polypeptide having aldehyde dehydrogenase and/or aldehyde oxidase activity. As used herein, "aldehyde dehydrogenase activity" refers to any polypeptide having a biological function of an aldehyde dehydrogenase. Such polypeptides include a polypeptide that catalyzes the oxidation (dehydrogenation) of aldehydes. Such polypeptides include a polypeptide that catalyzes the conversion of isobutyraldehyde to isobutyric acid. Such polypeptides also include a polypeptide that corresponds to Enzyme Commission Numbers EC 1.2.1.3, EC 1.2.1.4 or EC 1.2.1.5. Such polypeptides can be determined by methods well known in the art and disclosed herein. As used herein, "aldehyde oxidase activity" refers to any polypeptide having a biological function of an aldehyde oxidase. Such polypeptides include a polypeptide that catalyzes production of carboxylic acids from aldehydes. Such polypeptides include a polypeptide that catalyzes the conversion of isobutyraldehyde to isobutyric acid. Such polypeptides also include a polypeptide that corresponds to Enzyme Commission Number EC 1.2.3.1. Such polypeptides can be determined by methods well known in the art and disclosed herein. In some embodiments, the polypeptide having aldehyde dehydrogenase activity is ALD6 from *Saccharomyces cerevisiae* or a homolog thereof.

A genetic modification which has the effect of reducing glucose repression wherein the yeast production host cell is pdc− is described in U.S. Patent Application Publication No. 2011/0124060, incorporated herein by reference. In some embodiments, the pyruvate decarboxylase that is deleted or down-regulated is selected from the group consisting of: PDC1, PDC5, PDC6, and combinations thereof. In some embodiments, the pyruvate decarboxylase is selected from PDC1 pyruvate decarboxylase from *Saccharomyces cerevisiae*, PDC5 pyruvate decarboxylase from *Saccharomyces cerevisiae*, PDC6 pyruvate decarboxylase from *Saccharomyces cerevisiae*, pyruvate decarboxylase from *Candida glabrata*, PDC1 pyruvate decarboxylase from *Pichia stipites*, PDC2 pyruvate decarboxylase from *Pichia stipites*, pyruvate decarboxylase from *Kluveromyces lactis*, pyruvate decarboxylase from *Yarrowia lipolytica*, pyruvate decarboxylase from *Schizosaccharomyces pombe*, and pyruvate decarboxylase from *Zygosaccharomyces rouxii*. In some embodiments, host cells contain a deletion or down-regulation of a polynucleotide encoding a polypeptide that catalyzes the conversion of glyceraldehyde-3-phosphate to glycerate 1,3, bisphosphate. In some embodiments, the enzyme that catalyzes this reaction is glyceraldehyde-3-phosphate dehydrogenase.

WIPO publication number WO 2011/103300 discloses recombinant host cells comprising (a) at least one heterologous polynucleotide encoding a polypeptide having dihydroxy-acid dehydratase activity; and (b)(i) at least one deletion, mutation, and/or substitution in an endogenous gene encoding a polypeptide affecting Fe—S cluster biosynthesis; and/or (ii) at least one heterologous polynucleotide encoding a polypeptide affecting Fe—S cluster biosynthesis. In embodiments, the polypeptide affecting Fe—S cluster biosynthesis is encoded by AFT1, AFT2, FRA2, GRX3, or CCC1. In embodiments, the polypeptide affecting Fe—S cluster biosynthesis is constitutive mutant AFT1 L99A, AFT1 L102A, AFT1 C291F, or AFT1 C293F.

Additionally, host cells may comprise heterologous polynucleotides encoding a polypeptide with phosphoketolase activity and/or a heterologous polynucleotide encoding a polypeptide with phosphotransacetylase activity as described in U.S. Patent Application No. 2012/0156735, incorporated herein by reference.

In some embodiments, any particular nucleic acid molecule or polypeptide may be at least 80%, 85%, 90%, 95%, 96%, 97%, 98%, or 99% identical to a nucleotide sequence or polypeptide sequence described herein. The term "percent identity" as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those disclosed in: 1.) *Computational Molecular Biology* (Lesk, A. M., Ed.) Oxford University: NY (1988); 2.) *Biocomputing: Informatics and Genome Projects* (Smith, D. W., Ed.) Academic: NY (1993); 3.) *Computer Analysis of Sequence Data, Part I* (Griffin, A. M., and Griffin, H. G., Eds.) Humania: NJ (1994); 4.) *Sequence Analysis in Molecular Biology* (von Heinje, G., Ed.) Academic (1987); and 5.) *Sequence Analysis Primer* (Gribskov, M. and Devereux, J., Eds.) Stockton: NY (1991).

Standard recombinant DNA and molecular cloning techniques are well known in the art and are described by Sambrook, et al. (Sambrook, J., Fritsch, E. F. and Maniatis, T. (Molecular Cloning: A Laboratory Manual; Cold Spring Harbor Laboratory Press, Cold Spring Harbor, 1989, here in referred to as Maniatis) and by Ausubel, et al. (Ausubel, et al., *Current Protocols in Molecular Biology*, pub. by Greene Publishing Assoc. and Wiley-Interscience, 1987). Examples of methods to construct microorganisms that comprise a butanol biosynthetic pathway are disclosed, for example, in U.S. Pat. No. 7,851,188, and U.S. Patent Application Publication Nos. 2007/0092957; 2007/0259410; 2007/0292927; 2008/0182308; 2008/0274525; 2009/0155870; 2009/0305363; and 2009/0305370, the entire contents of each are herein incorporated by reference.

Expression of a Butanol Biosynthetic Pathway in *Saccharomyces cerevisiae*

Methods for gene expression in *Saccharomyces cerevisiae* are known in the art (e.g., *Methods in Enzymology*, Volume 194, *Guide to Yeast Genetics and Molecular and Cell Biology*, Part A, 2004, Christine Guthrie and Gerald R. Fink, eds., Elsevier Academic Press, San Diego, Calif.). Expression of genes in yeast typically requires a promoter, followed by the gene of interest, and a transcriptional terminator. A number of yeast promoters, including those used in the Examples herein, can be used in constructing expression cassettes for genes encoding an isobutanol biosynthetic pathway, including, but not limited to constitutive promoters FBA, GPD, ADH1, and GPM, and the inducible promoters GAL 1, GAL 10, and CUP1. Suitable transcriptional terminators include, but are not limited to FBAt, GPDt, GPMt, ERG10t, GAL1t, CYC1, and ADH1. For example, suitable promoters, transcriptional terminators, and the genes of an isobutanol biosynthetic pathway can be cloned into *E. coli*-yeast shuttle vectors and transformed into yeast cells as described in U.S. App. Pub. No. 2010/0129886. These vectors allow strain propagation in both *E. coli* and yeast strains. Typically the vector contains a selectable marker and sequences allowing autonomous replication or chromosomal integration in the desired host. Typically used plasmids in yeast are shuttle vectors pRS423, pRS424, pRS425, and pRS426 (American Type Culture Collection, Rockville, Md.), which contain an *E. coli* replication origin (e.g., pMB1), a yeast 2μ origin of replication, and a marker for nutritional selection. The selection markers for these four vectors are His3 (vector pRS423), Trp1 (vector pRS424), Leu2 (vector pRS425) and Ura3 (vector pRS426). Construction of expression vectors with genes encoding polypeptides of interest can be performed by either standard molecular cloning techniques in *E. coli* or by the gap repair recombination method in yeast.

The gap repair cloning approach takes advantage of the highly efficient homologous recombination in yeast. Typically, a yeast vector DNA is digested (e.g., in its multiple cloning site) to create a "gap" in its sequence. A number of insert DNAs of interest are generated that contain a ≥21 bp sequence at both the 5' and the 3' ends that sequentially overlap with each other, and with the 5' and 3' terminus of the vector DNA. For example, to construct a yeast expression vector for "Gene X', a yeast promoter and a yeast terminator are selected for the expression cassette. The promoter and terminator are amplified from the yeast genomic DNA, and Gene X is either PCR amplified from its source organism or obtained from a cloning vector comprising Gene X sequence. There is at least a 21 bp overlapping sequence between the 5' end of the linearized vector and the promoter sequence, between the promoter and Gene X, between Gene X and the terminator sequence, and between the terminator and the 3' end of the linearized vector. The "gapped" vector and the insert DNAs are then co-transformed into a yeast strain and plated on the medium containing the appropriate compound mixtures that allow complementation of the nutritional selection markers on the plasmids. The presence of correct insert combinations can be confirmed by PCR mapping using plasmid DNA prepared from the selected cells. The plasmid DNA isolated from yeast (usually low in concentration) can then be transformed into an *E. coli* strain, e.g., TOP10, followed by mini preps and restriction mapping to further verify the plasmid construct. Finally the construct can be verified by sequence analysis.

Like the gap repair technique, integration into the yeast genome also takes advantage of the homologous recombination system in yeast. Typically, a cassette containing a coding region plus control elements (promoter and terminator) and auxotrophic marker is PCR-amplified with a high-fidelity DNA polymerase using primers that hybridize to the cassette and contain 40-70 base pairs of sequence homology to the regions 5' and 3' of the genomic area where insertion is desired. The PCR product is then transformed into yeast and plated on medium containing the appropriate compound mixtures that allow selection for the integrated auxotrophic marker. For example, to integrate "Gene X" into chromosomal location "Y", the promoter-coding regionX-terminator construct is PCR amplified from a plasmid DNA construct and joined to an autotrophic marker (such as URA3) by either SOE PCR or by common restriction digests and cloning. The full cassette, containing the promoter-coding regionX-terminator-URA3 region, is PCR amplified with primer sequences that contain 40-70 bp of homology to the regions 5' and 3' of location "Y" on the yeast chromosome. The PCR product is transformed into yeast and selected on growth media lacking uracil. Transformants can be verified either by colony PCR or by direct sequencing of chromosomal DNA.

Growth for Production

Recombinant host cells disclosed herein are contacted with suitable carbon substrates, typically in fermentation media. Additional carbon substrates may include, but are not limited to, monosaccharides such as fructose, oligosaccharides such as lactose, maltose, galactose, or sucrose, polysaccharides such as starch or cellulose or mixtures thereof and unpurified mixtures from renewable feedstocks such as cheese whey permeate, cornsteep liquor, sugar beet molasses, and barley malt. Other carbon substrates can include ethanol, lactate, succinate, or glycerol.

Additionally the carbon substrate may also be one-carbon substrates such as carbon dioxide, or methanol for which metabolic conversion into key biochemical intermediates has been demonstrated. In addition to one and two carbon substrates, methylotrophic organisms are also known to utilize a number of other carbon containing compounds such as methylamine, glucosamine and a variety of amino acids for metabolic activity. For example, methylotrophic yeasts are known to utilize the carbon from methylamine to form trehalose or glycerol (Bellion et al., *Microb. Growth C1 Compd*., [Int. Symp.], $7^{th}$ (1993), 415-32, Editors: Murrell, J. Collin, Kelly, Don P.; Publisher: Intercept, Andover, UK). Similarly, various species of *Candida* will metabolize alanine or oleic acid (Sulter et al., *Arch. Microbiol.* 153:485-

489 (1990)). Hence it is contemplated that the source of carbon utilized in the present invention may encompass a wide variety of carbon containing substrates and will only be limited by the choice of organism.

Although it is contemplated that all of the above mentioned carbon substrates and mixtures thereof are suitable in the present invention, in some embodiments, the carbon substrates are glucose, fructose, and sucrose, or mixtures of these with C5 sugars such as xylose and/or arabinose for yeasts cells modified to use C5 sugars. Sucrose may be derived from renewable sugar sources such as sugar cane, sugar beets, cassava, sweet sorghum, and mixtures thereof. Glucose and dextrose can be derived from renewable grain sources through saccharification of starch based feedstocks including grains such as corn, wheat, rye, barley, oats, and mixtures thereof. In addition, fermentable sugars can be derived from renewable cellulosic or lignocellulosic biomass through processes of pretreatment and saccharification, as described, for example, in U.S. Patent Application Publication No. 2007/0031918 A1, which is herein incorporated by reference. Biomass, when used in reference to carbon substrate, refers to any cellulosic or lignocellulosic material and includes materials comprising cellulose, and optionally further comprising hemicellulose, lignin, starch, oligosaccharides and/or monosaccharides. Biomass can also comprise additional components, such as protein and/or lipid. Biomass can be derived from a single source, or biomass can comprise a mixture derived from more than one source; for example, biomass may comprise a mixture of corn cobs and corn stover, or a mixture of grass and leaves. Biomass includes, but is not limited to, bioenergy crops, agricultural residues, municipal solid waste, industrial solid waste, sludge from paper manufacture, yard waste, wood and forestry waste. Examples of biomass include, but are not limited to, corn grain, corn cobs, crop residues such as corn husks, corn stover grasses, wheat, wheat straw, barley, barley straw, hay, rice straw, switchgrass, waste paper, sugar cane bagasse, sorghum, soy, components obtained from milling of grains, trees, branches, roots, leaves, wood chips, sawdust, shrubs and bushes, vegetables, fruits, flowers, animal manure, and mixtures thereof.

In addition to an appropriate carbon source, fermentation media must contain suitable minerals, salts, cofactors, buffers and other components, known to those skilled in the art, suitable for the growth of the cultures and promotion of an enzymatic pathway described herein.

Culture Conditions

Typically cells are grown at a temperature in the range of about 20° C. to about 40° C. in an appropriate medium. Suitable growth media in the present invention are common commercially prepared media such as Luria Bertani (LB) broth, Sabouraud Dextrose (SD) broth or Yeast Medium (YM) broth or broth that includes yeast nitrogen base, ammonium sulfate, and dextrose (as the carbon/energy source) or YPD Medium, a blend of peptone, yeast extract, and dextrose in optimal proportions for growing most *Saccharomyces cerevisiae* strains. Other defined or synthetic growth media can also be used, and the appropriate medium for growth of the particular microorganism will be known by one skilled in the art of microbiology or fermentation science. The use of agents known to modulate catabolite repression directly or indirectly, e.g., cyclic adenosine 2',3'-monophosphate (cAMP), can also be incorporated into the fermentation medium.

Suitable pH ranges for the fermentation are between pH 5.0 to pH 9.0, where pH 6.0 to pH 8.0 is preferred for the initial condition. Suitable pH ranges for the fermentation of yeast are typically between about pH 3.0 to about pH 9.0. In one embodiment, about pH 5.0 to about pH 8.0 is used for the initial condition. Suitable pH ranges for the fermentation of other microorganisms are between about pH 3.0 to about pH 7.5. In one embodiment, about pH 4.5 to about pH 6.5 is used for the initial condition.

Fermentations can be performed under aerobic or anaerobic conditions. In one embodiment, anaerobic or microaerobic conditions are used for fermentation.

Industrial Batch and Continuous Fermentations

Butanol, or other products, can be produced using a batch method of fermentation. A classical batch fermentation is a closed system where the composition of the medium is set at the beginning of the fermentation and not subject to artificial alterations during the fermentation. A variation on the standard batch system is the fed-batch system. Fed-batch fermentation processes are also suitable in the present invention and comprise a typical batch system with the exception that the substrate is added in increments at the fermentation progresses. Fed-batch systems are useful when catabolite repression is apt to inhibit the metabolism of the cells and where it is desirable to have limited amounts of substrate in the media. Batch and fed-batch fermentations are common and well known in the art and examples can be found in Thomas D. Brock in *Biotechnology: A Textbook of Industrial Microbiology*, Second Edition (1989) Sinauer Associates, Inc., Sunderland, Mass., or Deshpande, Mukund V., *Appl. Biochem. Biotechnol.,* 36:227, (1992), herein incorporated by reference.

Butanol, or other products, may also be produced using continuous fermentation methods. Continuous fermentation is an open system where a defined fermentation medium is added continuously to a bioreactor and an equal amount of conditioned media is removed simultaneously for processing. Continuous fermentation generally maintains the cultures at a constant high density where cells are primarily in log phase growth. Continuous fermentation allows for the modulation of one factor or any number of factors that affect cell growth or end product concentration. Methods of modulating nutrients and growth factors for continuous fermentation processes as well as techniques for maximizing the rate of product formation are well known in the art of industrial microbiology and a variety of methods are detailed by Brock, supra.

It is contemplated that the production of butanol, or other products, can be practiced using batch, fed-batch or continuous processes and that any known mode of fermentation would be suitable. Additionally, it is contemplated that cells can be immobilized on a substrate as whole cell catalysts and subjected to fermentation conditions for butanol production.

Methods for Butanol Isolation from the Fermentation Medium

Bioproduced butanol may be isolated from the fermentation medium using methods known in the art for ABE fermentations (see, e.g., Durre, *Appl. Microbiol. Biotechnol.* 49:639-648 (1998), Groot et al., *Process. Biochem.* 27:61-75 (1992), and references therein). For example, solids may be removed from the fermentation medium by centrifugation, filtration, decantation, or the like. The butanol may be isolated from the fermentation medium using methods such as distillation, azeotropic distillation, liquid-liquid extraction, adsorption, gas stripping, membrane evaporation, or pervaporation.

Because butanol forms a low boiling point, azeotropic mixture with water, distillation can be used to separate the mixture up to its azeotropic composition. Distillation may be used in combination with the processes described herein to obtain separation around the azeotrope. Methods that may be used in combination with distillation to isolate and purify butanol include, but are not limited to, decantation, liquid-liquid extraction, adsorption, and membrane-based techniques. Additionally, butanol may be isolated using azeotropic distillation using an entrainer (see, e.g., Doherty and Malone, *Conceptual Design of Distillation Systems*, McGraw Hill, New York, 2001).

The butanol-water mixture forms a heterogeneous azeotrope so that distillation may be used in combination with decantation to isolate and purify the isobutanol. In this method, the butanol containing fermentation broth is distilled to near the azeotropic composition. Then, the azeotropic mixture is condensed, and the butanol is separated from the fermentation medium by decantation. The decanted aqueous phase may be returned to the first distillation column as reflux or to a separate stripping column. The butanol-rich decanted organic phase may be further purified by distillation in a second distillation column.

The butanol can also be isolated from the fermentation medium using liquid-liquid extraction in combination with distillation. In this method, the butanol is extracted from the fermentation broth using liquid-liquid extraction with a suitable solvent. The butanol-containing organic phase is then distilled to separate the butanol from the solvent.

Distillation in combination with adsorption can also be used to isolate butanol from the fermentation medium. In this method, the fermentation broth containing the butanol is distilled to near the azeotropic composition and then the remaining water is removed by use of an adsorbent, such as molecular sieves (Aden et al., *Lignocellulosic Biomass to Ethanol Process Design and Economics Utilizing Co-Current Dilute Acid Prehydrolysis and Enzymatic Hydrolysis for Corn Stover*, Report NREL/TP-510-32438, National Renewable Energy Laboratory, June 2002).

Additionally, distillation in combination with pervaporation can be used to isolate and purify the butanol from the fermentation medium. In this method, the fermentation broth containing the butanol is distilled to near the azeotropic composition, and then the remaining water is removed by pervaporation through a hydrophilic membrane (Guo et al., *J. Membr. Sci.* 245, 199-210 (2004)).

In situ product removal (ISPR) (also referred to as extractive fermentation) can be used to remove butanol (or other fermentative alcohol) from the fermentation vessel as it is produced, thereby allowing the microorganism to produce butanol at high yields. One method for ISPR for removing fermentative alcohol that has been described in the art is liquid-liquid extraction. In general, with regard to butanol fermentation, for example, the fermentation medium, which includes the microorganism, is contacted with an organic extractant at a time before the butanol concentration reaches a toxic level. The organic extractant and the fermentation medium form a biphasic mixture. The butanol partitions into the organic extractant phase, decreasing the concentration in the aqueous phase containing the microorganism, thereby limiting the exposure of the microorganism to the inhibitory butanol.

Liquid-liquid extraction can be performed, for example, according to the processes described in U.S. Patent Appl. Pub. Nos. 2009/0305370 and 2011/0097773, the disclosures of which are hereby incorporated in their entirety. U.S. Patent Appl. Pub. Nos. 2009/0305370 and 2011/0097773 describe methods for producing and recovering butanol from a fermentation broth using liquid-liquid extraction, the methods comprising the step of contacting the fermentation broth with a water immiscible extractant to form a two-phase mixture comprising an aqueous phase and an organic phase. Typically, the extractant can be an organic extractant selected from the group consisting of saturated, mono-unsaturated, polyunsaturated (and mixtures thereof) $C_{12}$ to $C_{22}$ fatty alcohols, $C_{12}$ to $C_{22}$ fatty acids, esters of $C_{12}$ to $C_{22}$ fatty acids, $C_{12}$ to $C_{22}$ fatty aldehydes, and mixtures thereof. The extractant(s) for ISPR can be non-alcohol extractants. The ISPR extractant can be an exogenous organic extractant such as oleyl alcohol, behenyl alcohol, cetyl alcohol, lauryl alcohol, myristyl alcohol, stearyl alcohol, 1-undecanol, oleic acid, lauric acid, myristic acid, stearic acid, methyl myristate, methyl oleate, undecanal, lauric aldehyde, 20-methylundecanal, and mixtures thereof.

In some embodiments, an alcohol ester can be formed by contacting the alcohol in a fermentation medium with an organic acid (e.g., fatty acids) and a catalyst capable of esterifying the alcohol with the organic acid. In such embodiments, the organic acid can serve as an ISPR extractant into which the alcohol esters partition. The organic acid can be supplied to the fermentation vessel and/or derived from the biomass supplying fermentable carbon fed to the fermentation vessel. Lipids present in the feedstock can be catalytically hydrolyzed to organic acid, and the same catalyst (e.g., enzymes) can esterify the organic acid with the alcohol. In certain embodiments, lipids present in the feedstock can be converted into fatty acids and glycerol utilizing the catalysts (e.g., enzymes) described above. The glycerol can, for example, be provided to the fermentation vessel to supplement the microorganisms with reduced glycerol production described herein. Supplementing the microorganisms can, for example, improve biomass production and microorganism cell health. The glycerol will be provided in sufficient amounts beyond that produced by yeast under fermentation conditions. Carboxylic acids that are produced during the fermentation can additionally be esterified with the alcohol produced by the same or a different catalyst. The catalyst can be supplied to the feedstock prior to fermentation, or can be supplied to the fermentation vessel before or contemporaneously with the supplying of the feedstock. When the catalyst is supplied to the fermentation vessel, alcohol esters can be obtained by hydrolysis of the lipids into organic acid and substantially simultaneous esterification of the organic acid with butanol present in the fermentation vessel. Organic acid and/or native oil not derived from the feedstock can also be fed to the fermentation vessel, with the native oil being hydrolyzed into organic acid. Any organic acid not esterified with the alcohol can serve as part of the ISPR extractant. The extractant containing alcohol esters can be separated from the fermentation medium, and the alcohol can be recovered from the extractant. The extractant can be recycled to the fermentation vessel. Thus, in the case of butanol production, for example, the conversion of the butanol to an ester reduces the free butanol concentration in the fermentation medium, shielding the microorganism from the toxic effect of increasing butanol concentration. In addition, unfractionated grain can be used as feedstock without separation of lipids therein, since the lipids can be catalytically hydrolyzed to organic acid, thereby decreasing the rate of build-up of lipids in the ISPR extractant.

In situ product removal can be carried out in a batch mode or a continuous mode. In a continuous mode of in situ product removal, product is continually removed from the reactor. In a batchwise mode of in situ product removal, a volume of organic extractant is added to the fermentation vessel and the extractant is not removed during the process. For in situ product removal, the organic extractant can contact the fermentation medium at the start of the fermentation forming a biphasic fermentation medium. Alternatively, the organic extractant can contact the fermentation medium after the microorganism has achieved a desired amount of growth, which can be determined by measuring the optical density of the culture. Further, the organic extractant can contact the fermentation medium at a time at which the product alcohol level in the fermentation medium reaches a preselected level. In the case of butanol production according to some embodiments of the present invention, the organic acid extractant can contact the fermentation medium at a time before the butanol concentration reaches a toxic level, so as to esterify the butanol with the organic acid to produce butanol esters and consequently reduce the concentration of butanol in the fermentation vessel. The ester-containing organic phase can then be removed from the fermentation vessel (and separated from the fermentation broth which constitutes the aqueous phase) after a desired effective titer of the butanol esters is achieved. In some embodiments, the ester-containing organic phase is separated from the aqueous phase after fermentation of the available fermentable sugar in the fermentation vessel is substantially complete.

Confirmation of Isobutanol Production

The presence and/or concentration of isobutanol in the culture medium can be determined by a number of methods known in the art (see, for example, U.S. Pat. No. 7,851,188, incorporated by reference). For example, a specific high performance liquid chromatography (HPLC) method utilizes a Shodex SH-1011 column with a Shodex SHG guard column, both may be purchased from Waters Corporation (Milford, Mass.), with refractive index (RI) detection. Chromatographic separation is achieved using 0.01 M $H_2SO_4$ as the mobile phase with a flow rate of 0.5 mL/min and a column temperature of 50° C. Isobutanol has a retention time of 46.6 min under the conditions used.

Alternatively, gas chromatography (GC) methods are available. For example, a specific GC method utilizes an HP-INNOWax column (30 m×0.53 mm id, 1 μm film thickness, Agilent Technologies, Wilmington, Del.), with a flame ionization detector (FID). The carrier gas is helium at a flow rate of 4.5 mL/min, measured at 150° C. with constant head pressure; injector split is 1:25 at 200° C.; oven temperature is 45° C. for 1 min, 45 to 220° C. at 10° C./min, and 220° C. for 5 min; and FID detection is employed at 240° C. with 26 mL/min helium makeup gas. The retention time of isobutanol is 4.5 min.

While various embodiments of the present invention have been described herein, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the claims and their equivalents.

All publications, patents, and patent applications mentioned in this specification are indicative of the level of those skilled in the art to which this invention pertains, and are herein incorporated by reference to the same extent as if each individual publication, patent, or patent application was specifically and individually indicated to be incorporated by reference.

EXAMPLES

The present invention is further defined in the following Examples. It should be understood that these Examples, while indicating embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

General Methods

Standard recombinant DNA, molecular cloning techniques and transformation protocols used in the Examples are well known in the art and are described by Sambrook et al. (Sambrook, J., Fritsch, E. F. and Maniatis, T. (Molecular Cloning: A Laboratory Manual; Cold Spring Harbor Laboratory Press, Cold Spring Harbor, 1989, here in referred to as Maniatis), by Ausubel et al. (Ausubel et al., Current Protocols in Molecular Biology, pub. by Greene Publishing Assoc. and Wiley-Interscience, 1987) and by Amberg et al (Amberg, D.C., Burke, D. J. and Strathern, J. N. (Methods in Yeast Genetics: A Cold Spring Harbor Laboratory Course Manual, Cold Spring Harbor Press, 2005). Materials and methods suitable for the maintenance and growth of bacterial cultures are well known in the art. Techniques suitable for use in the following examples may be found as set out in Manual of Methods for General Bacteriology (Phillipp et al., eds., American Society for Microbiology, Washington, D.C., 1994) or by Thomas D. Brock in (Brock, Biotechnology: A Textbook of Industrial Microbiology, Second Edition, Sinauer Associates, Inc., Sunderland, Mass. (1989). All reagents, restriction enzymes and materials used for the growth and maintenance of bacterial cells were obtained from Sigma-Aldrich Chemicals (St. Louis, Mo.), BD Diagnostic Systems (Sparks, Md.), Invitrogen (Carlsbad, Calif.), HiMedia (Mumbai, India), SD Fine chemicals (India), or Takara Bio Inc. (Shiga, Japan), unless otherwise specified.

The meaning of abbreviations is as follows: "sec" means second(s), "min" means minute(s), "h" means hour(s), "nm" means nanometers, "uL" means microliter(s), "mL" means milliliter(s), "mg/mL" means milligram per milliliter, "L" means liter(s), "nm" means nanometers, "mM" means millimolar, "M" means molar, "mmol" means millimole(s), "μmole" means micromole(s), "kg" means kilogram, "g" means gram(s), "μg" means microgram(s) and "ng" means nanogram(s), "PCR" means polymerase chain reaction, "OD" means optical density, "OD600" means the optical density measured at a wavelength of 600 nm, "kDa" means kilodaltons, "g" can also mean the gravitation constant, "bp" means base pair(s), "kbp" means kilobase pair(s), "kb" means kilobase, "%" means percent, "% w/v" means weight/volume percent, "% v/v" means volume/volume percent, "HPLC" means high performance liquid chromatography, "g/L" means gram per liter, "μg/L" means microgram per liter, "ng/μL" means nanogram per microliter, "pmol/μL" means picomol per microliter, "RPM" means rotation per minute, "μmol/min/mg" means micromole per minute per milligram, "w/v" means weight per volume, "v/v" means volume per volume.

Strain Construction

Construction of Strain PNY2115

*Saccharomyces cerevisiae* strain PNY0827 is used as the host cell for further genetic manipulation for PNY2115. PNY0827 refers to a strain derived from *Saccharomyces cerevisiae* which has been deposited at the ATCC under the Budapest Treaty on Sep. 22, 2011 at the American Type Culture Collection, Patent Depository 10801 University Boulevard, Manassas, Va. 20110-2209 and has the patent deposit designation PTA-12105.

Deletion of URA3 and Sporulation into Haploids

In order to delete the endogenous URA3 coding region, a deletion cassette was PCR-amplified from pLA54 (SEQ ID NO: 95) which contains a $P_{TEF1}$-kanMX4-TEF1t cassette flanked by loxP sites to allow homologous recombination in vivo and subsequent removal of the KANMX4 marker. PCR was done by using Phusion High Fidelity PCR Master Mix (New England BioLabs; Ipswich, Mass.) and primers BK505 (SEQ ID NO: 96) and BK506 (SEQ ID NO: 97). The URA3 portion of each primer was derived from the 5' region 180 bp upstream of the URA3 ATG and 3' region 78 bp downstream of the coding region such that integration of the kanMX4 cassette results in replacement of the URA3 coding region. The PCR product was transformed into PNY0827 using standard genetic techniques (Methods in Yeast Genetics, 2005, Cold Spring Harbor Laboratory Press, Cold Spring Harbor, N.Y., pp. 201-202) and transformants were selected on YEP medium supplemented 2% glucose and 100 μg/ml Geneticin at 30° C. Transformants were screened by colony PCR with primers LA468 (SEQ ID NO: 98) and LA492 (SEQ ID NO: 99) to verify presence of the integration cassette. A heterozygous diploid was obtained: NYLA98, which has the genotype MATa/α URA3/ura3::loxP-kanMX4-loxP. To obtain haploids, NYLA98 was sporulated using standard methods (Codón A C, Gasent-Ramírez J M, Benítez T. Factors which affect the frequency of sporulation and tetrad formation in *Saccharomyces cerevisiae* baker's yeast. Appl Environ Microbiol. 1995 PMID: 7574601). Tetrads were dissected using a micromanipulator and grown on rich YPE medium supplemented with 2% glucose. Tetrads containing four viable spores were patched onto synthetic complete medium lacking uracil supplemented with 2% glucose, and the mating type was verified by multiplex colony PCR using primers AK109-1 (SEQ ID NO: 100), AK109-2 (SEQ ID NO: 101), and AK109-3 (SEQ ID NO: 102). The resulting identified haploid strain called NYLA103, which has the genotype: MATα ura3Δ::loxP-kanMX4-loxP, and NYLA106, which has the genotype: MATa ura3Δ::loxP-kanMX4-loxP.

Deletion of His3

To delete the endogenous HIS3 coding region, a scarless deletion cassette was used. The four fragments for the PCR cassette for the scarless HIS3 deletion were amplified using Phusion High Fidelity PCR Master Mix (New England BioLabs; Ipswich, Mass.) and CEN.PK 113-7D genomic DNA as template, prepared with a Gentra Puregene Yeast/Bact kit (Qiagen; Valencia, Calif.). HIS3 Fragment A was amplified with primer oBP452 (SEQ ID NO: 103) and primer oBP453 (SEQ ID NO: 104), containing a 5' tail with homology to the 5' end of HIS3 Fragment B. HIS3 Fragment B was amplified with primer oBP454 (SEQ ID NO: 105), containing a 5' tail with homology to the 3' end of HIS3 Fragment A, and primer oBP455 (SEQ ID NO: 106) containing a 5' tail with homology to the 5' end of HIS3 Fragment U. HIS3 Fragment U was amplified with primer oBP456 (SEQ ID NO: 107), containing a 5' tail with homology to the 3' end of HIS3 Fragment B, and primer oBP457 (SEQ ID NO: 108), containing a 5' tail with homology to the 5' end of HIS3 Fragment C. HIS3 Fragment C was amplified with primer oBP458 (SEQ ID NO: 109), containing a 5' tail with homology to the 3' end of HIS3 Fragment U, and primer oBP459 (SEQ ID NO: 110). PCR products were purified with a PCR Purification kit (Qiagen). HIS3 Fragment AB was created by overlapping PCR by mixing HIS3 Fragment A and HIS3 Fragment B and amplifying with primers oBP452 (SEQ ID NO: 103) and oBP455 (SEQ ID NO: 106). HIS3 Fragment UC was created by overlapping PCR by mixing HIS3 Fragment U and HIS3 Fragment C and amplifying with primers oBP456 (SEQ ID NO: 107) and oBP459 (SEQ ID NO: 110). The resulting PCR products were purified on an agarose gel followed by a Gel Extraction kit (Qiagen). The HIS3 ABUC cassette was created by overlapping PCR by mixing HIS3 Fragment AB and HIS3 Fragment UC and amplifying with primers oBP452 (SEQ ID NO: 103) and oBP459 (SEQ ID NO: 110). The PCR product was purified with a PCR Purification kit (Qiagen). Competent cells of NYLA106 were transformed with the HIS3 ABUC PCR cassette and were plated on synthetic complete medium lacking uracil supplemented with 2% glucose at 30° C. Transformants were screened to verify correct integration by replica plating onto synthetic complete medium lacking histidine and supplemented with 2% glucose at 30° C. Genomic DNA preps were made to verify the integration by PCR using primers oBP460 (SEQ ID NO: 111) and LA135 (SEQ ID NO: 112) for the 5' end and primers oBP461 (SEQ ID NO: 113) and LA92 (SEQ ID NO: 114) for the 3' end. The URA3 marker was recycled by plating on synthetic complete medium supplemented with 2% glucose and 5-FOA at 30° C. following standard protocols. Marker removal was confirmed by patching colonies from the 5-FOA plates onto SD-URA medium to verify the absence of growth. The resulting identified strain, called PNY2003 has the genotype: MATa ura3Δ::loxP-kanMX4-loxP his3Δ.

Deletion of PDC1

To delete the endogenous PDC1 coding region, a deletion cassette was PCR-amplified from pLA59 (SEQ ID NO: 115), which contains a URA3 marker flanked by degenerate loxP sites to allow homologous recombination in vivo and subsequent removal of the URA3 marker. PCR was done by using Phusion High Fidelity PCR Master Mix (New England BioLabs; Ipswich, Mass.) and primers LA678 (SEQ ID NO: 116) and LA679 (SEQ ID NO: 117). The PDC1 portion of each primer was derived from the 5' region 50 bp downstream of the PDC1 start codon and 3' region 50 bp upstream of the stop codon such that integration of the URA3 cassette results in replacement of the PDC1 coding region but leaves the first 50 bp and the last 50 bp of the coding region. The PCR product was transformed into PNY2003 using standard genetic techniques and transformants were selected on synthetic complete medium lacking uracil and supplemented with 2% glucose at 30° C. Transformants were screened to verify correct integration by colony PCR using primers LA337 (SEQ ID NO: 118), external to the 5' coding region and LA135 (SEQ ID NO: 112), an internal primer to URA3. Positive transformants were then screened by colony PCR using primers LA692 (SEQ ID NO: 119) and LA693 (SEQ ID NO: 120), internal to the PDC1 coding region. The URA3 marker was recycled by transforming with pLA34 (SEQ ID NO: 121) containing the CRE recombinase under the GAL1 promoter and plated on synthetic complete medium lacking histidine and supplemented with 2% glucose at 30° C. Transformants were plated on rich medium supplemented with 0.5% galactose to induce the recombinase. Marker removal was confirmed by patching colonies to synthetic complete medium lacking uracil and supplemented with 2% glucose to verify absence of growth. The resulting identified strain, called PNY2008 has the genotype: MATa ura3Δ::loxP-kanMX4-loxP his3Δpdc1Δ::loxP71/66.

Deletion of PDC5

To delete the endogenous PDC5 coding region, a deletion cassette was PCR-amplified from pLA59 (SEQ ID NO: 115), which contains a URA3 marker flanked by degenerate loxP sites to allow homologous recombination in vivo and subsequent removal of the URA3 marker. PCR was done by using Phusion High Fidelity PCR Master Mix (New England BioLabs; Ipswich, Mass.) and primers LA722 (SEQ ID NO: 122) and LA733 (SEQ ID NO: 123). The PDC5 portion of each primer was derived from the 5' region 50 bp upstream of the PDC5 start codon and 3' region 50 bp downstream of the stop codon such that integration of the URA3 cassette results in replacement of the entire PDC5 coding region. The PCR product was transformed into PNY2008 using standard genetic techniques and transformants were selected on synthetic complete medium lacking uracil and supplemented with 1% ethanol at 30° C. Transformants were screened to verify correct integration by colony PCR using primers LA453 (SEQ ID NO: 124), external to the 5' coding region and LA135 (SEQ ID NO: 112), an internal primer to URA3. Positive transformants were then screened by colony PCR using primers LA694 (SEQ ID NO: 125) and LA695 (SEQ ID NO: 126), internal to the PDC5 coding region. The URA3 marker was recycled by transforming with pLA34 (SEQ ID NO: 121) containing the CRE recombinase under the GAL1 promoter and plated on synthetic complete medium lacking histidine and supplemented with 1% ethanol at 30° C. Transformants were plated on rich YEP medium supplemented with 1% ethanol and 0.5% galactose to induce the recombinase. Marker removal was confirmed by patching colonies to synthetic complete medium lacking uracil and supplemented with 1% ethanol to verify absence of growth. The resulting identified strain, called PNY2009 has the genotype: MATa ura3Δ::loxP-kanMX4-loxP his3Δ pdc1Δ::loxP71/66 pdc5Δ::loxP71/66.

Deletion of FRA2

The FRA2 deletion was designed to delete 250 nucleotides from the 3' end of the coding sequence, leaving the first 113 nucleotides of the FRA2 coding sequence intact. An in-frame stop codon was present 7 nucleotides downstream of the deletion. The four fragments for the PCR cassette for the scarless FRA2 deletion were amplified using Phusion High Fidelity PCR Master Mix (New England BioLabs; Ipswich, Mass.) and CEN.PK 113-7D genomic DNA as template, prepared with a Gentra Puregene Yeast/Bact kit (Qiagen; Valencia, Calif.). FRA2 Fragment A was amplified with primer oBP594 (SEQ ID NO: 127) and primer oBP595 (SEQ ID NO: 128), containing a 5' tail with homology to the 5' end of FRA2 Fragment B. FRA2 Fragment B was amplified with primer oBP596 (SEQ ID NO: 129), containing a 5' tail with homology to the 3' end of FRA2 Fragment A, and primer oBP597 (SEQ ID NO: 130), containing a 5' tail with homology to the 5' end of FRA2 Fragment U. FRA2 Fragment U was amplified with primer oBP598 (SEQ ID NO: 131), containing a 5' tail with homology to the 3' end of FRA2 Fragment B, and primer oBP599 (SEQ ID NO: 132), containing a 5' tail with homology to the 5' end of FRA2 Fragment C. FRA2 Fragment C was amplified with primer oBP600 (SEQ ID NO: 133), containing a 5' tail with homology to the 3' end of FRA2 Fragment U, and primer oBP601 (SEQ ID NO: 134). PCR products were purified with a PCR Purification kit (Qiagen). FRA2 Fragment AB was created by overlapping PCR by mixing FRA2 Fragment A and FRA2 Fragment B and amplifying with primers oBP594 (SEQ ID NO: 127) and oBP597 (SEQ ID NO: 130). FRA2 Fragment UC was created by overlapping PCR by mixing FRA2 Fragment U and FRA2 Fragment C and amplifying with primers oBP598 (SEQ ID NO: 131) and oBP601 (SEQ ID NO: 134). The resulting PCR products were purified on an agarose gel followed by a Gel Extraction kit (Qiagen). The FRA2 ABUC cassette was created by overlapping PCR by mixing FRA2 Fragment AB and FRA2 Fragment UC and amplifying with primers oBP594 (SEQ ID NO: 127) and oBP601 (SEQ ID NO: 134). The PCR product was purified with a PCR Purification kit (Qiagen).

To delete the endogenous FRA2 coding region, the scarless deletion cassette obtained above was transformed into PNY2009 using standard techniques and plated on synthetic complete medium lacking uracil and supplemented with 1% ethanol. Genomic DNA preps were made to verify the integration by PCR using primers oBP602 (SEQ ID NO: 135) and LA135 (SEQ ID NO: 112) for the 5' end, and primers oBP602 (SEQ ID NO: 135) and oBP603 (SEQ ID NO: 136) to amplify the whole locus. The URA3 marker was recycled by plating on synthetic complete medium supplemented with 1% ethanol and 5-FOA (5-Fluoroorotic Acid) at 30° C. following standard protocols. Marker removal was confirmed by patching colonies from the 5-FOA plates onto synthetic complete medium lacking uracil and supplemented with 1% ethanol to verify the absence of growth. The resulting identified strain, PNY2037, has the genotype: MATa ura3Δ::loxP-kanMX4-loxP his3Δ pdc1Δ::loxP71/66 pdc5Δ::loxP71/66 fra2Δ.

Addition of Native 2 Micron Plasmid

The loxP71-URA3-loxP66 marker was PCR-amplified using Phusion DNA polymerase (New England BioLabs; Ipswich, Mass.) from pLA59 (SEQ ID NO: 115), and transformed along with the LA811x817 (SEQ ID NOs: 137, 138) and LA812x818 (SEQ ID NOs: 139, 140) 2-micron plasmid fragments (amplified from the native 2-micron plasmid from CEN.PK 113-7D; Centraalbureau voor Schimmelcultures (CBS) Fungal Biodiversity Centre) into strain PNY2037 on SE-URA plates at 30° C. The resulting strain PNY2037 2μ::loxP71-URA3-loxP66 was transformed with pLA34 (pRS423::cre) (also called, pLA34) (SEQ ID NO: 121) and selected on SE-HIS-URA plates at 30° C. Transformants were patched onto YP-1% galactose plates and allowed to grow for 48 hrs at 30° C. to induce Cre recombinase expression. Individual colonies were then patched onto SE-URA, SE-HIS, and YPE plates to confirm URA3 marker removal. The resulting identified strain, PNY2050, has the genotype: MATa ura3Δ::loxP-kanMX4-loxP, his3Δ pdc1Δ::loxP71/66 pdc5Δ::loxP71/66 fra2Δ 2-micron.

Construction of PNY2115 from PNY2050

Construction of PNY2115 [MATa ura3Δ::loxP his3Δ pdc5Δ::loxP66/71 fra2Δ 2-micron plasmid (CEN.PK2) pdc1Δ::P[PDC1]-ALS|alsS_Bs-CYC1t-loxP71/66 pdc6Δ::(UAS)PGK1-P[FBA1]-KIVD|Lg(y)-TDH3t-loxP71/66 adh1Δ::P[ADH1]-ADH|Bi(y)-ADHt-loxP71/66 fra2Δ::P[ILV5]-ADH|Bi(y)-ADHt-loxP71/66 gpd2Δ::loxP71/66] from PNY2050 was as follows.

Pdc1Δ::P[PDC1]-ALS|alsS_Bs-CYC1t-loxP71/66

To integrate alsS into the pdc1Δ::loxP66/71 locus of PNY2050 using the endogenous PDC1 promoter, An integration cassette was PCR-amplified from pLA71 (SEQ ID NO: 146), which contains the gene acetolactate synthase from the species *Bacillus subtilis* with a FBA1 promoter and a CYC1 terminator, and a URA3 marker flanked by degenerate loxP sites to allow homologous recombination in vivo and subsequent removal of the URA3 marker. PCR was done by using KAPA HiFi and primers 895 (SEQ ID NO: 149) and 679 (SEQ ID NO: 150). The PDC1 portion of each primer was derived from 60 bp of the upstream of the coding sequence and 50 bp that are 53 bp upstream of the stop codon. The PCR product was transformed into PNY2050 using standard genetic techniques and transformants were selected on synthetic complete media lacking uracil and supplemented with 1% ethanol at 30° C. Transformants were screened to verify correct integration by colony PCR using primers 681 (SEQ ID NO: 151), external to the 3' coding region and 92 (SEQ ID NO: 152), internal to the URA3 gene. Positive transformants were then prepped for genomic DNA and screened by PCR using primers N245 (SEQ ID NO: 153) and N246 (SEQ ID NO: 154). The URA3 marker was recycled by transforming with pLA34 (SEQ ID NO: 121) containing the CRE recombinase under the GAL1 promoter and plated on synthetic complete media lacking histidine and supplemented with 1% ethanol at 30° C. Transformants were plated on rich media supplemented with 1% ethanol and 0.5% galactose to induce the recombinase. Marker removal was confirmed by patching colonies to synthetic complete media lacking uracil and supplemented with 1% ethanol to verify absence of growth. The resulting identified strain, called PNY2090 has the genotype MATa ura3Δ::loxP, his3Δ, pdc1Δ::loxP71/66, pdc5Δ::loxP71/66 fra2Δ 2-micron pdc1Δ::P[PDC1]-ALS|alsS_Bs-CYC1t-loxP71/66.

Pdc6Δ::(UAS)PGK1-P[FBA1]-KIVD|Lg(v)-TDH3t-loxP71/66

To delete the endogenous PDC6 coding region, an integration cassette was PCR-amplified from pLA78 (SEQ ID NO: 147), which contains the kivD gene from the species *Listeria grayi* with a hybrid FBA1 promoter and a TDH3 terminator, and a URA3 marker flanked by degenerate loxP sites to allow homologous recombination in vivo and subsequent removal of the URA3 marker. PCR was done by using KAPA HiFi and primers 896 (SEQ ID NO: 155) and 897 (SEQ ID NO: 156). The PDC6 portion of each primer was derived from 60 bp upstream of the coding sequence and 59 bp downstream of the coding region. The PCR product was transformed into PNY2090 using standard genetic techniques and transformants were selected on synthetic complete media lacking uracil and supplemented with 1% ethanol at 30° C. Transformants were screened to verify correct integration by colony PCR using primers 365 (SEQ ID NO: 157) and 366 (SEQ ID NO: 158), internal primers to the PDC6 gene. Transformants with an absence of product were then screened by colony PCR N638 (SEQ ID NO: 159), external to the 5' end of the gene, and 740 (SEQ ID NO: 160), internal to the FBA1 promoter. Positive transformants were than the prepped for genomic DNA and screened by PCR with two external primers to the PDC6 coding sequence. Positive integrants would yield a 4720 bp product, while PDC6 wild type transformants would yield a 2130 bp product. The URA3 marker was recycled by transforming with pLA34 containing the CRE recombinase under the GAL 1 promoter and plated on synthetic complete media lacking histidine and supplemented with 1% ethanol at 30° C. Transformants were plated on rich media supplemented with 1% ethanol and 0.5% galactose to induce the recombinase. Marker removal was confirmed by patching colonies to synthetic complete media lacking uracil and supplemented with 1% ethanol to verify absence of growth. The resulting identified strain is called PNY2093 and has the genotype MATa ura3Δ::loxP his3Δ pdc5Δ::loxP71/66 fra2Δ 2-micron pdc1Δ::P[PDC1]-ALS|alsS_Bs-CYC1t-loxP71/66 pdc6Δ::(UAS)PGK1-P[FBA1]-KIVD|Lg(y)-TDH3t-loxP71/66.

Adh1Δ::P[ADH1]-ADH|Bi(v)-ADHt-loxP71/66

To delete the endogenous ADH1 coding region and integrate BiADH using the endogenous ADH1 promoter, an integration cassette was PCR-amplified from pLA65 (SEQ ID NO: 148), which contains the alcohol dehydrogenase from the species *Beijerinckii* with an ILV5 promoter and a ADH1 terminator, and a URA3 marker flanked by degenerate loxP sites to allow homologous recombination in vivo and subsequent removal of the URA3 marker. PCR was done by using KAPA HiFi and primers 856 (SEQ ID NO: 161) and 857 (SEQ ID NO: 162). The ADH1 portion of each primer was derived from the 5' region 50 bp upstream of the ADH1 start codon and the last 50 bp of the coding region. The PCR product was transformed into PNY2093 using standard genetic techniques and transformants were selected on synthetic complete media lacking uracil and supplemented with 1% ethanol at 30° C. Transformants were screened to verify correct integration by colony PCR using primers BK415 (SEQ ID NO: 163), external to the 5' coding region and N1092 (SEQ ID NO: 164), internal to the BiADH gene. Positive transformants were then screened by colony PCR using primers 413 (SEQ ID NO: 169), external to the 3' coding region, and 92 (SEQ ID NO: 152), internal to the URA3 marker. The URA3 marker was recycled by transforming with pLA34 (SEQ ID NO: 121) containing the CRE recombinase under the GAL 1 promoter and plated on synthetic complete media lacking histidine and supplemented with 1% ethanol at 30° C. Transformants were plated on rich media supplemented with 1% ethanol and 0.5% galactose to induce the recombinase. Marker removal was confirmed by patching colonies to synthetic complete media lacking uracil and supplemented with 1% ethanol to verify absence of growth. The resulting identified strain, called PNY2101 has the genotype MATa ura3Δ::loxP his3Δ pdc5Δ::loxP71/66 fra2Δ 2-micron pdc1Δ::P[PDC1]-ALS|alsS_Bs-CYC1t-loxP71/66 pdc6Δ::(UAS)PGK1-P[FBA1]-KIVD|Lg(y)-TDH3t-loxP71/66 adh1Δ::P[ADH1]-ADH|Bi(y)-ADHt-loxP71/66.

Fra2Δ::P[ILV5]-ADH|Bi(v)-ADHt-loxP71/66

To integrate BiADH into the fra2Δ locus of PNY2101, an integration cassette was PCR-amplified from pLA65 (SEQ ID NO: 148), which contains the alcohol dehydrogenase from the species *Beijerinckii indica* with an ILV5 promoter and an ADH1 terminator, and a URA3 marker flanked by degenerate loxP sites to allow homologous recombination in vivo and subsequent removal of the URA3 marker. PCR was done by using KAPA HiFi and primers 906 (SEQ ID NO: 165) and 907 (SEQ ID NO: 166). The FRA2 portion of each primer was derived from the first 60 bp of the coding sequence starting at the ATG and 56 bp downstream of the stop codon. The PCR product was transformed into PNY2101 using standard genetic techniques and transformants were selected on synthetic complete media lacking uracil and supplemented with 1% ethanol at 30° C. Transformants were screened to verify correct integration by colony PCR using primers 667 (SEQ ID NO: 167), external to the 5' coding region and 749 (SEQ ID NO: 168), internal to the ILV5 promoter. The URA3 marker was recycled by transforming with pLA34 (SEQ ID NO: 121) containing the CRE recombinase under the GAL1 promoter and plated on synthetic complete media lacking histidine and supplemented with 1% ethanol at 30° C. Transformants were plated on rich media supplemented with 1% ethanol and 0.5% galactose to induce the recombinase. Marker removal was confirmed by patching colonies to synthetic complete media lacking uracil and supplemented with 1% ethanol to verify absence of growth. The resulting identified strain, called PNY2110 has the genotype MATa ura3Δ::loxP his3Δ pdc5Δ::loxP66/71 2-micron pdc1Δ::P[PDC1]-ALS|alsS_Bs-CYC1t-loxP71/66 pdc6Δ:(UAS)PGK1-P[FBA1]-

KIVD|Lg(y)-TDH3t-loxP71/66 adh1Δ::P[ADH1]-ADH|Bi(y)-ADHt-loxP71/66 fra2Δ::P[ILV5]-ADH|Bi(y)-ADHt-loxP71/66.

GPD2 Deletion

To delete the endogenous GPD2 coding region, a deletion cassette was PCR amplified from pLA59 (SEQ ID NO: 115), which contains a URA3 marker flanked by degenerate loxP sites to allow homologous recombination in vivo and subsequent removal of the URA3 marker. PCR was done by using KAPA HiFi and primers LA512 (SEQ ID NO: 141) and LA513 (SEQ ID NO: 142). The GPD2 portion of each primer was derived from the 5' region 50 bp upstream of the GPD2 start codon and 3' region 50 bp downstream of the stop codon such that integration of the URA3 cassette results in replacement of the entire GPD2 coding region. The PCR product was transformed into PNY2110 using standard genetic techniques and transformants were selected on synthetic complete medium lacking uracil and supplemented with 1% ethanol at 30° C. Transformants were screened to verify correct integration by colony PCR using primers LA516 (SEQ ID NO: 143) external to the 5' coding region and LA135 (SEQ ID NO: 112), internal to URA3. Positive transformants were then screened by colony PCR using primers LA514 (SEQ ID NO: 144) and LA515 (SEQ ID NO: 145), internal to the GPD2 coding region. The URA3 marker was recycled by transforming with pLA34 (SEQ ID NO: 121) containing the CRE recombinase under the GAL1 promoter and plated on synthetic complete medium lacking histidine and supplemented with 1% ethanol at 30° C. Transformants were plated on rich medium supplemented with 1% ethanol and 0.5% galactose to induce the recombinase. Marker removal was confirmed by patching colonies to synthetic complete medium lacking uracil and supplemented with 1% ethanol to verify absence of growth. The resulting identified strain, called PNY2115, has the genotype MATa ura3Δ::loxP his3Δ pdc5Δ::loxP66/71 fra2Δ 2-micron pdc1Δ::P[PDC1]-ALS|alsS_Bs-CYC1t-loxP71/66 pdc6Δ::(UAS)PGK1-P[FBA1]-KIVD|Lg(y)-TDH3t-loxP71/66 adh1Δ::P[ADH1]-ADH|Bi(y)-ADHt-loxP71/66 fra2Δ::P[ILV5]-ADH|Bi(y)-ADHt-loxP71/66 gpd2Δ::loxP71/66.

Creation of PNY2145 from PNY2115

PNY2145 was constructed from PNY2115 by the additional integration of a phosphoketolase gene cassette at the pdc5Δ locus and by replacing the native AMN1 gene with a codon optimized version of the ortholog from CEN.PK. Integration constructs are further described below.

pdc5Δ::FBA(L8)-xpk1-CYC1t-loxP71/66

The TEF(M4)-xpk1-CYC1t gene from pRS423::TEF(M4)-xpk1+ENO1-eutD (SEQ ID NO: 170) was PCR amplified using primers N1341 and N1338 (SEQ ID NOS: 171 and 172), generating a 3.1 kb product. The loxP-flanked URA3 gene cassette from pLA59 (SEQ ID NO: 115) was amplified with primers N1033c and N1342 (SEQ ID NOS: 173 and 174), generating a 1.6 kb product. The xpk1 and URA3 PCR products were fused by combining them without primers for an additional 10 cycles of PCR using Phusion DNA polymerase. The resulting reaction mix was then used as a template for a PCR reaction with KAPA Hi Fi and primers N1342 and N1364 (SEQ ID NOS: 174 and 175). A 4.2 kb PCR product was recovered by purification from an electrophoresis agarose gel (Zymo kit). FBA promoter variant L8 (SEQ ID NO: 176) was amplified using primers N1366 and N1368 (SEQ ID NOS: 177 and 178). The xpk1::URA3 PCR product was combined with the FBA promoter by additional rounds of PCR. The resulting product was phosphorylated with polynucleotide kinase and ligated into pBR322 that had been digested with EcoRV and treated with calf intestinal phosphatase. The ligation reaction was transformed into *E. coli* cells (Stbl3 competent cells from Invitrogen). The integration cassette was confirmed by sequencing. To prepare DNA for integration, the plasmid was used as a template in a PCR reaction with Kapa HiFi and primers N1371 and N1372 (SEQ ID NOS: 179 and 180). The PCR product was isolated by phenol-chloroform extraction and ethanol precipitation (using standard methods; eg. Maniatas, et al.). Five micrograms of DNA were used to transform strain PNY2115. Transformants were selected on medium lacking uracil (synthetic complete medium minus uracil with 1% ethanol as the carbon source). Colonies were screened for the integration event using PCR (JumpStart) with primers BK93 and N1114 (SEQ ID NOS: 181 and 182). Two clones were selected to carry forward. The URA3 marker was recycled by transforming with pJT254 (SEQ ID NO: 183) containing the CRE recombinase under the GAL1 promoter and plating on synthetic complete medium lacking histidine and supplemented with 1% ethanol at 30° C. Transformants were grown in rich medium supplemented with 1% ethanol to derepress the recombinase. Marker removal was confirmed for single colony isolates by patching to synthetic complete medium lacking uracil and supplemented with 1% ethanol to verify absence of growth. Loss of the recombinase plasmid, pJT254, was confirmed by patching the colonies to synthetic complete medium lacking histidine and supplemented with 1% ethanol. Proper marker removal was confirmed by PCR (primers N160SeqF5 (SEQ ID NO: 184) and BK380. One resulting clone was designated PNY2293.

amn1Δ::AMN1(y)-loxP71/66

To replace the endogenous copy of AMN1 with a codon-optimized version of the AMN1 gene from CEN.PK2, an integration cassette containing the CEN.PK AMN1 promoter, AMN1(y) gene (nucleic acid SEQ ID NO: 185; amino acid SEQ ID NO: 186), and CEN.PK AMN1 terminator was assembled by SOE PCR and subcloned into the shuttle vector pLA59. The AMN1(y) gene was ordered from DNA 2.0 with codon-optimization for *S. cerevisiae*. The completed pLA67 plasmid (SEQ ID NO: 187) contained: 1) pUC19 vector backbone sequence containing an *E. coli* replication origin and ampicillin resistance gene; 2) URA3 selection marker flanked by loxP71 and loxP66 sites; and 3) $P_{AMN1(CEN.PK)}$-AMN1(y)-$term_{AMN1(CEN.PK)}$ expression cassette. PCR amplification of the AMN1(y)-loxP71-URA3-loxP66 cassette was done by using KAPA HiFi from Kapa Biosystems, Woburn, Mass. and primers LA712 (SEQ ID NO: 188) and LA746 (SEQ ID NO: 189). The PCR product was transformed into PNY2293 using standard genetic techniques and transformants were selected on synthetic complete medium lacking uracil and supplemented with 1% ethanol at 30° C. Transformants were observed under magnification for the absence of a clumping phenotype with respect to the control (PNY2293). The URA3 marker was recycled using the pJT254 Cre recombinase plasmid as described above. After marker recycle, clones were again observed under magnification to confirm absence of the clumping phenotype. A resulting identified strain, PNY2145, has the genotype: MATa ura3Δ::loxP his3Δ pdc5Δ::P[FBA(L8)]-XPK|xpk1_Lp-CYCt-loxP66/71 fra2Δ 2-micron plasmid (CEN.PK2) pdc1Δ::P[PDC1]-ALS|alsS_Bs-CYC1t-loxP71/66 pdc6Δ::(UAS)PGK1-P[FBA1]-KIVD|Lg(y)-TDH3t-loxP71/66 adh1Δ::P[ADH1]-ADH|Bi(y)-ADHt-loxP71/66 fra2Δ::P[ILV5]-ADH|Bi(y)-ADHt-loxP71/66 gpd2Δ::loxP71/66 amn1Δ::AMN1(y).

Creation of PNY2310 from PNY2145

PNY2310 was generated by transforming strain PNY2145 with plasmids pLH804-L2V4 and pRS413::BiADH-kivD. Plasmid pLH804-L2V4 (SEQ ID NO: 12) is a yeast-*E. coli* shuttle vector based on pHR81 (ATCC#87541). It contains genes for the expression of KARI variant K9JB4P and DHAD variant L2V4. Plasmid pRS413::BiADH-kivD (SEQ ID NO: 13) is a yeast-*E. coli* shuttle vector based on pRS413 (ATCC#87518). It contains genes for the expression of BiADH and kivD. The positions of the relevant gene features in both plasmids are listed in the Tables 3 and 4. Plasmid transformants were selected by plating on synthetic complete medium lacking uracil and histidine with 1% (v/v) ethanol as the carbon source. Colonies were transferred to fresh plates by patching. After two days, cells from the patches were transferred to plates containing synthetic complete medium (minus uracil and histidine) with 2% (w/v) glucose as the carbon source. The resulting strain was designated PNY2310.

TABLE 3

Nucleotide positions of pathway gene features in plasmid pLH804-L2V4

| Element | Description | Start | End | Strand |
|---|---|---|---|---|
| Promoter | ILV5p | 427 | 1620 | T |
| CDS | JB4P | 1628 | 2659 | T |
| Terminator | ILV5t | 2685 | 3307 | T |
| Terminator | FBAt | 3320 | 3632 | B |
| CDS | ILVD-L2V4 | 3641 | 5356 | B |
| Promoter | TEF1(M7)p | 5366 | 5766 | B |

TABLE 4

Nucleotide positions of pathway gene features in plasmid pRS413::BiADH-kivD

| Element | Description | Start | End | Strand |
|---|---|---|---|---|
| Promoter | FBA1p | 2293 | 2893 | T |
| CDS | kivD_Lg(y) | 2902 | 4548 | T |
| Terminator | TDH3t | 4560 | 5139 | T |
| Promoter | PDC1p | 5983 | 6852 | T |
| CDS | adhBiy | 6853 | 7896 | T |
| Terminator | ADH1t | 7905 | 8220 | T |

Creation of CPN97 from PNY2145

To replace the endogenous GPD1 of *Saccharomyces cerevisiae* with *E. coli* gpsA, primers were designed to amplify the *E. coli* gpsA open reading frame to insert in the endogenous GPD1 chromosomal location maintaining the region upstream of the ATG start codon and the endogenous *Saccharomyces cerevisiae* GPD1 stop codon. Overlapping PCR was used to obtain a PCR product containing 50 base pairs upstream of the *Saccharomyces cerevisiae* GPD1 for recombination, the *E. coli* gpsA gene, a loxP-URA3-loxP cassette, and 50 base pairs downstream of the *Saccharomyces cerevisiae* GPD1 for recombination in PNY2145. The *E. coli* gpsA ORF (PCR product 1) was amplified utilizing *E. coli* BL21 chromosomal DNA as a template with primers F1 (SEQ ID NO: 234) and R1 (SEQ ID NO: 235). The loxP-URA3-loxP cassette (PCR product 2) was amplified utilizing pLA59 (SEQ ID NO:27) as a template using primers F2 (SEQ ID NO: 236) and R2 (SEQ ID NO: 237). The PCR product (PCR product 3) containing 50 base pairs upstream of the *Saccharomyces cerevisiae* GPD1, the *E. coli* gpsA gene, a loxP-URA3-loxP cassette, and 50 base pairs downstream of the *Saccharomyces cerevisiae* GPD1 was amplified utilizing the PCR products 1 and 2 as templates and primers F1 (SEQ ID NO: 234) and R2 (SEQ ID NO: 237). All PCR reactions were performed using the enzyme Herculase (Agilent; Santa Clara, Calif.) according to manufacturer's conditions.

PCR product 3 was recovered by purification and transformed into PNY2145 using a yeast transformation kit (Sigma-Aldrich; St. Louis, Mo.). Colonies were selected on yeast synthetic medium containing 1% ethanol but no uracil. Yeast synthetic medium: 6.7 g/L yeast nitrogen base without amino acids (Becton Dickinson; East Rutherford, N.J.), 1.85 g/L Kaiser dropout His-Ura (Formedium; Norfolk, UK). Histidine or uracil were added at 76 mg/L when needed.

To recycle the URA3 marker, one colony was selected and transformed with plasmid pJT254 (SEQ ID NO: 183) containing CRE recombinase under the GAL1 promoter and was plated on yeast synthetic medium containing 1% ethanol and no histidine. One colony was selected and grown overnight in YPE medium (20 g/L peptone, 10 g/L yeast extract, 10 g/L ethanol) and restreaked on YPE plates (20 g/L peptone, 10 g/L yeast extract, 10 g/L ethanol, 15 g/L agar). Colonies were selected and patched on plates of yeast synthetic medium containing 1% ethanol and no uracil, 1% ethanol and no histidine, and YPE plates. A colony unable to grow on plates lacking uracil and histidine was selected and screened for marker removal and insertion of *E. coli* gpsA by PCR. The colony was designated CPN82.

To produce a strain with an isobutanol production pathway, CPN82 was transformed with pLH804::L2V4 (SEQ ID NO: 12) and pRS413::BiADH-kivD (SEQ ID NO: 13), described above. The transformation was plated on yeast synthetic medium lacking uracil and histidine and with 1% ethanol, and three colonies were selected and restreaked on yeast synthetic medium lacking histidine and uracil with 3 g/L glucose, 3 g/L ethanol. The colonies were tested for isobutanol production, and one colony was selected and designated CPN97.

Creation of Yeast Codon Optimized GPD1 M, M3, and M8 Variant Strains from PNY2145 Integration of Yeast Codon Optimized GPD1 Variants In order to test GPD1 mutants in the host *Saccharomyces cerevisiae* strain, native GPD1 was swapped with a codon optimized version of GPD1 synthesized by DNA 2.0 using *S. cerevisiae* codon usage.

Preparation of Integration Cassette

The gene swap cassette was prepared by cloning 2 fragments (upstream GPD1 upstream homology region and codon optimized yeast GPD1 fragment) in vector pBP3518 (SEQ ID NO:9) containing the URA3 marker gene along with the promoter and terminator and GPD downstream homology region cloned downstream of the URA3 marker gene.

Fragment 1 for the integration cassette was amplified using Phusion High Fidelity PCR Master Mix (New England Biolabs Inc.; Ipswich, Mass.), primers oBP1329 (SEQ ID NO:1) and oBP1333 (SEQ ID NO:2) and PNY2145 genomic DNA as template prepared using YeaStar™ Genomic DNA kit (Zymo Research). Fragment 2 was amplified using primers oBP1334 (SEQ ID NO:3) and oBP1335 (SEQ ID NO:4) and synthetic codon optimized Yeast GPD1 or appropriate GPD1 variants as the templates. Primer oBP1333 (SEQ ID NO:2) has a 5' tail with homology to the 5' region of Fragment 2 (synthetic codon optimized GPD1) and primer oBP1334 (SEQ ID NO:3) has a 5' tail with homology to the 3' end of Fragment 1 (GPD upstream region). The two fragments were combined using overlap PCR using primer oBP1329 (SEQ ID NO:1) and oBP1335 (SEQ ID NO:4). This combined fragment was cloned in AscI and PmeI sites in vector pBP3518 (SEQ ID NO:9) and the resulting vector referred as pBP3518GPD* (SEQ ID NO:10) was transformed into Agilent XL1Blue competent cells (Agilent Technologies, USA).

Transformation of Integration Cassette in PNY2145

Plasmid oBP3518GPD* (SEQ ID NO:10) was isolated using QIAprep Spin miniprep Kit (Qiagen, GmbH) and restricted using SacI and PacI restriction enzymes (New England Biolabs Inc. Ipswich, Mass.). The resulting 4.2 kb fragments (containing the entire integration cassette, GPD Upstream homology region, Codon Opt GPD, URA3 marker gene and Downstream GPD region) was transformed into PNY2145 using Frozen EZ Yeast Transformation II Kit (Zymo Research). The transformation mix was plated on synthetic complete lacking Uracil with 0.5% ethanol at 30° C. for 48 hours. For confirmation of integration site, transformants were screened using two sets of primers oBP1342 (SEQ ID NO:6) and oBP1344 (SEQ ID NO:7) and oBP1341 (SEQ ID NO:5) and oBP1345 (SEQ ID NO:8) for confirmation of integration at both ends. The primers oBP1342 (SEQ ID NO:6) and oBP1345 (SEQ ID NO:8) were designed from a region outside the cassette to confirm integration at the right site.

Removal of URA3 Marker

The confirmed transformants (strain PNY2145 GPD1Δ::CO GPD1 URA3) were transformed with pRS423::$P_{GAL1}$-cre using a Frozen-EZ Yeast Transformation II™ kit (Zymo Research Corporation, Irvine, Calif.) and plating on synthetic complete medium lacking histidine and uracil supplemented with 0.5% ethanol and incubated at 30° C. for 48 hours. Transformants were grown in synthetic complete medium lacking histidine with 0.5% ethanol overnight and plated on synthetic complete medium with 0.5% ethanol and 0.1% 5FOA for URA3 marker. Marker removal was confirmed by colony PCR using primers oBP1341 (SEQ ID NO:5) and oBP1345 (SEQ ID NO:8).

Transformation of Pathway Plasmid

The strain PNY2145 GPD1Δ::CO GPD1 was then transformed with plasmid pLMH11-JM44 (SEQ ID NO:240) using Frozen-EZ Yeast Transformation II™ kit (Zymo Research Corporation, Irvine, Calif.) and plated on synthetic complete medium without uracil with 0.5% ethanol. The resulting strains were designated M, M3 (F73A), and M8 (F73G/F129G).

Creation of *E. coli* Codon Optimized Yeast GPD1 EC1, E3, and E8 Strains from PNY2145 Integration of Yeast GPD1 Codon Optimized for *E. coli*

In order to test GPD1 mutants in the host *Saccharomyces cerevisiae* strain, native GPD1 was swapped with an *E. coli* codon optimized version of GPD1 synthesized by DNA 2.0 using *E. coli* codon usage.

Preparation of Integration Cassette

The gene swap cassette was prepared by cloning 2 fragments (upstream GPD1 upstream homology region and codon optimized yeast GPD1 fragment) in vector pBP3518 (SEQ ID NO:9) containing the URA3 marker gene along with the promoter and terminator and GPD downstream homology region cloned downstream of the URA3 marker gene.

Fragment 1 for the integration cassette was amplified using Phusion High Fidelity PCR Master Mix (New England Biolabs Inc.; Ipswich, Mass.), primers oBP1329 (SEQ ID NO:1) and oBP1350 (SEQ ID NO:241) and PNY2145 genomic DNA as template prepared using YeaStar™ Genomic DNA kit (Zymo Research). Fragment 2 was amplified using primers oBP1351 (SEQ ID NO:242) and oBP1352 (SEQ ID NO:243) and synthetic *E. coli* codon Yeast optimized GPD1 gene and E3 and E8 variants as the templates. Primer oBP1350 (SEQ ID NO:241) has a 5' tail with homology to the 5' region of Fragment 2 (synthetic codon optimized GPD1) and primer oBP1351 (SEQ ID NO:242) has a 5' tail with homology to the 3' end of Fragment 1 (GPD upstream region). The two fragments were combined using overlap PCR using primer oBP1329 (SEQ ID NO:1) and oBP1352 (SEQ ID NO:243). This combined fragment was cloned in AscI and PmeI sites in vector pBP3518 (SEQ ID NO:9) and the resulting vector referred as pBP3518GPD1_EcOpt (SEQ ID NO:249) was transformed into Agilent XL1Blue competent cells (Agilent Technologies, USA).

Transformation of Integration Cassette in PNY2145

Plasmid pBP3518GPD1_EcOpt (SEQ ID NO:249) was isolated using QIAprep Spin miniprep Kit (Qiagen, GmbH) and restricted using SacI and PacI restriction enzymes (New England Biolabs Inc. Ipswich, Mass.). The resulting 4.2 kb fragments (containing the entire integration cassette, GPD Upstream homology region, *E. coli* codon optimized GPD1, URA3 marker gene and Downstream GPD region) was transformed into PNY2145 using Frozen EZ Yeast Transformation II Kit (Zymo Research). The transformation mix was plated on synthetic complete lacking Uracil with 0.5% ethanol at 30° C. for 48 hours. For confirmation of integration site, transformants were screened using two sets of primers oBP1342 (SEQ ID NO:6) and oBP1352 (SEQ ID NO:243) and oBP1357 (SEQ ID NO:248) and oBP1345 (SEQ ID NO:8) for confirmation of integration at both ends. The primers oBP1342 (SEQ ID NO:6) and oBP1345 (SEQ ID NO:8) were designed from a region outside the cassette to confirm integration at the right site.

Removal of URA3 Marker

The confirmed transformants (strain PNY2145 GPD1Δ::EC CO GPD1 URA3) were transformed with pRS423::$P_{GAL1}$-cre using a Frozen-EZ Yeast Transformation II™ kit (Zymo Research Corporation, Irvine, Calif.) and plating on synthetic complete medium lacking histidine and uracil supplemented with 0.5% ethanol and incubated at 30° C. for 48 hours. Transformants were grown in synthetic complete medium lacking histidine with 0.5% ethanol overnight and plated on synthetic complete medium with 0.5% ethanol and 0.1% 5FOA for URA3 marker. Marker removal was confirmed by colony PCR using primers oBP1357 (SEQ ID NO:248) and oBP1345 (SEQ ID NO:8).

Transformation of Pathway Plasmid

The strain PNY2145 GPD1Δ::EC CO GPD1 was then transformed with plasmid pLMH11-JM44 (SEQ ID NO:240) using Frozen-EZ Yeast Transformation II™ kit (Zymo Research Corporation, Irvine, Calif.) and plated on synthetic complete medium without uracil with 0.5% ethanol. The resulting strains were designated EC1, E3 (F73A), and E8 (F73G/F129G).

Creation of Native Yeast GPD1 N, N3, and N8 Strains from PNY2145

Integration of Yeast Native GPD1 Variants

In order to test yeast native GPD1 mutants in the host *Saccharomyces cerevisiae* strain, yeast codon optimized GPD1 was swapped with yeast native version of GPD1 in strain PNY2145 GPD1Δ::CO GPD1.

Preparation of Integration Cassette

The gene swap cassette was prepared by cloning 2 fragments (upstream GPD1 upstream homology region and yeast native GPD1 fragment) in vector pBP3518 (SEQ ID NO:9) containing the URA3 marker gene along with the promoter and terminator and GPD downstream homology region cloned downstream of the URA3 marker gene.

Fragment 1 for the integration cassette was amplified using Phusion High Fidelity PCR Master Mix (New England Biolabs Inc.; Ipswich, Mass.), primers oBP1329 (SEQ ID NO:1) and oBP1353 (SEQ ID NO:244) and PNY2145 genomic DNA as template prepared using YeaStar™ Genomic DNA kit (Zymo Research). Fragment 2 was amplified using primers oBP1354 (SEQ ID NO:245) and oBP1355 (SEQ ID NO:246) and PNY2145 genomic DNA and appropriate variants as the templates. Primer oBP1353 (SEQ ID NO:244) has a 5' tail with homology to the 5' region of Fragment 2 (yeast native GPD1) and primer oBP1354 (SEQ ID NO:245) has a 5' tail with homology to the 3' end of Fragment 1 (GPD upstream region). The two fragments were combined using overlap PCR using primer oBP1329 (SEQ ID NO: 1) and oBP1355 (SEQ ID NO:246). This combined fragment was cloned in AscI and PmeI sites in vector pBP3518 (SEQ ID NO:9) and the resulting vector referred as pBP3518GPD1_Native (SEQ ID NO:250) was transformed into Agilent XL1Blue competent cells (Agilent Technologies, USA).

Transformation of Integration Cassette in PNY2145

Plasmid pBP3518GPD1_Native (SEQ ID NO:250) was isolated using QIAprep Spin miniprep Kit (Qiagen, GmbH) and restricted using SacI and PacI restriction enzymes (New England Biolabs Inc. Ipswich, Mass.). The resulting 4.2 kb fragments (containing the entire integration cassette, GPD upstream homology region, yeast native GPD1, URA3 marker gene and downstream GPD region) was transformed into PNY2145 GPD1Δ::CO GPD1 using Frozen EZ Yeast Transformation II Kit (Zymo Research). The transformation mix was plated on synthetic complete lacking Uracil with 0.5% ethanol at 30° C. for 48 hours. For confirmation of integration site, transformants were screened using two sets of primers oBP1342 (SEQ ID NO:6) and oBP1355 (SEQ ID NO:246) and oBP1356 (SEQ ID NO:247) and oBP1345 (SEQ ID NO:8) for confirmation of integration at both ends.

Removal of URA3 Marker

The confirmed transformants (strain PNY2145 CO GPD1Δ::Native GPD1 URA3) were transformed with pRS423::$P_{GAL1}$-cre using a Frozen-EZ Yeast Transformation II™ kit (Zymo Research Corporation, Irvine, Calif.) and plating on synthetic complete medium lacking histidine and uracil supplemented with 0.5% ethanol and incubated at 30° C. for 48 hours. Transformants were grown in synthetic complete medium lacking histidine with 0.5% ethanol overnight and plated on synthetic complete medium with 0.5% ethanol and 0.1% 5FOA for URA3 marker. Marker removal was confirmed by colony PCR using primers oBP1356 (SEQ ID NO:247) and oBP1345 (SEQ ID NO:8).

Transformation of Pathway Plasmids

The strain PNY2145 CO GPD1Δ::Native GPD1 was then transformed with plasmid pLMH11-JM44 (SEQ ID NO:240) using Frozen-EZ Yeast Transformation II™ kit (Zymo Research Corporation, Irvine, Calif.) and plated on synthetic complete medium without uracil with 0.5% ethanol. The resulting strains were designated N, N3 (F73A), and N8 (F73G/F129G).

Integration of GPD1 Variants

Integration cassettes for GPD1 variants were prepared in the same way as described above for codon optimized GPD1 swap except that the template used for amplifying fragment 2 for each GPD1 variant was the corresponding coding sequence with the mutation listed in Table 5.

TABLE 5

GPD variants with corresponding mutations

| GPD Variant | Mutation | Strain |
|---|---|---|
| GPD2 | F129G | |
| GPD3 | F73A | E3, M3, N3 |
| GPD4 | F73G | |
| GPD7 | F73A/F129G | |
| GPD8 | F73G/F129G | E8, M8, N8 |

E3 and E8 are variants of GPD1 using *E. coli* codon optimization; M3 and M8 are variants GPD1 using *S. cerevisiae* codon optimization; and N3 and N8 are variants GPD1 with native *S. cerevisiae* codon usage.

Integration of Heterologous GPDs

Integration cassettes for heterologous GPDs can be prepared in the same way as described above for codon optimized GPD1 except one skilled in the art would redesign the primers based on the heterologous GPD1 to be inserted to get proper assembly of the integration cassette.

Example 1

Variant GPD1 Enzymes

In this example, variant versions of *Saccharomyces* GPD1 were created and tested by expression in *E. coli* followed by enzymatic assays on the crude cell extract.

GPD1 Mutagenesis

Mutagenesis of yeast GPD1 was directed by the desire to increase the $K_M$ for NADH without having an impact on other kinetic parameters of the enzyme. The approach to mutagenesis was based on the high resolution crystal structures of human GPD1 (Ou et al, 2005, J. Mol. Biol. 357: 858-869), which allowed for the determination of the amino acids within contact distance of NAD in the cofactor binding pocket. By analyzing the amino acid residues and the type of contact made, it was possible to limit the number of amino acid changes to result in an increase in the NADH $K_M$ value. Table 6 shows the results of this analysis, where the amino acid residues within 5 Angstroms of the bound NAD have been enumerated, and the role in NAD binding was interpreted. Because of their role in the pi-stacking stabilization of bound NAD, an initial focus was placed on mutagenesis of positions homologous to the phe41 and phe97 of truncated human GPD1 (SEQ ID NO:84) (phe73 and phe129 of yeast GPD1)

TABLE 6

Amino acid residues within 5 angstroms (Å) of bound NAD in the human crystal structure, and potential mutagenesis targets to increase NADH $K_M$ value.

| Residue (Number Human GPD1) | Yeast GPD Number (Residue if diff.) | No. of Contacts with NAD | Interaction Type | Possible Role | Equiv. Alt. Residues | Increase KM with | Rationale |
|---|---|---|---|---|---|---|---|
| Ser(11) | 42 | 3 | | | | | |
| Asn(13) | 44 | 18 | Polar | H-bonds with NAD | | A, C, G, I, L, M, S, V | A non-bulky non-polar residue can reduce attraction to NAD |

TABLE 6-continued

Amino acid residues within 5 angstroms (Å) of bound NAD in the human crystal structure, and potential mutagenesis targets to increase NADH $K_M$ value.

| Residue (Number Human GPD1) | Yeast GPD Number (Residue if diff.) | No. of Contacts with NAD | Interaction Type | Possible Role | Equiv. Alt. Residues | Increase KM with | Rationale |
|---|---|---|---|---|---|---|---|
| Trp(14) | 45 | 66 | π-stacking | Possibly stabilizes pyrimidine ring for stable electron transfer | Phe, Tyr | A, C, G, H, I, K, L, M, N, Q, R, S, T, V | A non-ring residue which does not create too much of a Van der Waal clash and is non-negative can increase $K_M$ for NAD but destabilize the electron transfer by removing the π-stacking fixing. May also alter $K_{cat}$. |
| Trp(39) | 71 | 6 | | | | | |
| Phe(41) | 73 | 64 | π-stacking | Stabilizes after binding | Tyr, Trp, possibly Arg, Lys due to cation-π | G, A, R, K | Small residues can increase adenine entropy. Large residues can make it difficult to get in. Long positive residues close gate with other ring due to cation-π. |
| Glu(43) | 75 | 2 | | | | | |
| Tyr(63) | 95 | 39 | | Water stabilization | | | |
| Val(92) | 124 (Gln) | 6 | | | | | |
| Pro(94) | 126 | 25 | | | | | |
| Phe(97) | 129 | 64 | π-stacking | Stabilizes after binding | Tyr, Trp, possibly Arg, Lys due to cation-π | G, A, R, K | Small residues can increase adenine entropy. Large residues can make it difficult to get in. Long positive residues close gate with other ring due to cation-π. |
| Ile(119) | 151 (leu) | 5 | | | | | |
| Lys(120) | 152 | 20 | Polar | H-bonds with DHAP and stabilizes it | | | Reversing or removing polarity can increase $K_M$ for NAD, but can alter $K_{cat}$ or $K_M$ for DHAP |
| Asn(151) | 183 | 3 | | | | | |
| Ile(152) | 184 | 2 | | | | | |
| Ala(153) | 185 | 4 | | | | | |
| Asn(205) | 246 | 1 | | Possibly assists in electron transfer | | | Can alter $K_{cat}$ or $K_M$ for DHAP |
| Arg(269) | 310 | 33 | | Stabilizes electron transfer. Likely can create attraction for diphosphate of NAD | | | Changing to a non-positive residue can make the diphosphate of NAD uneasy, but can alter $K_{cat}$ or $K_M$ for DHAP |
| Gln(295) | 336 | 14 | | | | | |
| Lys(296) | 337 (Ser) | 17 | | H-bonds with NAD | | A, C, D, E, G, I, L, M, N, Q, S, V | Prevent h-bond formation, reverse polarity and reduce attraction for NAD |
| Gln(298) | 339 | 14 | | H-bonds and stabilizes residues around NAD | | A, C, G, I, L, M, S, V | A non-bulky non-polar residue can reduce attraction to NAD |

Strain and Media

*Escherichia coli* TOP10 was obtained from Life Technologies Corp. (Cat. # C404003, Grand Island, N.Y.). Expression plasmid pBAD was previously described (U.S. Pat. No. 7,910,342). Synthetic yeast GPD1 gene, optimized for yeast expression, was obtained from DNA2.0 (Menlo Park, Calif.). Cells were grown at 37° C. in Miller's LB broth (Cat. #46-050-CM, Mediatech, Inc., Herndon, Va.) with 0.02% L-(+)-arabinose (Cat. # A3256, Sigma-Aldrich, Inc., St. Louis, Mo.) and 100 μg/mL ampicillin (Cat. # A1066, Sigma-Aldrich, Inc., St. Louis, Mo.). Cells were plated on LB agar plates with 100 μg/mL ampicillin (Cat. # L1004, Teknova, Inc., Hollister, Calif.).

Construction of GPD1 Variants

Mutations were introduced at 4 different amino acid positions, according to Table 7. Mutagenesis was performed using a QuikChange Lightning Kit (Cat. #210519, Agilent Technologies, La Jolla, Calif.), according to manufacturer's directions. Mutagenesis primers were obtained from Sigma-Aldrich Co. LLC, St. Louis Mo. Reactions were thermocycled in a Gene Amp 9700 (Perkin Elmer Applied Biosystems, Norwalk, Conn.). *Escherichia coli* TOP10 were transformed with 1 μl of QuikChange reaction product according to manufacturer's directions, and transformants were selected on LB agar plates with 100 μg/mL ampicillin. DNA sequences were obtained for multiple isolates from each transformation in order to identify those with the desired mutations.

Double mutants were constructed in the same manner, except that the template in the mutagenesis reaction already contained one of the mutations, and the appropriate primers were used to introduce the second mutation.

TABLE 7

GPD1 Variants and Primers Used in Their Construction

| Position | SEQ ID NO: | Forward Primer SEQ ID NO: | Reverse Primer SEQ ID NO: |
|---|---|---|---|
| Asn44 | | 20 | |
| N44A | 212 | 21 | 54 |
| N44C | 213 | 22 | 55 |
| N44G | 214 | 23 | 56 |
| N44I | 215 | 24 | 57 |
| N44L | 216 | 25 | 58 |
| N44M | 217 | 26 | 59 |
| N44S | 218 | 27 | 60 |
| N44V | 219 | 28 | 61 |
| Trp45 | | 29 | |
| W45A | 220 | 30 | 62 |
| W45C | 221 | 31 | 63 |
| W45G | 222 | 32 | 64 |
| W45H | 223 | 33 | 65 |
| W45I | 224 | 34 | 66 |
| W45K | 225 | 35 | 67 |
| W45L | 226 | 36 | 68 |
| W45M | 227 | 37 | 69 |
| W45N | 228 | 38 | 70 |
| W45Q | 229 | 39 | 71 |
| W45R | 230 | 40 | 72 |
| W45S | 231 | 41 | 73 |
| W45T | 232 | 42 | 74 |
| W45V | 233 | 43 | 75 |
| Phe73 | | 44 | |
| F73G | 196 | 45 | 76 |
| F73A | 197 | 46 | 77 |
| F73R | 198 | 47 | 78 |
| F73K | 199 | 48 | 79 |
| Phe129 | | 49 | |
| F129G | 200 | 50 | 80 |
| F129A | 201 | 51 | 81 |
| F129R | 202 | 52 | 82 |
| F129K | 203 | 53 | 83 |

GPD1 Assay

Soluble fraction cell extracts were prepared from 5 ml of culture by bead beating 2×10 seconds in 100 mM MOPS pH 6.8, 10 mM $MgCl_2$, 1 mM EDTA in a Mini-Bead-beater (Cat. #3110BX, Biospec Products, Bartlesville, Okla.). Cell extract protein concentration was determined by Pierce BCA assay (Cat. #23224 and 23228, Thermo Fisher Scientific, Inc., Rockford, Ill.).

Assays were performed in a 100 μl volume containing 100 mM MOPS pH6.8, 1 mM EDTA, 1 mM glucose-6-phosphate, 3 m U/μl glucose-6-phosphate dehydrogenase (Cat. #G8404, Sigma-Aldrich, Inc., St. Louis, Mo.), 1 mM dihydroxyacetone phosphate (Cat. #D7137, Sigma-Aldrich, Inc., St. Louis, Mo.), varying concentrations of NADH, and varying concentrations of cell extract. Reactions were terminated by 4-fold dilution into 0.1% formic acid (Suprapur, #1167-1, EMD Chemicals, Gibbstown, N.J.) in water (Omnisolv, #WX0001-1, EMD Chemicals, Gibbstown, N.J.). Glycerol-3-phosphate production was measured by LC/MS.

LC/MS Method

2 μL of each sample was injected on a Waters Acuity UPLC/SQD System, using a HSS T3 column (2.1×100 mm, 1.8 μm, #186003539, Waters, Milford, Mass.) at a temperature of 30° C. UPLC mobile phases consisted of 0.1% formic acid in water (Mobile A) and 0.1% formic acid in acetonitrile (Omnisolv, #AX0156-1, EMD Chemicals, Gibbstown, N.J.) (Mobile B) with a constant flow rate of 0.3 mL/min. The gradient consisted of an initial 1 minute period at 99% A, followed by a 0.5 minute linear gradient ending at 75% B, and then a 0.5 minute linear gradient back down to 99% A, before injecting the next sample. MS analysis was performed by electrospray negative ionization at a cone voltage of 30V and m/z=171. Retention time and peak intensities were determined using MassLynx4.1 software (Waters, Milford, Mass.). External standard (glycerol-3-phosphate, Cat. #G7886, Sigma-Aldrich, Inc., St. Louis, Mo.) was analyzed in the same manner was used for quantitation.

Analysis of GPD1 Variants

The activity of the GPD1 variants was initially screened by measuring the initial rate of formation of glycerol 3 phosphate (G3P) at two concentrations of NADH (30 and 300 μM). This serves as a measurement indicating the $K_M$ of the variants for NADH: for a $K_M$ much less than 30 μM, the ratio would be 1.0, for a $K_M$ much higher than 300 μM the ratio would be 10. The results for the individual single mutants are shown in Table 8.

TABLE 8

Activity of GPD1 Variants Measured by Initial G3P Formation Rate

| Variant | Activity Ratio |
|---|---|
| 129R | 78.0 |
| 129K | 73.1 |
| 129G | 67.8 |
| 129A | 65.9 |
| 44G | 2.4 |
| 44M | 2.4 |
| 44S | 2.3 |
| 45G | 2.2 |
| 44V | 2.2 |
| 73A | 2.0 |
| 44A | 1.8 |
| 73G | 1.8 |
| 44C | 1.8 |
| 44L | 1.8 |
| 44I | 1.7 |

TABLE 8-continued

Activity of GPD1 Variants Measured by Initial G3P Formation Rate

| Variant | Activity Ratio |
|---|---|
| 45C | 1.7 |
| 73R | 1.5 |
| 45M | 1.4 |
| 45A | 1.4 |
| 45H | 1.3 |
| 73K | 1.2 |
| 45I | 1.0 |
| 45S | 1.0 |
| 45V | 1.0 |
| 45T | 0.9 |
| 45K | 0.8 |
| 45L | 0.7 |
| 45N | 0.6 |
| 45Q | 0.6 |
| 45R | 0.6 |
| GPD1 wt | 1.3 +/− 0.3 |

This data can be interpreted to indicate that any variant with a ratio greater than 1.6 (average value of three control measurements plus standard deviation) has a higher NADH $K_M$ than the wild-type GPD1. Double mutants of the individual high-$K_M$ single mutants were created as described above. Full-scale analysis of the NADH $K_M$ values for a selection of the double and single mutants is shown in Table 9.

TABLE 9

Michaelis constants ($K_M$) for NADH of GPD1 Variants

| Variant | Vmax (U/ml) | $K_M$ (μM) |
|---|---|---|
| GPD1 WT_y | 9 | 13 |
| F129A | 14 | 234 |
| F129G | 21 | 200 |
| F129K | 14 | 136 |
| F129R | 11 | 76 |
| F73A | 11 | 101 |
| F73G | 9 | 42 |
| N44A | 6 | 14 |
| N44C | 3 | 5 |
| N44G | 29 | 26 |
| N44L | 1 | 8 |
| N44M | 9 | 8 |
| N44S | 6 | 51 |
| N44V | 3 | 3 |
| F129A | 33 | 199 |
| F129R | 32 | 70 |
| F73A129G (SEQ ID NO: 204) | 30 | 605 |
| F73A129A (SEQ ID NO: 205) | 12 | 595 |
| F73A129R (SEQ ID NO: 206) | 14 | 734 |
| F73A129K (SEQ ID NO: 207) | 9 | 2989 |
| F73G129G (SEQ ID NO: 208) | 29 | 515 |
| F73G129A (SEQ ID NO: 209) | 15 | 554 |
| F73G129R (SEQ ID NO: 210) | 7 | 1364 |
| F73G129K (SEQ ID NO: 211) | 6 | 1671 |

These data indicate that mutations of amino acids corresponding to residues 44, 45, 73, and 129 (alone or in combination) of *S. cerevisiae* GPD can increase the $K_M$ of GPD for NADH. As shown in FIG. 2, amino acids 73 and 129 of *S. cerevisiae* GPD correspond to amino acids 41 and 97 of human GPD, respectively.

Example 2

Heterologous GPD Enzymes with Higher $K_M$ for NADH than *S. cerevisiae* GPD In this example, alternate glycerol-3-phosphate dehydrogenase enzymes with Michaelis constants ($K_M$) for NADH that are higher than yeast GPD1 were identified.

One strategy to identify higher NADH $K_M$ enzymes is to use values published in literature for those enzymes that have been previously identified. Table 10 enumerates publications where the NADH $K_M$ is higher than that reported for *Saccharomyces* GPD1.

TABLE 10

Published NADH $K_M$ for GPDs

| NADH $K_M$ (mM) | Source | Reference |
|---|---|---|
| 0.023 | *Saccharomyces Cerevisiae* GPD1 | Albertyn et al. 1992, *FEBS Lett.* 308: 130 |
| 0.024 | *Leishmania mexicana* | Marche et al, 2000, *Mol Biochem Parasitol.* 106: 83-91 |
| 0.032 | *Jaculus orientalis* | Berrada et al, 2002 *Mol Cell Biochem.* 231: 117-27 |
| 0.0589 | *Dunaliella viridis* GPDH1 | He et al, 2009, *Plant Mol Biol.* 71: 193-205 |
| 0.0592 | *Dunaliella viridis* GPDH2 | He et al, 2009, *Plant Mol Biol.* 71: 193-205 |
| 0.078 | *Drosophila melanogaster* | Niesel et al, 1982, *Methods Enzymol.* 89, 296-301 |

The enzyme in the *Drosophila melanogaster* reference cited above identified "GPDH1" as coming from the *Drosophila* flight muscle. However, the reference predates sequence information about the gene encoding the enzyme. Subsequently, the sequence for this enzyme was identified (gi: 22945708) as glycerol 3 phosphate dehydrogenase, isoform C from the *Drosophila* genomic sequence (Carmon & MacIntyre, 2010, Journal of Heredity 101: 225-234). Using the techniques outlined in Example 1, this enzyme was expressed in *E. coli*, and the $K_M$ value was measured in parallel with, and under the same conditions, used to measure *E. coli* expressed *Saccharomyces* GPD1. In one experiment, the NADH $K_M$ was measured as 5 μM for both enzymes, i.e., not significantly different.

An alternate strategy to identify naturally occurring GPDs with a high $K_M$ for NADH is to evaluate members of the GPDs as defined by the enzyme commission nomenclature EC 1.1.1.94. While some of these enzymes use both NADH and NADPH equally well (e.g., Edgar & Bell, 1980, *J Biol Chem* 255: 3492-34-97), others have been characterized as having a preference for NADPH (Frohlich et al, 2010, *J Bacteriol* 192: 4281-4288; Watanabe et al, 2008, *Yeast* 25:107-116; Sakasegawa et al, 2004, *Protein Science* 13: 1361-1371; Ruijter et al, 2004, *Microbiology* 150: 1095-1101). It is possible that this preference might be manifest as a high $K_M$ for NADH (as compared to the $K_M$ for NADPH of the same enzyme). Using the techniques outlined in Example 1, synthetic genes in the pBad expression vector for the following GPD enzymes were prepared: (a) *Archaeoglobus fulgidus* DSM 4304 (gi|11497621:c775889-774882) (SEQ ID NO:14); (b) *Candida versatilis* CvGPD1 gene for glycerol-3-phosphate dehydrogenase (gi|157060214|dbj|AB296385.1) (SEQ ID NO:15); and (c) *Rickettsia prowazekii* str. BuV67-CWPP chromosome (gi|383499256:539930-540880) (SEQ ID NO:16).

As in Example 1, these proteins were expressed in *E. coli*, and crude cell extracts were used to measure NADH $K_M$ values. *Candida versatilis* GPD did not yield significant measurable activity. The *Archeoglobus fulgidus* enzyme had measurable activity with a $K_M$=7 μM for NADPH and 5 μM for NADH, and the *Rickettsia prowazekii* enzyme had measurable activity with a $K_M$=4 μM for NADPH and 664 μM for NADH.

The *Rickettsia prowazekii* enzyme $K_M$ for NADH was higher than the $K_M$ for *Saccharomyces*. In order to further evaluate what aspect of the enzyme might be contributing to this decreased affinity for NADH, the sequence of the *Rickettsia* enzyme was compared to the crystal structure of the human enzyme with NAD+ in the binding site. A notable feature of the human enzyme:NAD complex is the pi-stacking of phe41 and phe97 sandwiched around the adenine ring of NAD+ (pdb: 1X0X; Ou et al, 2006 *J Mol Biol* 357: 858-869). The pi-stacking is a very stable structure, and sequence alignment reveals that the homologous positions are conserved in yeast GPD1 sequence (phe73, phe129). However in *Rickettsia*, the homologous positions in an alignment are arg35 and ala85 (see FIG. 2). These amino acids would be expected to destabilize NADH binding, thus leading to an increased NADH $K_M$. This was confirmed by mutagenesis at these positions in Example 1.

As further confirmation of the role of these amino acid positions in increasing NADH $K_M$, two of the most closely related GPD sequences outside of the *Rickettsia* genus were identified by BLAST search of the NCBI database. Two of the most closely related sequences are from *Beggiatoa alba* (BLAST E value=2e-51, 37% sequence identity; SEQ ID NO:17) and *Kangiella koreensis* (BLAST E value=2e-50, 37% sequence identity; SEQ ID NO:18). These proteins were synthesized and tested as previously described.

Although the expression level in *E coli* for these enzymes was low, the values measured with the *Beggiatoa* enzyme were $K_M$=6 μM for NADPH and 101 μM for NADH, while the *Kangiella* enzyme values were $K_M$=1 μM for NADPH and 2018 μM for NADH. The amino acids in homologous positions to the two phenylalanines forming the pi-stacking in the human enzyme are lys85 and gly86 in the *Beggiatoa* enzyme, and arg35 and ala86 in the *Kangiella* enzyme (see FIG. 2).

These results confirm that certain GPDs from other organisms have a higher $K_M$ for NADH and also further support that the $K_M$ for NADH can be raised by engineering GPD enzymes, for example, by modification of amino acids involved in the pi-stacking phenylalanine pair.

Example 3

Isobutanol and Glycerol Production for Yeast Strains Comprising GPD1 Enzyme Variants In this example, yeast strains with variant GPD1 enzymes produced and described above were tested for isobutanol and glycerol production.

PNY2145 GPD and GPD variant strains with isobutanol pathway plasmid were plated on synthetic complete agar plates [1× yeast nitrogen base without amino acids (Difco), 1× amino acid drop-out without uracil (Clone-tech) containing 2% agar (Difco), 0.2% ethanol] and incubated for 72 hours at 300 C incubator (New Brunswick)

Cells were patched on synthetic complete medium [1× yeast nitrogen base without amino acids (Difco), 1× amino acid drop-out without uracil (Clonetech) containing 2% agar (Difco), 1% glucose (sigma), 0.2% ethanol] and incubated for 72 hours at 30° C. incubator (New Brunswick). Cells were adapted by repetitive plating every three days on same media for 30 days.

Patches of the adapted cells were inoculated in 10 ml of synthetic complete liquid medium [1× yeast nitrogen base without amino acids (Difco), 1× amino acid drop-out without uracil (Clonetech) containing 2% agar (Difco), 1% glucose (Sigma), 0.2% ethanol] as primary cultures in 125 ml flasks (BD) and incubated at 30° C. for 24 hours in an incubator shaker (New Brunswick) at 250 rpm. Secondary cultures were inoculated from the primary cultures in the same medium with an initial OD of 0.5 and allowed to grow for another 24 hours. After 24 hours tertiary cultures were inoculated in the same medium from the secondary cultures with an initial O.D of 0.5 and allowed to grow for another 24 hours. These cells were then used for evaluation studies of GPD variants.

Cells were harvested by centrifugation at 3600 rpm for 5 minutes at room temperature in a centrifuge (Eppendorf) and suspended in production medium (1× yeast nitrogen base without amino acids (Difco), 1× amino acid drop-out without uracil (Clonetech), 35 g/L glucose (Sigma), 2 g/L ethanol, 100 mM MES (Sigma) 1× peptone (Difco), 1× yeast extract (Difco), 1M HCL (Sigma) at pH 5.2) and initial OD of 2 in 15 ml falcon tubes. Cultures were then incubated at 30° C. in an incubator shaker (New Brunswick) at 225 rpm for 20 hours. Samples were collected at 20 hours and analyzed by HPLC (Agilent Life Sciences) (FIG. 3).

Sample Preparation

Cultures were harvested at the end of production at 20 hours and each cell pellet was resuspended in 100 mM of MOPS pH 6.8 which contains 1× protease inhibitor (Roche). Lysis was achieved by subjecting cells to bead beating (Mini-Beadbeater-16, Biospec) for 5 cycles of 30 seconds each with an interval of 2 min between each cycle. Lysed sample was subjected to centrifugation at 13,000 rpm for 30 min in centrifuge at 40° C. Supernatant was carefully transferred to another tube. Protein estimation was done using Bradford reagent (Cat. #500-0205, Bio-Rad). GPD assay was done immediately on fresh samples without any freeze-thaw step.

Assay Condition

Glycerol-3-phosphate (GPD) assays were performed using Cary 100 UV-Vis spectrophotometer in a 1 ml volume containing 100 mM MOPS (Sigma) pH 6.8, 1 mM EDTA, 1 mM glucose-6-phosphate, 3 mU/μl glucose-6-phosphate dehydrogenase (Cat. #G8404, Sigma-Aldrich, Inc., St. Louis, Mo.), 1 mM dihydroxyacetone phosphate (Cat. #D51269,Sigma-Aldrich, Inc., St. Louis, Mo.), 0.3 mM NADH, and varying concentrations of cell extract. Rate of the reaction was calculated by taking slope of first 1 min for decrease in NADH concentration at 340 nm. Extinction coefficient of NADH was taken as 6.22 $mM^{-1}cm^{-1}$. For variants N8_1, E8_1 and M8_1 (i.e. those with the double mutant F73G/F129G) the NADH concentration was increased to 0.45 mM. This is non-saturating level of NADH for these variants.

Regression Analysis of Results

The data used in this section are provided in Table 11, and includes measurements of the metabolic products and the in vitro measurements of GPD as described above. To account for differences in the measured GPD activity that arises from measurement at subsaturating amounts of NADH, the total activity at $V_{max}$ was calculated by solving the single substrate Michaelis-Menton equation for $V_{max}$, using GPD (U/mg) for rate and the $K_M$ value as determined in Table 9.

TABLE 11

In vitro measurement of metabolic products and specific activity of GPD in various control and variant isobutanologen strains harboring different substitution in heterologous/native GPD sequence.

| Strain | Glucose Cons. (g/L) | Gly (g/L) | EtOH (g/L) | *i*BuOH (g/L) | Yield (g/g) | *i*BuOH/Gly ratio | GPD (U/mg) | GPD $K_M$ (μM) | GPD $V_{max}$ (U/mg) |
|---|---|---|---|---|---|---|---|---|---|
| EC_1 | 21.52 | 1.55 | 0.4 | 4.14 | 0.19 | 2.67 | 0.0014 | 11 | 0.0015 |
| E3_1 | 18.82 | 1.91 | 0.13 | 3.63 | 0.19 | 1.90 | 0.0018 | 101 | 0.0024 |
| E8_1 | 12.16 | 0.75 | 0.13 | 3.11 | 0.26 | 4.15 | 0.0003 | 554 | 0.0007 |
| M3_1 | 23.81 | 2.44 | 0.35 | 4.36 | 0.18 | 1.79 | 0.0053 | 101 | 0.0071 |
| M8_1 | 22.91 | 2.89 | 0.2 | 4.64 | 0.20 | 1.61 | 0.0035 | 554 | 0.0078 |
| N3_1 | 22.32 | 3.4 | 0.49 | 3.3 | 0.15 | 0.97 | 0.0097 | 101 | 0.0130 |
| N8_1 | 13.95 | 2.1 | 0.19 | 2.16 | 0.15 | 1.03 | 0.0084 | 554 | 0.0187 |
| 2145 | 30.68 | 3.43 | 0.2 | 5.46 | 0.18 | 1.59 | 0.0025 | 11 | 0.0026 |

Initially, it was observed that integration of both unaltered and variant GPDs following the methods described above led to varying amounts of GPD activity, as analyzed in the yeast cell extract following isobutanol production. The specific activity of GPD could vary by as much as 10-fold. The isobutanol/glycerol ratio also exhibited an inverse correlation with the level of GPD activity detected as shown in FIG. 4. As shown in the figure, the $R^2$ value for the linear regression of this relationship was 60.1%, but the cross-validated R-$Sq_{(pred)}$ value, which indicates the ability of the GPD activity data to predict unknown values of the isobutanol/glycerol ratio, was only 25.04%. This result indicated that while there was a correlation, the GPD activity alone was not a good predictor of this ratio.

This factor made it difficult to detect changes in the contribution of the high $K_M$ GPD variants to the production of glycerol and isobutanol, as the beneficial effect of the increased NADH $K_M$ was masked by the unpredictable activity levels. In order to further understand these effects, multiple linear regression analysis was applied to the data in Table 11 to determine if the contribution of the variant properties could be more clearly quantified. Modeled parameters were subjected to multiple rounds of linear regression using Minitab (Minitab V16.2.1, Minitab Inc.; State College, Pa.), manually removing the contributing parameter with the greatest P value until the P value of the remaining coefficients were all below 0.05. This produced a regression equation with a maximum R-sq(pred) value, which indicated the ability of the model to predict the value of new observations. Two of the metabolic measurements in Table 11 yielded models with independent contributing parameters that could be interpreted physiologically.

Isobutanol titer was modeled using the following parameters from Table 11: glucose consumed, ethanol, glycerol, yield, GPD $K_M$, and GPD $V_{max}$. Eliminating the least significant parameters yielded a regression model with 3 parameters (predictors): glucose consumed, GPD $K_M$, and GPD $V_{max}$ (shown in the FIG. 5 and Table 12). The R-Sq value for this model is 98.6%. The R-$Sq_{(pred)}$ value for this model is 94.32% indicating that this regression equation provides a high degree of predictive value. Interpreting the regression model physiologically, it suggests that isobutanol titer is predicted by positive contributions from the glucose consumed and GPD $K_M$ values, and a negative contribution from the GPD $V_{max}$ value. Thus, at any amount of glucose consumed, a higher GPD $K_M$ will result in an increase in isobutanol titer. Similarly, increases in the level of the measured activity of the GPD enzyme (as $V_{max}$ value) will result in a decrease in the isobutanol titer.

TABLE 12

Regression model for isobutanol titer (g/L).

| Predictor | Coefficient | SE Coefficient | T | P | VIF |
|---|---|---|---|---|---|
| Constant | 0.3316 | 0.3499 | 0.95 | 0.397 | |
| Glucose Consumed (g/L) | 0.17741 | 0.01382 | 12.83 | 0.000 | 1.804 |
| GPD $K_M$ (μM) | 0.0013789 | 0.0003309 | 4.17 | 0.014 | 1.977 |
| GPD $V_{max}$ (U/mg) | −75.81 | 10.10 | −7.50 | 0.002 | 1.146 |

The regression model allowed an estimate of the magnitude of these effects. At a glucose consumption level of 30 g/L, and GPD $V_{max}$ of 0.0026 U/mg, increasing the $K_M$ from 11 μM (wild type) to 550 μM resulted in a 14% increase in isobutanol titer. However, at a glucose consumption level of 30 g/L, $K_M$ at 11 μM, and increase in the GPD level from 0.0015 U/mg to 0.019 U/mg (the maximum change in activity from Table 11) resulted in a 25% decrease in isobutanol titer. This regression model therefore demonstrated that decreasing GPD affinity for NADH (increased $K_M$), increased the isobutanol titer in the samples shown here.

Isobutanol yield (grams isobutanol/gram glucose consumed) was similarly modeled using the following parameters from Table 12: glucose consumed, ethanol, glycerol, isobutanol, GPD $K_M$, and GPD $V_{max}$. Elimination of the least significant parameters yielded a regression model using 2 parameters, GPD $K_M$, and GPD $V_{max}$ (see FIG. 6 and Table 13). This regression model had an R-Sq value of 93.9%. This regression model predicted yield with R-$Sq_{(pred)}$ value of 76.3%, and notably is solely dependent on the activity level and $K_M$ of the GPD enzyme. Similar to the regression model for isobutanol titer, the GPD $V_{max}$ has a negative contribution to yield. In this regression model, increasing the $K_M$ of GPD from 11 μM (wild type) to 550 μM, at the lowest observed GPD activity level of 0.0015 U/mg, resulted in a yield improvement of 28%. At the highest GPD activity level observed here (0.019 U/mg) the yield improvement was 78%.

TABLE 13

| Regression model for yield (g/g). | | | | | |
|---|---|---|---|---|---|
| Predictor | Coefficient | SE Coefficient | T | P | VIF |
| Constant | 0.199176 | 0.005908 | 33.71 | 0.000 | |
| GPD $K_M$ (μM) | 0.00009410 | 0.00001597 | 5.89 | 0.002 | 1.144 |
| GPD $V_{max}$ (U/mg) | −5.2197 | 0.6404 | −8.15 | 0.000 | 1.144 |

Example 4

Prophetic

In this example, heterologous GPD1 yeast integrants described above are tested for isobutanol and glycerol production.

Growth Media and Procedure

Two types of media are used during the growth procedure of yeast strains: an aerobic pre-culture media and an anaerobic culture media. All chemicals are obtained from Sigma unless otherwise noted (St. Louis, Mo.)

Aerobic pre-culture media (SE-Ura-His): 6.7 g/L yeast nitrogen base without amino acids (Difco, 291940, Sparks, Md.), 1.4 g/L yeast synthetic drop-out medium supplement without histidine, leucine, tryptophan and uracil, 0.2% ethanol, 0.2% glucose, 0.01% w/v leucine and 0.002% w/v tryptophan.

Anaerobic culture media (SEG-Ura-His): 50 mM MES (pH 5.5, 6.7 g/L yeast nitrogen base without amino acids (Difco, 291940, Sparks, Md.), 1.4 g/L yeast synthetic drop-out medium supplement without histidine, leucine, tryptophan and uracil, 0.1% ethanol, 3% glucose, 0.01% leucine, 0.002% tryptophan, 30 mg/L nicotinic acid, 30 mg/L thiamine and 10 mg/L ergosterol made up in 50/50 v/v Tween/ethanol solution.

The patched cells are inoculated into 25 mL SEG-Ura,His media with 0.2% glucose and 0.2% ethanol, and grown under progressively oxygen-limited conditions with lid closed for approximately 48 hours at 30° C. with shaking, until a target $OD_{600}$ value of approximately 1.5 to 2 is achieved. $OD_{600}$ values are recorded. Cells are pelleted via centrifugation and the supernatant is discarded. Cell pellets are transferred into a Coy Anaerobic Bag (Grass Lake, Mich.) where pellets are resuspended in 1.0 mL anaerobic growth media (SEG-Ura-His). The resuspended cell pellets are used to inoculate 30 mL SEG-Ura-His media in 50 mL serum bottles (Wheaton, 223748, Millville, N.J.) to a target initial $OD_{600}$ value of 0.2. All anaerobic media, serum vials, stoppers and crimps are allowed to degas in the anaerobic bag for at least 24 hours prior to inoculation. Serum bottles are stoppered, crimped and transferred out of the anaerobic bag and grown at 30° C. with shaking at 240 rpm. Anaerobic cultures are grown for 24 to 72 hours with a target $OD_{600}$ value of at least 1.2. Additional anaerobic growth steps used the cells from the previous anaerobic culture step as inoculant. Three transformants were evaluated for each variant.

HPLC Analysis of Variant and Heterologous Yeast GPD1 Strains

Samples are taken for HPLC analysis and to obtain $OD_{600}$ values at the end of the anaerobic growth period. HPLC analysis is performed using a Waters 2695 separations unit, 2996 photodiode array detector, and 2414 refractive index detector (Waters, Milford, Mass.) with a Shodex Sugar SH-G pre-column and Shodex Sugar SH1011 separations column (Shodex, JM Science, Grand Island, N.Y.). Compounds are separated by isocratic elution at 0.01 N sulfuric acid with a flow rate of 0.5 mL/min. Chromatograms are analyzed using the Waters Empower Pro software.

Molar yields for glycerol, isobutanol and the isobutanol/glycerol ratio are determined. Mean and standard deviations are calculated from triplicate analyses for each variant and heterologous GPD. Student's t-test is employed to determine if the difference in the values are statistically significant from the codon-optimized GPD1 control values.

Example 5

Effect of gpsA on Isobutanol Production

Strains CPN97 and PNY2310 were grown on yeast synthetic medium containing 100 mM MES (2-(N-morpholino) ethanesulfonic acid), 3 g/L glucose and 3 g/L ethanol and lacking histidine and uracil. A colony from each strain was selected and inoculated in 10 ml yeast synthetic medium containing 10 g/l glucose and 100 mM MES without histidine and uracil and incubated overnight at 30° C. at 200 rpm. After overnight incubation, the cells were resuspended to an $OD_{600}$=0.4 in 10 mL yeast synthetic medium containing 20 g/l glucose and 100 mM MES without histidine and uracil and incubated for 4 hours at 30° C. and 200 rpm. The cells were then harvested and resuspended to an $OD_{600}$=0.2 in 10 mL yeast synthetic medium containing 20 g/l glucose and 100 mM MES without histidine and uracil in a 20 ml serum vial (Wheaton; Millville, N.J.), capped with a butylrubber stopper and sealed. Vials were placed in a 30° C. incubator, rotated at 200 rpm, and incubated for 28 and 42.5 hours. Two vials were prepared for each strain tested.

After 28 and 42.5 hours, the cap of one of the vials was opened, $OD_{600}$ was measured and the broth was analyzed by HPLC. HPLC analysis was performed on an Agilent 1100 series HPLC system containing a refractive index detector using a 300 mm×7.8 mm BioRad-Aminex HPX-87H exclusion column (BioRad; Hercules, Calif.) incubated at 50° C. and equipped with a BioRad-Microguard Cation H refill 30 mm×4.6 mm. Samples were run at a flow rate of 0.6 ml/min in 0.01 N sulfuric acid running buffer. From the HPLC analysis, it was observed that isobutanol yield (FIG. 7) and isobutanol/glycerol ratio (FIG. 8) were increased in CPN97 as compared to PNY2310 and glucose consumption was decreased (FIG. 9) in CPN97 as compared to PNY2310. While grown in aerobic conditions, the optical densities (ODs) as a function of time were similar.

Example 6

Generation of Feedback Resistant gpsA

Prophetic

The gpsA allele was amplified using *E. coli* MG1655 chromosomal DNA and primers Ptrc-gpsA NcoI F (SEQ ID NO:238) and Ptrc-gpsA PstI R (SEQ ID NO:239). The gpsA allele was cloned into NcoI/PstI-digested pTrcHis2B (Invitrogen; Carlsbad, Calif.) using the GeneArt seamless cloning and assembly kit (Life Technologies, Carlsbad, Calif.), to form pCPN124.

pCPN124 is submitted to error-prone mutagenesis using GeneMorphII Random Mutagenesis kit from Agilent (Santa Clara, Calif.). Plasmids that are obtained are transformed into strain BB26-36 (Bell, J. Bact. 117:1065-1076 (1974)).

Strain BB26-36 contains a mutation in the plsB gene. Additionally, the strain does not have the glycerol-3-phosphate auxotrophy of parent strain BB26 because of the loss of inhibition of glycerol kinase (GlpK) by fructose-1,6-diphosphate (fru-1,6-diP), so BB26-36 can produce glycerol-3-phosphate and grow on minimal media M9 plus glycerol 3 g/L and glucose 3 g/L (M9 contains 12.8 g sodium phosphate heptahydrate, 3 g potassium phosphate monobasic, 0.5 g sodium chloride, 1 g ammonium chloride, 0.24 g magnesium sulfate, and 11.1 mg calcium chloride, per liter).

The transformation reaction is plated on M9 medium containing 5 g/L glucose and 50 mg/L carbenicillin. Plasmids are extracted from the colonies growing on these plates and the gpsA gene is sequenced. GpsA activity of the mutated protein was determined and the $K_i$ for glycerol-3-phosphate is measured. Proteins with increased $K_i$ compared to wild-type protein are then used to replace GPD1 in the yeast chromosome and isobutanol and glycerol production are measured.

What is claimed is:

1. A recombinant microorganism comprising:

(a) an isobutanol biosynthetic pathway comprising at least one polypeptide that is heterologous to the recombinant microorganism;

(b) a heterologous glycerol-3-phosphate dehydrogenase (GPD), wherein the heterologous GPD has at least 90% identity to SEQ ID NO: 195 and comprises at least one substitution at a residue corresponding to position 44, 45, 73, or 129 of SEQ ID NO: 195, and wherein the heterologous GPD has a higher $K_M$ for NADH as compared to the $K_M$ of the endogenous GPD of the microorganism; and (c) a deletion or disruption in an endogenous gene encoding GPD;

wherein the recombinant microorganism has improved production of isobutanol as compared to a control recombinant microorganism that lacks the heterologous GPD.

2. The recombinant microorganism of claim 1, wherein the isobutanol biosynthetic pathway comprises at least one gene encoding a polypeptide that performs at least one of the following substrate to product conversions:

(a) pyruvate to acetolactate, as catalyzed by acetolactate synthase;

(b) acetolactate to 2,3-dihydroxyisovalerate, as catalyzed by acetohydroxy acid isomeroreductase;

(c) 2,3-dihydroxyisovalerate to a-ketoisovalerate, as catalyzed by dihydroxyacid dehydratase;

(d) α-ketoisovalerate to isobutyraldehyde, as catalyzed by a branched chain keto acid decarboxylase; and (e) isobutyraldehyde to isobutanol, as catalyzed by branched-chain alcohol dehydrogenase.

3. The recombinant microorganism of claim 1, wherein the microorganism is from a genus selected from the group consisting of *Clostridium, Zymomonas, Escherichia, Salmonella, Serratia, Erwinia, Klebsiella, Shigella, Rhodococcus, Pseudomonas, Bacillus, Lactobacillus, Enterococcus, Alcaligenes, Paenibacillus, Arthrobacter, Corynebacterium, Brevibacterium, Schizosaccharomyces, Kluveromyces, Yarrowia, Pichia, Zygosaccharomyces, Debaryomyces, Candida, Brettanomyces, Pachysolen, Hansenula, Issatchenkia, Trichosporon Yamadazyma*, and *Saccharomyces*.

4. The recombinant microorganism of claim 3, wherein the microorganism is from the genus *Saccharomyces*.

5. The recombinant microorganism of claim 1, wherein the engineered GPD comprises a substitution at a residue corresponding to position 73 of SEQ ID NO:195.

6. The recombinant microorganism of claim 1, wherein the engineered GPD comprises a substitution at a residue corresponding to position 129 of SEQ ID NO:195.

7. The recombinant microorganism of claim 1, wherein the engineered GPD comprises a substitution at a residue corresponding to position 73 of SEQ ID NO:195 and a substitution at a residue corresponding to position 129 of SEQ ID NO:195.

8. The recombinant microorganism of claim 1, wherein the microorganism comprises a ketol-acid reductoisomerase (KARI) that utilizes NADH.

* * * * *

SEQUENCE LISTING

```
<160> NUMBER OF SEQ ID NOS: 250

<210> SEQ ID NO 1
<211> LENGTH: 38
<212> TYPE: DNA
<213> ORGANISM: Artificial Sequence
<220> FEATURE:
<223> OTHER INFORMATION: oBP1329

<400> SEQUENCE: 1

aattggcgcg ccgtgtagac gtagtataac agtatatc                              38


<210> SEQ ID NO 2
<211> LENGTH: 48
<212> TYPE: DNA
<213> ORGANISM: Artificial Sequence
<220> FEATURE:
<223> OTHER INFORMATION: oBP1333

<400> SEQUENCE: 2

atctgtcagc agcagcggac atctttatat tatcaatatt tgtgtttg                   48


<210> SEQ ID NO 3
<211> LENGTH: 50
<212> TYPE: DNA
<213> ORGANISM: Artificial Sequence
<220> FEATURE:
<223> OTHER INFORMATION: oBP1334

<400> SEQUENCE: 3

aaacacaaat attgataata taaagatgtc cgctgctgct gacagattga                 50


<210> SEQ ID NO 4
<211> LENGTH: 36
<212> TYPE: DNA
<213> ORGANISM: Artificial Sequence
<220> FEATURE:
<223> OTHER INFORMATION: oBP1335

<400> SEQUENCE: 4

ttaagtttaa acttagtcct cgtgtaagtc taattc                                36


<210> SEQ ID NO 5
<211> LENGTH: 25
<212> TYPE: DNA
<213> ORGANISM: Artificial Sequence
<220> FEATURE:
<223> OTHER INFORMATION: oBP1341

<400> SEQUENCE: 5

gacctaataa ccacctgtgc tggtg                                            25


<210> SEQ ID NO 6
<211> LENGTH: 25
<212> TYPE: DNA
```

<213> ORGANISM: Artificial Sequence
<220> FEATURE:
<223> OTHER INFORMATION: oBP1342

<400> SEQUENCE: 6
agcccgaaag agttatcgtt actcc 25

<210> SEQ ID NO 7
<211> LENGTH: 21
<212> TYPE: DNA
<213> ORGANISM: Artificial Sequence
<220> FEATURE:
<223> OTHER INFORMATION: oBP1344

<400> SEQUENCE: 7
aatatcaacg tccttgacac t 21

<210> SEQ ID NO 8
<211> LENGTH: 25
<212> TYPE: DNA
<213> ORGANISM: Artificial Sequence
<220> FEATURE:
<223> OTHER INFORMATION: oBP1345

<400> SEQUENCE: 8
cacatctgaa atcatcgtaa ggaac 25

<210> SEQ ID NO 9
<211> LENGTH: 5036
<212> TYPE: DNA
<213> ORGANISM: Artificial Sequence
<220> FEATURE:
<223> OTHER INFORMATION: pBP3518

<400> SEQUENCE: 9
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcaggcgcc 240
attcgccatt caggctgcgc aactgttggg aagggcgatc ggtgcgggcc tcttcgctat 300
tacgccagct ggcgaaaggg ggatgtgctg caaggcgatt aagttgggta acgccagggt 360
tttcccagtc acgacgttgt aaaacgacgg ccagtgaatt cgagctcggt acccggggat 420
ccggcgcgcc gtttaaactc atgtaattag ttatgtcacg cttacattca cgccctcctc 480
ccacatccgc tctaaccgaa aaggaaggag ttagacaacc tgaagtctag gtccctattt 540 attttttttta atagttatgt tagtattaag aacgttattt atatttcaaa tttttctttt 600
ttttctgtac aaacgcgtgt acgcatgtaa cattatactg aaaaccttgc ttgagaaggt 660
tttgggacgc tcgaaggctt taatttgcgg ggccggccgc attgcggatt acgtattcta 720
atgttcagta ccgttcgtat aatgtatgct atacgaagtt atgcagattg tactgagagt 780
gcaccatacc accttttcaa ttcatcattt ttttttattt cttttttttg atttcggttt 840
ccttgaaatt tttttgattc ggtaatctcc gaacagaagg aagaacgaag gaaggagcac 900
agacttagat tggtatatat acgcatatgt agtgttgaag aaacatgaaa ttgcccagta 960
ttcttaaccc aactgcacag aacaaaaacc tgcaggaaac gaagataaat catgtcgaaa 1020
gctacatata aggaacgtgc tgctactcat cctagtcctg ttgctgccaa gctatttaat 1080
atcatgcacg aaaagcaaac aaacttgtgt gcttcattgg atgttcgtac caccaaggaa 1140

```
ttactggagt tagttgaagc attaggtccc aaaatttgtt tactaaaaac acatgtggat   1200
atcttgactg atttttccat ggagggcaca gttaagccgc taaaggcatt atccgccaag   1260
tacaattttt tactcttcga agacagaaaa tttgctgaca ttggtaatac agtcaaattg   1320
cagtactctg cgggtgtata cagaatagca gaatgggcag acattacgaa tgcacacggt   1380
gtggtgggcc caggtattgt tagcggtttg aagcaggcgg cagaagaagt aacaaaggaa   1440
cctagaggcc ttttgatgtt agcagaattg tcatgcaagg gctccctatc tactggagaa   1500
tatactaagg gtactgttga cattgcgaag agcgacaaag attttgttat cggctttatt   1560
gctcaaagag acatgggtgg aagagatgaa ggttacgatt ggttgattat gacacccggt   1620
gtgggtttag atgacaaggg agacgcattg ggtcaacagt atagaaccgt ggatgatgtg   1680
gtctctacag gatctgacat tattattgtt ggaagaggac tatttgcaaa gggaagggat   1740
gctaaggtag agggtgaacg ttacagaaaa gcaggctggg aagcatattt gagaagatgc   1800
ggccagcaaa actaaaaaac tgtattataa gtaaatgcat gtatactaaa ctcacaaatt   1860
agagcttcaa tttaattata tcagttatta ccctatgcgg tgtgaaatac cgcacagatg   1920
cgtaaggaga aaataccgca tcaggaaatt gtaagcgtta atattttgtt aaaattcgcg   1980
ttaaattttt gttaaatcag ctcatttttt aaccaatagg ccgaaatcgg caaaatccct   2040
tataaatcaa aagaatagac cgagataggg ttgagtgttg ttccagtttg gaacaagagt   2100
ccactattaa agaacgtgga ctccaacgtc aaagggcgaa aaaccgtcta tcagggcgat   2160
ggcccactac gtgaaccatc accctaatca agataacttc gtataatgta tgctatacga   2220
acggtaccag tgatgataca acgagttagc caaggtggcg gccgcattta ttggagaaag   2280
ataacatatc atactttccc ccactttttt cgaggctctt ctatatcata ttcataaatt   2340
agcattatgt catttctcat aactacttta tcacgttaga aattacttat tattattaaa   2400
ttaatacaaa atttagtaac caaataaata taaataaata tgcatattta aattttaaaa   2460
aaaaatccta tagagcaaaa ggattctcca ttataatatg agctatacac ctcttacgca   2520
tttttgagg gtggttacaa caccactcat tcagaggctg tcggcacagt tgcttccagc   2580
atctggcgtc cgtatgtatg ggtgtatttt aaataataaa caaagtgcca caccttcacc   2640
aattatgtct ttaagaaatg gacaagttcc aaagagcttg cccaaggctc gacaaggatg   2700
tactttagaa tatctatatt caagtacgtg gcgcgcatat gtttgagtgt gcacacaata   2760
aaggttaatt aatctagagt cgacctgcag gcatgcaagc ttggcgtaat catggtcata   2820
gctgtttcct gtgtgaaatt gttatccgct cacaattcca cacaacatac gagccggaag   2880
cataaagtgt aaagcctggg gtgcctaatg agtgagctaa ctcacattaa ttgcgttgcg   2940
ctcactgccc gctttccagt cgggaaacct gtcgtgccag ctgcattaat gaatcggcca   3000
acgcgcgggg agaggcggtt tgcgtattgg gcgctcttcc gcttcctcgc tcactgactc   3060
gctgcgctcg gtcgttcggc tgcggcgagc ggtatcagct cactcaaagg cggtaatacg   3120
gttatccaca gaatcagggg ataacgcagg aaagaacatg tgagcaaaag gccagcaaaa   3180
ggccaggaac cgtaaaaagg ccgcgttgct ggcgtttttc cataggctcc gcccccctga   3240
cgagcatcac aaaaatcgac gctcaagtca gaggtggcga aacccgacag gactataaag   3300
ataccaggcg tttccccctg gaagctccct cgtgcgctct cctgttccga ccctgccgct   3360
taccggatac ctgtccgcct ttctcccttc gggaagcgtg gcgctttctc atagctcacg   3420
ctgtaggtat ctcagttcgg tgtaggtcgt tcgctccaag ctgggctgtg tgcacgaacc   3480
```

```
ccccgttcag cccgaccgct gcgccttatc cggtaactat cgtcttgagt ccaacccggt   3540
aagacacgac ttatcgccac tggcagcagc cactggtaac aggattagca gagcgaggta   3600
tgtaggcggt gctacagagt tcttgaagtg gtggcctaac tacggctaca ctagaaggac   3660
agtatttggt atctgcgctc tgctgaagcc agttaccttc ggaaaaagag ttggtagctc   3720
ttgatccggc aaacaaacca ccgctggtag cggtggtttt tttgtttgca agcagcagat   3780
tacgcgcaga aaaaaaggat ctcaagaaga tcctttgatc ttttctacgg ggtctgacgc   3840
tcagtggaac gaaaactcac gttaagggat tttggtcatg agattatcaa aaaggatctt   3900
cacctagatc cttttaaatt aaaaatgaag ttttaaatca atctaaagta tatatgagta   3960
aacttggtct gacagttacc aatgcttaat cagtgaggca cctatctcag cgatctgtct   4020
atttcgttca tccatagttg cctgactccc cgtcgtgtag ataactacga tacgggaggg   4080
cttaccatct ggccccagtg ctgcaatgat accgcgagac ccacgctcac cggctccaga   4140
tttatcagca ataaaccagc cagccggaag ggccgagcgc agaagtggtc ctgcaacttt   4200
atccgcctcc atccagtcta ttaattgttg ccgggaagct agagtaagta gttcgccagt   4260
taatagtttg cgcaacgttg ttgccattgc tacaggcatc gtggtgtcac gctcgtcgtt   4320
tggtatggct tcattcagct ccggttccca acgatcaagg cgagttacat gatcccccat   4380
gttgtgcaaa aaagcggtta gctccttcgg tcctccgatc gttgtcagaa gtaagttggc   4440
cgcagtgtta tcactcatgg ttatggcagc actgcataat tctcttactg tcatgccatc   4500
cgtaagatgc ttttctgtga ctggtgagta ctcaaccaag tcattctgag aatagtgtat   4560
gcggcgaccg agttgctctt gcccggcgtc aatacgggat aataccgcgc cacatagcag   4620
aactttaaaa gtgctcatca ttggaaaacg ttcttcgggg cgaaaactct caaggatctt   4680
accgctgttg agatccagtt cgatgtaacc cactcgtgca cccaactgat cttcagcatc   4740
ttttactttc accagcgttt ctgggtgagc aaaaacagga aggcaaaatg ccgcaaaaaa   4800
gggaataagg gcgacacgga aatgttgaat actcatactc ttcctttttc aatattattg   4860
aagcatttat cagggttatt gtctcatgag cggatacata tttgaatgta tttagaaaaa   4920
taaacaaata ggggttccgc gcacatttcc ccgaaaagtg ccacctgacg tctaagaaac   4980
cattattatc atgacattaa cctataaaaa taggcgtatc acgaggccct ttcgtc       5036
```

```
<210> SEQ ID NO 10
<211> LENGTH: 7063
<212> TYPE: DNA
<213> ORGANISM: Artificial Sequence
<220> FEATURE:
<223> OTHER INFORMATION: pBP3518GPD*

<400> SEQUENCE: 10
```

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgaatt cgagctcggt acccggggat    420
ccggcgcgcc gtgtagacgt agtataacag tatatctgac acgcacgtga tgaccacgta    480
atcgcatcgc ccctcacatc tcacctctca ccgctgactc agcttcacta aaaaggaaaa    540
```

```
tatatactct ttcccaggca aggtgacagc ggtccccgtc tcctccacaa aggcctctcc    600
tggggtttga gcaagtctaa gtttacgtag cataaaaatt ctcggattgc gtcaaataat    660
aaaaaaagta actccacttc tacttctaca tcggaaaaac attccattca catatcgtct    720
ttggcctatc ttgttttgtc cttggtagat caggtcagta caaacgcaac acgaaagaac    780
aaaaaaagaa gaaaacagaa ggccaagaca gggtcaatga gactgttgtc ctcctactgt    840
ccctatgtct ctggccgatc acgcgccatt gtccctcaga aacaaatcaa acacccacac    900
cccgggcacc caaagtcccc acccacacca ccaatacgta aacggggcgc cccctgcagg    960
ccctcctgcg cgcggcctcc cgccttgctt ctctcccctc ccttttcttt ttccagtttt   1020
ccctattttg tcccttttc cgcacaacaa gtatcagaat gggttcatca aatctatcca    1080
acctaattcg cacgtagact ggcttggtat tggcagtttc gcagttatat atatactacc   1140
atgagtgaaa ctgttacgtt accttaaatt ctttctccct ttaattttct tttatcttac   1200
tctcctacat aagacatcaa gaaacaattg tatattgtac accccccccc tccacaaaca   1260
caaatattga taatataaag atgtccgctg ctgctgacag attgaacttg acatctggtc   1320
acttgaacgc tggtagaaag agatcatcct cctctgtctc tttgaaggct gccgaaaagc   1380
cattcaaggt caccgttatc ggttctggta actggggtac caccattgcc aaggtcgtcg   1440
ccgaaaactg caagggttac ccagaagttt ttgctccaat cgttcaaatg tgggtttttg   1500
aagaggaaat taacggtgaa aagttgactg aaattatcaa cactagacac caaaacgtga   1560
agtacttgcc cggtattacc ttgccagaca atttggttgc caatccagac ttgatcgata   1620
gtgtcaagga cgttgatatt atcgttttta acatcccaca ccaattccta ccacgtattt   1680
gttctcaatt gaagggtcat gtcgattctc acgttagagc tatctcctgc ttgaagggtt   1740
tcgaagttgg tgctaagggt gttcaattgt tatcctctta catcactgaa gagctaggta   1800
tccaatgtgg tgctttgtct ggtgctaaca tcgctaccga agtcgctcaa gagcactggt   1860
ctgaaaccac tgtcgcttac catatcccaa aggactttag aggtgaaggt aaagacgttg   1920
accacaaggt cctaaaggct ttgttccaca gaccatactt tcacgtttct gtcatcgaag   1980
atgtcgccgg tatctctatc tgtggcgctt taaagaacgt cgtcgccttg ggttgtggtt   2040
ttgttgaagg attgggttgg ggtaacaacg cctctgctgc tatccaacgt gtcggtttgg   2100
gtgaaatcat tagatttggt caaatgtttt tccctgaatc cagagaggaa acctactacc   2160
aagagtctgc cggtgttgct gacctaataa ccacctgtgc tggtggtaga aacgttaagg   2220
ttgccagatt gatggctact tccggtaagg acgcttggga atgtgaaaag gaattgttga   2280
acggtcaatc cgctcaaggt ttgattactt gtaaggaagt tcacgaatgg ttggaaactt   2340
gtggcagcgt tgaagatttt ccattattcg aagctgtcta ccaaatcgtc tacaataact   2400
accctatgaa aaacttgcca gatatgatcg aggaattaga cttacacgag gactaagttt   2460
aaactcatgt aattagttat gtcacgctta cattcacgcc ctcctcccac atccgctcta   2520
accgaaaagg aaggagttag acaacctgaa gtctaggtcc ctatttattt tttttaatag   2580
ttatgttagt attaagaacg ttatttatat ttcaaatttt tcttttttt ctgtacaaac    2640
gcgtgtacgc atgtaacatt atactgaaaa ccttgcttga gaaggttttg ggacgctcga   2700
aggctttaat ttgcggggcc ggccgcattg cggattacgt attctaatgt tcagtaccgt   2760
tcgtataatg tatgctatac gaagttatgc agattgtact gagagtgcac cataccacct   2820
tttcaattca tcattttttt tttattcttt tttttgattt cggtttcctt gaaatttttt   2880
```

```
tgattcggta atctccgaac agaaggaaga acgaaggaag gagcacagac ttagattggt   2940
atatatacgc atatgtagtg ttgaagaaac atgaaattgc ccagtattct taacccaact   3000
gcacagaaca aaaacctgca ggaaacgaag ataaatcatg tcgaaagcta catataagga   3060
acgtgctgct actcatccta gtcctgttgc tgccaagcta tttaatatca tgcacgaaaa   3120
gcaaacaaac ttgtgtgctt cattggatgt tcgtaccacc aaggaattac tggagttagt   3180
tgaagcatta ggtcccaaaa tttgtttact aaaaacacat gtggatatct tgactgattt   3240
ttccatggag ggcacagtta agccgctaaa ggcattatcc gccaagtaca atttttttact   3300
cttcgaagac agaaaatttg ctgacattgg taatacagtc aaattgcagt actctgcggg   3360
tgtatacaga atagcagaat gggcagacat tacgaatgca cacggtgtgg tgggcccagg   3420
tattgttagc ggtttgaagc aggcggcaga agaagtaaca aaggaaccta gaggcctttt   3480
gatgttagca gaattgtcat gcaagggctc cctatctact ggagaatata ctaagggtac   3540
tgttgacatt gcgaagagcg acaaagattt tgttatcggc tttattgctc aaagagacat   3600
gggtggaaga gatgaaggtt acgattggtt gattatgaca cccggtgtgg gtttagatga   3660
caagggagac gcattgggtc aacagtatag aaccgtggat gatgtggtct ctacaggatc   3720
tgacattatt attgttggaa gaggactatt tgcaaaggga agggatgcta aggtagaggg   3780
tgaacgttac agaaaagcag gctgggaagc atatttgaga agatgcggcc agcaaaacta   3840
aaaaactgta ttataagtaa atgcatgtat actaaactca caaattagag cttcaattta   3900
attatatcag ttattaccct atgcggtgtg aaataccgca cagatgcgta aggagaaaat   3960
accgcatcag gaaattgtaa gcgttaatat tttgttaaaa ttcgcgttaa atttttgtta   4020
aatcagctca ttttttaacc aataggccga aatcggcaaa atcccttata aatcaaaaga   4080
atagaccgag atagggttga gtgttgttcc agtttggaac aagagtccac tattaaagaa   4140
cgtggactcc aacgtcaaag ggcgaaaaac cgtctatcag ggcgatggcc cactacgtga   4200
accatcaccc taatcaagat aacttcgtat aatgtatgct atacgaacgg taccagtgat   4260
gatacaacga gttagccaag gtggcggccg catttattgg agaaagataa catatcatac   4320
tttcccccac ttttttcgag gctcttctat atcatattca taaattagca ttatgtcatt   4380
tctcataact actttatcac gttagaaatt acttattatt attaaattaa tacaaaattt   4440
agtaaccaaa taaatataaa taaatatgca tatttaaatt ttaaaaaaaa aatcctatag   4500
agcaaaagga ttctccatta taatatgagc tatacacctc ttacgcattt tttgagggtg   4560
gttacaacac cactcattca gaggctgtcg gcacagttgc ttccagcatc tggcgtccgt   4620
atgtatgggt gtattttaaa taataaacaa agtgccacac cttcaccaat tatgtcttta   4680
agaaatggac aagttccaaa gagcttgccc aaggctcgac aaggatgtac tttagaatat   4740
ctatattcaa gtacgtggcg cgcatatgtt tgagtgtgca cacaataaag gttaattaat   4800
ctagagtcga cctgcaggca tgcaagcttg gcgtaatcat ggtcatagct gtttcctgtg   4860
tgaaattgtt atccgctcac aattccacac aacatacgag ccggaagcat aaagtgtaaa   4920
gcctggggtg cctaatgagt gagctaactc acattaattg cgttgcgctc actgcccgct   4980
ttccagtcgg gaaacctgtc gtgccagctg cattaatgaa tcggccaacg cgcggggaga   5040
ggcggtttgc gtattgggcg ctcttccgct tcctcgctca ctgactcgct gcgctcggtc   5100
gttcggctgc ggcgagcggt atcagctcac tcaaaggcgg taatacggtt atccacagaa   5160
tcaggggata acgcaggaaa gaacatgtga gcaaaaggcc agcaaaaggc caggaaccgt   5220
aaaaaggccg cgttgctggc gtttttccat aggctccgcc cccctgacga gcatcacaaa   5280
```

```
aatcgacgct caagtcagag gtggcgaaac ccgacaggac tataaagata ccaggcgttt   5340

cccccctggaa gctccctcgt gcgctctcct gttccgaccc tgccgcttac cggatacctg  5400

tccgcctttc tcccttcggg aagcgtggcg ctttctcata gctcacgctg taggtatctc   5460

agttcggtgt aggtcgttcg ctccaagctg ggctgtgtgc acgaaccccc cgttcagccc   5520

gaccgctgcg ccttatccgg taactatcgt cttgagtcca acccggtaag acacgactta   5580

tcgccactgg cagcagccac tggtaacagg attagcagag cgaggtatgt aggcggtgct   5640

acagagttct tgaagtggtg gcctaactac ggctacacta gaaggacagt atttggtatc   5700

tgcgctctgc tgaagccagt taccttcgga aaaagagttg gtagctcttg atccggcaaa   5760

caaaccaccg ctggtagcgg tggttttttt gtttgcaagc agcagattac gcgcagaaaa   5820

aaaggatctc aagaagatcc tttgatcttt tctacggggt ctgacgctca gtggaacgaa   5880

aactcacgtt aagggatttt ggtcatgaga ttatcaaaaa ggatcttcac ctagatcctt   5940

ttaaattaaa aatgaagttt taaatcaatc taaagtatat atgagtaaac ttggtctgac   6000

agttaccaat gcttaatcag tgaggcacct atctcagcga tctgtctatt tcgttcatcc   6060

atagttgcct gactccccgt cgtgtagata actacgatac gggagggctt accatctggc   6120

cccagtgctg caatgatacc gcgagaccca cgctcaccgg ctccagattt atcagcaata   6180

aaccagccag ccggaagggc cgagcgcaga agtggtcctg caactttatc cgcctccatc   6240

cagtctatta attgttgccg ggaagctaga gtaagtagtt cgccagttaa tagtttgcgc   6300

aacgttgttg ccattgctac aggcatcgtg gtgtcacgct cgtcgtttgg tatggcttca   6360

ttcagctccg gttcccaacg atcaaggcga gttacatgat cccccatgtt gtgcaaaaaa   6420

gcggttagct ccttcggtcc tccgatcgtt gtcagaagta agttggccgc agtgttatca   6480

ctcatggtta tggcagcact gcataattct cttactgtca tgccatccgt aagatgcttt   6540

tctgtgactg gtgagtactc aaccaagtca ttctgagaat agtgtatgcg gcgaccgagt   6600

tgctcttgcc cggcgtcaat acgggataat accgcgccac atagcagaac tttaaaagtg   6660

ctcatcattg gaaaacgttc ttcggggcga aaactctcaa ggatcttacc gctgttgaga   6720

tccagttcga tgtaacccac tcgtgcaccc aactgatctt cagcatcttt tactttcacc   6780

agcgtttctg ggtgagcaaa aacaggaagg caaaatgccg caaaaaaggg aataagggcg   6840

acacggaaat gttgaatact catactcttc ctttttcaat attattgaag catttatcag   6900

ggttattgtc tcatgagcgg atacatattt gaatgtattt agaaaaataa acaaataggg   6960

gttccgcgca catttccccg aaaagtgcca cctgacgtct aagaaaccat tattatcatg   7020

acattaacct ataaaaatag gcgtatcacg aggccctttc gtc                     7063
```

<210> SEQ ID NO 11
<211> LENGTH: 7555
<212> TYPE: DNA
<213> ORGANISM: Artificial Sequence
<220> FEATURE:
<223> OTHER INFORMATION: p423:Gal1p-CRE-ADHt

<400> SEQUENCE: 11

```
tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accatcaaatt cccgttttaa gagcttggtg agcgctagga gtcactgcca ggtatcgttt   240
```

-continued

```
gaacacggca ttagtcaggg aagtcataac acagtccttt cccgcaattt tctttttcta    300
ttactcttgg cctcctctag tacactctat attttttat gcctcggtaa tgattttcat    360
ttttttttt cccctagcgg atgactcttt ttttttctta gcgattggca ttatcacata    420
atgaattata cattatataa agtaatgtga tttcttcgaa gaatatacta aaaaatgagc    480
aggcaagata aacgaaggca aagatgacag agcagaaagc cctagtaaag cgtattacaa    540
atgaaaccaa gattcagatt gcgatctctt taaagggtgg tcccctagcg atagagcact    600
cgatcttccc agaaaaagag gcagaagcag tagcagaaca ggccacacaa tcgcaagtga    660
ttaacgtcca cacaggtata gggtttctgg accatatgat acatgctctg gccaagcatt    720
ccggctggtc gctaatcgtt gagtgcattg gtgacttaca catagacgac catcacacca    780
ctgaagactg cgggattgct ctcggtcaag cttttaaaga ggccctactg gcgcgtggag    840
taaaaaggtt tggatcagga tttgcgcctt tggatgaggc actttccaga gcggtggtag    900
atctttcgaa caggccgtac gcagttgtcg aacttggttt gcaaagggag aaagtaggag    960
atctctcttg cgagatgatc ccgcattttc ttgaaagctt tgcagaggct agcagaatta   1020
ccctccacgt tgattgtctg cgaggcaaga atgatcatca ccgtagtgag agtgcgttca   1080
aggctcttgc ggttgccata agagaagcca cctcgcccaa tggtaccaac gatgttccct   1140
ccaccaaagg tgttcttatg tagtgacacc gattatttaa agctgcagca tacgatatat   1200
atacatgtgt atatatgtat acctatgaat gtcagtaagt atgtatacga acagtatgat   1260
actgaagatg acaaggtaat gcatcattct atacgtgtca ttctgaacga ggcgcgcttt   1320
ccttttttct ttttgctttt tctttttttt tctcttgaac tcgacggatc tatgcggtgt   1380
gaaataccgc acagatgcgt aaggagaaaa taccgcatca ggaaattgta aacgttaata   1440
ttttgttaaa attcgcgtta aatttttgtt aaatcagctc attttttaac caataggccg   1500
aaatcggcaa aatcccttat aaatcaaaag aatagaccga gatagggttg agtgttgttc   1560
cagtttggaa caagagtcca ctattaaaga acgtggactc caacgtcaaa gggcgaaaaa   1620
ccgtctatca gggcgatggc ccactacgtg aaccatcacc ctaatcaagt tttttggggt   1680
cgaggtgccg taaagcacta aatcggaacc ctaaagggag cccccgattt agagcttgac   1740
ggggaaagcc ggcgaacgtg gcgagaaagg aagggaagaa agcgaaagga gcgggcgcta   1800
gggcgctggc aagtgtagcg gtcacgctgc gcgtaaccac cacacccgcc gcgcttaatg   1860
cgccgctaca gggcgcgtcg cgccattcgc cattcaggct gcgcaactgt tgggaagggc   1920
gatcggtgcg ggcctcttcg ctattacgcc agctggcgaa aggggggatgt gctgcaaggc   1980
gattaagttg ggtaacgcca gggttttccc agtcacgacg ttgtaaaacg acggccagtg   2040
agcgcgcgta atacgactca ctatagggcg aattgggtac cgggcccccc ctcgaggtcg   2100
acggtatcga taagcttgat tagaagccgc cgagcgggcg acagccctcc gacggaagac   2160
tctcctccgt gcgtcctcgt cttcaccggt cgcgttcctg aaacgcagat gtgcctcgcg   2220
ccgcactgct ccgaacaata aagattctac aatactagct tttatggtta tgaagaggaa   2280
aaattggcag taacctggcc ccacaaacct tcaaattaac gaatcaaatt aacaaccata   2340
ggatgataat gcgattagtt ttttagcctt atttctgggg taattaatca gcgaagcgat   2400
gatttttgat ctattaacag atatataaat ggaaaagctg cataaccact ttaactaata   2460
ctttcaacat tttcagtttg tattacttct tattcaaatg tcataaaagt atcaacaaaa   2520
aattgttaat atacctctat actttaacgt caaggagaaa aatgtccaat ttactgcccg   2580
tacaccaaaa tttgcctgca ttaccggtcg atgcaacgag tgatgaggtt cgcaagaacc   2640
```

```
tgatggacat gttcagggat cgccaggcgt tttctgagca tacctggaaa atgcttctgt   2700
ccgtttgccg gtcgtgggcg gcatggtgca agttgaataa ccggaaatgg tttcccgcag   2760
aacctgaaga tgttcgcgat tatcttctat atcttcaggc gcgcggtctg gcagtaaaaa   2820
ctatccagca acatttgggc cagctaaaca tgcttcatcg tcggtccggg ctgccacgac   2880
caagtgacag caatgctgtt tcactggtta tgcggcggat ccgaaaagaa aacgttgatg   2940
ccggtgaacg tgcaaaacag gctctagcgt tcgaacgcac tgatttcgac caggttcgtt   3000
cactcatgga aaatagcgat cgctgccagg atatacgtaa tctggcattt ctggggattg   3060
cttataacac cctgttacgt atagccgaaa ttgccaggat cagggttaaa gatatctcac   3120
gtactgacgg tgggagaatg ttaatccata ttggcagaac gaaaacgctg gttagcaccg   3180
caggtgtaga gaaggcactt agcctggggg taactaaact ggtcgagcga tggatttccg   3240
tctctggtgt agctgatgat ccgaataact acctgttttg ccgggtcaga aaaaatggtg   3300
ttgccgcgcc atctgccacc agccagctat caactcgcgc cctggaaggg atttttgaag   3360
caactcatcg attgatttac ggcgctaagg atgactctgg tcagagatac ctggcctggt   3420
ctggacacag tgcccgtgtc ggagccgcgc gagatatggc ccgcgctgga gtttcaatac   3480
cggagatcat gcaagctggt ggctggacca atgtaaatat tgtcatgaac tatatccgta   3540
acctggatag tgaaacaggg gcaatggtgc gcctgctgga agatggcgat taggagtaag   3600
cgaatttctt atgatttatg atttttatta ttaaataagt tataaaaaaa ataagtgtat   3660
acaaatttta aagtgactct taggttttaa aacgaaaatt cttattcttg agtaactctt   3720
tcctgtaggt caggttgctt tctcaggtat agcatgaggt cgctcttatt gaccacacct   3780
ctaccggcat gccgagcaaa tgcctgcaaa tcgctcccca tttcacccaa ttgtagatat   3840
gctaactcca gcaatgagtt gatgaatctc ggtgtgtatt ttatgtcctc agaggacaac   3900
acctgtggtg ttctagagcg gccgccaccg cggtggagct ccagcttttg ttccctttag   3960
tgagggttaa ttgcgcgctt ggcgtaatca tggtcatagc tgtttcctgt gtgaaattgt   4020
tatccgctca caattccaca caacatagga gccggaagca taaagtgtaa agcctggggt   4080
gcctaatgag tgaggtaact cacattaatt gcgttgcgct cactgcccgc tttccagtcg   4140
ggaaacctgt cgtgccagct gcattaatga atcggccaac gcgcggggag aggcggtttg   4200
cgtattgggc gctcttccgc ttcctcgctc actgactcgc tgcgctcggt cgttcggctg   4260
cggcgagcgg tatcagctca ctcaaaggcg gtaatacggt tatccacaga atcaggggat   4320
aacgcaggaa agaacatgtg agcaaaaggc cagcaaaagg ccaggaaccg taaaaaggcc   4380
gcgttgctgg cgtttttcca taggctccgc ccccctgacg agcatcacaa aaatcgacgc   4440
tcaagtcaga ggtggcgaaa cccgacagga ctataaagat accaggcgtt tccccctgga   4500
agctccctcg tgcgctctcc tgttccgacc ctgccgctta ccggatacct gtccgccttt   4560
ctcccttcgg gaagcgtggc gctttctcat agctcacgct gtaggtatct cagttcggtg   4620
taggtcgttc gctccaagct gggctgtgtg cacgaacccc ccgttcagcc cgaccgctgc   4680
gccttatccg gtaactatcg tcttgagtcc aacccggtaa gacacgactt atcgccactg   4740
gcagcagcca ctggtaacag gattagcaga gcgaggtatg taggcggtgc tacagagttc   4800
ttgaagtggt ggcctaacta cggctacact agaaggacag tatttggtat ctgcgctctg   4860
ctgaagccag ttaccttcgg aaaaagagtt ggtagctctt gatccggcaa acaaaccacc   4920
gctggtagcg gtggtttttt tgtttgcaag cagcagatta cgcgcagaaa aaaaggatct   4980
```

```
caagaagatc ctttgatctt ttctacgggg tctgacgctc agtggaacga aaactcacgt   5040
taagggattt tggtcatgag attatcaaaa aggatcttca cctagatcct tttaaattaa   5100
aaatgaagtt ttaaatcaat ctaaagtata tatgagtaaa cttggtctga cagttaccaa   5160
tgcttaatca gtgaggcacc tatctcagcg atctgtctat ttcgttcatc catagttgcc   5220
tgactccccg tcgtgtagat aactacgata cgggagggct taccatctgg ccccagtgct   5280
gcaatgatac cgcgagaccc acgctcaccg gctccagatt tatcagcaat aaaccagcca   5340
gccggaaggg ccgagcgcag aagtggtcct gcaactttat ccgcctccat ccagtctatt   5400
aattgttgcc gggaagctag agtaagtagt tcgccagtta atagtttgcg caacgttgtt   5460
gccattgcta caggcatcgt ggtgtcacgc tcgtcgtttg gtatggcttc attcagctcc   5520
ggttcccaac gatcaaggcg agttacatga tcccccatgt tgtgcaaaaa agcggttagc   5580
tccttcggtc ctccgatcgt tgtcagaagt aagttggccg cagtgttatc actcatggtt   5640
atggcagcac tgcataattc tcttactgtc atgccatccg taagatgctt ttctgtgact   5700
ggtgagtact caaccaagtc attctgagaa tagtgtatgc ggcgaccgag ttgctcttgc   5760
ccggcgtcaa tacgggataa taccgcgcca catagcagaa ctttaaaagt gctcatcatt   5820
ggaaaacgtt cttcggggcg aaaactctca aggatcttac cgctgttgag atccagttcg   5880
atgtaaccca ctcgtgcacc caactgatct tcagcatctt ttactttcac cagcgtttct   5940
gggtgagcaa aaacaggaag gcaaaatgcc gcaaaaaagg gaataagggc gacacggaaa   6000
tgttgaatac tcatactctt cctttttcaa tattattgaa gcatttatca gggttattgt   6060
ctcatgagcg gatacatatt tgaatgtatt tagaaaaata aacaaatagg ggttccgcgc   6120
acatttcccc gaaaagtgcc acctgaacga agcatctgtg cttcattttg tagaacaaaa   6180
atgcaacgcg agagcgctaa tttttcaaac aaagaatctg agctgcattt ttacagaaca   6240
gaaatgcaac gcgaaagcgc tattttacca acgaagaatc tgtgcttcat ttttgtaaaa   6300
caaaaatgca acgcgagagc gctaattttt caaacaaaga atctgagctg catttttaca   6360
gaacagaaat gcaacgcgag agcgctattt taccaacaaa gaatctatac ttcttttttg   6420
ttctacaaaa atgcatcccg agagcgctat ttttctaaca aagcatctta gattactttt   6480
tttctccttt gtgcgctcta taatgcagtc tcttgataac tttttgcact gtaggtccgt   6540
taaggttaga agaaggctac tttggtgtct attttctctt ccataaaaaa agcctgactc   6600
cacttcccgc gtttactgat tactagcgaa gctgcgggtg catttttttca agataaaggc   6660
atccccgatt atattctata ccgatgtgga ttgcgcatac tttgtgaaca gaaagtgata   6720
gcgttgatga ttcttcattg gtcagaaaat tatgaacggt ttcttctatt ttgtctctat   6780
atactacgta taggaaatgt ttacattttc gtattgtttt cgattcactc tatgaatagt   6840
tcttactaca atttttttgt ctaaagagta atactagaga taaacataaa aaatgtagag   6900
gtcgagttta gatgcaagtt caaggagcga aaggtggatg ggtaggttat atagggatat   6960
agcacagaga tatatagcaa agagatactt ttgagcaatg tttgtggaag cggtattcgc   7020
aatattttag tagctcgtta cagtccggtg cgtttttggt tttttgaaag tgcgtcttca   7080
gagcgctttt ggttttcaaa agcgctctga agttcctata ctttctagag aataggaact   7140
tcggaatagg aacttcaaag cgtttccgaa aacgagcgct tccgaaaatg caacgcgagc   7200
tgcgcacata cagctcactg ttcacgtcgc acctatatct gcgtgttgcc tgtatatata   7260
tatacatgag aagaacggca tagtgcgtgt ttatgcttaa atgcgtactt atatgcgtct   7320
atttatgtag gatgaaaggt agtctagtac ctcctgtgat attatcccat tccatgcggg   7380
```

```
gtatcgtatg cttccttcag cactaccctt tagctgttct atatgctgcc actcctcaat   7440

tggattagtc tcatccttca atgctatcat ttcctttgat attggatcat ctaagaaacc   7500

attattatca tgacattaac ctataaaaat aggcgtatca cgaggccctt tcgtc        7555


<210> SEQ ID NO 12
<211> LENGTH: 12298
<212> TYPE: DNA
<213> ORGANISM: Artificial Sequence
<220> FEATURE:
<223> OTHER INFORMATION: pLH804::L2V4

<400> SEQUENCE: 12

tcccattacc gacatttggg cgctatacgt gcatatgttc atgtatgtat ctgtatttaa     60

aacacttttg tattattttt cctcatatat gtgtataggt ttatacggat gatttaatta    120

ttacttcacc accctttatt tcaggctgat atcttagcct tgttactaga ttaatcatgt    180

aattagttat gtcacgctta cattcacgcc ctccccccac atccgctcta accgaaaagg    240

aaggagttag acaacctgaa gtctaggtcc ctatttattt ttttatagtt atgttagtat    300

taagaacgtt atttatattt caaatttttc ttttttttct gtacagacgc gtgtacgcat    360

gtaacattat actgaaaacc ttgcttgaga aggttttggg acgctcgaag gctttaattt    420

gcgggcggcc gcacctggta aaacctctag tggagtagta gatgtaatca atgaagcgga    480

agccaaaaga ccagagtaga ggcctataga agaaactgcg ataccttttg tgatggctaa    540

acaaacagac atctttttat atgtttttac ttctgtatat cgtgaagtag taagtgataa    600

gcgaatttgg ctaagaacgt tgtaagtgaa caagggacct cttttgcctt tcaaaaaagg    660

attaaatgga gttaatcatt gagatttagt tttcgttaga ttctgtatcc ctaaataact    720

cccttacccg acgggaaggc acaaaagact tgaataatag caaacggcca gtagccaaga    780

ccaaataata ctagagttaa ctgatggtct taaacaggca ttacgtggtg aactccaaga    840

ccaatataca aaatatcgat aagttattct tgcccaccaa tttaaggagc ctacatcagg    900

acagtagtac cattcctcag agaagaggta tacataacaa gaaaatcgcg tgaacacctt    960

atataactta gcccgttatt gagctaaaaa accttgcaaa atttcctatg aataagaata   1020

cttcagacgt gataaaaatt tactttctaa ctcttctcac gctgccccta tctgttcttc   1080

cgctctaccg tgagaaataa agcatcgagt acggcagttc gctgtcactg aactaaaaca   1140

ataaggctag ttcgaatgat gaacttgctt gctgtcaaac ttctgagttg ccgctgatgt   1200

gacactgtga caataaattc aaaccggtta tagcggtctc ctccggtacc ggttctgcca   1260

cctccaatag agctcagtag gagtcagaac ctctgcggtg gctgtcagtg actcatccgc   1320

gtttcgtaag ttgtgcgcgt gcacatttcg cccgttcccg ctcatcttgc agcaggcgga   1380

aattttcatc acgctgtagg acgcaaaaaa aaaataatta atcgtacaag aatcttggaa   1440

aaaaaattga aaaattttgt ataaaaggga tgacctaact tgactcaatg gcttttacac   1500

ccagtatttt ccctttcctt gtttgttaca attatagaag caagacaaaa acatatagac   1560

aacctattcc taggagttat attttttttac cctaccagca atataagtaa aaaactgttt   1620

aaacagtatg gaagaatgta agatggctaa gatttactac caagaagact gtaacttgtc   1680

cttgttggat ggtaagacta tcgccgttat cggttacggt tctcaaggtc acgctcatgc   1740

cctgaatgct aaggaatccg gttgtaacgt tatcattggt ttatacgaag gtgcggagga   1800

gtggaaaaga gctgaagaac aaggtttcga agtctacacc gctgctgaag ctgctaagaa   1860
```

-continued

```
ggctgacatc attatgatct tgatcccaga tgaaaagcag gctaccatgt acaaaaacga   1920
catcgaacca aacttggaag ccggtaacat gttgatgttc gctcacggtt tcaacatcca   1980
tttcggttgt attgttccac caaaggacgt tgatgtcact atgatcgctc caaagggtcc   2040
aggtcacacc gttagatccg aatacgaaga aggtaaaggt gtcccatgct tggttgctgt   2100
cgaacaagac gctactggca aggctttgga tatggctttg gcctacgctt tagccatcgg   2160
tggtgctaga gccggtgtct tggaaactac cttcagaacc gaaactgaaa ccgacttgtt   2220
cggtgaacaa gctgttttat gtggtggtgt ctgcgctttg atgcaggccg gttttgaaac   2280
cttggttgaa gccggttacg acccaagaaa cgcttacttc gaatgtatcc acgaaatgaa   2340
gttgatcgtt gacttgatct accaatctgg tttctccggt atgcgttact ctatctccaa   2400
cactgctgaa tacggtgact acattaccgg tccaaagatc attactgaag ataccaagaa   2460
ggctatgaag aagattttgt ctgacattca agatggtacc tttgccaagg acttcttggt   2520
tgacatgtct gatgctggtt cccaggtcca cttcaaggct atgagaaagt tggcctccga   2580
acacccagct gaagttgtcg gtgaagaaat tagatccttg tactcctggt ccgacgaaga   2640
caagttgatt aacaactgag gccctgcagg ccagaggaaa ataatatcaa gtgctggaaa   2700
ctttttctct tggaattttt gcaacatcaa gtcatagtca attgaattga cccaatttca   2760
catttaagat ttttttttt tcatccgaca tacatctgta cactaggaag ccctgttttt   2820
ctgaagcagc ttcaaatata tatatttttt acatatttat tatgattcaa tgaacaatct   2880
aattaaatcg aaaacaagaa ccgaaacgcg aataaataat ttatttagat ggtgacaagt   2940
gtataagtcc tcatcgggac agctacgatt tctctttcgg ttttggctga gctactggtt   3000
gctgtgacgc agcggcatta gcgcggcgtt atgagctacc ctcgtggcct gaaagatggc   3060
gggaataaag cggaactaaa aattactgac tgagccatat tgaggtcaat ttgtcaactc   3120
gtcaagtcac gtttggtgga cggcccctt ccaacgaatc gtatatacta acatgcgcgc   3180
gcttcctata tacacatata catatatata tatatatata tgtgtgcgtg tatgtgtaca   3240
cctgtattta atttccttac tcgcgggttt ttctttttttc tcaattcttg gcttcctctt   3300
tctcgagcgg accggatcct cgcgaactcc aaaatgagct atcaaaaacg atagatcgat   3360
taggatgact ttgaaatgac tccgcagtgg actggccgtt aatttcaagc gtgagtaaaa   3420
tagtgcatga caaaagatga gctaggcttt tgtaaaaata tcttacgttg taaaatttta   3480
gaaatcatta tttccttcat atcattttgt cattgacctt cagaagaaaa gagccgacca   3540
ataaatataa taaataaata aaaataatat tccattattt ctaaacagat tcaatactca   3600
ttaaaaaact atatcaatta atttgaatta acttaattaa ttatttttg ccagtttctt   3660
caggcttcca aaagtctgtt acggctcccc tagaagcaga cgaaacgatg tgagcatatt   3720
taccaaggat accgcgtgaa tagagcggtg gcaattcaat ggtctcttga cgatgtttta   3780
actcttcatc ggagatatca aagtgtaatt ccttagtgtc ttggtcaata gtgactatgt   3840
ctcctgtttg caggtaggcg attggaccgc catcttgtgc ttcaggagcg atatgaccca   3900
cgacaagacc ataagtacca cctgagaagc ggccatctgt cagaagggca actttttcac   3960
cttgcccttt accaacaatc attgatgaaa gggaaagcat ttcaggcata ccaggaccgc   4020
cctttggtcc tacaaaacgt acgacaacaa catcaccatc aacaatatca tcattcaaga   4080
cagcttcaat ggcttcttct tcagaattaa agaccttagc aggaccgaca tgacgacgca   4140
cttttacacc agaaactttg gcaacggcac cgtctggagc caagttacca tggagaataa   4200
tgaccggacc atcttcacgt ttaggatttt caagcggcat aataaccttt tgaccaggtg   4260
```

```
ttaaatcatc aaaagccttc aaattttcag cgactgtttt gccagtacaa gtgatacggt   4320

caccatgaag gaagccattt ttaaggagat atttcataac tgctggtacc cctccgacct   4380

tgtaaaggtc ttggaataca tattgaccag aaggtttcaa atcagccaaa tgaggaactt   4440

tttcttggaa agtattgaaa tcatcaagtg tcaattccac attagcagca tgggcaatag   4500

ctaagaggtg aagggttgag ttggttgaac ctcccagagc catagttaca gtaatagcat   4560

cttcaaaagc ttcacgcgtt aaaatgtcag aaggttttaa gcccatttcg agcattttga   4620

caacagcgcg accagcttct tcaatatctg ctttcttttc tgcggattca gccgggtgag   4680

aagatgaacc cggaaggcta agtcccaaaa cttcaatagc tgtcgccatt gtgttagcag   4740

tatacatacc accgcagcct ccaggaccgg gacaagcatt acattccaaa gctttaactt   4800

cttctttggt catatcgccg tggttccaat ggccgacacc ttcaaagaca gagactaaat   4860

cgatatcttt gccgtctaaa ttaccaggtg caattgttcc gccgtaagca aaaatggctg   4920

ggatatccat gttagccata gcgataacag aaccgggcat gtttttatca caaccgccaa   4980

tggctacaaa agcatccgca ttatgacctc ccatggctgc ttcaatagaa tctgcaataa   5040

tatcacgaga tgtcaaggag aaacgcattc cttgggttcc catggcgatt ccatcagaaa   5100

ccgtgattgt tccgaactga actggccaag caccagcttc cttaacaccg actttggcta   5160

gtttaccaaa gtcatgtaag tggatattac aaggtgtgtt ttcagcccaa gttgaaatga   5220

caccgacgat aggtttttca aagtcttcat cttgcatacc agttgcacgc aacatagcac   5280

gattaggtga tttaaccatt gaatcgtaaa cagaactacg atttcttaag tctttaagag   5340

ttttttgtc agtcatactc acgtgaaact tagattagat tgctatgctt tctttccaat   5400

gagcaagaag taaaaaaagt tgtaatagaa caggaaaaat gaagctgaaa cttgagaaat   5460

tgaagaccgt ttgttaactc aaatatcaat gggaggtcgt cgaaagagaa caaaatcgaa   5520

aaaaaagttt tcaagagaaa gaaacgtgat aaaaattttt attgccttct ccgacgaaga   5580

aaaagggacg aggcggtctc tttttccttt tccaaacctt tagtacgggt aattaacggc   5640

accctagagg aaggaggagg gggaatttag tatgctgtgc ttgggtgttt tgaagtggta   5700

cggcggtgcg cggagtccga gaaaatctgg aagagtaaaa aaggagtaga gacattttga   5760

agctatgccg gcagatctat ttaaatggcg cgccgacgtc aggtggcact tttcggggaa   5820

atgtgcgcgg aacccctatt tgtttatttt tctaaataca ttcaaatatg tatccgctca   5880

tgagacaata accctgataa atgcttcaat aatattgaaa aaggaagagt atgagtattc   5940

aacatttccg tgtcgccctt attccctttt ttgcggcatt ttgccttcct gtttttgctc   6000

acccagaaac gctggtgaaa gtaaaagatg ctgaagatca gttgggtgca cgagtgggtt   6060

acatcgaact ggatctcaac agcggtaaga tccttgagag ttttcgcccc gaagaacgtt   6120

ttccaatgat gagcactttt aaagttctgc tatgtggcgc ggtattatcc cgtattgacg   6180

ccgggcaaga gcaactcggt cgccgcatac actattctca gaatgacttg gttgagtact   6240

caccagtcac agaaaagcat cttacggatg gcatgacagt aagagaatta tgcagtgctg   6300

ccataaccat gagtgataac actgcggcca acttacttct gacaacgatc ggaggaccga   6360

aggagctaac cgcttttttg cacaacatgg gggatcatgt aactcgcctt gatcgttggg   6420

aaccggagct gaatgaagcc ataccaaacg acgagcgtga caccacgatg cctgtagcaa   6480

tggcaacaac gttgcgcaaa ctattaactg gcgaactact tactctagct tcccggcaac   6540

aattaataga ctggatggag gcggataaag ttgcaggacc acttctgcgc tcggcccttc   6600
```

```
cggctggctg gtttattgct gataaatctg gagccggtga gcgtgggtct cgcggtatca   6660
ttgcagcact ggggccagat ggtaagccct cccgtatcgt agttatctac acgacgggga   6720
gtcaggcaac tatggatgaa cgaaatagac agatcgctga gataggtgcc tcactgatta   6780
agcattggta actgtcagac caagtttact catatatact ttagattgat ttaaaacttc   6840
atttttaatt taaaaggatc taggtgaaga tcctttttga taatctcatg accaaaatcc   6900
cttaacgtga gttttcgttc cactgagcgt cagaccccgt agaaaagatc aaaggatctt   6960
cttgagatcc tttttttctg cgcgtaatct gctgcttgca aacaaaaaaa ccaccgctac   7020
cagcggtggt ttgtttgccg gatcaagagc taccaactct ttttccgaag gtaactggct   7080
tcagcagagc gcagatacca aatactgttc ttctagtgta gccgtagtta ggccaccact   7140
tcaagaactc tgtagcaccg cctacatacc tcgctctgct aatcctgtta ccagtggctg   7200
ctgccagtgg cgataagtcg tgtcttaccg ggttggactc aagacgatag ttaccggata   7260
aggcgcagcg gtcgggctga acggggggtt cgtgcacaca gcccagcttg gagcgaacga   7320
cctacaccga actgagatac ctacagcgtg agctatgaga aagcgccacg cttcccgaag   7380
ggagaaaggc ggacaggtat ccggtaagcg gcagggtcgg aacaggagag cgcacgaggg   7440
agcttccagg gggaaacgcc tggtatcttt atagtcctgt cgggtttcgc cacctctgac   7500
ttgagcgtcg atttttgtga tgctcgtcag gggggcggag cctatggaaa aacgccagca   7560
acgcggcctt tttacggttc ctggcctttt gctggccttt tgctcacatg ttctttcctg   7620
cgttatcccc tgattctgtg gataaccgta ttaccgcctt tgagtgagct gataccgctc   7680
gccgcagccg aacgaccgag cgcagcgagt cagtgagcga ggaagcggaa gagcgcccaa   7740
tacgcaaacc gcctctcccc gcgcgttggc cgattcatta atgcagctgg cacgacaggt   7800
ttcccgactg gaaagcgggc agtgagcgca acgcaattaa tgtgagttag ctcactcatt   7860
aggcacccca ggctttacac tttatgcttc cggctcgtat gttgtgtgga attgtgagcg   7920
gataacaatt tcacacagga aacagctatg accatgatta cgccaagctt tttctttcca   7980
attttttttt tttcgtcatt ataaaaatca ttacgaccga gattcccggg taataactga   8040
tataattaaa ttgaagctct aatttgtgag tttagtatac atgcatttac ttataataca   8100
gtttttttagt tttgctggcc gcatcttctc aaatatgctt cccagcctgc ttttctgtaa   8160
cgttcaccct ctaccttagc atcccttccc tttgcaaata gtcctcttcc aacaataata   8220
atgtcagatc ctgtagagac cacatcatcc acggttctat actgttgacc caatgcgtct   8280
cccttgtcat ctaaacccac accgggtgtc ataatcaacc aatcgtaacc ttcatctctt   8340
ccacccatgt ctctttgagc aataaagccg ataacaaaat ctttgtcgct cttcgcaatg   8400
tcaacagtac ccttagtata ttctccagta gatagggagc ccttgcatga caattctgct   8460
aacatcaaaa ggcctctagg ttcctttgtt acttcttctg ccgcctgctt caaaccgcta   8520
acaatacctg ggcccaccac accgtgtgca ttcgtaatgt ctgcccattc tgctattctg   8580
tatacacccg cagagtactg caatttgact gtattaccaa tgtcagcaaa ttttctgtct   8640
tcgaagagta aaaaattgta cttggcggat aatgccttta gcggcttaac tgtgccctcc   8700
atggaaaaat cagtcaagat atccacatgt gtttttagta aacaaatttt gggacctaat   8760
gcttcaacta actccagtaa ttccttggtg gtacgaacat ccaatgaagc acacaagttt   8820
gtttgctttt cgtgcatgat attaaatagc ttggcagcaa caggactagg atgagtagca   8880
gcacgttcct tatatgtagc tttcgacatg atttatcttc gtttcctgca ggtttttgtt   8940
ctgtgcagtt gggttaagaa tactgggcaa tttcatgttt cttcaacact acatatgcgt   9000
```

```
atatatacca atctaagtct gtgctccttc cttcgttctt ccttctgttc ggagattacc   9060
gaatcaaaaa aatttcaagg aaaccgaaat caaaaaaaag aataaaaaaa aaatgatgaa   9120
ttgaaaagct tgcatgcctg caggtcgact ctagtatact ccgtctactg tacgatacac   9180
ttccgctcag gtccttgtcc tttaacgagg ccttaccact cttttgttac tctattgatc   9240
cagctcagca aaggcagtgt gatctaagat tctatcttcg cgatgtagta aaactagcta   9300
gaccgagaaa gagactagaa atgcaaaagg cacttctaca atggctgcca tcattattat   9360
ccgatgtgac gctgcatttt tttttttttt tttttttttt tttttttttt tttttttttt   9420
tttttttgt acaaatatca taaaaaaaga gaatcttttt aagcaaggat tttcttaact   9480
tcttcggcga cagcatcacc gacttcggtg gtactgttgg aaccacctaa atcaccagtt   9540
ctgatacctg catccaaaac ctttttaact gcatcttcaa tggctttacc ttcttcaggc   9600
aagttcaatg acaatttcaa catcattgca gcagacaaga tagtggcgat agggttgacc   9660
ttattctttg gcaaatctgg agcggaacca tggcatggtt cgtacaaacc aaatgcggtg   9720
ttcttgtctg gcaaagaggc caaggacgca gatggcaaca aacccaagga gcctgggata   9780
acggaggctt catcggagat gatatcacca aacatgttgc tggtgattat aataccattt   9840
aggtgggttg ggttcttaac taggatcatg gcggcagaat caatcaattg atgttgaact   9900
ttcaatgtag ggaattcgtt cttgatggtt tcctccacag tttttctcca taatcttgaa   9960
gaggccaaaa cattagcttt atccaaggac caaataggca atggtggctc atgttgtagg  10020
gccatgaaag cggccattct tgtgattctt tgcacttctg gaacggtgta ttgttcacta  10080
tcccaagcga caccatcacc atcgtcttcc tttctcttac caaagtaaat acctcccact  10140
aattctctaa caacaacgaa gtcagtacct ttagcaaatt gtggcttgat tggagataag  10200
tctaaaagag agtcggatgc aaagttacat ggtcttaagt tggcgtacaa ttgaagttct  10260
ttacggattt ttagtaaacc ttgttcaggt ctaacactac cggtacccca tttaggacca  10320
cccacagcac ctaacaaaac ggcatcagcc ttcttggagg cttccagcgc ctcatctgga  10380
agtggaacac ctgtagcatc gatagcagca ccaccaatta aatgattttc gaaatcgaac  10440
ttgacattgg aacgaacatc agaaatagct ttaagaacct taatggcttc ggctgtgatt  10500
tcttgaccaa cgtggtcacc tggcaaaacg acgatcttct taggggcaga cattacaatg  10560
gtatatcctt gaaatatata taaaaaaaaa aaaaaaaaaa aaaaaaaaaa atgcagcttc  10620
tcaatgatat tcgaatacgc tttgaggaga tacagcctaa tatccgacaa actgttttac  10680
agatttacga tcgtacttgt tacccatcat tgaattttga acatccgaac ctgggagttt  10740
tccctgaaac agatagtata tttgaacctg tataataata tatagtctag cgctttacgg  10800
aagacaatgt atgtatttcg gttcctggag aaactattgc atctattgca taggtaatct  10860
tgcacgtcgc atccccggtt cattttctgc gtttccatct tgcacttcaa tagcatatct  10920
ttgttaacga agcatctgtg cttcattttg tagaacaaaa atgcaacgcg agagcgctaa  10980
tttttcaaac aaagaatctg agctgcattt ttacagaaca gaaatgcaac gcgaaagcgc  11040
tattttacca acgaagaatc tgtgcttcat ttttgtaaaa caaaaatgca acgcgagagc  11100
gctaattttt caaacaaaga atctgagctg catttttaca gaacagaaat gcaacgcgag  11160
agcgctattt taccaacaaa gaatctatac ttcttttttg ttctacaaaa atgcatcccg  11220
agagcgctat ttttctaaca aagcatctta gattactttt tttctccttt gtgcgctcta  11280
taatgcagtc tcttgataac tttttgcact gtaggtccgt taaggttaga agaaggctac  11340
```

```
tttggtgtct attttctctt ccataaaaaa agcctgactc cacttcccgc gtttactgat  11400
tactagcgaa gctgcgggtg catttttttca agataaaggc atccccgatt atattctata  11460
ccgatgtgga ttgcgcatac tttgtgaaca gaaagtgata gcgttgatga ttcttcattg  11520
gtcagaaaat tatgaacggt ttcttctatt ttgtctctat atactacgta taggaaatgt  11580
ttacattttc gtattgtttt cgattcactc tatgaatagt tcttactaca atttttttgt  11640
ctaaagagta atactagaga taaacataaa aaatgtagag gtcgagttta gatgcaagtt  11700
caaggagcga aaggtggatg ggtaggttat atagggatat agcacagaga tatatagcaa  11760
agagatactt ttgagcaatg tttgtggaag cggtattcgc aatattttag tagctcgtta  11820
cagtccggtg cgtttttggt tttttgaaag tgcgtcttca gagcgctttt ggttttcaaa  11880
agcgctctga agttcctata ctttctagag aataggaact tcggaatagg aacttcaaag  11940
cgtttccgaa aacgagcgct tccgaaaatg caacgcgagc tgcgcacata cagctcactg  12000
ttcacgtcgc acctatatct gcgtgttgcc tgtatatata tatacatgag aagaacggca  12060
tagtgcgtgt ttatgcttaa atgcgtactt atatgcgtct atttatgtag gatgaaaggt  12120
agtctagtac ctcctgtgat attatcccat tccatgcggg gtatcgtatg cttccttcag  12180
cactaccctt tagctgttct atatgctgcc actcctcaat tggattagtc tcatccttca  12240
atgctatcat ttcctttgat attggatcat atgcatagta ccgagaaact agaggatc    12298
```

<210> SEQ ID NO 13
<211> LENGTH: 11013
<212> TYPE: DNA
<213> ORGANISM: Artificial Sequence
<220> FEATURE:
<223> OTHER INFORMATION: pRS413::BiADH-KivD Lg(y)

<400> SEQUENCE: 13

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgcgtg    120
ttggcgggtg tcggggctgg cttaactatg cggcatcaga gcagattgta ctgagagtgc    180
accataaatt cccgttttaa gagcttggtg agcgctagga gtcactgcca ggtatcgttt    240
gaacacggca ttagtcaggg aagtcataac acagtccttt cccgcaattt tctttttcta    300
ttactcttgg cctcctctag tacactctat attttttttat gcctcggtaa tgattttcat    360
tttttttttt cccctagcgg atgactcttt ttttttctta gcgattggca ttatcacata    420
atgaattata cattatataa agtaatgtga tttcttcgaa gaatatacta aaaaatgagc    480
aggcaagata aacgaaggca aagatgacag agcagaaagc cctagtaaag cgtattacaa    540
atgaaaccaa gattcagatt gcgatctctt taaagggtgg tcccctagcg atagagcact    600
cgatcttccc agaaaaagag gcagaagcag tagcagaaca ggccacacaa tcgcaagtga    660
ttaacgtcca cacaggtata gggtttctgg accatatgat acatgctctg gccaagcatt    720
ccggctggtc gctaatcgtt gagtgcattg gtgacttaca catagacgac catcacacca    780
ctgaagactg cgggattgct ctcggtcaag cttttaaaga ggccctactg gcgcgtggag    840
taaaaaggtt tggatcagga tttgcgcctt tggatgaggc actttccaga gcggtggtag    900
atctttcgaa caggccgtac gcagttgtcg aacttggttt gcaaagggag aaagtaggag    960
atctctcttg cgagatgatc ccgcattttc ttgaaagctt tgcagaggct agcagaatta   1020
ccctccacgt tgattgtctg cgaggcaaga atgatcatca ccgtagtgag agtgcgttca   1080
aggctcttgc ggttgccata agagaagcca cctcgcccaa tggtaccaac gatgttccct   1140
```

```
ccaccaaagg tgttcttatg tagtgacacc gattatttaa agctgcagca tacgatatat   1200
atacatgtgt atatatgtat acctatgaat gtcagtaagt atgtatacga acagtatgat   1260
actgaagatg acaaggtaat gcatcattct atacgtgtca ttctgaacga ggcgcgcttt   1320
ccttttttct ttttgctttt tcttttttt tctcttgaac tcgacggatc tatgcggtgt    1380
gaaataccgc acagatgcgt aaggagaaaa taccgcatca ggaaattgta aacgttaata   1440
ttttgttaaa attcgcgtta aatttttgtt aaatcagctc attttttaac caataggccg   1500
aaatcggcaa aatcccttat aaatcaaaag aatagaccga gatagggttg agtgttgttc   1560
cagtttggaa caagagtcca ctattaaaga acgtggactc caacgtcaaa gggcgaaaaa   1620
ccgtctatca gggcgatggc ccactacgtg aaccatcacc ctaatcaagt tttttggggt   1680
cgaggtgccg taaagcacta aatcggaacc ctaaagggag cccccgattt agagcttgac   1740
ggggaaagcc ggcgaacgtg gcgagaaagg aagggaagaa agcgaaagga gcgggcgcta   1800
gggcgctggc aagtgtagcg gtcacgctgc gcgtaaccac cacacccgcc gcgcttaatg   1860
cgccgctaca gggcgcgtcg cgccattcgc cattcaggct gcgcaactgt tgggaagggc   1920
gatcggtgcg ggcctcttcg ctattacgcc agctggcgaa aggggggatgt gctgcaaggc  1980
gattaagttg ggtaacgcca gggttttccc agtcacgacg ttgtaaaacg acggccagtg   2040
agcgcgcgta atacgactca ctatagggcg aattgggtac cgggcccccc ctgtacgcat   2100
gtaacattat actgaaaacc ttgcttgaga aggttttggg acgctcgaag gctttaattt   2160
cctgcaggaa ttaccgtcgc tcgtgatttg tttgcaaaaa gaacaaaact gaaaaaaccc   2220
agacacgctc gacttcctgt cttcctattg attgcagctt ccaatttcgt cacacaacaa   2280
ggtcctgtcg acgcctactt ggcttcacat acgttgcata cgtcgatata gataataatg   2340
ataatgacag caggattatc gtaatacgta atagttgaaa atctcaaaaa tgtgtgggtc   2400
attacgtaaa taatgatagg aatgggattc ttctattttt cctttttcca ttctagcagc   2460
cgtcgggaaa acgtggcatc ctctctttcg ggctcaattg gagtcacgct gccgtgagca   2520
tcctctcttt ccatatctaa caactgagca cgtaaccaat ggaaaagcat gagcttagcg   2580
ttgctccaaa aaagtattgg atggttaata ccatttgtct gttctcttct gactttgact   2640
cctcaaaaaa aaaaaatcta caatcaacag atcgcttcaa ttacgccctc acaaaaactt   2700
ttttccttct tcttcgccca cgttaaattt tatccctcat gttgtctaac ggatttctgc   2760
acttgattta ttataaaaag acaaagacat aatacttctc tatcaatttc agttattgtt   2820
cttccttgcg ttattcttct gttcttcttt ttcttttgtc atatataacc ataaccaagt   2880
aatacatatt caagtttaaa catgtatacc gtaggacagt acttggtaga tagactagaa   2940
gagattggta tcgataaggt tttcggtgtg ccaggggatt acaatttgac ttttctagat   3000
tacattcaaa atcacgaagg actttcctgg caagggaata ctaatgaact aaacgcagca   3060
tatgcagcag atggctacgc ccgtgaaaga ggcgtatcag ctcttgttac tacattcgga   3120
gtgggtgaac tgtcagccat taacggaaca gctggtagtt ttgcagaaca agtccctgtc   3180
atccacatcg tgggttctcc aactatgaat gtgcaatcca acaaaaagct ggttcatcat   3240
tccttaggaa tgggtaactt tcataacttt agtgaaatgg ctaaggaagt cactgccgct   3300
acaaccatgc ttactgaaga gaatgcagct tcagagatcg acagagtatt agaaacagcc   3360
ttgttggaaa agaggccagt atacatcaat cttccaattg atatagctca taaagcaata   3420
gttaaacctg caaaagcact acaaacagag aaatcatctg gtgagagaga ggcacaactt   3480
```

```
gcagaaatca tactatcaca cttagaaaag gccgctcaac ctatcgtaat cgccggtcat   3540
gagatcgccc gtttccagat aagagaaaga tttgaaaact ggataaacca aacaaagttg   3600
ccagtaacca atttggcata tggcaaaggc tctttcaatg aagagaacga acatttcatt   3660
ggtacctatt acccagcttt ttctgacaaa aacgttctgg attacgttga caatagtgac   3720
ttcgttttac attttggtgg gaaaatcatt gacaattcta cctcctcatt ttctcaaggc   3780
tttaagactg aaaacacttt aaccgctgca aatgacatca ttatgctgcc agatgggtct   3840
acttactctg ggatttctct taacggtctt ttggcagagc tggaaaaact aaactttact   3900
tttgctgata ctgctgctaa acaagctgaa ttagctgttt tcgaaccaca ggccgaaaca   3960
ccactaaagc aagacagatt tcaccaagct gttatgaact tttgcaagc tgatgatgtg    4020
ttggtcactg agcaggggac atcatctttc ggtttgatgt tggcacctct gaaaaagggt   4080
atgaatttga tcagtcaaac attatggggc tccataggat acacattacc tgctatgatt   4140
ggttcacaaa ttgctgcccc agaaaggaga cacattctat ccatcggtga tggatctttt   4200
caactgacag cacaggaaat gtccaccatc ttcagagaga aattgacacc agtgatattc   4260
attatcaata acgatggcta tacagtcgaa agagccatcc atggagagga tgagagttac   4320
aatgatatac caacttggaa cttgcaatta gttgctgaaa catttggtgg tgatgccgaa   4380
actgtcgaca ctcacaacgt tttcacagaa acagacttcg ctaatacttt agctgctatc   4440
gatgctactc ctcaaaaagc acatgtcgtt gaagttcata tggaacaaat ggatatgcca   4500
gaatcattga gacagattgg cttagcctta tctaagcaaa actcttaacc tgcagggccg   4560
tgaatttact ttaaatcttg catttaaata aattttcttt ttatagcttt atgacttagt   4620
ttcaatttat atactatttt aatgacattt tcgattcatt gattgaaagc tttgtgtttt   4680
ttcttgatgc gctattgcat tgttcttgtc tttttcgcca catgtaatat ctgtagtaga   4740
tacctgatac attgtggatg ctgagtgaaa ttttagttaa taatggaggc gctcttaata   4800
attttgggga tattggcttt ttttttaaa gtttacaaat gaatttttc cgccaggata    4860
acgattctga agttactctt agcgttccta tcggtacagc catcaaatca tgcctataaa   4920
tcatgcctat atttgcgtgc agtcagtatc atctacatga aaaaaactcc cgcaatttct   4980
tatagaatac gttgaaaatt aaatgtacgc gccaagataa gataacatat atctagatgc   5040
agtaatatac acagattccc gcggacgtgg gaaggaaaaa attagataac aaaatctgag   5100
tgatatggaa attccgctgt atagctcata tctttcccta cctggtaaaa cctctagtgg   5160
agtagtagat gtaatcaatg aagcggaagc caaaagacca gagtagaggc ctatagaaga   5220
aactgcgata ccttttgtga tggctaaaca aacagacatc tttttatatg tttttacttc   5280
tgtatatcgt gaagtagtaa gtgataagcg aatttggcta agaacgttgt aagtgaacaa   5340
gggacctctt ttgcctttca aaaaaggatt aaatggagtt aatcattgag atttagtttt   5400
cgttagattc tgtatcccta aataactccc ttacccgacg ggaaggcaca aaagacttga   5460
ataatagcaa acggccagta gccaagacca aataatacta gagttaactg atggtcttaa   5520
acaggcatta cgtggtgaac tccaagacca atatacaaaa tatcgataag ttattcttgc   5580
ccaccaattt aaggagccta catcaggaca gtagtaccat tcctcagaga agaggtatac   5640
ataacaagaa aatcgcgtga acaccttata taacttagcc cgttattgag ctaaaaaacc   5700
ttgcaaaatt tcctatgaat aagaatactt cagacgtgat aaaaatttac tttctaactc   5760
ttctcacgct gcccctatct gttcttccgc tctaccgtga gaaataaagc atcgagtacg   5820
gcagttcgct gtcactgaac taaaacaata aggctagttc gaatgatgaa cttgcttgct   5880
```

```
gtcaaacttc tgagttgccg ctgatgtgac actgtgacaa taaattcaaa ccggttatag   5940
cggtctcctc cggtaccggt tctgccacct ccaatagagc tcccgcacgc cgaaatgcat   6000
gcaagtaacc tattcaaagt aatatctcat acatgtttca tgagggtaac aacatgcgac   6060
tgggtgagca tatgttccgc tgatgtgatg tgcaagataa acaagcaagg cagaaactaa   6120
cttcttcttc atgtaataaa cacaccccgc gtttatttac ctatctctaa acttcaacac   6180
cttatatcat aactaatatt tcttgagata agcacactgc acccatacct tccttaaaaa   6240
cgtagcttcc agtttttggt ggttccggct tccttcccga ttccgcccgc taaacgcata   6300
tttttgttgc ctggtggcat ttgcaaaatg cataacctat gcatttaaaa gattatgtat   6360
gctcttctga cttttcgtgt gatgaggctc gtggaaaaaa tgaataattt atgaatttga   6420
gaacaatttt gtgttgttac ggtattttac tatggaataa tcaatcaatt gaggatttta   6480
tgcaaatatc gtttgaatat ttttccgacc ctttgagtac ttttcttcat aattgcataa   6540
tattgtccgc tgcccctttt tctgttagac ggtgtcttga tctacttgct atcgttcaac   6600
accaccttat tttctaacta ttttttttt agctcatttg aatcagctta tggtgatggc   6660
acatttttgc ataaacctag ctgtcctcgt tgaacatagg aaaaaaaaat atataaacaa   6720
ggctctttca ctctccttgc aatcagattt gggtttgttc cctttatttt catatttctt   6780
gtcatattcc tttctcaatt attattttct actcataacc tcacgcaaaa taacacagtc   6840
aaatcaatca aaatgaaagc attagtgtat aggggcccag gccagaagtt ggtggaagag   6900
agacagaagc cagagcttaa ggaacctggt gacgctatag tgaaggtaac aaagactaca   6960
atttgcggaa ccgatctaca cattcttaaa ggtgacgttg cgacttgtaa acccggtcgt   7020
gtattagggc atgaaggagt gggggttatt gaatcagtcg gatctggggt tactgctttc   7080
caaccaggcg atagagtttt gatatcatgt atatcgagtt gcggaaagtg ctcattttgt   7140
agaagaggaa tgttcagtca ctgtacgacc gggggttgga ttctgggcaa cgaaattgat   7200
ggtacccaag cagagtacgt aagagtacca catgctgaca catcccttta tcgtattccg   7260
gcaggtgcgg atgaagaggc cttagtcatg ttatcagata ttctaccaac gggttttgag   7320
tgcggagtcc taaacggcaa agtcgcacct ggttcttcgg tggctatagt aggtgctggt   7380
cccgttggtt tggccgcctt actgacagca caattctact ccccagctga aatcataatg   7440
atcgatcttg atgataacag gctgggatta gccaaacaat ttggtgccac cagaacagta   7500
aactccacgg gtggtaacgc cgcagccgaa gtgaaagctc ttactgaagg cttaggtgtt   7560
gatactgcga ttgaagcagt tgggatacct gctacatttg aattgtgtca gaatatcgta   7620
gctcccggtg gaactatcgc taatgtcggc gttcacggta gcaaagttga tttgcatctt   7680
gaaagtttat ggtcccataa tgtcacgatt actacaaggt tggttgacac ggctaccacc   7740
ccgatgttac tgaaaactgt tcaaagtcac aagctagatc catctagatt gataacacat   7800
agattcagcc tggaccagat cttggacgca tatgaaactt ttggccaagc tgcgtctact   7860
caagcactaa aagtcatcat ttcgatggag gcttgattaa ttaagagtaa gcgaatttct   7920
tatgatttat gatttttatt attaaataag ttataaaaaa aataagtgta tacaaatttt   7980
aaagtgactc ttaggtttta aaacgaaaat tcttattctt gagtaactct ttcctgtagg   8040
tcaggttgct ttctcaggta tagcatgagg tcgctcttat tgaccacacc tctaccggca   8100
tgccgagcaa atgcctgcaa atcgctcccc atttcaccca attgtagata tgctaactcc   8160
agcaatgagt tgatgaatct cggtgtgtat tttatgtcct cagaggacaa cacctgtggt   8220
```

```
gagctccagc ttttgttccc tttagtgagg gttaattgcg cgcttggcgt aatcatggtc   8280
atagctgttt cctgtgtgaa attgttatcc gctcacaatt ccacacaaca taggagccgg   8340
aagcataaag tgtaaagcct ggggtgccta atgagtgagg taactcacat taattgcgtt   8400
gcgctcactg cccgctttcc agtcgggaaa cctgtcgtgc cagctgcatt aatgaatcgg   8460
ccaacgcgcg gggagaggcg gtttgcgtat tgggcgctct tccgcttcct cgctcactga   8520
ctcgctgcgc tcggtcgttc ggctgcggcg agcggtatca gctcactcaa aggcggtaat   8580
acggttatcc acagaatcag gggataacgc aggaaagaac atgtgagcaa aaggccagca   8640
aaaggccagg aaccgtaaaa aggccgcgtt gctggcgttt ttccataggc tccgcccccc   8700
tgacgagcat cacaaaaatc gacgctcaag tcagaggtgg cgaaacccga caggactata   8760
aagataccag gcgtttcccc ctggaagctc cctcgtgcgc tctcctgttc cgaccctgcc   8820
gcttaccgga tacctgtccg cctttctccc ttcgggaagc gtggcgcttt ctcatagctc   8880
acgctgtagg tatctcagtt cggtgtaggt cgttcgctcc aagctgggct gtgtgcacga   8940
accccccgtt cagcccgacc gctgcgcctt atccggtaac tatcgtcttg agtccaaccc   9000
ggtaagacac gacttatcgc cactggcagc agccactggt aacaggatta gcagagcgag   9060
gtatgtaggc ggtgctacag agttcttgaa gtggtggcct aactacggct acactagaag   9120
gacagtattt ggtatctgcg ctctgctgaa gccagttacc ttcggaaaaa gagttggtag   9180
ctcttgatcc ggcaaacaaa ccaccgctgg tagcggtggt ttttttgttt gcaagcagca   9240
gattacgcgc agaaaaaaag gatctcaaga agatcctttg atcttttcta cggggtctga   9300
cgctcagtgg aacgaaaact cacgttaagg gattttggtc atgagattat caaaaaggat   9360
cttcacctag atccttttaa attaaaaatg aagttttaaa tcaatctaaa gtatatatga   9420
gtaaacttgg tctgacagtt accaatgctt aatcagtgag gcacctatct cagcgatctg   9480
tctatttcgt tcatccatag ttgcctgact ccccgtcgtg tagataacta cgatacggga   9540
gggcttacca tctggcccca gtgctgcaat gataccgcga gacccacgct caccggctcc   9600
agatttatca gcaataaacc agccagccgg aagggccgag cgcagaagtg gtcctgcaac   9660
tttatccgcc tccatccagt ctattaattg ttgccgggaa gctagagtaa gtagttcgcc   9720
agttaatagt ttgcgcaacg ttgttgccat tgctacaggc atcgtggtgt cacgctcgtc   9780
gtttggtatg gcttcattca gctccggttc ccaacgatca aggcgagtta catgatcccc   9840
catgttgtgc aaaaaagcgg ttagctcctt cggtcctccg atcgttgtca gaagtaagtt   9900
ggccgcagtg ttatcactca tggttatggc agcactgcat aattctctta ctgtcatgcc   9960
atccgtaaga tgcttttctg tgactggtga gtactcaacc aagtcattct gagaatagtg  10020
tatgcggcga ccgagttgct cttgcccggc gtcaatacgg gataataccg cgccacatag  10080
cagaacttta aaagtgctca tcattggaaa acgttcttcg gggcgaaaac tctcaaggat  10140
cttaccgctg ttgagatcca gttcgatgta acccactcgt gcacccaact gatcttcagc  10200
atcttttact ttcaccagcg tttctgggtg agcaaaaaca ggaaggcaaa atgccgcaaa  10260
aaagggaata agggcgacac ggaaatgttg aatactcata ctcttccttt ttcaatatta  10320
ttgaagcatt tatcagggtt attgtctcat gagcggatac atatttgaat gtatttagaa  10380
aaataaacaa ataggggttc cgcgcacatt tccccgaaaa gtgccacctg ggtccttttc  10440
atcacgtgct ataaaaataa ttataattta aattttttaa tataaatata taaattaaaa  10500
atagaaagta aaaaaagaaa ttaaagaaaa aatagttttt gttttccgaa gatgtaaaag  10560
actctagggg gatcgccaac aaatactacc ttttatcttg ctcttcctgc tctcaggtat  10620
```

taatgccgaa ttgtttcatc ttgtctgtgt agaagaccac acacgaaaat cctgtgattt 10680
tacattttac ttatcgttaa tcgaatgtat atctatttaa tctgcttttc ttgtctaata 10740
aatatatatg taaagtacgc tttttgttga aattttttaa acctttgttt attttttttt 10800
cttcattccg taactcttct accttcttta tttactttct aaaatccaaa tacaaaacat 10860
aaaaataaat aaacacagag taaattccca aattattcca tcattaaaag atacgaggcg 10920
cgtgtaagtt acaggcaagc gatccgtcct aagaaaccat tattatcatg acattaacct 10980
ataaaaatag gcgtatcacg aggccctttc gtc 11013

<210> SEQ ID NO 14
<211> LENGTH: 1008
<212> TYPE: DNA
<213> ORGANISM: Archaeoglobus fulgidus

<400> SEQUENCE: 14
atgattgttt cgatactggg agcgggtgca atgggctcag ccctctccgt cccgctcgta 60
gataacggca acgaagtgag aatctggggg accgagttcg atacggagat tttaaaatca 120
atctcagccg gcagagagca tccaaggctt ggtgtaaagc tcaatggcgt ggaaattttc 180
tggccagagc agcttgaaaa atgtttggag aatgcagagg ttgtacttct gggtgttagc 240
acggatggcg tgctgcccgt aatgagcaga attctcccgt atctcaagga ccagtacatc 300
gtactcatct ctaaagggct gattgatttt gataacagtg ttctgacggt tcccgaagct 360
gtatggaggt taaagcacga tttgagggaa aggactgtgg cgataaccgg gcccgctatt 420
gcaagagagg tggcgaaacg catgcccaca accgttgttt tcagcagccc atccgaaagc 480
tcggccaata aaatgaaaga aatctttgag acagagtact ttggcgttga agtaacaaca 540
gacataattg gcacggaaat aacctccgcc ctcaaaaacg tttattccat agccattgca 600
tggataaggg gctacgagag cagaaaaaac gttgagatga gcaatgcaaa gggagtgatt 660
gcaacgagag ccataaacga gatggcagag ctgatagaga ttctcggagg ggatagagag 720
accgcctttg gcctttccgg atttggagac ctcatcgcaa ccttcagggg aggaaggaac 780
gggatgctgg gagagctgct tggaaagggg cttagcatcg atgaggcgat ggaggagctt 840
gagaggagag gagttggtgt ggttgagggc tacaaaacgg cagagaaagc atacaggctg 900
tccagcaaaa taaatgcaga cacaaagctg ctcgacagca tctacagagt cctttatgaa 960
ggactgaagg ttgaggaagt gctgtttgaa ctcgctacat ttaaataa 1008

<210> SEQ ID NO 15
<211> LENGTH: 1137
<212> TYPE: DNA
<213> ORGANISM: Candida versatilis

<400> SEQUENCE: 15
atgcctactc ctcaagagag actcgctcag ttgcgtggaa atgaagacgc gccagcgtcg 60
gtagcatcga aatataacaa aagattccgt gtaggtgtca ttggttctgg taactggggt 120
acggcagtcg cgaagattgt cgccgaaaac tgcctggaaa agccatatct gtttcaccgt 180
gatgtgaaga tgtgggttcg tgaggaagag gtctctgaca tgaagctgac ggacatcatt 240
aattcctacc atgagaacgt gaagtacctg ccggaggtaa ctctgccgtt taatctgttt 300
gctgagccag acattcgcaa ggttgctgat ggtgcagacc tgctggttat caatctgccc 360
caccagttct tggggtctgt atgcgaccag atgaagggca tcgacttctc taagtcctca 420

```
gccatttctt gtctaaaggg tatcaatgta tctgcagatg gtgtggagct tcttcatgat    480

gtcgtggaaa agaagcttgg cttgcattgc ggtgtcctga gtggtgcgaa tattgcgtcc    540

gaggtggccc gtgaacgttg gtctgagacc accattgcct tcccattgcc ttcgtggtac    600

cagcagggtg atgctgatga taatctgatc aaggagttgt tctacaggcc ctatttccat    660

gttcaagtat cggatgatgt gtgtggtgcg tcaattagcg gtgcacttaa gaacgtggtc    720

gctcttggcg caggtcttgt tgagggcgca ggctggggtg ataatgccaa ggctgctgtc    780

atgcgtcgtg gcttgctcga agtgattatg ttcggcaacg ttttcttccc aggtaagtgc    840

cgcccagaga ccttcaccac tgaatcggca ggtgtggccg atttgatcac ctcgtgtgct    900

ggtggacgta acgtcaaggt tggacgtgca tttgctcgta caggaaagcc acttgaggtc    960

atcgagaagg agctcctaaa tggccagtca gcccagggta ttattaccgg acgtgaggtg   1020

atggagcttc taacggcaac caagaaggag gacgagttcc ctctgcttgg tgctatttac   1080

gatattgtgc ataacaagtt gcacatctca aatctgccag agcggatcgc agactaa      1137
```

```
<210> SEQ ID NO 16
<211> LENGTH: 951
<212> TYPE: DNA
<213> ORGANISM: Rickettsia prowazekii

<400> SEQUENCE: 16

atgaacaaat ttaagaatat tgcagtttat ggaggaggta gtttcggcac tagtcttgct     60

tctttagtag cacgaaactg taataatgtt actttatttt tacgtgacga gataatttta    120

aaagaaattt tatataaaaa aactaacgca caatacttag gtgatattga attacctact    180

aatttgcaag ctactacaaa cttaagtgta atcaaggatt ttgaattaat tattattgca    240

gtgccatctt atgcttttga tgattcaata aaattattga aaacgtacgg catctctaaa    300

gagcatacta ttctagtagc gacaaaaggc ttggctgata atcctactga attattttct    360

gatagactta acactttatt acccgataat cctataggat tttatctgg tccaaatcta    420

gcaaaggaac ttgctaaaaa tttgcctgct tcggcaagta ttgcaagttt agatatagat    480

atcgcaaata aaatagctta taacttcagt tcaaaaactt tttcaacaaa tacgaccata    540

gatattgtaa cgttacaaat tgctggagct ttaaaaaata tttttgctat taaaagtgga    600

attgatttag caagagagca gggagcaaat tcaagagcaa cgcttatagt aggggcctta    660

aaagaaatta ctactttatc taaggttctt ggaggtatgc aaaaaaattc tgatatttta    720

cttgaagcag gagtattagg cgatttagta cttacttgtt actctttagg ttcgcgtaat    780

acaaaatttg gttatgaatt tgaaattagt agggataaaa agaaattttt atgcgaatat    840

aaagaattag tagaaggacg agaagcatta aaattagttt tggatctaat aaaaaaatat    900

aatttacaca tgcctatagt tgctgaagta gcttcactca ttttaatttg a             951
```

```
<210> SEQ ID NO 17
<211> LENGTH: 1008
<212> TYPE: DNA
<213> ORGANISM: Beggiatoa alba

<400> SEQUENCE: 17

atgttatcgc cgtccgcctt attagtctta ggggcagggt catggggcac tgcactggct     60

cttgcgcttg cccgtcgaca ataccctatt tacctttggg gtaaagaccc tgcgcatgtt    120

catactttac aaatacaacg ttgtaatcaa cgatttttgc cgaatgcggt tttcccgat    180

aatttatacg ccattacgga cttcgtaacc ctcatgccga ttgtggaaga cattattatt    240
```

```
gtcgttccta gccatggctt ccgcgaaacc ttaaaaaaaa taaagcccta cattacaaaa    300

aatcatcgtt tatgctgggc aacaaaaggc ttggaatatc aaacagggtt gcttttacac    360

gaagtagcgc gtgcagaatt aggcgataac atccctctcg cggttttgtc aggtccttca    420

tttgccggtg aagtcgctgc cgccttaccg acagcggtca cgattgccgc acaagacatc    480

gaaaacgctc atcatgtcgc ccaattattt catcaagcct cattccgtgc ttataccagt    540

aatgacatgg tcggggtaca aattgggggc gcggttaaaa atgtcattgc cattgctgca    600

ggtatcgcag atggtttaaa aatgggagca aatacccgtg ccgctttaat tacacgtgga    660

ctgagcgaaa ttgtacgttt aggcattgcc ctcggtggac aacgcgaaac ctttatgggt    720

ttagcaggct taggcgattt agtcctaact tgcactgata accaatcccg caatcgacgc    780

tttggctacg cactcgcgca aggcatcagc ctagaagctg cacaagctca agttggacaa    840

gtggtcgaag gcatacatgc tgcaaccatc acccaccaac tcgcccaaca gcacggtgta    900

gaaatgccca tagtcaacca tgtcaaccaa gtattaacag gacaaagcac cccactagaa    960

gccgctcaag ccctgttagc ccgtgaaccc aagccagaaa tgctataa                1008
```

```
<210> SEQ ID NO 18
<211> LENGTH: 1005
<212> TYPE: DNA
<213> ORGANISM: Kangiella koreensis

<400> SEQUENCE: 18

atgtctgcac aactttcctt tgcggttctt ggggcaggtt cttatggaac cgcattggca     60

gttttgcttg cccgtaatgg ccatagtgtt cagttatggg ctcgcaactc tcagcatgtt    120

gttgaaatgc agcaggcaaa acagaatacg aaataccttc ctgatgtcgc tttccctgac    180

aatctatcag taaccgatca aattgatgta gctttaaagc atcatcctat tattcttgta    240

gcggtcccaa gtcatgcgtt tcgcgataca ctgtacctca tcaaacctct tgtaaaccaa    300

gatagtaagc tagtatgggc gagcaaaggg ctcgatcccg atagtggtga tttgttaggt    360

aatgtgctga aaaatatttt aggcgataat atgccacacg ccattttatc tgggccaact    420

ttcgccaagg aaatggctat tggtatgcct accgctatca ctttagcagc taataatgac    480

gactttgctg agcaattagc tttggcttta cataatgagc gtttcagagt ctataccagt    540

gatgacatcg ttggtgttca agtcggtggt gcggttaaaa atgtagtagc tatcggtgct    600

ggaattgctg acggactagg ttatggtgcg aacgcaagaa cagccttgat cactcggggt    660

ttggctgaaa tgactcgctt aggtgttgcc gcaggcggaa agcaggaaac tttcaatgga    720

atggcaggca tgggcgattt ggtcttaacc tgtaccgata atcagtcgcg taataggcgt    780

tttggtttag ctttaggtaa aggtgctaat agagatgagg ctgagcatgc cattgggcag    840

gtagtagaag gtgttcgtaa tgccaaggaa gttaagatgc tggcggagcg actaggggtc    900

gaaatgccaa tcagcgatgc gatttatcgc ataatttatg aaggcgtcga cgcccgtcag    960

gccgcacatg aattattaac tcgagacctt aaatctgaag gttag                   1005

<210> SEQ ID NO 19
<211> LENGTH: 1176
<212> TYPE: DNA
<213> ORGANISM: Artificial Sequence
<220> FEATURE:
<223> OTHER INFORMATION: Yeast GPD1_opt

<400> SEQUENCE: 19
```

```
atgtccgctg ctgctgacag attgaacttg acatctggtc acttgaacgc tggtagaaag     60

agatcatcct cctctgtctc tttgaaggct gccgaaaagc cattcaaggt caccgttatc    120

ggttctggta actggggtac caccattgcc aaggtcgtcg ccgaaaactg caagggttac    180

ccagaagttt ttgctccaat cgttcaaatg tgggtttttg aagaggaaat taacggtgaa    240

aagttgactg aaattatcaa cactagacac caaaacgtga agtacttgcc cggtattacc    300

ttgccagaca atttggttgc caatccagac ttgatcgata gtgtcaagga cgttgatatt    360

atcgttttta acatcccaca ccaattccta ccacgtattt gttctcaatt gaagggtcat    420

gtcgattctc acgttagagc tatctcctgc ttgaagggtt tcgaagttgg tgctaagggt    480

gttcaattgt tatcctctta catcactgaa gagctaggta tccaatgtgg tgctttgtct    540

ggtgctaaca tcgctaccga agtcgctcaa gagcactggt ctgaaaccac tgtcgcttac    600

catatcccaa aggactttag aggtgaaggt aaagacgttg accacaaggt cctaaaggct    660

ttgttccaca gaccatactt tcacgtttct gtcatcgaag atgtcgccgg tatctctatc    720

tgtggcgctt taaagaacgt cgtcgccttg ggttgtggtt ttgttgaagg attgggttgg    780

ggtaacaacg cctctgctgc tatccaacgt gtcggtttgg gtgaaatcat tagatttggt    840

caaatgtttt tccctgaatc cagagaggaa acctactacc aagagtctgc cggtgttgct    900

gacctaataa ccacctgtgc tggtggtaga aacgttaagg ttgccagatt gatggctact    960

tccggtaagg acgcttggga atgtgaaaag gaattgttga acggtcaatc cgctcaaggt   1020

ttgattactt gtaaggaagt tcacgaatgg ttggaaactt gtggcagcgt tgaagatttt   1080

ccattattcg aagctgtcta ccaaatcgtc tacaataact accctatgaa aaacttgcca   1140

gatatgatcg aggaattaga cttacacgag gactaa                             1176
```

```
<210> SEQ ID NO 20
<211> LENGTH: 38
<212> TYPE: DNA
<213> ORGANISM: Artificial Sequence
<220> FEATURE:
<223> OTHER INFORMATION: Asn44F

<400> SEQUENCE: 20

ccgttatcgg ttctggtaac tggggtacca ccattgcc                            38


<210> SEQ ID NO 21
<211> LENGTH: 38
<212> TYPE: DNA
<213> ORGANISM: Artificial Sequence
<220> FEATURE:
<223> OTHER INFORMATION: N44AF

<400> SEQUENCE: 21

ccgttatcgg ttctggtgct tggggtacca ccattgcc                            38


<210> SEQ ID NO 22
<211> LENGTH: 38
<212> TYPE: DNA
<213> ORGANISM: Artificial Sequence
<220> FEATURE:
<223> OTHER INFORMATION: N44CF

<400> SEQUENCE: 22

ccgttatcgg ttctggttgt tggggtacca ccattgcc                            38


<210> SEQ ID NO 23
<211> LENGTH: 38
```

<212> TYPE: DNA
<213> ORGANISM: Artificial Sequence
<220> FEATURE:
<223> OTHER INFORMATION: N44GF

<400> SEQUENCE: 23
ccgttatcgg ttctggtggt tggggtacca ccattgcc 38

<210> SEQ ID NO 24
<211> LENGTH: 38
<212> TYPE: DNA
<213> ORGANISM: Artificial Sequence
<220> FEATURE:
<223> OTHER INFORMATION: N44IF

<400> SEQUENCE: 24
ccgttatcgg ttctggtatc tggggtacca ccattgcc 38

<210> SEQ ID NO 25
<211> LENGTH: 38
<212> TYPE: DNA
<213> ORGANISM: Artificial Sequence
<220> FEATURE:
<223> OTHER INFORMATION: N44LF

<400> SEQUENCE: 25
ccgttatcgg ttctggtcta tggggtacca ccattgcc 38

<210> SEQ ID NO 26
<211> LENGTH: 38
<212> TYPE: DNA
<213> ORGANISM: Artificial Sequence
<220> FEATURE:
<223> OTHER INFORMATION: N44MF

<400> SEQUENCE: 26
ccgttatcgg ttctggtatg tggggtacca ccattgcc 38

<210> SEQ ID NO 27
<211> LENGTH: 38
<212> TYPE: DNA
<213> ORGANISM: Artificial Sequence
<220> FEATURE:
<223> OTHER INFORMATION: N44SF

<400> SEQUENCE: 27
ccgttatcgg ttctggttct tggggtacca ccattgcc 38

<210> SEQ ID NO 28
<211> LENGTH: 38
<212> TYPE: DNA
<213> ORGANISM: Artificial Sequence
<220> FEATURE:
<223> OTHER INFORMATION: N44VF

<400> SEQUENCE: 28
ccgttatcgg ttctggtgtt tggggtacca ccattgcc 38

<210> SEQ ID NO 29
<211> LENGTH: 38
<212> TYPE: DNA
<213> ORGANISM: Artificial Sequence
<220> FEATURE:
<223> OTHER INFORMATION: Trp45F

<400> SEQUENCE: 29
ccgttatcgg ttctggtaac tggggtacca ccattgcc 38

<210> SEQ ID NO 30
<211> LENGTH: 38
<212> TYPE: DNA
<213> ORGANISM: Artificial Sequence
<220> FEATURE:
<223> OTHER INFORMATION: W45AF

<400> SEQUENCE: 30
ccgttatcgg ttctggtaac gctggtacca ccattgcc 38

<210> SEQ ID NO 31
<211> LENGTH: 38
<212> TYPE: DNA
<213> ORGANISM: Artificial Sequence
<220> FEATURE:
<223> OTHER INFORMATION: W45CF

<400> SEQUENCE: 31
ccgttatcgg ttctggtaac tgtggtacca ccattgcc 38

<210> SEQ ID NO 32
<211> LENGTH: 38
<212> TYPE: DNA
<213> ORGANISM: Artificial Sequence
<220> FEATURE:
<223> OTHER INFORMATION: W45GF

<400> SEQUENCE: 32
ccgttatcgg ttctggtaac ggtggtacca ccattgcc 38

<210> SEQ ID NO 33
<211> LENGTH: 38
<212> TYPE: DNA
<213> ORGANISM: Artificial Sequence
<220> FEATURE:
<223> OTHER INFORMATION: W45HF

<400> SEQUENCE: 33
ccgttatcgg ttctggtaac cacggtacca ccattgcc 38

<210> SEQ ID NO 34
<211> LENGTH: 38
<212> TYPE: DNA
<213> ORGANISM: Artificial Sequence
<220> FEATURE:
<223> OTHER INFORMATION: W45IF

<400> SEQUENCE: 34
ccgttatcgg ttctggtaac atcggtacca ccattgcc 38

<210> SEQ ID NO 35
<211> LENGTH: 38
<212> TYPE: DNA
<213> ORGANISM: Artificial Sequence
<220> FEATURE:
<223> OTHER INFORMATION: W45RF

<400> SEQUENCE: 35
ccgttatcgg ttctggtaac aagggtacca ccattgcc 38

<210> SEQ ID NO 36
<211> LENGTH: 38
<212> TYPE: DNA
<213> ORGANISM: Artificial Sequence

<220> FEATURE:
<223> OTHER INFORMATION: W45LF

<400> SEQUENCE: 36
ccgttatcgg ttctggtaac ctaggtacca ccattgcc 38

<210> SEQ ID NO 37
<211> LENGTH: 38
<212> TYPE: DNA
<213> ORGANISM: Artificial Sequence
<220> FEATURE:
<223> OTHER INFORMATION: W45MF

<400> SEQUENCE: 37
ccgttatcgg ttctggtaac atgggtacca ccattgcc 38

<210> SEQ ID NO 38
<211> LENGTH: 38
<212> TYPE: DNA
<213> ORGANISM: Artificial Sequence
<220> FEATURE:
<223> OTHER INFORMATION: W45NF

<400> SEQUENCE: 38
ccgttatcgg ttctggtaac aacggtacca ccattgcc 38

<210> SEQ ID NO 39
<211> LENGTH: 38
<212> TYPE: DNA
<213> ORGANISM: Artificial Sequence
<220> FEATURE:
<223> OTHER INFORMATION: W45QF

<400> SEQUENCE: 39
ccgttatcgg ttctggtaac caaggtacca ccattgcc 38

<210> SEQ ID NO 40
<211> LENGTH: 38
<212> TYPE: DNA
<213> ORGANISM: Artificial Sequence
<220> FEATURE:
<223> OTHER INFORMATION: W45RF

<400> SEQUENCE: 40
ccgttatcgg ttctggtaac cgtggtacca ccattgcc 38

<210> SEQ ID NO 41
<211> LENGTH: 38
<212> TYPE: DNA
<213> ORGANISM: Artificial Sequence
<220> FEATURE:
<223> OTHER INFORMATION: W45SF

<400> SEQUENCE: 41
ccgttatcgg ttctggtaac tctggtacca ccattgcc 38

<210> SEQ ID NO 42
<211> LENGTH: 38
<212> TYPE: DNA
<213> ORGANISM: Artificial Sequence
<220> FEATURE:
<223> OTHER INFORMATION: W45TF

<400> SEQUENCE: 42
ccgttatcgg ttctggtaac accggtacca ccattgcc 38

<210> SEQ ID NO 43
<211> LENGTH: 38
<212> TYPE: DNA
<213> ORGANISM: Artificial Sequence
<220> FEATURE:
<223> OTHER INFORMATION: W45VF

<400> SEQUENCE: 43
ccgttatcgg ttctggtaac gttggtacca ccattgcc 38

<210> SEQ ID NO 44
<211> LENGTH: 43
<212> TYPE: DNA
<213> ORGANISM: Artificial Sequence
<220> FEATURE:
<223> OTHER INFORMATION: Phe73F

<400> SEQUENCE: 44
ccaatcgttc aaatgtgggt ttttgaagag gaaattaacg gtg 43

<210> SEQ ID NO 45
<211> LENGTH: 43
<212> TYPE: DNA
<213> ORGANISM: Artificial Sequence
<220> FEATURE:
<223> OTHER INFORMATION: F73GF

<400> SEQUENCE: 45
ccaatcgttc aaatgtgggt tggtgaagag gaaattaacg gtg 43

<210> SEQ ID NO 46
<211> LENGTH: 43
<212> TYPE: DNA
<213> ORGANISM: Artificial Sequence
<220> FEATURE:
<223> OTHER INFORMATION: F73AF

<400> SEQUENCE: 46
ccaatcgttc aaatgtgggt tgctgaagag gaaattaacg gtg 43

<210> SEQ ID NO 47
<211> LENGTH: 43
<212> TYPE: DNA
<213> ORGANISM: Artificial Sequence
<220> FEATURE:
<223> OTHER INFORMATION: F73RF

<400> SEQUENCE: 47
ccaatcgttc aaatgtgggt tcgtgaagag gaaattaacg gtg 43

<210> SEQ ID NO 48
<211> LENGTH: 43
<212> TYPE: DNA
<213> ORGANISM: Artificial Sequence
<220> FEATURE:
<223> OTHER INFORMATION: F73KF

<400> SEQUENCE: 48
ccaatcgttc aaatgtgggt taaggaagag gaaattaacg gtg 43

<210> SEQ ID NO 49
<211> LENGTH: 43
<212> TYPE: DNA
<213> ORGANISM: Artificial Sequence
<220> FEATURE:
<223> OTHER INFORMATION: Phe129F

<400> SEQUENCE: 49
gtttttaaca tcccacacca attcctacca cgtatttgtt ctc 43

<210> SEQ ID NO 50
<211> LENGTH: 43
<212> TYPE: DNA
<213> ORGANISM: Artificial Sequence
<220> FEATURE:
<223> OTHER INFORMATION: F129GF

<400> SEQUENCE: 50
gtttttaaca tcccacacca aggtctacca cgtatttgtt ctc 43

<210> SEQ ID NO 51
<211> LENGTH: 43
<212> TYPE: DNA
<213> ORGANISM: Artificial Sequence
<220> FEATURE:
<223> OTHER INFORMATION: F129AF

<400> SEQUENCE: 51
gtttttaaca tcccacacca agctctacca cgtatttgtt ctc 43

<210> SEQ ID NO 52
<211> LENGTH: 43
<212> TYPE: DNA
<213> ORGANISM: Artificial Sequence
<220> FEATURE:
<223> OTHER INFORMATION: F129RF

<400> SEQUENCE: 52
gtttttaaca tcccacacca acgtctacca cgtatttgtt ctc 43

<210> SEQ ID NO 53
<211> LENGTH: 43
<212> TYPE: DNA
<213> ORGANISM: Artificial Sequence
<220> FEATURE:
<223> OTHER INFORMATION: F129KF

<400> SEQUENCE: 53
gtttttaaca tcccacacca aaagctacca cgtatttgtt ctc 43

<210> SEQ ID NO 54
<211> LENGTH: 38
<212> TYPE: DNA
<213> ORGANISM: Artificial Sequence
<220> FEATURE:
<223> OTHER INFORMATION: N44AR

<400> SEQUENCE: 54
ggcaatggtg gtaccccaag caccagaacc gataacgg 38

<210> SEQ ID NO 55
<211> LENGTH: 38
<212> TYPE: DNA
<213> ORGANISM: Artificial Sequence
<220> FEATURE:
<223> OTHER INFORMATION: N44CR

<400> SEQUENCE: 55
ggcaatggtg gtaccccaac aaccagaacc gataacgg 38

<210> SEQ ID NO 56

<211> LENGTH: 38
<212> TYPE: DNA
<213> ORGANISM: Artificial Sequence
<220> FEATURE:
<223> OTHER INFORMATION: N44GR

<400> SEQUENCE: 56
ggcaatggtg gtaccccaac caccagaacc gataacgg 38

<210> SEQ ID NO 57
<211> LENGTH: 38
<212> TYPE: DNA
<213> ORGANISM: Artificial Sequence
<220> FEATURE:
<223> OTHER INFORMATION: N44IR

<400> SEQUENCE: 57
ggcaatggtg gtaccccaga taccagaacc gataacgg 38

<210> SEQ ID NO 58
<211> LENGTH: 38
<212> TYPE: DNA
<213> ORGANISM: Artificial Sequence
<220> FEATURE:
<223> OTHER INFORMATION: N44LR

<400> SEQUENCE: 58
ggcaatggtg gtaccccata gaccagaacc gataacgg 38

<210> SEQ ID NO 59
<211> LENGTH: 38
<212> TYPE: DNA
<213> ORGANISM: Artificial Sequence
<220> FEATURE:
<223> OTHER INFORMATION: N44MR

<400> SEQUENCE: 59
ggcaatggtg gtaccccaca taccagaacc gataacgg 38

<210> SEQ ID NO 60
<211> LENGTH: 38
<212> TYPE: DNA
<213> ORGANISM: Artificial Sequence
<220> FEATURE:
<223> OTHER INFORMATION: N44SR

<400> SEQUENCE: 60
ggcaatggtg gtaccccaag aaccagaacc gataacgg 38

<210> SEQ ID NO 61
<211> LENGTH: 38
<212> TYPE: DNA
<213> ORGANISM: Artificial Sequence
<220> FEATURE:
<223> OTHER INFORMATION: N44VR

<400> SEQUENCE: 61
ggcaatggtg gtaccccaaa caccagaacc gataacgg 38

<210> SEQ ID NO 62
<211> LENGTH: 38
<212> TYPE: DNA
<213> ORGANISM: Artificial Sequence
<220> FEATURE:
<223> OTHER INFORMATION: W45AR

<400> SEQUENCE: 62
ggcaatggtg gtaccagcgt taccagaacc gataacgg 38

<210> SEQ ID NO 63
<211> LENGTH: 38
<212> TYPE: DNA
<213> ORGANISM: Artificial Sequence
<220> FEATURE:
<223> OTHER INFORMATION: W45CR

<400> SEQUENCE: 63
ggcaatggtg gtaccacagt taccagaacc gataacgg 38

<210> SEQ ID NO 64
<211> LENGTH: 38
<212> TYPE: DNA
<213> ORGANISM: Artificial Sequence
<220> FEATURE:
<223> OTHER INFORMATION: W45GR

<400> SEQUENCE: 64
ggcaatggtg gtaccaccgt taccagaacc gataacgg 38

<210> SEQ ID NO 65
<211> LENGTH: 38
<212> TYPE: DNA
<213> ORGANISM: Artificial Sequence
<220> FEATURE:
<223> OTHER INFORMATION: W45HR

<400> SEQUENCE: 65
ggcaatggtg gtaccgtggt taccagaacc gataacgg 38

<210> SEQ ID NO 66
<211> LENGTH: 38
<212> TYPE: DNA
<213> ORGANISM: Artificial Sequence
<220> FEATURE:
<223> OTHER INFORMATION: W45IR

<400> SEQUENCE: 66
ggcaatggtg gtaccgatgt taccagaacc gataacgg 38

<210> SEQ ID NO 67
<211> LENGTH: 38
<212> TYPE: DNA
<213> ORGANISM: Artificial Sequence
<220> FEATURE:
<223> OTHER INFORMATION: W45KR

<400> SEQUENCE: 67
ggcaatggtg gtacccttgt taccagaacc gataacgg 38

<210> SEQ ID NO 68
<211> LENGTH: 38
<212> TYPE: DNA
<213> ORGANISM: Artificial Sequence
<220> FEATURE:
<223> OTHER INFORMATION: W45LR

<400> SEQUENCE: 68
ggcaatggtg gtacctaggt taccagaacc gataacgg 38

<210> SEQ ID NO 69
<211> LENGTH: 38
<212> TYPE: DNA

<213> ORGANISM: Artificial Sequence
<220> FEATURE:
<223> OTHER INFORMATION: W45MR

<400> SEQUENCE: 69
ggcaatggtg gtacccatgt taccagaacc gataacgg 38

<210> SEQ ID NO 70
<211> LENGTH: 38
<212> TYPE: DNA
<213> ORGANISM: Artificial Sequence
<220> FEATURE:
<223> OTHER INFORMATION: W45NR

<400> SEQUENCE: 70
ggcaatggtg gtaccgttgt taccagaacc gataacgg 38

<210> SEQ ID NO 71
<211> LENGTH: 38
<212> TYPE: DNA
<213> ORGANISM: Artificial Sequence
<220> FEATURE:
<223> OTHER INFORMATION: W45QR

<400> SEQUENCE: 71
ggcaatggtg gtaccttggt taccagaacc gataacgg 38

<210> SEQ ID NO 72
<211> LENGTH: 38
<212> TYPE: DNA
<213> ORGANISM: Artificial Sequence
<220> FEATURE:
<223> OTHER INFORMATION: W45RR

<400> SEQUENCE: 72
ggcaatggtg gtaccacggt taccagaacc gataacgg 38

<210> SEQ ID NO 73
<211> LENGTH: 38
<212> TYPE: DNA
<213> ORGANISM: Artificial Sequence
<220> FEATURE:
<223> OTHER INFORMATION: W45SR

<400> SEQUENCE: 73
ggcaatggtg gtaccagagt taccagaacc gataacgg 38

<210> SEQ ID NO 74
<211> LENGTH: 38
<212> TYPE: DNA
<213> ORGANISM: Artificial Sequence
<220> FEATURE:
<223> OTHER INFORMATION: W45TR

<400> SEQUENCE: 74
ggcaatggtg gtaccggtgt taccagaacc gataacgg 38

<210> SEQ ID NO 75
<211> LENGTH: 38
<212> TYPE: DNA
<213> ORGANISM: Artificial Sequence
<220> FEATURE:
<223> OTHER INFORMATION: W45VR

<400> SEQUENCE: 75
ggcaatggtg gtaccaacgt taccagaacc gataacgg 38

<210> SEQ ID NO 76
<211> LENGTH: 43
<212> TYPE: DNA
<213> ORGANISM: Artificial Sequence
<220> FEATURE:
<223> OTHER INFORMATION: F73GR

<400> SEQUENCE: 76
caccgttaat ttcctcttca ccaacccaca tttgaacgat tgg 43

<210> SEQ ID NO 77
<211> LENGTH: 43
<212> TYPE: DNA
<213> ORGANISM: Artificial Sequence
<220> FEATURE:
<223> OTHER INFORMATION: F73AR

<400> SEQUENCE: 77
caccgttaat ttcctcttca gcaacccaca tttgaacgat tgg 43

<210> SEQ ID NO 78
<211> LENGTH: 43
<212> TYPE: DNA
<213> ORGANISM: Artificial Sequence
<220> FEATURE:
<223> OTHER INFORMATION: F73RR

<400> SEQUENCE: 78
caccgttaat ttcctcttca cgaacccaca tttgaacgat tgg 43

<210> SEQ ID NO 79
<211> LENGTH: 43
<212> TYPE: DNA
<213> ORGANISM: Artificial Sequence
<220> FEATURE:
<223> OTHER INFORMATION: F73KR

<400> SEQUENCE: 79
caccgttaat ttcctcttcc ttaacccaca tttgaacgat tgg 43

<210> SEQ ID NO 80
<211> LENGTH: 43
<212> TYPE: DNA
<213> ORGANISM: Artificial Sequence
<220> FEATURE:
<223> OTHER INFORMATION: F129GR

<400> SEQUENCE: 80
gagaacaaat acgtggtaga ccttggtgtg ggatgttaaa aac 43

<210> SEQ ID NO 81
<211> LENGTH: 43
<212> TYPE: DNA
<213> ORGANISM: Artificial Sequence
<220> FEATURE:
<223> OTHER INFORMATION: F129AR

<400> SEQUENCE: 81
gagaacaaat acgtggtaga gcttggtgtg ggatgttaaa aac 43

<210> SEQ ID NO 82
<211> LENGTH: 43
<212> TYPE: DNA
<213> ORGANISM: Artificial Sequence
<220> FEATURE:

<223> OTHER INFORMATION: F129RR

<400> SEQUENCE: 82
gagaacaaat acgtggtaga cgttggtgtg ggatgttaaa aac 43

<210> SEQ ID NO 83
<211> LENGTH: 43
<212> TYPE: DNA
<213> ORGANISM: Artificial Sequence
<220> FEATURE:
<223> OTHER INFORMATION: F129KR

<400> SEQUENCE: 83
gagaacaaat acgtggtagc ttttggtgtg ggatgttaaa aac 43

<210> SEQ ID NO 84
<211> LENGTH: 349
<212> TYPE: PRT
<213> ORGANISM: Homo sapiens

<400> SEQUENCE: 84

```
Met Ala Ser Lys Lys Val Cys Ile Val Gly Ser Gly Asn Trp Gly Ser
1               5                   10                  15

Ala Ile Ala Lys Ile Val Gly Gly Asn Ala Ala Gln Leu Ala Gln Phe
            20                  25                  30

Asp Pro Arg Val Thr Met Trp Val Phe Glu Glu Asp Ile Gly Gly Lys
        35                  40                  45

Lys Leu Thr Glu Ile Ile Asn Thr Gln His Glu Asn Val Lys Tyr Leu
    50                  55                  60

Pro Gly His Lys Leu Pro Pro Asn Val Val Ala Val Pro Asp Val Val
65                  70                  75                  80

Gln Ala Ala Glu Asp Ala Asp Ile Leu Ile Phe Val Val Pro His Gln
                85                  90                  95

Phe Ile Gly Lys Ile Cys Asp Gln Leu Lys Gly His Leu Lys Ala Asn
            100                 105                 110

Pro Thr Gly Ile Ser Leu Ile Lys Gly Val Asp Glu Gly Pro Asn Gly
        115                 120                 125

Leu Lys Leu Ile Ser Glu Val Ile Gly Glu Arg Leu Gly Ile Pro Met
    130                 135                 140

Ser Val Leu Met Gly Ala Asn Ile Ala Ser Glu Val Ala Asp Glu Lys
145                 150                 155                 160

Phe Cys Glu Thr Thr Ile Gly Cys Lys Asp Pro Ala Gln Gly Gln Leu
                165                 170                 175

Leu Lys Glu Leu Met Gln Thr Pro Asn Phe Arg Ile Thr Val Val Gln
            180                 185                 190

Glu Val Asp Thr Val Glu Ile Cys Gly Ala Leu Lys Asn Val Val Ala
        195                 200                 205

Val Gly Ala Gly Phe Cys Asp Gly Leu Gly Phe Gly Asp Asn Thr Lys
    210                 215                 220

Ala Ala Val Ile Arg Leu Gly Leu Met Glu Met Ile Ala Phe Ala Lys
225                 230                 235                 240

Leu Phe Cys Ser Gly Pro Val Ser Ser Ala Thr Phe Leu Glu Ser Cys
                245                 250                 255

Gly Val Ala Asp Leu Ile Thr Thr Cys Tyr Gly Gly Arg Asn Arg Lys
            260                 265                 270

Val Ala Glu Ala Phe Ala Arg Thr Gly Lys Ser Ile Glu Gln Leu Glu
        275                 280                 285
```

```
Lys Glu Leu Leu Asn Gly Gln Lys Leu Gln Gly Pro Glu Thr Ala Arg
    290                 295                 300

Glu Leu Tyr Ser Ile Leu Gln His Lys Gly Leu Val Asp Lys Phe Pro
305                 310                 315                 320

Leu Phe Met Ala Val Tyr Lys Val Cys Tyr Glu Gly Gln Pro Val Gly
                325                 330                 335

Glu Phe Ile His Cys Leu Gln Asn His Pro Glu His Met
            340                 345


<210> SEQ ID NO 85
<211> LENGTH: 343
<212> TYPE: PRT
<213> ORGANISM: Artificial Sequence
<220> FEATURE:
<223> OTHER INFORMATION: KG9G

<400> SEQUENCE: 85

Met Glu Glu Cys Lys Met Ala Lys Ile Tyr Tyr Gln Glu Asp Cys Asn
1               5                   10                  15

Leu Ser Leu Leu Asp Gly Lys Thr Ile Ala Val Ile Gly Tyr Gly Ser
            20                  25                  30

Gln Gly His Ala His Ala Leu Asn Ala Lys Glu Ser Gly Cys Asn Val
        35                  40                  45

Ile Ile Gly Leu Tyr Glu Gly Ala Lys Glu Trp Lys Arg Ala Glu Glu
    50                  55                  60

Gln Gly Phe Glu Val Tyr Thr Ala Ala Glu Ala Ala Lys Lys Ala Asp
65                  70                  75                  80

Ile Ile Met Ile Leu Ile Asn Asp Glu Lys Gln Ala Thr Met Tyr Lys
                85                  90                  95

Asn Asp Ile Glu Pro Asn Leu Glu Ala Gly Asn Met Leu Met Phe Ala
            100                 105                 110

His Gly Phe Asn Ile His Phe Gly Cys Ile Val Pro Pro Lys Asp Val
        115                 120                 125

Asp Val Thr Met Ile Ala Pro Lys Gly Pro Gly His Thr Val Arg Ser
    130                 135                 140

Glu Tyr Glu Glu Gly Lys Gly Val Pro Cys Leu Val Ala Val Glu Gln
145                 150                 155                 160

Asp Ala Thr Gly Lys Ala Leu Asp Met Ala Leu Ala Tyr Ala Leu Ala
                165                 170                 175

Ile Gly Gly Ala Arg Ala Gly Val Leu Glu Thr Thr Phe Arg Thr Glu
            180                 185                 190

Thr Glu Thr Asp Leu Phe Gly Glu Gln Ala Val Leu Cys Gly Gly Val
        195                 200                 205

Cys Ala Leu Met Gln Ala Gly Phe Glu Thr Leu Val Glu Ala Gly Tyr
    210                 215                 220

Asp Pro Arg Asn Ala Tyr Phe Glu Cys Ile His Glu Met Lys Leu Ile
225                 230                 235                 240

Val Asp Leu Ile Tyr Gln Ser Gly Phe Ser Gly Met Arg Tyr Ser Ile
                245                 250                 255

Ser Asn Thr Ala Glu Tyr Gly Asp Tyr Ile Thr Gly Pro Lys Ile Ile
            260                 265                 270

Thr Glu Asp Thr Lys Lys Ala Met Lys Lys Ile Leu Ser Asp Ile Gln
        275                 280                 285

Asp Gly Thr Phe Ala Lys Asp Phe Leu Val Asp Met Ser Asp Ala Gly
    290                 295                 300
```

```
Ser Gln Val His Phe Lys Ala Met Arg Lys Leu Ala Ser Glu His Pro
305                 310                 315                 320

Ala Glu Val Val Gly Glu Glu Ile Arg Ser Leu Tyr Ser Trp Ser Asp
                325                 330                 335

Glu Asp Lys Leu Ile Asn Asn
            340


<210> SEQ ID NO 86
<211> LENGTH: 343
<212> TYPE: PRT
<213> ORGANISM: Artificial Sequence
<220> FEATURE:
<223> OTHER INFORMATION: K9D3

<400> SEQUENCE: 86

Met Glu Glu Cys Lys Met Ala Lys Ile Tyr Tyr Gln Glu Asp Cys Asn
1               5                   10                  15

Leu Ser Leu Leu Asp Gly Lys Thr Ile Ala Val Ile Gly Tyr Gly Ser
            20                  25                  30

Gln Gly His Ala His Ala Leu Asn Ala Lys Glu Ser Gly Cys Asn Val
        35                  40                  45

Ile Ile Gly Leu Tyr Glu Gly Ala Lys Asp Trp Lys Arg Ala Glu Glu
    50                  55                  60

Gln Gly Phe Glu Val Tyr Thr Ala Ala Glu Ala Ala Lys Lys Ala Asp
65                  70                  75                  80

Ile Ile Met Ile Leu Ile Asn Asp Glu Lys Gln Ala Thr Met Tyr Lys
                85                  90                  95

Asn Asp Ile Glu Pro Asn Leu Glu Ala Gly Asn Met Leu Met Phe Ala
            100                 105                 110

His Gly Phe Asn Ile His Phe Gly Cys Ile Val Pro Pro Lys Asp Val
        115                 120                 125

Asp Val Thr Met Ile Ala Pro Lys Gly Pro Gly His Thr Val Arg Ser
    130                 135                 140

Glu Tyr Glu Glu Gly Lys Gly Val Pro Cys Leu Val Ala Val Glu Gln
145                 150                 155                 160

Asp Ala Thr Gly Lys Ala Leu Asp Met Ala Leu Ala Tyr Ala Leu Ala
                165                 170                 175

Ile Gly Gly Ala Arg Ala Gly Val Leu Glu Thr Thr Phe Arg Thr Glu
            180                 185                 190

Thr Glu Thr Asp Leu Phe Gly Glu Gln Ala Val Leu Cys Gly Gly Val
        195                 200                 205

Cys Ala Leu Met Gln Ala Gly Phe Glu Thr Leu Val Glu Ala Gly Tyr
    210                 215                 220

Asp Pro Arg Asn Ala Tyr Phe Glu Cys Ile His Glu Met Lys Leu Ile
225                 230                 235                 240

Val Asp Leu Ile Tyr Gln Ser Gly Phe Ser Gly Met Arg Tyr Ser Ile
                245                 250                 255

Ser Asn Thr Ala Glu Tyr Gly Asp Tyr Ile Thr Gly Pro Lys Ile Ile
            260                 265                 270

Thr Glu Asp Thr Lys Lys Ala Met Lys Lys Ile Leu Ser Asp Ile Gln
        275                 280                 285

Asp Gly Thr Phe Ala Lys Asp Phe Leu Val Asp Met Ser Asp Ala Gly
    290                 295                 300

Ser Gln Val His Phe Lys Ala Met Arg Lys Leu Ala Ser Glu His Pro
305                 310                 315                 320
```

```
Ala Glu Val Val Gly Glu Glu Ile Arg Ser Leu Tyr Ser Trp Ser Asp
                325                 330                 335

Glu Asp Lys Leu Ile Asn Asn
            340


<210> SEQ ID NO 87
<211> LENGTH: 343
<212> TYPE: PRT
<213> ORGANISM: Artificial Sequence
<220> FEATURE:
<223> OTHER INFORMATION: K9JB4P

<400> SEQUENCE: 87

Met Glu Glu Cys Lys Met Ala Lys Ile Tyr Tyr Gln Glu Asp Cys Asn
1               5                   10                  15

Leu Ser Leu Leu Asp Gly Lys Thr Ile Ala Val Ile Gly Tyr Gly Ser
            20                  25                  30

Gln Gly His Ala His Ala Leu Asn Ala Lys Glu Ser Gly Cys Asn Val
        35                  40                  45

Ile Ile Gly Leu Tyr Glu Gly Ala Glu Glu Trp Lys Arg Ala Glu Glu
    50                  55                  60

Gln Gly Phe Glu Val Tyr Thr Ala Ala Glu Ala Ala Lys Lys Ala Asp
65                  70                  75                  80

Ile Ile Met Ile Leu Ile Pro Asp Glu Lys Gln Ala Thr Met Tyr Lys
                85                  90                  95

Asn Asp Ile Glu Pro Asn Leu Glu Ala Gly Asn Met Leu Met Phe Ala
            100                 105                 110

His Gly Phe Asn Ile His Phe Gly Cys Ile Val Pro Pro Lys Asp Val
        115                 120                 125

Asp Val Thr Met Ile Ala Pro Lys Gly Pro Gly His Thr Val Arg Ser
    130                 135                 140

Glu Tyr Glu Glu Gly Lys Gly Val Pro Cys Leu Val Ala Val Glu Gln
145                 150                 155                 160

Asp Ala Thr Gly Lys Ala Leu Asp Met Ala Leu Ala Tyr Ala Leu Ala
                165                 170                 175

Ile Gly Gly Ala Arg Ala Gly Val Leu Glu Thr Thr Phe Arg Thr Glu
            180                 185                 190

Thr Glu Thr Asp Leu Phe Gly Glu Gln Ala Val Leu Cys Gly Gly Val
        195                 200                 205

Cys Ala Leu Met Gln Ala Gly Phe Glu Thr Leu Val Glu Ala Gly Tyr
    210                 215                 220

Asp Pro Arg Asn Ala Tyr Phe Glu Cys Ile His Glu Met Lys Leu Ile
225                 230                 235                 240

Val Asp Leu Ile Tyr Gln Ser Gly Phe Ser Gly Met Arg Tyr Ser Ile
                245                 250                 255

Ser Asn Thr Ala Glu Tyr Gly Asp Tyr Ile Thr Gly Pro Lys Ile Ile
            260                 265                 270

Thr Glu Asp Thr Lys Lys Ala Met Lys Lys Ile Leu Ser Asp Ile Gln
        275                 280                 285

Asp Gly Thr Phe Ala Lys Asp Phe Leu Val Asp Met Ser Asp Ala Gly
    290                 295                 300

Ser Gln Val His Phe Lys Ala Met Arg Lys Leu Ala Ser Glu His Pro
305                 310                 315                 320

Ala Glu Val Val Gly Glu Glu Ile Arg Ser Leu Tyr Ser Trp Ser Asp
                325                 330                 335
```

```
Glu Asp Lys Leu Ile Asn Asn
            340


<210> SEQ ID NO 88
<211> LENGTH: 570
<212> TYPE: PRT
<213> ORGANISM: Lactococcus lactis

<400> SEQUENCE: 88

Met Glu Phe Lys Tyr Asn Gly Lys Val Glu Ser Ile Glu Leu Asn Lys
1               5                   10                  15

Tyr Ser Lys Thr Leu Thr Gln Asp Pro Thr Gln Pro Ala Thr Gln Ala
            20                  25                  30

Met His Tyr Gly Ile Gly Phe Lys Asp Glu Asp Phe Lys Lys Ala Gln
        35                  40                  45

Val Gly Ile Val Ser Met Asp Trp Asp Gly Asn Pro Cys Asn Met His
    50                  55                  60

Leu Gly Thr Leu Gly Ser Lys Ile Lys Asn Ser Val Asn Gln Thr Asp
65                  70                  75                  80

Gly Leu Ile Gly Leu Gln Phe His Thr Ile Gly Val Ser Asp Gly Ile
                85                  90                  95

Ala Asn Gly Lys Leu Gly Met Arg Tyr Ser Leu Val Ser Arg Glu Val
            100                 105                 110

Ile Ala Asp Ser Ile Glu Thr Asn Ala Gly Ala Glu Tyr Tyr Asp Ala
        115                 120                 125

Ile Val Ala Val Pro Gly Cys Asp Lys Asn Met Pro Gly Ser Ile Ile
    130                 135                 140

Gly Met Ala Arg Leu Asn Arg Pro Ser Ile Met Val Tyr Gly Gly Thr
145                 150                 155                 160

Ile Glu His Gly Glu Tyr Lys Gly Glu Lys Leu Asn Ile Val Ser Ala
                165                 170                 175

Phe Glu Ala Leu Gly Gln Lys Ile Thr Gly Asn Ile Ser Glu Glu Asp
            180                 185                 190

Tyr His Gly Val Ile Cys Asn Ala Ile Pro Gly Gln Gly Ala Cys Gly
        195                 200                 205

Gly Met Tyr Thr Ala Asn Thr Leu Ala Ser Ala Ile Glu Thr Leu Gly
    210                 215                 220

Met Ser Leu Pro Tyr Ser Ala Ser Asn Pro Ala Val Ser Gln Glu Lys
225                 230                 235                 240

Glu Asp Glu Cys Asp Glu Ile Gly Leu Ala Ile Lys Asn Leu Leu Glu
                245                 250                 255

Lys Asp Ile Lys Pro Ser Asp Ile Met Thr Lys Glu Ala Phe Glu Asn
            260                 265                 270

Ala Ile Thr Ile Val Met Val Leu Gly Gly Ser Thr Asn Ala Val Leu
        275                 280                 285

His Ile Ile Ala Met Ala Asn Ala Ile Gly Val Glu Ile Thr Gln Asp
    290                 295                 300

Asp Phe Gln Arg Ile Ser Asp Val Thr Pro Val Leu Gly Asp Phe Lys
305                 310                 315                 320

Pro Ser Gly Lys Tyr Met Met Glu Asp Leu His Lys Ile Gly Gly Val
                325                 330                 335

Pro Ala Val Leu Lys Tyr Leu Leu Lys Glu Gly Lys Leu His Gly Asp
            340                 345                 350

Cys Leu Thr Val Thr Gly Lys Thr Leu Ala Glu Asn Val Glu Thr Ala
```

```
        355                 360                 365

Leu Asp Leu Asp Phe Asp Ser Gln Asp Ile Ile Arg Pro Leu Glu Asn
    370                 375                 380

Pro Ile Lys Ala Thr Gly His Leu Gln Ile Leu Tyr Gly Asn Leu Ala
385                 390                 395                 400

Glu Gly Gly Ser Val Ala Lys Ile Ser Gly Lys Glu Gly Glu Phe Phe
                405                 410                 415

Lys Gly Thr Ala Arg Val Phe Asp Gly Glu Gln His Phe Ile Asp Gly
            420                 425                 430

Ile Glu Ser Gly Arg Leu His Ala Gly Asp Val Ala Val Ile Arg Asn
        435                 440                 445

Ile Gly Pro Val Gly Gly Pro Gly Met Pro Glu Met Leu Lys Pro Thr
    450                 455                 460

Ser Ala Leu Ile Gly Ala Gly Leu Gly Lys Ser Cys Ala Leu Ile Thr
465                 470                 475                 480

Asp Gly Arg Phe Ser Gly Gly Thr His Gly Phe Val Val Gly His Ile
                485                 490                 495

Val Pro Glu Ala Val Glu Gly Gly Leu Ile Gly Leu Val Glu Asp Asp
            500                 505                 510

Asp Ile Ile Glu Ile Asp Ala Val Asn Asn Ser Ile Ser Leu Lys Val
        515                 520                 525

Ala Asp Asp Glu Ile Ala Arg Arg Arg Ala Asn Tyr Gln Lys Pro Ala
    530                 535                 540

Pro Lys Ala Thr Arg Gly Val Leu Ala Lys Phe Ala Lys Leu Thr Arg
545                 550                 555                 560

Pro Ala Ser Glu Gly Cys Val Thr Asp Leu
                565                 570


<210> SEQ ID NO 89
<211> LENGTH: 571
<212> TYPE: PRT
<213> ORGANISM: Streptococcus mutans

<400> SEQUENCE: 89

Met Thr Asp Lys Lys Thr Leu Lys Asp Leu Arg Asn Arg Ser Ser Val
1               5                   10                  15

Tyr Asp Ser Met Val Lys Ser Pro Asn Arg Ala Met Leu Arg Ala Thr
            20                  25                  30

Gly Met Gln Asp Glu Asp Phe Glu Lys Pro Ile Val Gly Val Ile Ser
        35                  40                  45

Thr Trp Ala Glu Asn Thr Pro Cys Asn Ile His Leu His Asp Phe Gly
    50                  55                  60

Lys Leu Ala Lys Val Gly Val Lys Glu Ala Gly Ala Trp Pro Val Gln
65                  70                  75                  80

Phe Gly Thr Ile Thr Val Ser Asp Gly Ile Ala Met Gly Thr Gln Gly
                85                  90                  95

Met Arg Phe Ser Leu Thr Ser Arg Asp Ile Ile Ala Asp Ser Ile Glu
            100                 105                 110

Ala Ala Met Gly Gly His Asn Ala Asp Ala Phe Val Ala Ile Gly Gly
        115                 120                 125

Cys Asp Lys Asn Met Pro Gly Ser Val Ile Ala Met Ala Asn Met Asp
    130                 135                 140

Ile Pro Ala Ile Phe Ala Tyr Gly Gly Thr Ile Ala Pro Gly Asn Leu
145                 150                 155                 160
```

```
Asp Gly Lys Asp Ile Asp Leu Val Ser Val Phe Glu Gly Val Gly His
                165                 170                 175

Trp Asn His Gly Asp Met Thr Lys Glu Glu Val Lys Ala Leu Glu Cys
            180                 185                 190

Asn Ala Cys Pro Gly Pro Gly Gly Cys Gly Gly Met Tyr Thr Ala Asn
        195                 200                 205

Thr Met Ala Thr Ala Ile Glu Val Leu Gly Leu Ser Leu Pro Gly Ser
    210                 215                 220

Ser Ser His Pro Ala Glu Ser Ala Glu Lys Lys Ala Asp Ile Glu Glu
225                 230                 235                 240

Ala Gly Arg Ala Val Val Lys Met Leu Glu Met Gly Leu Lys Pro Ser
                245                 250                 255

Asp Ile Leu Thr Arg Glu Ala Phe Glu Asp Ala Ile Thr Val Thr Met
            260                 265                 270

Ala Leu Gly Gly Ser Thr Asn Ser Thr Leu His Leu Leu Ala Ile Ala
        275                 280                 285

His Ala Ala Asn Val Glu Leu Thr Leu Asp Asp Phe Asn Thr Phe Gln
    290                 295                 300

Glu Lys Val Pro His Leu Ala Asp Leu Lys Pro Ser Gly Gln Tyr Val
305                 310                 315                 320

Phe Gln Asp Leu Tyr Lys Val Gly Gly Val Pro Ala Val Met Lys Tyr
                325                 330                 335

Leu Leu Lys Asn Gly Phe Leu His Gly Asp Arg Ile Thr Cys Thr Gly
            340                 345                 350

Lys Thr Val Ala Glu Asn Leu Lys Ala Phe Asp Asp Leu Thr Pro Gly
        355                 360                 365

Gln Lys Val Ile Met Pro Leu Glu Asn Pro Lys Arg Glu Asp Gly Pro
    370                 375                 380

Leu Ile Ile Leu His Gly Asn Leu Ala Pro Asp Gly Ala Val Ala Lys
385                 390                 395                 400

Val Ser Gly Val Lys Val Arg Arg His Val Gly Pro Ala Lys Val Phe
                405                 410                 415

Asn Ser Glu Glu Glu Ala Ile Glu Ala Val Leu Asn Asp Asp Ile Val
            420                 425                 430

Asp Gly Asp Val Val Val Val Arg Phe Val Gly Pro Lys Gly Gly Pro
        435                 440                 445

Gly Met Pro Glu Met Leu Ser Leu Ser Ser Met Ile Val Gly Lys Gly
    450                 455                 460

Gln Gly Glu Lys Val Ala Leu Leu Thr Asp Gly Arg Phe Ser Gly Gly
465                 470                 475                 480

Thr Tyr Gly Leu Val Val Gly His Ile Ala Pro Glu Ala Gln Asp Gly
                485                 490                 495

Gly Pro Ile Ala Tyr Leu Gln Thr Gly Asp Ile Val Thr Ile Asp Gln
            500                 505                 510

Asp Thr Lys Glu Leu His Phe Asp Ile Ser Asp Glu Glu Leu Lys His
        515                 520                 525

Arg Gln Glu Thr Ile Glu Leu Pro Pro Leu Tyr Ser Arg Gly Ile Leu
    530                 535                 540

Gly Lys Tyr Ala His Ile Val Ser Ser Ala Ser Arg Gly Ala Val Thr
545                 550                 555                 560

Asp Phe Trp Lys Pro Glu Glu Thr Gly Lys Lys
                565                 570
```

```
<210> SEQ ID NO 90
<211> LENGTH: 548
<212> TYPE: PRT
<213> ORGANISM: Lactococcus lactis

<400> SEQUENCE: 90

Met Tyr Thr Val Gly Asp Tyr Leu Leu Asp Arg Leu His Glu Leu Gly
1               5                   10                  15

Ile Glu Glu Ile Phe Gly Val Pro Gly Asp Tyr Asn Leu Gln Phe Leu
            20                  25                  30

Asp Gln Ile Ile Ser His Lys Asp Met Lys Trp Val Gly Asn Ala Asn
        35                  40                  45

Glu Leu Asn Ala Ser Tyr Met Ala Asp Gly Tyr Ala Arg Thr Lys Lys
    50                  55                  60

Ala Ala Ala Phe Leu Thr Thr Phe Gly Val Gly Glu Leu Ser Ala Val
65                  70                  75                  80

Asn Gly Leu Ala Gly Ser Tyr Ala Glu Asn Leu Pro Val Val Glu Ile
                85                  90                  95

Val Gly Ser Pro Thr Ser Lys Val Gln Asn Glu Gly Lys Phe Val His
            100                 105                 110

His Thr Leu Ala Asp Gly Asp Phe Lys His Phe Met Lys Met His Glu
        115                 120                 125

Pro Val Thr Ala Ala Arg Thr Leu Leu Thr Ala Glu Asn Ala Thr Val
    130                 135                 140

Glu Ile Asp Arg Val Leu Ser Ala Leu Leu Lys Glu Arg Lys Pro Val
145                 150                 155                 160

Tyr Ile Asn Leu Pro Val Asp Val Ala Ala Ala Lys Ala Glu Lys Pro
                165                 170                 175

Ser Leu Pro Leu Lys Lys Glu Asn Ser Thr Ser Asn Thr Ser Asp Gln
            180                 185                 190

Glu Ile Leu Asn Lys Ile Gln Glu Ser Leu Lys Asn Ala Lys Lys Pro
        195                 200                 205

Ile Val Ile Thr Gly His Glu Ile Ile Ser Phe Gly Leu Glu Lys Thr
    210                 215                 220

Val Thr Gln Phe Ile Ser Lys Thr Lys Leu Pro Ile Thr Thr Leu Asn
225                 230                 235                 240

Phe Gly Lys Ser Ser Val Asp Glu Ala Leu Pro Ser Phe Leu Gly Ile
                245                 250                 255

Tyr Asn Gly Thr Leu Ser Glu Pro Asn Leu Lys Glu Phe Val Glu Ser
            260                 265                 270

Ala Asp Phe Ile Leu Met Leu Gly Val Lys Leu Thr Asp Ser Ser Thr
        275                 280                 285

Gly Ala Phe Thr His His Leu Asn Glu Asn Lys Met Ile Ser Leu Asn
    290                 295                 300

Ile Asp Glu Gly Lys Ile Phe Asn Glu Arg Ile Gln Asn Phe Asp Phe
305                 310                 315                 320

Glu Ser Leu Ile Ser Ser Leu Leu Asp Leu Ser Glu Ile Glu Tyr Lys
                325                 330                 335

Gly Lys Tyr Ile Asp Lys Lys Gln Glu Asp Phe Val Pro Ser Asn Ala
            340                 345                 350

Leu Leu Ser Gln Asp Arg Leu Trp Gln Ala Val Glu Asn Leu Thr Gln
        355                 360                 365

Ser Asn Glu Thr Ile Val Ala Glu Gln Gly Thr Ser Phe Phe Gly Ala
    370                 375                 380
```

```
Ser Ser Ile Phe Leu Lys Ser Lys Ser His Phe Ile Gly Gln Pro Leu
385                 390                 395                 400

Trp Gly Ser Ile Gly Tyr Thr Phe Pro Ala Ala Leu Gly Ser Gln Ile
                405                 410                 415

Ala Asp Lys Glu Ser Arg His Leu Leu Phe Ile Gly Asp Gly Ser Leu
            420                 425                 430

Gln Leu Thr Val Gln Glu Leu Gly Leu Ala Ile Arg Glu Lys Ile Asn
        435                 440                 445

Pro Ile Cys Phe Ile Ile Asn Asn Asp Gly Tyr Thr Val Glu Arg Glu
    450                 455                 460

Ile His Gly Pro Asn Gln Ser Tyr Asn Asp Ile Pro Met Trp Asn Tyr
465                 470                 475                 480

Ser Lys Leu Pro Glu Ser Phe Gly Ala Thr Glu Asp Arg Val Val Ser
                485                 490                 495

Lys Ile Val Arg Thr Glu Asn Glu Phe Val Ser Val Met Lys Glu Ala
            500                 505                 510

Gln Ala Asp Pro Asn Arg Met Tyr Trp Ile Glu Leu Ile Leu Ala Lys
        515                 520                 525

Glu Gly Ala Pro Lys Val Leu Lys Lys Met Gly Lys Leu Phe Ala Glu
    530                 535                 540

Gln Asn Lys Ser
545


<210> SEQ ID NO 91
<211> LENGTH: 548
<212> TYPE: PRT
<213> ORGANISM: Listeria grayi

<400> SEQUENCE: 91

Met Tyr Thr Val Gly Gln Tyr Leu Val Asp Arg Leu Glu Glu Ile Gly
1               5                   10                  15

Ile Asp Lys Val Phe Gly Val Pro Gly Asp Tyr Asn Leu Thr Phe Leu
            20                  25                  30

Asp Tyr Ile Gln Asn His Glu Gly Leu Ser Trp Gln Gly Asn Thr Asn
        35                  40                  45

Glu Leu Asn Ala Ala Tyr Ala Ala Asp Gly Tyr Ala Arg Glu Arg Gly
    50                  55                  60

Val Ser Ala Leu Val Thr Thr Phe Gly Val Gly Glu Leu Ser Ala Ile
65                  70                  75                  80

Asn Gly Thr Ala Gly Ser Phe Ala Glu Gln Val Pro Val Ile His Ile
                85                  90                  95

Val Gly Ser Pro Thr Met Asn Val Gln Ser Asn Lys Lys Leu Val His
            100                 105                 110

His Ser Leu Gly Met Gly Asn Phe His Asn Phe Ser Glu Met Ala Lys
        115                 120                 125

Glu Val Thr Ala Ala Thr Thr Met Leu Thr Glu Glu Asn Ala Ala Ser
    130                 135                 140

Glu Ile Asp Arg Val Leu Glu Thr Ala Leu Leu Glu Lys Arg Pro Val
145                 150                 155                 160

Tyr Ile Asn Leu Pro Ile Asp Ile Ala His Lys Ala Ile Val Lys Pro
                165                 170                 175

Ala Lys Ala Leu Gln Thr Glu Lys Ser Ser Gly Glu Arg Glu Ala Gln
            180                 185                 190

Leu Ala Glu Ile Ile Leu Ser His Leu Glu Lys Ala Ala Gln Pro Ile
        195                 200                 205
```

```
Val Ile Ala Gly His Glu Ile Ala Arg Phe Gln Ile Arg Glu Arg Phe
    210                 215                 220

Glu Asn Trp Ile Asn Gln Thr Lys Leu Pro Val Thr Asn Leu Ala Tyr
225                 230                 235                 240

Gly Lys Gly Ser Phe Asn Glu Glu Asn Glu His Phe Ile Gly Thr Tyr
                245                 250                 255

Tyr Pro Ala Phe Ser Asp Lys Asn Val Leu Asp Tyr Val Asp Asn Ser
            260                 265                 270

Asp Phe Val Leu His Phe Gly Gly Lys Ile Ile Asp Asn Ser Thr Ser
        275                 280                 285

Ser Phe Ser Gln Gly Phe Lys Thr Glu Asn Thr Leu Thr Ala Ala Asn
    290                 295                 300

Asp Ile Ile Met Leu Pro Asp Gly Ser Thr Tyr Ser Gly Ile Ser Leu
305                 310                 315                 320

Asn Gly Leu Leu Ala Glu Leu Glu Lys Leu Asn Phe Thr Phe Ala Asp
                325                 330                 335

Thr Ala Ala Lys Gln Ala Glu Leu Ala Val Phe Glu Pro Gln Ala Glu
            340                 345                 350

Thr Pro Leu Lys Gln Asp Arg Phe His Gln Ala Val Met Asn Phe Leu
        355                 360                 365

Gln Ala Asp Asp Val Leu Val Thr Glu Gln Gly Thr Ser Ser Phe Gly
    370                 375                 380

Leu Met Leu Ala Pro Leu Lys Lys Gly Met Asn Leu Ile Ser Gln Thr
385                 390                 395                 400

Leu Trp Gly Ser Ile Gly Tyr Thr Leu Pro Ala Met Ile Gly Ser Gln
                405                 410                 415

Ile Ala Ala Pro Glu Arg Arg His Ile Leu Ser Ile Gly Asp Gly Ser
            420                 425                 430

Phe Gln Leu Thr Ala Gln Glu Met Ser Thr Ile Phe Arg Glu Lys Leu
        435                 440                 445

Thr Pro Val Ile Phe Ile Ile Asn Asn Asp Gly Tyr Thr Val Glu Arg
    450                 455                 460

Ala Ile His Gly Glu Asp Glu Ser Tyr Asn Asp Ile Pro Thr Trp Asn
465                 470                 475                 480

Leu Gln Leu Val Ala Glu Thr Phe Gly Gly Asp Ala Glu Thr Val Asp
                485                 490                 495

Thr His Asn Val Phe Thr Glu Thr Asp Phe Ala Asn Thr Leu Ala Ala
            500                 505                 510

Ile Asp Ala Thr Pro Gln Lys Ala His Val Val Glu Val His Met Glu
        515                 520                 525

Gln Met Asp Met Pro Glu Ser Leu Arg Gln Ile Gly Leu Ala Leu Ser
    530                 535                 540

Lys Gln Asn Ser
545


<210> SEQ ID NO 92
<211> LENGTH: 348
<212> TYPE: PRT
<213> ORGANISM: Achromobacter xyloxidans

<400> SEQUENCE: 92

Met Lys Ala Leu Val Tyr His Gly Asp His Lys Ile Ser Leu Glu Asp
1               5                   10                  15

Lys Pro Lys Pro Thr Leu Gln Lys Pro Thr Asp Val Val Val Arg Val
```

```
            20                  25                  30

Leu Lys Thr Thr Ile Cys Gly Thr Asp Leu Gly Ile Tyr Lys Gly Lys
        35                  40                  45

Asn Pro Glu Val Ala Asp Gly Arg Ile Leu Gly His Glu Gly Val Gly
    50                  55                  60

Val Ile Glu Glu Val Gly Glu Ser Val Thr Gln Phe Lys Lys Gly Asp
65                  70                  75                  80

Lys Val Leu Ile Ser Cys Val Thr Ser Cys Gly Ser Cys Asp Tyr Cys
                85                  90                  95

Lys Lys Gln Leu Tyr Ser His Cys Arg Asp Gly Gly Trp Ile Leu Gly
            100                 105                 110

Tyr Met Ile Asp Gly Val Gln Ala Glu Tyr Val Arg Ile Pro His Ala
        115                 120                 125

Asp Asn Ser Leu Tyr Lys Ile Pro Gln Thr Ile Asp Asp Glu Ile Ala
    130                 135                 140

Val Leu Leu Ser Asp Ile Leu Pro Thr Gly His Glu Ile Gly Val Gln
145                 150                 155                 160

Tyr Gly Asn Val Gln Pro Gly Asp Ala Val Ala Ile Val Gly Ala Gly
                165                 170                 175

Pro Val Gly Met Ser Val Leu Leu Thr Ala Gln Phe Tyr Ser Pro Ser
            180                 185                 190

Thr Ile Ile Val Ile Asp Met Asp Glu Asn Arg Leu Gln Leu Ala Lys
        195                 200                 205

Glu Leu Gly Ala Thr His Thr Ile Asn Ser Gly Thr Glu Asn Val Val
    210                 215                 220

Glu Ala Val His Arg Ile Ala Ala Glu Gly Val Asp Val Ala Ile Glu
225                 230                 235                 240

Ala Val Gly Ile Pro Ala Thr Trp Asp Ile Cys Gln Glu Ile Val Lys
                245                 250                 255

Pro Gly Ala His Ile Ala Asn Val Gly Val His Gly Val Lys Val Asp
            260                 265                 270

Phe Glu Ile Gln Lys Leu Trp Ile Lys Asn Leu Thr Ile Thr Thr Gly
        275                 280                 285

Leu Val Asn Thr Asn Thr Thr Pro Met Leu Met Lys Val Ala Ser Thr
    290                 295                 300

Asp Lys Leu Pro Leu Lys Lys Met Ile Thr His Arg Phe Glu Leu Ala
305                 310                 315                 320

Glu Ile Glu His Ala Tyr Gln Val Phe Leu Asn Gly Ala Lys Glu Lys
                325                 330                 335

Ala Met Lys Ile Ile Leu Ser Asn Ala Gly Ala Ala
            340                 345


<210> SEQ ID NO 93
<211> LENGTH: 375
<212> TYPE: PRT
<213> ORGANISM: Equus ferus caballus

<400> SEQUENCE: 93

Met Ser Thr Ala Gly Lys Val Ile Lys Cys Lys Ala Ala Val Leu Trp
1               5                   10                  15

Glu Glu Lys Lys Pro Phe Ser Ile Glu Glu Val Glu Val Ala Pro Pro
            20                  25                  30

Lys Ala His Glu Val Arg Ile Lys Met Val Ala Thr Gly Ile Cys Arg
        35                  40                  45
```

```
Ser Asp Asp His Val Val Ser Gly Thr Leu Val Thr Pro Leu Pro Val
    50                  55                  60

Ile Ala Gly His Glu Ala Ala Gly Ile Val Glu Ser Ile Gly Glu Gly
65                  70                  75                  80

Val Thr Thr Val Arg Pro Gly Asp Lys Val Ile Pro Leu Phe Thr Pro
                85                  90                  95

Gln Cys Gly Lys Cys Arg Val Cys Lys His Pro Glu Gly Asn Phe Cys
            100                 105                 110

Leu Lys Asn Asp Leu Ser Met Pro Arg Gly Thr Met Gln Asp Gly Thr
        115                 120                 125

Ser Arg Phe Thr Cys Arg Gly Lys Pro Ile His His Phe Leu Gly Thr
    130                 135                 140

Ser Thr Phe Ser Gln Tyr Thr Val Val Asp Glu Ile Ser Val Ala Lys
145                 150                 155                 160

Ile Asp Ala Ala Ser Pro Leu Glu Lys Val Cys Leu Ile Gly Cys Gly
                165                 170                 175

Phe Ser Thr Gly Tyr Gly Ser Ala Val Lys Val Ala Lys Val Thr Gln
            180                 185                 190

Gly Ser Thr Cys Ala Val Phe Gly Leu Gly Gly Val Gly Leu Ser Val
        195                 200                 205

Ile Met Gly Cys Lys Ala Ala Gly Ala Ala Arg Ile Ile Gly Val Asp
    210                 215                 220

Ile Asn Lys Asp Lys Phe Ala Lys Ala Lys Glu Val Gly Ala Thr Glu
225                 230                 235                 240

Cys Val Asn Pro Gln Asp Tyr Lys Lys Pro Ile Gln Glu Val Leu Thr
                245                 250                 255

Glu Met Ser Asn Gly Gly Val Asp Phe Ser Phe Glu Val Ile Gly Arg
            260                 265                 270

Leu Asp Thr Met Val Thr Ala Leu Ser Cys Cys Gln Glu Ala Tyr Gly
        275                 280                 285

Val Ser Val Ile Val Gly Val Pro Pro Asp Ser Gln Asn Leu Ser Met
    290                 295                 300

Asn Pro Met Leu Leu Leu Ser Gly Arg Thr Trp Lys Gly Ala Ile Phe
305                 310                 315                 320

Gly Gly Phe Lys Ser Lys Asp Ser Val Pro Lys Leu Val Ala Asp Phe
                325                 330                 335

Met Ala Lys Lys Phe Ala Leu Asp Pro Leu Ile Thr His Val Leu Pro
            340                 345                 350

Phe Glu Lys Ile Asn Glu Gly Phe Asp Leu Leu Arg Ser Gly Glu Ser
        355                 360                 365

Ile Arg Thr Ile Leu Thr Phe
    370                 375
```

<210> SEQ ID NO 94
<211> LENGTH: 347
<212> TYPE: PRT
<213> ORGANISM: Beijerinckia indica

<400> SEQUENCE: 94

```
Met Lys Ala Leu Val Tyr Arg Gly Pro Gly Gln Lys Leu Val Glu Glu
1               5                   10                  15

Arg Gln Lys Pro Glu Leu Lys Glu Pro Gly Asp Ala Ile Val Lys Val
            20                  25                  30

Thr Lys Thr Thr Ile Cys Gly Thr Asp Leu His Ile Leu Lys Gly Asp
        35                  40                  45
```

```
Val Ala Thr Cys Lys Pro Gly Arg Val Leu Gly His Glu Gly Val Gly
    50                  55                  60

Val Ile Glu Ser Val Gly Ser Gly Val Thr Ala Phe Gln Pro Gly Asp
65                  70                  75                  80

Arg Val Leu Ile Ser Cys Ile Ser Ser Cys Gly Lys Cys Ser Phe Cys
                85                  90                  95

Arg Arg Gly Met Phe Ser His Cys Thr Thr Gly Gly Trp Ile Leu Gly
            100                 105                 110

Asn Glu Ile Asp Gly Thr Gln Ala Glu Tyr Val Arg Val Pro His Ala
        115                 120                 125

Asp Thr Ser Leu Tyr Arg Ile Pro Ala Gly Ala Asp Glu Glu Ala Leu
    130                 135                 140

Val Met Leu Ser Asp Ile Leu Pro Thr Gly Phe Glu Cys Gly Val Leu
145                 150                 155                 160

Asn Gly Lys Val Ala Pro Gly Ser Ser Val Ala Ile Val Gly Ala Gly
                165                 170                 175

Pro Val Gly Leu Ala Ala Leu Leu Thr Ala Gln Phe Tyr Ser Pro Ala
            180                 185                 190

Glu Ile Ile Met Ile Asp Leu Asp Asp Asn Arg Leu Gly Leu Ala Lys
        195                 200                 205

Gln Phe Gly Ala Thr Arg Thr Val Asn Ser Thr Gly Gly Asn Ala Ala
    210                 215                 220

Ala Glu Val Lys Ala Leu Thr Glu Gly Leu Gly Val Asp Thr Ala Ile
225                 230                 235                 240

Glu Ala Val Gly Ile Pro Ala Thr Phe Glu Leu Cys Gln Asn Ile Val
                245                 250                 255

Ala Pro Gly Gly Thr Ile Ala Asn Val Gly Val His Gly Ser Lys Val
            260                 265                 270

Asp Leu His Leu Glu Ser Leu Trp Ser His Asn Val Thr Ile Thr Thr
        275                 280                 285

Arg Leu Val Asp Thr Ala Thr Thr Pro Met Leu Leu Lys Thr Val Gln
    290                 295                 300

Ser His Lys Leu Asp Pro Ser Arg Leu Ile Thr His Arg Phe Ser Leu
305                 310                 315                 320

Asp Gln Ile Leu Asp Ala Tyr Glu Thr Phe Gly Gln Ala Ala Ser Thr
                325                 330                 335

Gln Ala Leu Lys Val Ile Ile Ser Met Glu Ala
            340                 345
```

<210> SEQ ID NO 95
<211> LENGTH: 4519
<212> TYPE: DNA
<213> ORGANISM: Artificial Sequence
<220> FEATURE:
<223> OTHER INFORMATION: pLA54

<400> SEQUENCE: 95

```
caccttggct aactcgttgt atcatcactg gataacttcg tataatgtat gctatacgaa     60

gttatcgaac agagaaacta aatccacatt aattgagagt tctatctatt agaaaatgca    120

aactccaact aaatgggaaa acagataacc tcttttattt ttttttaatg tttgatattc    180

gagtcttttt cttttgttag gtttatattc atcatttcaa tgaataaaag aagcttctta    240

ttttggttgc aaagaatgaa aaaaaaggat tttttcatac ttctaaagct tcaattataa    300

ccaaaaattt tataaatgaa gagaaaaaat ctagtagtat caagttaaac ttagaaaaac    360
```

```
tcatcgagca tcaaatgaaa ctgcaattta ttcatatcag gattatcaat accatatttt    420
tgaaaaagcc gtttctgtaa tgaaggagaa aactcaccga ggcagttcca taggatggca    480
agatcctggt atcggtctgc gattccgact cgtccaacat caatacaacc tattaatttc    540
ccctcgtcaa aaataaggtt atcaagtgag aaatcaccat gagtgacgac tgaatccggt    600
gagaatggca aaagcttatg catttctttc cagacttgtt caacaggcca gccattacgc    660
tcgtcatcaa aatcactcgc atcaaccaaa ccgttattca ttcgtgattg cgcctgagcg    720
agacgaaata cgcgatcgct gttaaaagga caattacaaa caggaatcga atgcaaccgg    780
cgcaggaaca ctgccagcgc atcaacaata ttttcacctg aatcaggata ttcttctaat    840
acctggaatg ctgttttgcc ggggatcgca gtggtgagta accatgcatc atcaggagta    900
cggataaaat gcttgatggt cggaagaggc ataaattccg tcagccagtt tagtctgacc    960
atctcatctg taacatcatt ggcaacgcta cctttgccat gtttcagaaa caactctggc   1020
gcatcgggct tcccatacaa tcgatagatt gtcgcacctg attgcccgac attatcgcga   1080
gcccatttat acccatataa atcagcatcc atgttggaat ttaatcgcgg cctcgaaacg   1140
tgagtctttt ccttacccat ctcgagtttt aatgttactt ctcttgcagt tagggaacta   1200
taatgtaact caaaataaga ttaaacaaac taaaataaaa agaagttata cagaaaaacc   1260
catataaacc agtactaatc cataataata atacacaaaa aaactatcaa ataaaaccag   1320
aaaacagatt gaatagaaaa atttttcga tctcctttta tattcaaaat tcgatatatg    1380
aaaaagggaa ctctcagaaa atcaccaaat caatttaatt agatttttct tttccttcta   1440
gcgttggaaa gaaaaatttt tctttttttt tttagaaatg aaaaattttt gccgtaggaa   1500
tcaccgtata aaccctgtat aaacgctact ctgttcacct gtgtaggcta tgattgaccc   1560
agtgttcatt gttattgcga gagagcggga gaaaagaacc gatacaagag atccatgctg   1620
gtatagttgt ctgtccaaca ctttgatgaa cttgtaggac gatgatgtgt atttagacga   1680
gtacgtgtgt gactattaag tagttatgat agagaggttt gtacggtgtg ttctgtgtaa   1740
ttcgattgag aaaatggtta tgaatcccta gataacttcg tataatgtat gctatacgaa   1800
gttatctgaa cattagaata cgtaatccgc aatgcgggga tcctctagag tcgacctgca   1860
ggcatgcaag cttggcgtaa tcatggtcat agctgtttcc tgtgtgaaat tgttatccgc   1920
tcacaattcc acacaacata cgagccggaa gcataaagtg taaagcctgg ggtgcctaat   1980
gagtgagcta actcacatta attgcgttgc gctcactgcc cgctttccag tcgggaaacc   2040
tgtcgtgcca gctgcattaa tgaatcggcc aacgcgcggg gagaggcggt ttgcgtattg   2100
ggcgctcttc cgcttcctcg ctcactgact cgctgcgctc ggtcgttcgg ctgcggcgag   2160
cggtatcagc tcactcaaag gcggtaatac ggttatccac agaatcaggg gataacgcag   2220
gaaagaacat gtgagcaaaa ggccagcaaa aggccaggaa ccgtaaaaag gccgcgttgc   2280
tggcgttttt ccataggctc cgcccccctg acgagcatca caaaaatcga cgctcaagtc   2340
agaggtggcg aaacccgaca ggactataaa gataccaggc gtttccccct ggaagctccc   2400
tcgtgcgctc tcctgttccg accctgccgc ttaccggata cctgtccgcc tttctccctt   2460
cgggaagcgt ggcgctttct catagctcac gctgtaggta tctcagttcg gtgtaggtcg   2520
ttcgctccaa gctgggctgt gtgcacgaac cccccgttca gcccgaccgc tgcgccttat   2580
ccggtaacta tcgtcttgag tccaacccgg taagacacga cttatcgcca ctggcagcag   2640
ccactggtaa caggattagc agagcgaggt atgtaggcgg tgctacagag ttcttgaagt   2700
```

```
ggtggcctaa ctacggctac actagaagga cagtatttgg tatctgcgct ctgctgaagc   2760

cagttacctt cggaaaaaga gttggtagct cttgatccgg caaacaaacc accgctggta   2820

gcggtggttt ttttgtttgc aagcagcaga ttacgcgcag aaaaaaagga tctcaagaag   2880

atcctttgat cttttctacg gggtctgacg ctcagtggaa cgaaaactca cgttaaggga   2940

ttttggtcat gagattatca aaaaggatct tcacctagat ccttttaaat taaaaatgaa   3000

gttttaaatc aatctaaagt atatatgagt aaacttggtc tgacagttac caatgcttaa   3060

tcagtgaggc acctatctca gcgatctgtc tatttcgttc atccatagtt gcctgactcc   3120

ccgtcgtgta gataactacg atacgggagg gcttaccatc tggccccagt gctgcaatga   3180

taccgcgaga cccacgctca ccggctccag atttatcagc aataaaccag ccagccggaa   3240

gggccgagcg cagaagtggt cctgcaactt tatccgcctc catccagtct attaattgtt   3300

gccgggaagc tagagtaagt agttcgccag ttaatagttt gcgcaacgtt gttgccattg   3360

ctacaggcat cgtggtgtca cgctcgtcgt ttggtatggc ttcattcagc tccggttccc   3420

aacgatcaag gcgagttaca tgatccccca tgttgtgcaa aaaagcggtt agctccttcg   3480

gtcctccgat cgttgtcaga agtaagttgg ccgcagtgtt atcactcatg gttatggcag   3540

cactgcataa ttctcttact gtcatgccat ccgtaagatg cttttctgtg actggtgagt   3600

actcaaccaa gtcattctga gaatagtgta tgcggcgacc gagttgctct tgcccggcgt   3660

caatacggga taataccgcg ccacatagca gaactttaaa agtgctcatc attggaaaac   3720

gttcttcggg gcgaaaactc tcaaggatct taccgctgtt gagatccagt tcgatgtaac   3780

ccactcgtgc acccaactga tcttcagcat cttttacttt caccagcgtt tctgggtgag   3840

caaaaacagg aaggcaaaat gccgcaaaaa agggaataag ggcgacacgg aaatgttgaa   3900

tactcatact cttccttttt caatattatt gaagcattta tcagggttat tgtctcatga   3960

gcggatacat atttgaatgt atttagaaaa ataaacaaat aggggttccg cgcacatttc   4020

cccgaaaagt gccacctgac gtctaagaaa ccattattat catgacatta acctataaaa   4080

ataggcgtat cacgaggccc tttcgtctcg cgcgtttcgg tgatgacggt gaaaacctct   4140

gacacatgca gctcccggag acggtcacag cttgtctgta agcggatgcc gggagcagac   4200

aagcccgtca gggcgcgtca gcgggtgttg gcgggtgtcg gggctggctt aactatgcgg   4260

catcagagca gattgtactg agagtgcacc atatgcggtg tgaaataccg cacagatgcg   4320

taaggagaaa ataccgcatc aggcgccatt cgccattcag gctgcgcaac tgttgggaag   4380

ggcgatcggt gcgggcctct tcgctattac gccagctggc gaaaggggga tgtgctgcaa   4440

ggcgattaag ttgggtaacg ccagggtttt cccagtcacg acgttgtaaa acgacggcca   4500

gtgaattcga gctcggtac                                                4519
```

```
<210> SEQ ID NO 96
<211> LENGTH: 80
<212> TYPE: DNA
<213> ORGANISM: Artificial Sequence
<220> FEATURE:
<223> OTHER INFORMATION: BK505

<400> SEQUENCE: 96

ttccggtttc tttgaaattt ttttgattcg gtaatctccg agcagaagga gcattgcgga     60

ttacgtattc taatgttcag                                                 80


<210> SEQ ID NO 97
<211> LENGTH: 81
```

<212> TYPE: DNA
<213> ORGANISM: Artificial Sequence
<220> FEATURE:
<223> OTHER INFORMATION: BK506

<400> SEQUENCE: 97
gggtaataac tgatataatt aaattgaagc tctaatttgt gagtttagta caccttggct 60
aactcgttgt atcatcactg g 81

<210> SEQ ID NO 98
<211> LENGTH: 38
<212> TYPE: DNA
<213> ORGANISM: Artificial Sequence
<220> FEATURE:
<223> OTHER INFORMATION: LA468

<400> SEQUENCE: 98
gcctcgagtt ttaatgttac ttctcttgca gttaggga 38

<210> SEQ ID NO 99
<211> LENGTH: 31
<212> TYPE: DNA
<213> ORGANISM: Artificial Sequence
<220> FEATURE:
<223> OTHER INFORMATION: LA492

<400> SEQUENCE: 99
gctaaattcg agtgaaacac aggaagacca g 31

<210> SEQ ID NO 100
<211> LENGTH: 23
<212> TYPE: DNA
<213> ORGANISM: Artificial Sequence
<220> FEATURE:
<223> OTHER INFORMATION: AK109-1

<400> SEQUENCE: 100
agtcacatca agatcgttta tgg 23

<210> SEQ ID NO 101
<211> LENGTH: 23
<212> TYPE: DNA
<213> ORGANISM: Artificial Sequence
<220> FEATURE:
<223> OTHER INFORMATION: AK109-2

<400> SEQUENCE: 101
gcacggaata tgggactact tcg 23

<210> SEQ ID NO 102
<211> LENGTH: 23
<212> TYPE: DNA
<213> ORGANISM: Artificial Sequence
<220> FEATURE:
<223> OTHER INFORMATION: AK109-3

<400> SEQUENCE: 102
actccacttc aagtaagagt ttg 23

<210> SEQ ID NO 103
<211> LENGTH: 24
<212> TYPE: DNA
<213> ORGANISM: Artificial Sequence
<220> FEATURE:
<223> OTHER INFORMATION: oBP452

<400> SEQUENCE: 103
ttctcgacgt gggccttttt cttg 24

<210> SEQ ID NO 104
<211> LENGTH: 49
<212> TYPE: DNA
<213> ORGANISM: Artificial Sequence
<220> FEATURE:
<223> OTHER INFORMATION: oBP453

<400> SEQUENCE: 104
tgcagcttta aataatcggt gtcactactt tgccttcgtt tatcttgcc 49

<210> SEQ ID NO 105
<211> LENGTH: 49
<212> TYPE: DNA
<213> ORGANISM: Artificial Sequence
<220> FEATURE:
<223> OTHER INFORMATION: oBP454

<400> SEQUENCE: 105
gagcaggcaa gataaacgaa ggcaaagtag tgacaccgat tatttaaag 49

<210> SEQ ID NO 106
<211> LENGTH: 49
<212> TYPE: DNA
<213> ORGANISM: Artificial Sequence
<220> FEATURE:
<223> OTHER INFORMATION: oBP455

<400> SEQUENCE: 106
tatggaccct gaaaccacag ccacattgta accaccacga cggttgttg 49

<210> SEQ ID NO 107
<211> LENGTH: 49
<212> TYPE: DNA
<213> ORGANISM: Artificial Sequence
<220> FEATURE:
<223> OTHER INFORMATION: oBP457

<400> SEQUENCE: 107
tttagcaaca accgtcgtgg tggttacaat gtggctgtgg tttcagggt 49

<210> SEQ ID NO 108
<211> LENGTH: 49
<212> TYPE: DNA
<213> ORGANISM: Artificial Sequence
<220> FEATURE:
<223> OTHER INFORMATION: oBP457

<400> SEQUENCE: 108
ccagaaaccc tatacctgtg tggacgtaag gccatgaagc tttttcttt 49

<210> SEQ ID NO 109
<211> LENGTH: 49
<212> TYPE: DNA
<213> ORGANISM: Artificial Sequence
<220> FEATURE:
<223> OTHER INFORMATION: oBP458

<400> SEQUENCE: 109
attggaaaga aaaagcttca tggccttacg tccacacagg tatagggtt 49

<210> SEQ ID NO 110
<211> LENGTH: 22

<212> TYPE: DNA
<213> ORGANISM: Artificial Sequence
<220> FEATURE:
<223> OTHER INFORMATION: oBP459

<400> SEQUENCE: 110
cataagaaca cctttggtgg ag 22

<210> SEQ ID NO 111
<211> LENGTH: 22
<212> TYPE: DNA
<213> ORGANISM: Artificial Sequence
<220> FEATURE:
<223> OTHER INFORMATION: oBP460

<400> SEQUENCE: 111
aggattatca ttcataagtt tc 22

<210> SEQ ID NO 112
<211> LENGTH: 20
<212> TYPE: DNA
<213> ORGANISM: Artificial Sequence
<220> FEATURE:
<223> OTHER INFORMATION: LA135

<400> SEQUENCE: 112
cttggcagca acaggactag 20

<210> SEQ ID NO 113
<211> LENGTH: 23
<212> TYPE: DNA
<213> ORGANISM: Artificial Sequence
<220> FEATURE:
<223> OTHER INFORMATION: oBP461

<400> SEQUENCE: 113
ttcttggagc tgggacatgt ttg 23

<210> SEQ ID NO 114
<211> LENGTH: 22
<212> TYPE: DNA
<213> ORGANISM: Artificial Sequence
<220> FEATURE:
<223> OTHER INFORMATION: LA92

<400> SEQUENCE: 114
gagaagatgc ggccagcaaa ac 22

<210> SEQ ID NO 115
<211> LENGTH: 4242
<212> TYPE: DNA
<213> ORGANISM: Artificial Sequence
<220> FEATURE:
<223> OTHER INFORMATION: pLA59

<400> SEQUENCE: 115
aaacgccagc aacgcggcct ttttacggtt cctggccttt tgctggcctt ttgctcacat 60
gttctttcct gcgttatccc ctgattctgt ggataaccgt attaccgcct ttgagtgagc 120
tgataccgct cgccgcagcc gaacgaccga gcgcagcgag tcagtgagcg aggaagcgga 180
agagcgccca atacgcaaac cgcctctccc cgcgcgttgg ccgattcatt aatgcagctg 240
gcacgacagg tttcccgact ggaaagcggg cagtgagcgc aacgcaatta atgtgagtta 300
gctcactcat taggcacccc aggctttaca ctttatgctt ccggctcgta tgttgtgtgg 360

```
aattgtgagc ggataacaat ttcacacagg aaacagctat gaccatgatt acgccaagct    420
tgcatgcctg caggtcgact ctagaggatc cgcaatgcgg atccgcattg cggattacgt    480
attctaatgt tcagtaccgt tcgtataatg tatgctatac gaagttatgc agattgtact    540
gagagtgcac cataccacct tttcaattca tcattttttt tttattcttt tttttgattt    600
cggtttcctt gaaatttttt tgattcggta atctccgaac agaaggaaga acgaaggaag    660
gagcacagac ttagattggt atatatacgc atatgtagtg ttgaagaaac atgaaattgc    720
ccagtattct taacccaact gcacagaaca aaaacctgca ggaaacgaag ataaatcatg    780
tcgaaagcta catataagga acgtgctgct actcatccta gtcctgttgc tgccaagcta    840
tttaatatca tgcacgaaaa gcaaacaaac ttgtgtgctt cattggatgt tcgtaccacc    900
aaggaattac tggagttagt tgaagcatta ggtcccaaaa tttgtttact aaaaacacat    960
gtggatatct tgactgattt ttccatggag ggcacagtta agccgctaaa ggcattatcc   1020
gccaagtaca atttttttact cttcgaagac agaaaatttg ctgacattgg taatacagtc   1080
aaattgcagt actctgcggg tgtatacaga atagcagaat gggcagacat tacgaatgca   1140
cacggtgtgg tgggcccagg tattgttagc ggtttgaagc aggcggcaga agaagtaaca   1200
aaggaaccta gaggcctttt gatgttagca gaattgtcat gcaagggctc cctatctact   1260
ggagaatata ctaagggtac tgttgacatt gcgaagagcg acaaagattt tgttatcggc   1320
tttattgctc aaagagacat gggtggaaga gatgaaggtt acgattggtt gattatgaca   1380
cccggtgtgg gtttagatga caagggagac gcattgggtc aacagtatag aaccgtggat   1440
gatgtggtct ctacaggatc tgacattatt attgttggaa gaggactatt tgcaaaggga   1500
agggatgcta aggtagaggg tgaacgttac agaaaagcag gctgggaagc atatttgaga   1560
agatgcggcc agcaaaacta aaaaactgta ttataagtaa atgcatgtat actaaactca   1620
caaattagag cttcaattta attatatcag ttattaccct atgcggtgtg aaataccgca   1680
cagatgcgta aggagaaaat accgcatcag gaaattgtaa acgttaatat tttgttaaaa   1740
ttcgcgttaa atttttgtta aatcagctca ttttttaacc aataggccga aatcggcaaa   1800
atcccttata aatcaaaaga atagaccgag atagggttga gtgttgttcc agtttggaac   1860
aagagtccac tattaaagaa cgtggactcc aacgtcaaag ggcgaaaaac cgtctatcag   1920
ggcgatggcc cactacgtga accatcaccc taatcaagat aacttcgtat aatgtatgct   1980
atacgaacgg taccagtgat gatacaacga gttagccaag gtgaattcac tggccgtcgt   2040
tttacaacgt cgtgactggg aaaaccctgg cgttacccaa cttaatcgcc ttgcagcaca   2100
tccccctttc gccagctggc gtaatagcga agaggcccgc accgatcgcc cttcccaaca   2160
gttgcgcagc ctgaatggcg aatggcgcct gatgcggtat tttctcctta cgcatctgtg   2220
cggtatttca caccgcatat ggtgcactct cagtacaatc tgctctgatg ccgcatagtt   2280
aagccagccc cgacacccgc caacacccgc tgacgcgccc tgacgggctt gtctgctccc   2340
ggcatccgct tacagacaag ctgtgaccgt ctccgggagc tgcatgtgtc agaggttttc   2400
accgtcatca ccgaaacgcg cgagacgaaa gggcctcgtg atacgcctat ttttataggt   2460
taatgtcatg ataataatgg tttcttagac gtcaggtggc acttttcggg gaaatgtgcg   2520
cggaacccct atttgtttat ttttctaaat acattcaaat atgtatccgc tcatgagaca   2580
ataaccctga taaatgcttc aataatattg aaaaaggaag agtatgagta ttcaacattt   2640
ccgtgtcgcc cttattccct tttttgcggc attttgcctt cctgtttttg ctcacccaga   2700
aacgctggtg aaagtaaaag atgctgaaga tcagttgggt gcacgagtgg gttacatcga   2760
```

```
actggatctc aacagcggta agatccttga gagttttcgc cccgaagaac gttttccaat   2820

gatgagcact tttaaagttc tgctatgtgg cgcggtatta tcccgtattg acgccgggca   2880

agagcaactc ggtcgccgca tacactattc tcagaatgac ttggttgagt actcaccagt   2940

cacagaaaag catcttacgg atggcatgac agtaagagaa ttatgcagtg ctgccataac   3000

catgagtgat aacactgcgg ccaacttact tctgacaacg atcggaggac cgaaggagct   3060

aaccgctttt ttgcacaaca tgggggatca tgtaactcgc cttgatcgtt gggaaccgga   3120

gctgaatgaa gccataccaa acgacgagcg tgacaccacg atgcctgtag caatggcaac   3180

aacgttgcgc aaactattaa ctggcgaact acttactcta gcttcccggc aacaattaat   3240

agactggatg gaggcggata aagttgcagg accacttctg cgctcggccc ttccggctgg   3300

ctggtttatt gctgataaat ctggagccgg tgagcgtggg tctcgcggta tcattgcagc   3360

actggggcca gatggtaagc cctcccgtat cgtagttatc tacacgacgg ggagtcaggc   3420

aactatggat gaacgaaata gacagatcgc tgagataggt gcctcactga ttaagcattg   3480

gtaactgtca gaccaagttt actcatatat actttagatt gatttaaaac ttcattttta   3540

atttaaaagg atctaggtga agatcctttt tgataatctc atgaccaaaa tcccttaacg   3600

tgagttttcg ttccactgag cgtcagaccc cgtagaaaag atcaaaggat cttcttgaga   3660

tccttttttt ctgcgcgtaa tctgctgctt gcaaacaaaa aaaccaccgc taccagcggt   3720

ggtttgtttg ccggatcaag agctaccaac tctttttccg aaggtaactg gcttcagcag   3780

agcgcagata ccaaatactg tccttctagt gtagccgtag ttaggccacc acttcaagaa   3840

ctctgtagca ccgcctacat acctcgctct gctaatcctg ttaccagtgg ctgctgccag   3900

tggcgataag tcgtgtctta ccgggttgga ctcaagacga tagttaccgg ataaggcgca   3960

gcggtcgggc tgaacggggg gttcgtgcac acagcccagc ttggagcgaa cgacctacac   4020

cgaactgaga tacctacagc gtgagctatg agaaagcgcc acgcttcccg aagggagaaa   4080

ggcggacagg tatccggtaa gcggcagggt cggaacagga gagcgcacga gggagcttcc   4140

agggggaaac gcctggtatc tttatagtcc tgtcgggttt cgccacctct gacttgagcg   4200

tcgatttttg tgatgctcgt caggggggcg gagcctatgg aa                      4242
```

<210> SEQ ID NO 116
<211> LENGTH: 80
<212> TYPE: DNA
<213> ORGANISM: Artificial Sequence
<220> FEATURE:
<223> OTHER INFORMATION: LA678

<400> SEQUENCE: 116

```
caacgttaac accgttttcg gtttgccagg tgacttcaac ttgtccttgt gcattgcgga     60

ttacgtattc taatgttcag                                                 80
```

<210> SEQ ID NO 117
<211> LENGTH: 81
<212> TYPE: DNA
<213> ORGANISM: Artificial Sequence
<220> FEATURE:
<223> OTHER INFORMATION: LA679

<400> SEQUENCE: 117

```
gtggagcatc gaagactggc aacatgattt caatcattct gatcttagag caccttggct     60

aactcgttgt atcatcactg g                                               81
```

<210> SEQ ID NO 118
<211> LENGTH: 23
<212> TYPE: DNA
<213> ORGANISM: Artificial Sequence
<220> FEATURE:
<223> OTHER INFORMATION: LA337

<400> SEQUENCE: 118
ctcatttgaa tcagcttatg gtg 23

<210> SEQ ID NO 119
<211> LENGTH: 24
<212> TYPE: DNA
<213> ORGANISM: Artificial Sequence
<220> FEATURE:
<223> OTHER INFORMATION: LA692

<400> SEQUENCE: 119
ggaagtcatt gacaccatct tggc 24

<210> SEQ ID NO 120
<211> LENGTH: 24
<212> TYPE: DNA
<213> ORGANISM: Artificial Sequence
<220> FEATURE:
<223> OTHER INFORMATION: LA693

<400> SEQUENCE: 120
agaagctggg acagcagcgt tagc 24

<210> SEQ ID NO 121
<211> LENGTH: 7523
<212> TYPE: DNA
<213> ORGANISM: Artificial Sequence
<220> FEATURE:
<223> OTHER INFORMATION: pLA34

<400> SEQUENCE: 121
ccagcttttg ttccctttag tgagggttaa ttgcgcgctt ggcgtaatca tggtcatagc 60
tgtttcctgt gtgaaattgt tatccgctca caattccaca caacatagga gccggaagca 120
taaagtgtaa agcctggggt gcctaatgag tgaggtaact cacattaatt gcgttgcgct 180
cactgcccgc tttccagtcg ggaaacctgt cgtgccagct gcattaatga atcggccaac 240
gcgcggggag aggcggtttg cgtattgggc gctcttccgc ttcctcgctc actgactcgc 300
tgcgctcggt cgttcggctg cggcgagcgg tatcagctca ctcaaaggcg gtaatacggt 360
tatccacaga atcaggggat aacgcaggaa agaacatgtg agcaaaaggc cagcaaaagg 420
ccaggaaccg taaaaaggcc gcgttgctgg cgtttttcca taggctccgc ccccctgacg 480
agcatcacaa aaatcgacgc tcaagtcaga ggtggcgaaa cccgacagga ctataaagat 540
accaggcgtt tccccctgga agctccctcg tgcgctctcc tgttccgacc ctgccgctta 600
ccggatacct gtccgccttt ctcccttcgg gaagcgtggc gctttctcat agctcacgct 660
gtaggtatct cagttcggtg taggtcgttc gctccaagct gggctgtgtg cacgaacccc 720
ccgttcagcc cgaccgctgc gccttatccg gtaactatcg tcttgagtcc aacccggtaa 780
gacacgactt atcgccactg gcagcagcca ctggtaacag gattagcaga gcgaggtatg 840
taggcggtgc tacagagttc ttgaagtggt ggcctaacta cggctacact agaaggacag 900
tatttggtat ctgcgctctg ctgaagccag ttaccttcgg aaaaagagtt ggtagctctt 960
gatccggcaa acaaaccacc gctggtagcg gtggtttttt tgtttgcaag cagcagatta 1020

```
cgcgcagaaa aaaaggatct caagaagatc ctttgatctt ttctacgggg tctgacgctc   1080
agtggaacga aaactcacgt taagggattt tggtcatgag attatcaaaa aggatcttca   1140
cctagatcct tttaaattaa aaatgaagtt ttaaatcaat ctaaagtata tatgagtaaa   1200
cttggtctga cagttaccaa tgcttaatca gtgaggcacc tatctcagcg atctgtctat   1260
ttcgttcatc catagttgcc tgactccccg tcgtgtagat aactacgata cgggagggct   1320
taccatctgg ccccagtgct gcaatgatac cgcgagaccc acgctcaccg gctccagatt   1380
tatcagcaat aaaccagcca gccggaaggg ccgagcgcag aagtggtcct gcaactttat   1440
ccgcctccat ccagtctatt aattgttgcc gggaagctag agtaagtagt tcgccagtta   1500
atagtttgcg caacgttgtt gccattgcta caggcatcgt ggtgtcacgc tcgtcgtttg   1560
gtatggcttc attcagctcc ggttcccaac gatcaaggcg agttacatga tcccccatgt   1620
tgtgcaaaaa agcggttagc tccttcggtc ctccgatcgt tgtcagaagt aagttggccg   1680
cagtgttatc actcatggtt atggcagcac tgcataattc tcttactgtc atgccatccg   1740
taagatgctt ttctgtgact ggtgagtact caaccaagtc attctgagaa tagtgtatgc   1800
ggcgaccgag ttgctcttgc ccggcgtcaa tacgggataa taccgcgcca catagcagaa   1860
ctttaaaagt gctcatcatt ggaaaacgtt cttcggggcg aaaactctca aggatcttac   1920
cgctgttgag atccagttcg atgtaaccca ctcgtgcacc caactgatct tcagcatctt   1980
ttactttcac cagcgtttct gggtgagcaa aaacaggaag gcaaaatgcc gcaaaaaagg   2040
gaataagggc gacacggaaa tgttgaatac tcatactctt cctttttcaa tattattgaa   2100
gcatttatca gggttattgt ctcatgagcg gatacatatt tgaatgtatt tagaaaaata   2160
aacaaatagg ggttccgcgc acatttcccc gaaaagtgcc acctgaacga agcatctgtg   2220
cttcattttg tagaacaaaa atgcaacgcg agagcgctaa tttttcaaac aaagaatctg   2280
agctgcattt ttacagaaca gaaatgcaac gcgaaagcgc tattttacca acgaagaatc   2340
tgtgcttcat ttttgtaaaa caaaaatgca acgcgagagc gctaattttt caaacaaaga   2400
atctgagctg catttttaca gaacagaaat gcaacgcgag agcgctattt taccaacaaa   2460
gaatctatac ttcttttttg ttctacaaaa atgcatcccg agagcgctat ttttctaaca   2520
aagcatctta gattactttt tttctccttt gtgcgctcta taatgcagtc tcttgataac   2580
tttttgcact gtaggtccgt taaggttaga agaaggctac tttggtgtct attttctctt   2640
ccataaaaaa agcctgactc cacttcccgc gtttactgat tactagcgaa gctgcgggtg   2700
catttttttca agataaaggc atccccgatt atattctata ccgatgtgga ttgcgcatac   2760
tttgtgaaca gaaagtgata gcgttgatga ttcttcattg gtcagaaaat tatgaacggt   2820
ttcttctatt ttgtctctat atactacgta taggaaatgt ttacattttc gtattgtttt   2880
cgattcactc tatgaatagt tcttactaca atttttttgt ctaaagagta atactagaga   2940
taaacataaa aaatgtagag gtcgagttta gatgcaagtt caaggagcga aaggtggatg   3000
ggtaggttat atagggatat agcacagaga tatatagcaa agagatactt ttgagcaatg   3060
tttgtggaag cggtattcgc aatattttag tagctcgtta cagtccggtg cgtttttggt   3120
tttttgaaag tgcgtcttca gagcgctttt ggttttcaaa agcgctctga agttcctata   3180
ctttctagag aataggaact tcggaatagg aacttcaaag cgtttccgaa aacgagcgct   3240
tccgaaaatg caacgcgagc tgcgcacata cagctcactg ttcacgtcgc acctatatct   3300
gcgtgttgcc tgtatatata tatacatgag aagaacggca tagtgcgtgt ttatgcttaa   3360
```

```
atgcgtactt atatgcgtct atttatgtag gatgaaaggt agtctagtac ctcctgtgat   3420
attatcccat tccatgcggg gtatcgtatg cttccttcag cactaccctt tagctgttct   3480
atatgctgcc actcctcaat tggattagtc tcatccttca atgctatcat ttcctttgat   3540
attggatcat ctaagaaacc attattatca tgacattaac ctataaaaat aggcgtatca   3600
cgaggccctt tcgtctcgcg cgtttcggtg atgacggtga aaacctctga cacatgcagc   3660
tcccggagac ggtcacagct tgtctgtaag cggatgccgg gagcagacaa gcccgtcagg   3720
gcgcgtcagc gggtgttggc gggtgtcggg gctggcttaa ctatgcggca tcagagcaga   3780
ttgtactgag agtgcaccat aaattcccgt tttaagagct tggtgagcgc taggagtcac   3840
tgccaggtat cgtttgaaca cggcattagt cagggaagtc ataacacagt cctttcccgc   3900
aattttcttt ttctattact cttggcctcc tctagtacac tctatatttt tttatgcctc   3960
ggtaatgatt ttcatttttt tttttcccct agcggatgac tctttttttt tcttagcgat   4020
tggcattatc acataatgaa ttatacatta tataaagtaa tgtgatttct tcgaagaata   4080
tactaaaaaa tgagcaggca agataaacga aggcaaagat gacagagcag aaagccctag   4140
taaagcgtat tacaaatgaa accaagattc agattgcgat ctctttaaag ggtggtcccc   4200
tagcgataga gcactcgatc ttcccagaaa aagaggcaga agcagtagca gaacaggcca   4260
cacaatcgca agtgattaac gtccacacag gtatagggtt tctggaccat atgatacatg   4320
ctctggccaa gcattccggc tggtcgctaa tcgttgagtg cattggtgac ttacacatag   4380
acgaccatca caccactgaa gactgcggga ttgctctcgg tcaagctttt aaagaggccc   4440
tactggcgcg tggagtaaaa aggtttggat caggatttgc gcctttggat gaggcacttt   4500
ccagagcggt ggtagatctt tcgaacaggc cgtacgcagt tgtcgaactt ggtttgcaaa   4560
gggagaaagt aggagatctc tcttgcgaga tgatcccgca ttttcttgaa agctttgcag   4620
aggctagcag aattaccctc cacgttgatt gtctgcgagg caagaatgat catcaccgta   4680
gtgagagtgc gttcaaggct cttgcggttg ccataagaga agccacctcg cccaatggta   4740
ccaacgatgt tccctccacc aaaggtgttc ttatgtagtg acaccgatta tttaaagctg   4800
cagcatacga tatatataca tgtgtatata tgtataccta tgaatgtcag taagtatgta   4860
tacgaacagt atgatactga agatgacaag gtaatgcatc attctatacg tgtcattctg   4920
aacgaggcgc gctttccttt ttcttttttg ctttttcttt ttttttctct tgaactcgac   4980
ggatctatgc ggtgtgaaat accgcacaga tgcgtaagga gaaaataccg catcaggaaa   5040
ttgtaaacgt taatattttg ttaaaattcg cgttaaattt ttgttaaatc agctcatttt   5100
ttaaccaata ggccgaaatc ggcaaaatcc cttataaatc aaaagaatag accgagatag   5160
ggttgagtgt tgttccagtt tggaacaaga gtccactatt aaagaacgtg gactccaacg   5220
tcaaagggcg aaaaaccgtc tatcagggcg atggcccact acgtgaacca tcaccctaat   5280
caagtttttt ggggtcgagg tgccgtaaag cactaaatcg gaaccctaaa gggagccccc   5340
gatttagagc ttgacgggga aagccggcga acgtggcgag aaaggaaggg aagaaagcga   5400
aaggagcggg cgctagggcg ctggcaagtg tagcggtcac gctgcgcgta accaccacac   5460
ccgccgcgct taatgcgccg ctacagggcg cgtcgcgcca ttcgccattc aggctgcgca   5520
actgttggga agggcgatcg gtgcgggcct cttcgctatt acgccagctg gcgaaagggg   5580
gatgtgctgc aaggcgatta agttgggtaa cgccagggtt ttcccagtca cgacgttgta   5640
aaacgacggc cagtgagcgc gcgtaatacg actcactata gggcgaattg ggtaccgggc   5700
ccccctcga ggtattagaa gccgccgagc gggcgacagc cctccgacgg aagactctcc   5760
```

```
tccgtgcgtc ctcgtcttca ccggtcgcgt tcctgaaacg cagatgtgcc tcgcgccgca   5820
ctgctccgaa caataaagat tctacaatac tagcttttat ggttatgaag aggaaaaatt   5880
ggcagtaacc tggccccaca aaccttcaaa ttaacgaatc aaattaacaa ccataggatg   5940
ataatgcgat tagtttttta gccttatttc tggggtaatt aatcagcgaa gcgatgattt   6000
ttgatctatt aacagatata taaatggaaa agctgcataa ccactttaac taatactttc   6060
aacattttca gtttgtatta cttcttattc aaatgtcata aaagtatcaa caaaaaattg   6120
ttaatatacc tctatacttt aacgtcaagg agaaaaatgt ccaatttact gcccgtacac   6180
caaaatttgc ctgcattacc ggtcgatgca acgagtgatg aggttcgcaa gaacctgatg   6240
gacatgttca gggatcgcca ggcgttttct gagcatacct ggaaaatgct tctgtccgtt   6300
tgccggtcgt gggcggcatg gtgcaagttg aataaccgga aatggtttcc cgcagaacct   6360
gaagatgttc gcgattatct tctatatctt caggcgcgcg gtctggcagt aaaaactatc   6420
cagcaacatt tgggccagct aaacatgctt catcgtcggt ccgggctgcc acgaccaagt   6480
gacagcaatg ctgtttcact ggttatgcgg cggatccgaa aagaaaacgt tgatgccggt   6540
gaacgtgcaa aacaggctct agcgttcgaa cgcactgatt tcgaccaggt tcgttcactc   6600
atggaaaata gcgatcgctg ccaggatata cgtaatctgg catttctggg gattgcttat   6660
aacaccctgt tacgtatagc cgaaattgcc aggatcaggg ttaaagatat ctcacgtact   6720
gacggtggga gaatgttaat ccatattggc agaacgaaaa cgctggttag caccgcaggt   6780
gtagagaagg cacttagcct gggggtaact aaactggtcg agcgatggat ttccgtctct   6840
ggtgtagctg atgatccgaa taactacctg ttttgccggg tcagaaaaaa tggtgttgcc   6900
gcgccatctg ccaccagcca gctatcaact cgcgccctgg aagggatttt tgaagcaact   6960
catcgattga tttacggcgc taaggatgac tctggtcaga gatacctggc ctggtctgga   7020
cacagtgccc gtgtcggagc cgcgcgagat atggcccgcg ctggagtttc aataccggag   7080
atcatgcaag ctggtggctg gaccaatgta aatattgtca tgaactatat ccgtaacctg   7140
gatagtgaaa caggggcaat ggtgcgcctg ctggaagatg gcgattagga gtaagcgaat   7200
ttcttatgat ttatgatttt tattattaaa taagttataa aaaaaataag tgtatacaaa   7260
ttttaaagtg actcttaggt tttaaaacga aaattcttat tcttgagtaa ctctttcctg   7320
taggtcaggt tgctttctca ggtatagcat gaggtcgctc ttattgacca cacctctacc   7380
ggcatgccga gcaaatgcct gcaaatcgct ccccatttca cccaattgta gatatgctaa   7440
ctccagcaat gagttgatga atctcggtgt gtattttatg tcctcagagg acaacacctg   7500
tggtccgcca ccgcggtgga gct                                           7523
```

<210> SEQ ID NO 122
<211> LENGTH: 96
<212> TYPE: DNA
<213> ORGANISM: Artificial Sequence
<220> FEATURE:
<223> OTHER INFORMATION: LA722

<400> SEQUENCE: 122

```
tgccaattat ttacctaaac atctataacc ttcaaaagta aaaaaataca caaacgttga     60
atcatcacct tggctaactc gttgtatcat cactgg                               96
```

<210> SEQ ID NO 123
<211> LENGTH: 80
<212> TYPE: DNA

<213> ORGANISM: Artificial Sequence
<220> FEATURE:
<223> OTHER INFORMATION: LA733

<400> SEQUENCE: 123
cataatcaat ctcaaagaga acaacacaat acaataacaa gaagaacaaa gcattgcgga 60
ttacgtattc taatgttcag 80

<210> SEQ ID NO 124
<211> LENGTH: 30
<212> TYPE: DNA
<213> ORGANISM: Artificial Sequence
<220> FEATURE:
<223> OTHER INFORMATION: LA453

<400> SEQUENCE: 124
caccgaagaa gaatgcaaaa atttcagctc 30

<210> SEQ ID NO 125
<211> LENGTH: 25
<212> TYPE: DNA
<213> ORGANISM: Artificial Sequence
<220> FEATURE:
<223> OTHER INFORMATION: LA694

<400> SEQUENCE: 125
gctgaagttg ttagaactgt tgttg 25

<210> SEQ ID NO 126
<211> LENGTH: 21
<212> TYPE: DNA
<213> ORGANISM: Artificial Sequence
<220> FEATURE:
<223> OTHER INFORMATION: LA695

<400> SEQUENCE: 126
tgttagctgg agtagacttg g 21

<210> SEQ ID NO 127
<211> LENGTH: 22
<212> TYPE: DNA
<213> ORGANISM: Artificial Sequence
<220> FEATURE:
<223> OTHER INFORMATION: oBP594

<400> SEQUENCE: 127
agctgtctcg tgttgtgggt tt 22

<210> SEQ ID NO 128
<211> LENGTH: 49
<212> TYPE: DNA
<213> ORGANISM: Artificial Sequence
<220> FEATURE:
<223> OTHER INFORMATION: oBP595

<400> SEQUENCE: 128
cttaataata gaacaatatc atcctttacg ggcatcttat agtgtcgtt 49

<210> SEQ ID NO 129
<211> LENGTH: 49
<212> TYPE: DNA
<213> ORGANISM: Artificial Sequence
<220> FEATURE:
<223> OTHER INFORMATION: oBP596

<400> SEQUENCE: 129
gcgccaacga cactataaga tgcccgtaaa ggatgatatt gttctatta 49

<210> SEQ ID NO 130
<211> LENGTH: 49
<212> TYPE: DNA
<213> ORGANISM: Artificial Sequence
<220> FEATURE:
<223> OTHER INFORMATION: oBP597

<400> SEQUENCE: 130
tatggaccct gaaaccacag ccacattgca acgacgacaa tgccaaacc 49

<210> SEQ ID NO 131
<211> LENGTH: 49
<212> TYPE: DNA
<213> ORGANISM: Artificial Sequence
<220> FEATURE:
<223> OTHER INFORMATION: oBP598

<400> SEQUENCE: 131
tccttggttt ggcattgtcg tcgttgcaat gtggctgtgg tttcagggt 49

<210> SEQ ID NO 132
<211> LENGTH: 49
<212> TYPE: DNA
<213> ORGANISM: Artificial Sequence
<220> FEATURE:
<223> OTHER INFORMATION: oBP599

<400> SEQUENCE: 132
atcctctcgc ggagtccctg ttcagtaaag gccatgaagc tttttcttt 49

<210> SEQ ID NO 133
<211> LENGTH: 49
<212> TYPE: DNA
<213> ORGANISM: Artificial Sequence
<220> FEATURE:
<223> OTHER INFORMATION: oBP600

<400> SEQUENCE: 133
attggaaaga aaaagcttca tggcctttac tgaacaggga ctccgcgag 49

<210> SEQ ID NO 134
<211> LENGTH: 22
<212> TYPE: DNA
<213> ORGANISM: Artificial Sequence
<220> FEATURE:
<223> OTHER INFORMATION: oBP601

<400> SEQUENCE: 134
tcataccaca atcttagacc at 22

<210> SEQ ID NO 135
<211> LENGTH: 21
<212> TYPE: DNA
<213> ORGANISM: Artificial Sequence
<220> FEATURE:
<223> OTHER INFORMATION: oBP602

<400> SEQUENCE: 135
tgttcaaacc cctaaccaac c 21

<210> SEQ ID NO 136
<211> LENGTH: 22
<212> TYPE: DNA

<213> ORGANISM: Artificial Sequence
<220> FEATURE:
<223> OTHER INFORMATION: oBP603

<400> SEQUENCE: 136
tgttcccaca atctattacc ta 22

<210> SEQ ID NO 137
<211> LENGTH: 31
<212> TYPE: DNA
<213> ORGANISM: Artificial Sequence
<220> FEATURE:
<223> OTHER INFORMATION: LA811

<400> SEQUENCE: 137
aacgaagcat ctgtgcttca ttttgtagaa c 31

<210> SEQ ID NO 138
<211> LENGTH: 59
<212> TYPE: DNA
<213> ORGANISM: Artificial Sequence
<220> FEATURE:
<223> OTHER INFORMATION: LA817

<400> SEQUENCE: 138
cgatccactt gtatatttgg atgaattttt gaggaattct gaaccagtcc taaaacgag 59

<210> SEQ ID NO 139
<211> LENGTH: 31
<212> TYPE: DNA
<213> ORGANISM: Artificial Sequence
<220> FEATURE:
<223> OTHER INFORMATION: LA812

<400> SEQUENCE: 139
aacaaagata tgctattgaa gtgcaagatg g 31

<210> SEQ ID NO 140
<211> LENGTH: 33
<212> TYPE: DNA
<213> ORGANISM: Artificial Sequence
<220> FEATURE:
<223> OTHER INFORMATION: LA818

<400> SEQUENCE: 140
ctcaaaaatt catccaaata tacaagtgga tcg 33

<210> SEQ ID NO 141
<211> LENGTH: 90
<212> TYPE: DNA
<213> ORGANISM: Artificial Sequence
<220> FEATURE:
<223> OTHER INFORMATION: LA512

<400> SEQUENCE: 141
gtattttggt agattcaatt ctctttccct ttccttttcc ttcgctcccc ttccttatca 60
gcattgcgga ttacgtattc taatgttcag 90

<210> SEQ ID NO 142
<211> LENGTH: 90
<212> TYPE: DNA
<213> ORGANISM: Artificial Sequence
<220> FEATURE:
<223> OTHER INFORMATION: LA513

<400> SEQUENCE: 142

```
ttggttgggg gaaaaagagg caacaggaaa gatcagaggg ggaggggggg ggagagtgtc     60

accttggcta actcgttgta tcatcactgg                                      90


<210> SEQ ID NO 143
<211> LENGTH: 29
<212> TYPE: DNA
<213> ORGANISM: Artificial Sequence
<220> FEATURE:
<223> OTHER INFORMATION: LA516

<400> SEQUENCE: 143

ctcgaaacaa taagacgacg atggctctg                                       29


<210> SEQ ID NO 144
<211> LENGTH: 30
<212> TYPE: DNA
<213> ORGANISM: Artificial Sequence
<220> FEATURE:
<223> OTHER INFORMATION: LA514

<400> SEQUENCE: 144

cactatctgg tgcaaacttg gcaccggaag                                      30


<210> SEQ ID NO 145
<211> LENGTH: 29
<212> TYPE: DNA
<213> ORGANISM: Artificial Sequence
<220> FEATURE:
<223> OTHER INFORMATION: LA515

<400> SEQUENCE: 145

tgtttgtagc cactcgtgaa cttctctgc                                       29


<210> SEQ ID NO 146
<211> LENGTH: 6903
<212> TYPE: DNA
<213> ORGANISM: Artificial Sequence
<220> FEATURE:
<223> OTHER INFORMATION: pLA71

<400> SEQUENCE: 146

aaacgccagc aacgcggcct ttttacggtt cctggccttt tgctggcctt ttgctcacat     60

gttctttcct gcgttatccc ctgattctgt ggataaccgt attaccgcct ttgagtgagc    120

tgataccgct cgccgcagcc gaacgaccga gcgcagcgag tcagtgagcg aggaagcgga    180

agagcgccca atacgcaaac cgcctctccc cgcgcgttgg ccgattcatt aatgcagctg    240

gcacgacagg tttcccgact ggaaagcggg cagtgagcgc aacgcaatta atgtgagtta    300

gctcactcat taggcacccc aggctttaca ctttatgctt ccggctcgta tgttgtgtgg    360

aattgtgagc ggataacaat ttcacacagg aaacagctat gaccatgatt acgccaagct    420

tgcatgcgat ctgaaatgaa taacaatact gacagtagat ctgaaatgaa taacaatact    480

gacagtacta aataattgcc tacttggctt cacatacgtt gcatacgtcg atatagataa    540

taatgataat gacagcagga ttatcgtaat acgtaatagt tgaaaatctc aaaaatgtgt    600

gggtcattac gtaaataatg ataggaatgg gattcttcta tttttccttt ttccattcta    660

gcagccgtcg ggaaaacgtg gcatcctctc tttcgggctc aattggagtc acgctgccgt    720

gagcatcctc tctttccata tctaacaact gagcacgtaa ccaatggaaa agcatgagct    780

tagcgttgct ccaaaaaagt attggatggt taataccatt tgtctgttct cttctgactt    840
```

-continued

```
tgactcctca aaaaaaaaaa atctacaatc aacagatcgc ttcaattacg ccctcacaaa    900
aactttttttc cttcttcttc gcccacgtta aattttatcc ctcatgttgt ctaacggatt    960
tctgcacttg atttattata aaaagacaaa gacataatac ttctctatca atttcagtta   1020
ttgttcttcc ttgcgttatt cttctgttct tctttttctt ttgtcatata taaccataac   1080
caagtaatac atattcaaat ctagagctga ggatgttgac aaaagcaaca aaagaacaaa   1140
aatcccttgt gaaaaacaga ggggcggagc ttgttgttga ttgcttagtg gagcaaggtg   1200
tcacacatgt atttggcatt ccaggtgcaa aaattgatgc ggtatttgac gctttacaag   1260
ataaaggacc tgaaattatc gttgcccggc acgaacaaaa cgcagcattc atggcccaag   1320
cagtcggccg tttaactgga aaaccgggag tcgtgttagt cacatcagga ccgggtgcct   1380
ctaacttggc aacaggcctg ctgacagcga acactgaagg agaccctgtc gttgcgcttg   1440
ctggaaacgt gatccgtgca gatcgtttaa aacggacaca tcaatctttg gataatgcgg   1500
cgctattcca gccgattaca aaatacagtg tagaagttca agatgtaaaa aatataccgg   1560
aagctgttac aaatgcattt aggatagcgt cagcagggca ggctggggcc gcttttgtga   1620
gctttccgca agatgttgtg aatgaagtca caaatacgaa aaacgtgcgt gctgttgcag   1680
cgccaaaact cggtcctgca gcagatgatg caatcagtgc ggccatagca aaaatccaaa   1740
cagcaaaact tcctgtcgtt ttggtcggca tgaaaggcgg aagaccggaa gcaattaaag   1800
cggttcgcaa gcttttgaaa aaggttcagc ttccatttgt tgaaacatat caagctgccg   1860
gtaccctttc tagagattta gaggatcaat attttggccg tatcggtttg ttccgcaacc   1920
agcctggcga tttactgcta gagcaggcag atgttgttct gacgatcggc tatgacccga   1980
ttgaatatga tccgaaattc tggaatatca atggagaccg gacaattatc catttagacg   2040
agattatcgc tgacattgat catgcttacc agcctgatct tgaattgatc ggtgacattc   2100
cgtccacgat caatcatatc gaacacgatg ctgtgaaagt ggaatttgca gagcgtgagc   2160
agaaaatcct ttctgattta aaacaatata tgcatgaagg tgagcaggtg cctgcagatt   2220
ggaaatcaga cagagcgcac cctcttgaaa tcgttaaaga gttgcgtaat gcagtcgatg   2280
atcatgttac agtaacttgc gatatcggtt cgcacgccat ttggatgtca cgttatttcc   2340
gcagctacga gccgttaaca ttaatgatca gtaacggtat gcaaacactc ggcgttgcgc   2400
ttccttgggc aatcggcgct tcattggtga aaccgggaga aaaagtggtt tctgtctctg   2460
gtgacggcgg tttcttattc tcagcaatgg aattagagac agcagttcga ctaaaagcac   2520
caattgtaca cattgtatgg aacgacagca catatgacat ggttgcattc cagcaattga   2580
aaaaatataa ccgtacatct gcggtcgatt tcggaaatat cgatatcgtg aaatatgcgg   2640
aaagcttcgg agcaactggc ttgcgcgtag aatcaccaga ccagctggca gatgttctgc   2700
gtcaaggcat gaacgctgaa ggtcctgtca tcatcgatgt cccggttgac tacagtgata   2760
acattaattt agcaagtgac aagcttccga aagaattcgg ggaactcatg aaaacgaaag   2820
ctctctagtt aattaatcat gtaattagtt atgtcacgct tacattcacg ccctcccccc   2880
acatccgctc taaccgaaaa ggaaggagtt agacaacctg aagtctaggt ccctatttat   2940
ttttttatag ttatgttagt attaagaacg ttatttatat ttcaaatttt tctttttttt   3000
ctgtacagac gcgtgtacgc atgtaacatt atactgaaaa ccttgcttga gaaggttttg   3060
ggacgctcga aggctttaat ttaggttttg ggacgctcga aggctttaat ttggatccgc   3120
attgcggatt acgtattcta atgttcagta ccgttcgtat aatgtatgct atacgaagtt   3180
atgcagattg tactgagagt gcaccatacc acagcttttc aattcaattc atcatttttt   3240
```

```
ttttattctt ttttttgatt tcggtttctt tgaaattttt ttgattcggt aatctccgaa   3300
cagaaggaag aacgaaggaa ggagcacaga cttagattgg tatatatacg catatgtagt   3360
gttgaagaaa catgaaattg cccagtattc ttaacccaac tgcacagaac aaaaacctgc   3420
aggaaacgaa gataaatcat gtcgaaagct acatataagg aacgtgctgc tactcatcct   3480
agtcctgttg ctgccaagct atttaatatc atgcacgaaa agcaaacaaa cttgtgtgct   3540
tcattggatg ttcgtaccac caaggaatta ctggagttag ttgaagcatt aggtcccaaa   3600
atttgtttac taaaaacaca tgtggatatc ttgactgatt tttccatgga gggcacagtt   3660
aagccgctaa aggcattatc cgccaagtac aatttttac tcttcgaaga cagaaaattt    3720
gctgacattg gtaatacagt caaattgcag tactctgcgg gtgtatacag aatagcagaa   3780
tgggcagaca ttacgaatgc acacggtgtg gtgggcccag gtattgttag cggtttgaag   3840
caggcggcag aagaagtaac aaaggaacct agaggccttt tgatgttagc agaattgtca   3900
tgcaagggct ccctatctac tggagaatat actaagggta ctgttgacat tgcgaagagc   3960
gacaaagatt ttgttatcgg ctttattgct caaagagaca tgggtggaag agatgaaggt   4020
tacgattggt tgattatgac acccggtgtg ggtttagatg acaagggaga cgcattgggt   4080
caacagtata gaaccgtgga tgatgtggtc tctacaggat ctgacattat tattgttgga   4140
agaggactat ttgcaaaggg aagggatgct aaggtagagg gtgaacgtta cagaaaagca   4200
ggctgggaag catatttgag aagatgcggc cagcaaaact aaaaaactgt attataagta   4260
aatgcatgta tactaaactc acaaattaga gcttcaattt aattatatca gttattaccc   4320
tatgcggtgt gaaataccgc acagatgcgt aaggagaaaa taccgcatca ggaaattgta   4380
aacgttaata ttttgttaaa attcgcgtta aatttttgtt aaatcagctc attttttaac   4440
caataggccg aaatcggcaa aatcccttat aaatcaaaag aatagaccga gatagggttg   4500
agtgttgttc cagtttggaa caagagtcca ctattaaaga acgtggactc caacgtcaaa   4560
gggcgaaaaa ccgtctatca gggcgatggc ccactacgtg aaccatcacc ctaatcaaga   4620
taacttcgta taatgtatgc tatacgaacg gtaccagtga tgatacaacg agttagccaa   4680
ggtgaattca ctggccgtcg ttttacaacg tcgtgactgg gaaaaccctg gcgttaccca   4740
acttaatcgc cttgcagcac atcccccttt cgccagctgg cgtaatagcg aagaggcccg   4800
caccgatcgc ccttcccaac agttgcgcag cctgaatggc gaatggcgcc tgatgcggta   4860
ttttctcctt acgcatctgt gcggtatttc acaccgcata tggtgcactc tcagtacaat   4920
ctgctctgat gccgcatagt taagccagcc ccgacacccg ccaacacccg ctgacgcgcc   4980
ctgacgggct tgtctgctcc cggcatccgc ttacagacaa gctgtgaccg tctccgggag   5040
ctgcatgtgt cagaggtttt caccgtcatc accgaaacgc gcgagacgaa agggcctcgt   5100
gatacgccta tttttatagg ttaatgtcat gataataatg gtttcttaga cgtcaggtgg   5160
cacttttcgg ggaaatgtgc gcggaacccc tatttgttta tttttctaaa tacattcaaa   5220
tatgtatccg ctcatgagac aataaccctg ataaatgctt caataatatt gaaaaaggaa   5280
gagtatgagt attcaacatt tccgtgtcgc ccttattccc ttttttgcgg cattttgcct   5340
tcctgttttt gctcacccag aaacgctggt gaaagtaaaa gatgctgaag atcagttggg   5400
tgcacgagtg ggttacatcg aactggatct caacagcggt aagatccttg agagttttcg   5460
ccccgaagaa cgttttccaa tgatgagcac ttttaaagtt ctgctatgtg gcgcggtatt   5520
atcccgtatt gacgccgggc aagagcaact cggtcgccgc atacactatt ctcagaatga   5580
```

```
cttggttgag tactcaccag tcacagaaaa gcatcttacg gatggcatga cagtaagaga   5640

attatgcagt gctgccataa ccatgagtga taacactgcg gccaacttac ttctgacaac   5700

gatcggagga ccgaaggagc taaccgcttt tttgcacaac atgggggatc atgtaactcg   5760

ccttgatcgt tgggaaccgg agctgaatga agccatacca aacgacgagc gtgacaccac   5820

gatgcctgta gcaatggcaa caacgttgcg caaactatta actggcgaac tacttactct   5880

agcttcccgg caacaattaa tagactggat ggaggcggat aaagttgcag gaccacttct   5940

gcgctcggcc cttccggctg gctggtttat tgctgataaa tctggagccg gtgagcgtgg   6000

gtctcgcggt atcattgcag cactggggcc agatggtaag ccctcccgta tcgtagttat   6060

ctacacgacg gggagtcagg caactatgga tgaacgaaat agacagatcg ctgagatagg   6120

tgcctcactg attaagcatt ggtaactgtc agaccaagtt tactcatata tactttagat   6180

tgatttaaaa cttcattttt aatttaaaag gatctaggtg aagatccttt ttgataatct   6240

catgaccaaa atcccttaac gtgagttttc gttccactga gcgtcagacc ccgtagaaaa   6300

gatcaaagga tcttcttgag atcctttttt tctgcgcgta atctgctgct tgcaaacaaa   6360

aaaaccaccg ctaccagcgg tggtttgttt gccggatcaa gagctaccaa ctctttttcc   6420

gaaggtaact ggcttcagca gagcgcagat accaaatact gtccttctag tgtagccgta   6480

gttaggccac cacttcaaga actctgtagc accgcctaca tacctcgctc tgctaatcct   6540

gttaccagtg gctgctgcca gtggcgataa gtcgtgtctt accgggttgg actcaagacg   6600

atagttaccg gataaggcgc agcggtcggg ctgaacgggg ggttcgtgca cacagcccag   6660

cttggagcga acgacctaca ccgaactgag atacctacag cgtgagctat gagaaagcgc   6720

cacgcttccc gaagggagaa aggcggacag gtatccggta agcggcaggg tcggaacagg   6780

agagcgcacg agggagcttc cagggggaaa cgcctggtat ctttatagtc ctgtcgggtt   6840

tcgccacctc tgacttgagc gtcgattttt gtgatgctcg tcaggggggc ggagcctatg   6900

gaa                                                                 6903
```

<210> SEQ ID NO 147
<211> LENGTH: 6924
<212> TYPE: DNA
<213> ORGANISM: Artificial Sequence
<220> FEATURE:
<223> OTHER INFORMATION: pLA78

<400> SEQUENCE: 147

```
gatccgcatt gcggattacg tattctaatg ttcagtaccg ttcgtataat gtatgctata     60

cgaagttatg cagattgtac tgagagtgca ccataccacc ttttcaattc atcatttttt    120

ttttattctt ttttttgatt tcggtttcct tgaaattttt ttgattcggt aatctccgaa    180

cagaaggaag aacgaaggaa ggagcacaga cttagattgg tatatatacg catatgtagt    240

gttgaagaaa catgaaattg cccagtattc ttaacccaac tgcacagaac aaaaacctgc    300

aggaaacgaa gataaatcat gtcgaaagct acatataagg aacgtgctgc tactcatcct    360

agtcctgttg ctgccaagct atttaatatc atgcacgaaa agcaaacaaa cttgtgtgct    420

tcattggatg ttcgtaccac caaggaatta ctggagttag ttgaagcatt aggtcccaaa    480

atttgtttac taaaaacaca tgtggatatc ttgactgatt tttccatgga gggcacagtt    540

aagccgctaa aggcattatc cgccaagtac aattttttac tcttcgaaga cagaaaattt    600

gctgacattg gtaatacagt caaattgcag tactctgcgg gtgtatacag aatagcagaa    660

tgggcagaca ttacgaatgc acacggtgtg gtgggcccag gtattgttag cggtttgaag    720
```

```
caggcggcag aagaagtaac aaaggaacct agaggccttt tgatgttagc agaattgtca    780
tgcaagggct ccctatctac tggagaatat actaagggta ctgttgacat tgcgaagagc    840
gacaaagatt ttgttatcgg ctttattgct caaagagaca tgggtggaag agatgaaggt    900
tacgattggt tgattatgac acccggtgtg ggtttagatg acaagggaga cgcattgggt    960
caacagtata gaaccgtgga tgatgtggtc tctacaggat ctgacattat tattgttgga   1020
agaggactat ttgcaaaggg aagggatgct aaggtagagg gtgaacgtta cagaaaagca   1080
ggctgggaag catatttgag aagatgcggc cagcaaaact aaaaaactgt attataagta   1140
aatgcatgta tactaaactc acaaattaga gcttcaattt aattatatca gttattaccc   1200
tatgcggtgt gaaataccgc acagatgcgt aaggagaaaa taccgcatca ggaaattgta   1260
aacgttaata ttttgttaaa attcgcgtta aatttttgtt aaatcagctc atttttaac    1320
caataggccg aaatcggcaa aatcccttat aaatcaaaag aatagaccga gatagggttg   1380
agtgttgttc cagtttggaa caagagtcca ctattaaaga acgtggactc caacgtcaaa   1440
gggcgaaaaa ccgtctatca gggcgatggc ccactacgtg aaccatcacc ctaatcaaga   1500
taacttcgta taatgtatgc tatacgaacg gtaccagtga tgatacaacg agttagccaa   1560
ggtgaattca ctggccgtcg ttttacaacg tcgtgactgg gaaaaccctg gcgttaccca   1620
acttaatcgc cttgcagcac atcccccttt cgccagctgg cgtaatagcg aagaggcccg   1680
caccgatcgc ccttcccaac agttgcgcag cctgaatggc gaatggcgcc tgatgcggta   1740
ttttctcctt acgcatctgt gcggtatttc acaccgcata tggtgcactc tcagtacaat   1800
ctgctctgat gccgcatagt taagccagcc ccgacacccg ccaacacccg ctgacgcgcc   1860
ctgacgggct tgtctgctcc cggcatccgc ttacagacaa gctgtgaccg tctccgggag   1920
ctgcatgtgt cagaggtttt caccgtcatc accgaaacgc gcgagacgaa agggcctcgt   1980
gatacgccta tttttatagg ttaatgtcat gataataatg gtttcttaga cgtcaggtgg   2040
cacttttcgg ggaaatgtgc gcggaacccc tatttgttta tttttctaaa tacattcaaa   2100
tatgtatccg ctcatgagac aataaccctg ataaatgctt caataatatt gaaaaaggaa   2160
gagtatgagt attcaacatt tccgtgtcgc ccttattccc ttttttgcgg cattttgcct   2220
tcctgttttt gctcacccag aaacgctggt gaaagtaaaa gatgctgaag atcagttggg   2280
tgcacgagtg ggttacatcg aactggatct caacagcggt aagatccttg agagttttcg   2340
ccccgaagaa cgttttccaa tgatgagcac ttttaaagtt ctgctatgtg gcgcggtatt   2400
atcccgtatt gacgccgggc aagagcaact cggtcgccgc atacactatt ctcagaatga   2460
cttggttgag tactcaccag tcacagaaaa gcatcttacg gatggcatga cagtaagaga   2520
attatgcagt gctgccataa ccatgagtga taacactgcg gccaacttac ttctgacaac   2580
gatcggagga ccgaaggagc taaccgcttt tttgcacaac atgggggatc atgtaactcg   2640
ccttgatcgt tgggaaccgg agctgaatga agccatacca aacgacgagc gtgacaccac   2700
gatgcctgta gcaatggcaa caacgttgcg caaactatta actggcgaac tacttactct   2760
agcttcccgg caacaattaa tagactggat ggaggcggat aaagttgcag gaccacttct   2820
gcgctcggcc cttccggctg gctggtttat tgctgataaa tctggagccg gtgagcgtgg   2880
gtctcgcggt atcattgcag cactggggcc agatggtaag ccctcccgta tcgtagttat   2940
ctacacgacg gggagtcagg caactatgga tgaacgaaat agacagatcg ctgagatagg   3000
tgcctcactg attaagcatt ggtaactgtc agaccaagtt tactcatata ctttagat    3060
```

-continued

```
tgatttaaaa cttcattttt aatttaaaag gatctaggtg aagatccttt ttgataatct   3120
catgaccaaa atcccttaac gtgagttttc gttccactga gcgtcagacc ccgtagaaaa   3180
gatcaaagga tcttcttgag atcctttttt tctgcgcgta atctgctgct tgcaaacaaa   3240
aaaaccaccg ctaccagcgg tggtttgttt gccggatcaa gagctaccaa ctctttttcc   3300
gaaggtaact ggcttcagca gagcgcagat accaaatact gtccttctag tgtagccgta   3360
gttaggccac cacttcaaga actctgtagc accgcctaca tacctcgctc tgctaatcct   3420
gttaccagtg gctgctgcca gtggcgataa gtcgtgtctt accgggttgg actcaagacg   3480
atagttaccg gataaggcgc agcggtcggg ctgaacgggg ggttcgtgca cacagcccag   3540
cttggagcga acgacctaca ccgaactgag atacctacag cgtgagctat gagaaagcgc   3600
cacgcttccc gaagggagaa aggcggacag gtatccggta agcggcaggg tcggaacagg   3660
agagcgcacg agggagcttc caggggggaaa cgcctggtat ctttatagtc ctgtcgggtt   3720
tcgccacctc tgacttgagc gtcgattttt gtgatgctcg tcaggggggc ggagcctatg   3780
gaaaaacgcc agcaacgcgg cctttttacg gttcctggcc ttttgctggc cttttgctca   3840
catgttcttt cctgcgttat cccctgattc tgtggataac cgtattaccg cctttgagtg   3900
agctgatacc gctcgccgca gccgaacgac cgagcgcagc gagtcagtga gcgaggaagc   3960
ggaagagcgc ccaatacgca aaccgcctct ccccgcgcgt tggccgattc attaatgcag   4020
ctggcacgac aggtttcccg actggaaagc gggcagtgag cgcaacgcaa ttaatgtgag   4080
ttagctcact cattaggcac cccaggcttt acactttatg cttccggctc gtatgttgtg   4140
tggaattgtg agcggataac aatttcacac aggaaacagc tatgaccatg attacgccaa   4200
gcttccaatt accgtcgctc gtgatttgtt tgcaaaaaga acaaaactga aaaaacccag   4260
acacgctcga cttcctgtct tcctattgat tgcagcttcc aatttcgtca cacaacaagg   4320
tcctgtcgac gcctacttgg cttcacatac gttgcatacg tcgatataga taataatgat   4380
aatgacagca ggattatcgt aatacgtaat agttgaaaat ctcaaaaatg tgtgggtcat   4440
tacgtaaata atgataggaa tgggattctt ctattttttcc tttttccatt ctagcagccg   4500
tcgggaaaac gtggcatcct ctctttcggg ctcaattgga gtcacgctgc cgtgagcatc   4560
ctctctttcc atatctaaca actgagcacg taaccaatgg aaaagcatga gcttagcgtt   4620
gctccaaaaa agtattggat ggttaatacc atttgtctgt tctcttctga ctttgactcc   4680
tcaaaaaaaa aaaatctaca atcaacagat cgcttcaatt acgccctcac aaaaactttt   4740
ttccttcttc ttcgcccacg ttaaatttta tccctcatgt tgtctaacgg atttctgcac   4800
ttgatttatt ataaaaagac aaagacataa tacttctcta tcaatttcag ttattgttct   4860
tccttgcgtt attcttctgt tcttcttttt cttttgtcat atataaccat aaccaagtaa   4920
tacatattca agtttaaaca tgtataccgt aggacagtac ttggtagata gactagaaga   4980
gattggtatc gataaggttt tcggtgtgcc aggggattac aatttgactt ttctagatta   5040
cattcaaaat cacgaaggac tttcctggca agggaatact aatgaactaa acgcagcata   5100
tgcagcagat ggctacgccc gtgaaagagg cgtatcagct cttgttacta cattcggagt   5160
gggtgaactg tcagccatta acggaacagc tggtagtttt gcagaacaag tccctgtcat   5220
ccacatcgtg ggttctccaa ctatgaatgt gcaatccaac aaaaagctgg ttcatcattc   5280
cttaggaatg ggtaactttc ataactttag tgaaatggct aaggaagtca ctgccgctac   5340
aaccatgctt actgaagaga atgcagcttc agagatcgac agagtattag aaacagcctt   5400
gttggaaaag aggccagtat acatcaatct tccaattgat atagctcata aagcaatagt   5460
```

```
taaacctgca aaagcactac aaacagagaa atcatctggt gagagagagg cacaacttgc   5520
agaaatcata ctatcacact tagaaaaggc cgctcaacct atcgtaatcg ccggtcatga   5580
gatcgcccgt ttccagataa gagaaagatt tgaaaactgg ataaaccaaa caaagttgcc   5640
agtaaccaat ttggcatatg gcaaaggctc tttcaatgaa gagaacgaac atttcattgg   5700
tacctattac ccagcttttt ctgacaaaaa cgttctggat tacgttgaca atagtgactt   5760
cgttttacat tttggtggga aaatcattga caattctacc tcctcatttt ctcaaggctt   5820
taagactgaa aacactttaa ccgctgcaaa tgacatcatt atgctgccag atgggtctac   5880
ttactctggg atttctctta acggtctttt ggcagagctg gaaaaactaa actttacttt   5940
tgctgatact gctgctaaac aagctgaatt agctgttttc gaaccacagg ccgaaacacc   6000
actaaagcaa gacagatttc accaagctgt tatgaacttt ttgcaagctg atgatgtgtt   6060
ggtcactgag caggggacat catctttcgg tttgatgttg gcacctctga aaaagggtat   6120
gaatttgatc agtcaaacat tatggggctc cataggatac acattacctg ctatgattgg   6180
ttcacaaatt gctgccccag aaaggagaca cattctatcc atcggtgatg gatcttttca   6240
actgacagca caggaaatgt ccaccatctt cagagagaaa ttgacaccag tgatattcat   6300
tatcaataac gatggctata cagtcgaaag agccatccat ggagaggatg agagttacaa   6360
tgatatacca acttggaact tgcaattagt tgctgaaaca tttggtggtg atgccgaaac   6420
tgtcgacact cacaacgttt tcacagaaac agacttcgct aatactttag ctgctatcga   6480
tgctactcct caaaaagcac atgtcgttga agttcatatg gaacaaatgg atatgccaga   6540
atcattgaga cagattggct tagccttatc taagcaaaac tcttaagttt aaactaagcg   6600
aatttcttat gatttatgat ttttattatt aaataagtta taaaaaaaat aagtgtatac   6660
aaattttaaa gtgactctta ggttttaaaa cgaaaattct tattcttgag taactctttc   6720
ctgtaggtca ggttgctttc tcaggtatag catgaggtcg ctcttattga ccacacctct   6780
accggcatgc cgagcaaatg cctgcaaatc gctccccatt tcacccaatt gtagatatgc   6840
taactccagc aatgagttga tgaatctcgg tgtgtatttt atgtcctcag aggacaacac   6900
ctgttgtaat cgttcttcca cacg                                           6924
```

```
<210> SEQ ID NO 148
<211> LENGTH: 6761
<212> TYPE: DNA
<213> ORGANISM: Artificial Sequence
<220> FEATURE:
<223> OTHER INFORMATION: pLA65

<400> SEQUENCE: 148
```

```
gatccgcatt gcggattacg tattctaatg ttcagtaccg ttcgtataat gtatgctata     60
cgaagttatg cagattgtac tgagagtgca ccataccacc ttttcaattc atcatttttt    120
ttttattctt ttttttgatt tcggtttcct tgaaattttt ttgattcggt aatctccgaa    180
cagaaggaag aacgaaggaa ggagcacaga cttagattgg tatatatacg catatgtagt    240
gttgaagaaa catgaaattg cccagtattc ttaacccaac tgcacagaac aaaaacctgc    300
aggaaacgaa gataaatcat gtcgaaagct acatataagg aacgtgctgc tactcatcct    360
agtcctgttg ctgccaagct atttaatatc atgcacgaaa agcaaacaaa cttgtgtgct    420
tcattggatg ttcgtaccac caaggaatta ctggagttag ttgaagcatt aggtcccaaa    480
atttgtttac taaaaacaca tgtggatatc ttgactgatt tttccatgga gggcacagtt    540
```

```
aagccgctaa aggcattatc cgccaagtac aattttttac tcttcgaaga cagaaaattt    600
gctgacattg gtaatacagt caaattgcag tactctgcgg gtgtatacag aatagcagaa    660
tgggcagaca ttacgaatgc acacggtgtg gtgggcccag gtattgttag cggtttgaag    720
caggcggcag aagaagtaac aaaggaacct agaggccttt tgatgttagc agaattgtca    780
tgcaagggct ccctatctac tggagaatat actaagggta ctgttgacat tgcgaagagc    840
gacaaagatt ttgttatcgg ctttattgct caaagagaca tgggtggaag agatgaaggt    900
tacgattggt tgattatgac acccggtgtg ggtttagatg acaagggaga cgcattgggt    960
caacagtata gaaccgtgga tgatgtggtc tctacaggat ctgacattat tattgttgga   1020
agaggactat ttgcaaaggg aagggatgct aaggtagagg gtgaacgtta cagaaaagca   1080
ggctgggaag catatttgag aagatgcggc cagcaaaact aaaaaactgt attataagta   1140
aatgcatgta tactaaactc acaaattaga gcttcaattt aattatatca gttattaccc   1200
tatgcggtgt gaaataccgc acagatgcgt aaggagaaaa taccgcatca ggaaattgta   1260
aacgttaata ttttgttaaa attcgcgtta aatttttgtt aaatcagctc attttttaac   1320
caataggccg aaatcggcaa aatcccttat aaatcaaaag aatagaccga gatagggttg   1380
agtgttgttc cagtttggaa caagagtcca ctattaaaga acgtggactc caacgtcaaa   1440
gggcgaaaaa ccgtctatca gggcgatggc ccactacgtg aaccatcacc ctaatcaaga   1500
taacttcgta taatgtatgc tatacgaacg gtaccagtga tgatacaacg agttagccaa   1560
ggtgaattca ctggccgtcg ttttacaacg tcgtgactgg gaaaaccctg gcgttaccca   1620
acttaatcgc cttgcagcac atcccccttt cgccagctgg cgtaatagcg aagaggcccg   1680
caccgatcgc ccttcccaac agttgcgcag cctgaatggc gaatggcgcc tgatgcggta   1740
ttttctcctt acgcatctgt gcggtatttc acaccgcata tggtgcactc tcagtacaat   1800
ctgctctgat gccgcatagt taagccagcc ccgacacccg ccaacacccg ctgacgcgcc   1860
ctgacgggct tgtctgctcc cggcatccgc ttacagacaa gctgtgaccg tctccgggag   1920
ctgcatgtgt cagaggtttt caccgtcatc accgaaacgc gcgagacgaa agggcctcgt   1980
gatacgccta tttttatagg ttaatgtcat gataataatg gtttcttaga cgtcaggtgg   2040
cacttttcgg ggaaatgtgc gcggaacccc tatttgttta tttttctaaa tacattcaaa   2100
tatgtatccg ctcatgagac aataaccctg ataaatgctt caataatatt gaaaaaggaa   2160
gagtatgagt attcaacatt tccgtgtcgc ccttattccc ttttttgcgg cattttgcct   2220
tcctgttttt gctcacccag aaacgctggt gaaagtaaaa gatgctgaag atcagttggg   2280
tgcacgagtg ggttacatcg aactggatct caacagcggt aagatccttg agagttttcg   2340
ccccgaagaa cgttttccaa tgatgagcac ttttaaagtt ctgctatgtg gcgcggtatt   2400
atcccgtatt gacgccgggc aagagcaact cggtcgccgc atacactatt ctcagaatga   2460
cttggttgag tactcaccag tcacagaaaa gcatcttacg gatggcatga cagtaagaga   2520
attatgcagt gctgccataa ccatgagtga taacactgcg gccaacttac ttctgacaac   2580
gatcggagga ccgaaggagc taaccgcttt tttgcacaac atgggggatc atgtaactcg   2640
ccttgatcgt tgggaaccgg agctgaatga agccatacca aacgacgagc gtgacaccac   2700
gatgcctgta gcaatggcaa caacgttgcg caaactatta actggcgaac tacttactct   2760
agcttcccgg caacaattaa tagactggat ggaggcggat aaagttgcag gaccacttct   2820
gcgctcggcc cttccggctg gctggtttat tgctgataaa tctggagccg gtgagcgtgg   2880
gtctcgcggt atcattgcag cactggggcc agatggtaag ccctcccgta tcgtagttat   2940
```

```
ctacacgacg gggagtcagg caactatgga tgaacgaaat agacagatcg ctgagatagg   3000
tgcctcactg attaagcatt ggtaactgtc agaccaagtt tactcatata tactttagat   3060
tgatttaaaa cttcattttt aatttaaaag gatctaggtg aagatccttt ttgataatct   3120
catgaccaaa atcccttaac gtgagttttc gttccactga gcgtcagacc ccgtagaaaa   3180
gatcaaagga tcttcttgag atcctttttt tctgcgcgta atctgctgct tgcaaacaaa   3240
aaaaccaccg ctaccagcgg tggtttgttt gccggatcaa gagctaccaa ctctttttcc   3300
gaaggtaact ggcttcagca gagcgcagat accaaatact gtccttctag tgtagccgta   3360
gttaggccac cacttcaaga actctgtagc accgcctaca tacctcgctc tgctaatcct   3420
gttaccagtg gctgctgcca gtggcgataa gtcgtgtctt accgggttgg actcaagacg   3480
atagttaccg gataaggcgc agcggtcggg ctgaacgggg ggttcgtgca cacagcccag   3540
cttggagcga acgacctaca ccgaactgag atacctacag cgtgagctat gagaaagcgc   3600
cacgcttccc gaagggagaa aggcggacag gtatccggta agcggcaggg tcggaacagg   3660
agagcgcacg agggagcttc cagggggaaa cgcctggtat ctttatagtc ctgtcgggtt   3720
tcgccacctc tgacttgagc gtcgattttt gtgatgctcg tcaggggggc ggagcctatg   3780
gaaaaacgcc agcaacgcgg cctttttacg gttcctggcc ttttgctggc cttttgctca   3840
catgttcttt cctgcgttat cccctgattc tgtggataac cgtattaccg cctttgagtg   3900
agctgatacc gctcgccgca gccgaacgac cgagcgcagc gagtcagtga gcgaggaagc   3960
ggaagagcgc ccaatacgca aaccgcctct ccccgcgcgt tggccgattc attaatgcag   4020
ctggcacgac aggtttcccg actggaaagc gggcagtgag cgcaacgcaa ttaatgtgag   4080
ttagctcact cattaggcac cccaggcttt acactttatg cttccggctc gtatgttgtg   4140
tggaattgtg agcggataac aatttcacac aggaaacagc tatgaccatg attacgccaa   4200
gcttacctgg taaaacctct agtggagtag tagatgtaat caatgaagcg gaagccaaaa   4260
gaccagagta gaggcctata gaagaaactg cgataccttt tgtgatggct aaacaaacag   4320
acatcttttt atatgttttt acttctgtat atcgtgaagt agtaagtgat aagcgaattt   4380
ggctaagaac gttgtaagtg aacaagggac ctcttttgcc tttcaaaaaa ggattaaatg   4440
gagttaatca ttgagattta gttttcgtta gattctgtat ccctaaataa ctcccttacc   4500
cgacgggaag gcacaaaaga cttgaataat agcaaacggc cagtagccaa gaccaaataa   4560
tactagagtt aactgatggt cttaaacagg cattacgtgg tgaactccaa gaccaatata   4620
caaaatatcg ataagttatt cttgcccacc aatttaagga gcctacatca ggacagtagt   4680
accattcctc agagaagagg tatacataac aagaaaatcg cgtgaacacc ttatataact   4740
tagcccgtta ttgagctaaa aaaccttgca aaatttccta tgaataagaa tacttcagac   4800
gtgataaaaa tttactttct aactcttctc acgctgcccc tatctgttct tccgctctac   4860
cgtgagaaat aaagcatcga gtacggcagt tcgctgtcac tgaactaaaa caataaggct   4920
agttcgaatg atgaacttgc ttgctgtcaa acttctgagt tgccgctgat gtgacactgt   4980
gacaataaat tcaaaccggt tatagcggtc tcctccggta ccggttctgc cacctccaat   5040
agagctcagt aggagtcaga acctctgcgg tggctgtcag tgactcatcc gcgtttcgta   5100
agttgtgcgc gtgcacattt cgcccgttcc cgctcatctt gcagcaggcg gaaattttca   5160
tcacgctgta ggacgcaaaa aaaaaataat taatcgtaca agaatcttgg aaaaaaaatt   5220
gaaaaatttt gtataaaagg gatgacctaa cttgactcaa tggcttttac acccagtatt   5280
```

```
ttccctttcc ttgtttgtta caattataga agcaagacaa aaacatatag acaacctatt   5340

cctaggagtt atattttttt accctaccag caatataagt aaaaaactgt ttatgaaagc   5400

attagtgtat aggggcccag gccagaagtt ggtggaagag agacagaagc cagagcttaa   5460

ggaacctggt gacgctatag tgaaggtaac aaagactaca atttgcggaa ccgatctaca   5520

cattcttaaa ggtgacgttg cgacttgtaa acccggtcgt gtattagggc atgaaggagt   5580

gggggttatt gaatcagtcg gatctggggt tactgctttc caaccaggcg atagagtttt   5640

gatatcatgt atatcgagtt gcggaaagtg ctcattttgt agaagaggaa tgttcagtca   5700

ctgtacgacc gggggttgga ttctgggcaa cgaaattgat ggtacccaag cagagtacgt   5760

aagagtacca catgctgaca catcccttta tcgtattccg gcaggtgcgg atgaagaggc   5820

cttagtcatg ttatcagata ttctaccaac gggttttgag tgcggagtcc taaacggcaa   5880

agtcgcacct ggttcttcgg tggctatagt aggtgctggt cccgttggtt tggccgcctt   5940

actgacagca caattctact ccccagctga aatcataatg atcgatcttg atgataacag   6000

gctgggatta gccaaacaat ttggtgccac cagaacagta aactccacgg gtggtaacgc   6060

cgcagccgaa gtgaaagctc ttactgaagg cttaggtgtt gatactgcga ttgaagcagt   6120

tgggatacct gctacatttg aattgtgtca gaatatcgta gctcccggtg gaactatcgc   6180

taatgtcggc gttcacggta gcaaagttga tttgcatctt gaaagtttat ggtcccataa   6240

tgtcacgatt actacaaggt tggttgacac ggctaccacc ccgatgttac tgaaaactgt   6300

tcaaagtcac aagctagatc catctagatt gataacacat agattcagcc tggaccagat   6360

cttggacgca tatgaaactt ttggccaagc tgcgtctact caagcactaa aagtcatcat   6420

ttcgatggag gcttgattaa ttaagagtaa gcgaatttct tatgatttat gatttttatt   6480

attaaataag ttataaaaaa aataagtgta tacaaatttt aaagtgactc ttaggtttta   6540

aaacgaaaat tcttattctt gagtaactct ttcctgtagg tcaggttgct ttctcaggta   6600

tagcatgagg tcgctcttat tgaccacacc tctaccggca tgccgagcaa atgcctgcaa   6660

atcgctcccc atttcaccca attgtagata tgctaactcc agcaatgagt tgatgaatct   6720

cggtgtgtat tttatgtcct cagaggacaa cacctgtggt g                        6761
```

<210> SEQ ID NO 149
<211> LENGTH: 90
<212> TYPE: DNA
<213> ORGANISM: Artificial Sequence
<220> FEATURE:
<223> OTHER INFORMATION: 895

<400> SEQUENCE: 149

```
tctcaattat tattttctac tcataacctc acgcaaaata acacagtcaa atcaatcaaa     60

atgttgacaa aagcaacaaa agaacaaaaa                                      90
```

<210> SEQ ID NO 150
<211> LENGTH: 81
<212> TYPE: DNA
<213> ORGANISM: Artificial Sequence
<220> FEATURE:
<223> OTHER INFORMATION: 679

<400> SEQUENCE: 150

```
gtggagcatc gaagactggc aacatgattt caatcattct gatcttagag caccttggct     60

aactcgttgt atcatcactg g                                               81
```

<210> SEQ ID NO 151
<211> LENGTH: 20
<212> TYPE: DNA
<213> ORGANISM: Artificial Sequence
<220> FEATURE:
<223> OTHER INFORMATION: 681

<400> SEQUENCE: 151
ttattgctta gcgttggtag 20

<210> SEQ ID NO 152
<211> LENGTH: 22
<212> TYPE: DNA
<213> ORGANISM: Artificial Sequence
<220> FEATURE:
<223> OTHER INFORMATION: 92

<400> SEQUENCE: 152
gagaagatgc ggccagcaaa ac 22

<210> SEQ ID NO 153
<211> LENGTH: 25
<212> TYPE: DNA
<213> ORGANISM: Artificial Sequence
<220> FEATURE:
<223> OTHER INFORMATION: N245

<400> SEQUENCE: 153
agggtagcct ccccataaca taaac 25

<210> SEQ ID NO 154
<211> LENGTH: 25
<212> TYPE: DNA
<213> ORGANISM: Artificial Sequence
<220> FEATURE:
<223> OTHER INFORMATION: N246

<400> SEQUENCE: 154
tctccaaata tatacctctt gtgtg 25

<210> SEQ ID NO 155
<211> LENGTH: 90
<212> TYPE: DNA
<213> ORGANISM: Artificial Sequence
<220> FEATURE:
<223> OTHER INFORMATION: 896

<400> SEQUENCE: 155
ttttatatac agtataaata aaaaacccac gtaatatagc aaaaacatat tgccaacaaa 60
aattaccgtc gctcgtgatt tgtttgcaaa 90

<210> SEQ ID NO 156
<211> LENGTH: 90
<212> TYPE: DNA
<213> ORGANISM: Artificial Sequence
<220> FEATURE:
<223> OTHER INFORMATION: 897

<400> SEQUENCE: 156
caaactgtgt aagtttattt atttgcaaca ataattcgtt tgagtacact actaatggcc 60
accttggcta actcgttgta tcatcactgg 90

<210> SEQ ID NO 157
<211> LENGTH: 28
<212> TYPE: DNA

<213> ORGANISM: Artificial Sequence
<220> FEATURE:
<223> OTHER INFORMATION: 365

<400> SEQUENCE: 157
ctctatctcc gctcaggcta agcaattg 28

<210> SEQ ID NO 158
<211> LENGTH: 26
<212> TYPE: DNA
<213> ORGANISM: Artificial Sequence
<220> FEATURE:
<223> OTHER INFORMATION: 366

<400> SEQUENCE: 158
cagccgactc aacggcctgt ttcacg 26

<210> SEQ ID NO 159
<211> LENGTH: 28
<212> TYPE: DNA
<213> ORGANISM: Artificial Sequence
<220> FEATURE:
<223> OTHER INFORMATION: N638

<400> SEQUENCE: 159
aaaagatagt gtagtagtga taaactgg 28

<210> SEQ ID NO 160
<211> LENGTH: 22
<212> TYPE: DNA
<213> ORGANISM: Artificial Sequence
<220> FEATURE:
<223> OTHER INFORMATION: 740

<400> SEQUENCE: 160
cgataatcct gctgtcatta tc 22

<210> SEQ ID NO 161
<211> LENGTH: 83
<212> TYPE: DNA
<213> ORGANISM: Artificial Sequence
<220> FEATURE:
<223> OTHER INFORMATION: 856

<400> SEQUENCE: 161
gcttatttag aagtgtcaac aacgtatcta ccaacgattt gaccctttc cacaccttgg 60 ctaactcgtt gtatcatcac tgg 83

<210> SEQ ID NO 162
<211> LENGTH: 80
<212> TYPE: DNA
<213> ORGANISM: Artificial Sequence
<220> FEATURE:
<223> OTHER INFORMATION: 857

<400> SEQUENCE: 162
gcacaatatt tcaagctata ccaagcatac aatcaactat ctcatataca atgaaagcat 60
tagtgtatag gggcccaggc 80

<210> SEQ ID NO 163
<211> LENGTH: 25
<212> TYPE: DNA
<213> ORGANISM: Artificial Sequence
<220> FEATURE:
<223> OTHER INFORMATION: BK415

<400> SEQUENCE: 163
gcctcattga tggtggtaca taacg 25

<210> SEQ ID NO 164
<211> LENGTH: 26
<212> TYPE: DNA
<213> ORGANISM: Artificial Sequence
<220> FEATURE:
<223> OTHER INFORMATION: N1092

<400> SEQUENCE: 164
agagttttga tatcatgtat atcgag 26

<210> SEQ ID NO 165
<211> LENGTH: 92
<212> TYPE: DNA
<213> ORGANISM: Artificial Sequence
<220> FEATURE:
<223> OTHER INFORMATION: 906

<400> SEQUENCE: 165
atgacaggtg aaagaattga aaaggtgaaa ataaatgacg aatttgcaaa atcacatttc 60
acctggtaaa acctctagtg gagtagtaga tg 92

<210> SEQ ID NO 166
<211> LENGTH: 87
<212> TYPE: DNA
<213> ORGANISM: Artificial Sequence
<220> FEATURE:
<223> OTHER INFORMATION: 907

<400> SEQUENCE: 166
aaaaagattc aatgccgtct cctttcgaaa cttaataata gaacaatatc atccttcacc 60
ttggctaact cgttgtatca tcactgg 87

<210> SEQ ID NO 167
<211> LENGTH: 70
<212> TYPE: DNA
<213> ORGANISM: Artificial Sequence
<220> FEATURE:
<223> OTHER INFORMATION: 667

<400> SEQUENCE: 167
tctcctttcg aaacttaata atagaacaat atcatccttt tgtaaaacga cggccagtga 60
attcaccttg 70

<210> SEQ ID NO 168
<211> LENGTH: 25
<212> TYPE: DNA
<213> ORGANISM: Artificial Sequence
<220> FEATURE:
<223> OTHER INFORMATION: 749

<400> SEQUENCE: 168
caagtctttt gtgccttccc gtcgg 25

<210> SEQ ID NO 169
<211> LENGTH: 25
<212> TYPE: DNA
<213> ORGANISM: Artificial Sequence
<220> FEATURE:
<223> OTHER INFORMATION: 413

<400> SEQUENCE: 169
ggacataaaa tacacaccga gattc 25

<210> SEQ ID NO 170
<211> LENGTH: 10934
<212> TYPE: DNA
<213> ORGANISM: Artificial Sequence
<220> FEATURE:
<223> OTHER INFORMATION: pRS423::TEF(M4)-xpk1+ENO1-eutD

<400> SEQUENCE: 170

```
ggtggagctc cagcttttgt tccctttagt gagggttaat tgcgcgcttg gcgtaatcat     60
ggtcatagct gtttcctgtg tgaaattgtt atccgctcac aattccacac aacataggag    120
ccggaagcat aaagtgtaaa gcctggggtg cctaatgagt gaggtaactc acattaattg    180
cgttgcgctc actgcccgct ttccagtcgg gaaacctgtc gtgccagctg cattaatgaa    240
tcggccaacg cgcggggaga ggcggtttgc gtattgggcg ctcttccgct tcctcgctca    300
ctgactcgct gcgctcggtc gttcggctgc ggcgagcggt atcagctcac tcaaaggcgg    360
taatacggtt atccacagaa tcaggggata acgcaggaaa gaacatgtga gcaaaaggcc    420
agcaaaaggc caggaaccgt aaaaaggccg cgttgctggc gtttttccat aggctccgcc    480
cccctgacga gcatcacaaa aatcgacgct caagtcagag gtggcgaaac ccgacaggac    540
tataaagata ccaggcgttt ccccctggaa gctccctcgt gcgctctcct gttccgaccc    600
tgccgcttac cggatacctg tccgcctttc tcccttcggg aagcgtggcg ctttctcata    660
gctcacgctg taggtatctc agttcggtgt aggtcgttcg ctccaagctg ggctgtgtgc    720
acgaaccccc cgttcagccc gaccgctgcg ccttatccgg taactatcgt cttgagtcca    780
acccggtaag acacgactta tcgccactgg cagcagccac tggtaacagg attagcagag    840
cgaggtatgt aggcggtgct acagagttct tgaagtggtg gcctaactac ggctacacta    900
gaaggacagt atttggtatc tgcgctctgc tgaagccagt taccttcgga aaaagagttg    960
gtagctcttg atccggcaaa caaaccaccg ctggtagcgg tggttttttt gtttgcaagc   1020
agcagattac gcgcagaaaa aaaggatctc aagaagatcc tttgatcttt tctacggggt   1080
ctgacgctca gtggaacgaa aactcacgtt aagggatttt ggtcatgaga ttatcaaaaa   1140
ggatcttcac ctagatcctt ttaaattaaa aatgaagttt taaatcaatc taaagtatat   1200
atgagtaaac ttggtctgac agttaccaat gcttaatcag tgaggcacct atctcagcga   1260
tctgtctatt tcgttcatcc atagttgcct gactccccgt cgtgtagata actacgatac   1320
gggagggctt accatctggc cccagtgctg caatgatacc gcgagaccca cgctcaccgg   1380
ctccagattt atcagcaata aaccagccag ccggaagggc cgagcgcaga agtggtcctg   1440
caactttatc cgcctccatc cagtctatta attgttgccg ggaagctaga gtaagtagtt   1500
cgccagttaa tagtttgcgc aacgttgttg ccattgctac aggcatcgtg gtgtcacgct   1560
cgtcgtttgg tatggcttca ttcagctccg gttcccaacg atcaaggcga gttacatgat   1620
cccccatgtt gtgcaaaaaa gcggttagct ccttcggtcc tccgatcgtt gtcagaagta   1680
agttggccgc agtgttatca ctcatggtta tggcagcact gcataattct cttactgtca   1740
tgccatccgt aagatgcttt tctgtgactg gtgagtactc aaccaagtca ttctgagaat   1800
agtgtatgcg gcgaccgagt tgctcttgcc cggcgtcaat acgggataat accgcgccac   1860
atagcagaac tttaaaagtg ctcatcattg gaaaacgttc ttcggggcga aaactctcaa   1920
ggatcttacc gctgttgaga tccagttcga tgtaacccac tcgtgcaccc aactgatctt   1980
```

```
cagcatcttt tactttcacc agcgtttctg ggtgagcaaa aacaggaagg caaaatgccg   2040
caaaaaaggg aataagggcg acacggaaat gttgaatact catactcttc ctttttcaat   2100
attattgaag catttatcag ggttattgtc tcatgagcgg atacatattt gaatgtattt   2160
agaaaaataa acaaataggg gttccgcgca catttccccg aaaagtgcca cctgaacgaa   2220
gcatctgtgc ttcattttgt agaacaaaaa tgcaacgcga gagcgctaat ttttcaaaca   2280
aagaatctga gctgcatttt tacagaacag aaatgcaacg cgaaagcgct attttaccaa   2340
cgaagaatct gtgcttcatt tttgtaaaac aaaaatgcaa cgcgagagcg ctaatttttc   2400
aaacaaagaa tctgagctgc atttttacag aacagaaatg caacgcgaga gcgctatttt   2460
accaacaaag aatctatact tcttttttgt tctacaaaaa tgcatcccga gagcgctatt   2520
tttctaacaa agcatcttag attacttttt ttctcctttg tgcgctctat aatgcagtct   2580
cttgataact ttttgcactg taggtccgtt aaggttagaa gaaggctact tggtgtctta   2640
ttttctcttc cataaaaaaa gcctgactcc acttcccgcg tttactgatt actagcgaag   2700
ctgcgggtgc atttttcaa gataaaggca tccccgatta tattctatac cgatgtggat   2760
tgcgcatact ttgtgaacag aaagtgatag cgttgatgat tcttcattgg tcagaaaatt   2820
atgaacggtt tcttctattt tgtctctata tactacgtat aggaaatgtt tacattttcg   2880
tattgttttc gattcactct atgaatagtt cttactacaa tttttttgtc taaagagtaa   2940
tactagagat aaacataaaa aatgtagagg tcgagtttag atgcaagttc aaggagcgaa   3000
aggtggatgg gtaggttata tagggatata gcacagagat atatagcaaa gagatacttt   3060
tgagcaatgt ttgtggaagc ggtattcgca atattttagt agctcgttac agtccggtgc   3120
gtttttggtt ttttgaaagt gcgtcttcag agcgcttttg gttttcaaaa gcgctctgaa   3180
gttcctatac tttctagaga ataggaactt cggaatagga acttcaaagc gtttccgaaa   3240
acgagcgctt ccgaaaatgc aacgcgagct gcgcacatac agctcactgt tcacgtcgca   3300
cctatatctg cgtgttgcct gtatatatat atacatgaga agaacggcat agtgcgtgtt   3360
tatgcttaaa tgcgtactta tatgcgtcta tttatgtagg atgaaaggta gtctagtacc   3420
tcctgtgata ttatcccatt ccatgcgggg tatcgtatgc ttccttcagc actacccttt   3480
agctgttcta tatgctgcca ctcctcaatt ggattagtct catccttcaa tgctatcatt   3540
tcctttgata ttggatcatc taagaaacca ttattatcat gacattaacc tataaaaata   3600
ggcgtatcac gaggcccttt cgtctcgcgc gtttcggtga tgacggtgaa aacctctgac   3660
acatgcagct cccggagacg gtcacagctt gtctgtaagc ggatgccggg agcagacaag   3720
cccgtcaggg cgcgtcagcg ggtgttggcg ggtgtcgggg ctggcttaac tatgcggcat   3780
cagagcagat tgtactgaga gtgcaccata aattcccgtt ttaagagctt ggtgagcgct   3840
aggagtcact gccaggtatc gtttgaacac ggcattagtc agggaagtca taacacagtc   3900
ctttcccgca attttctttt tctattactc ttggcctcct ctagtacact ctatattttt   3960
ttatgcctcg gtaatgattt tcattttttt ttttccccta gcggatgact cttttttttt   4020
cttagcgatt ggcattatca cataatgaat tatacattat ataaagtaat gtgatttctt   4080
cgaagaatat actaaaaaat gagcaggcaa gataaacgaa ggcaaagatg acagagcaga   4140
aagccctagt aaagcgtatt acaaatgaaa ccaagattca gattgcgatc tctttaaagg   4200
gtggtcccct agcgatagag cactcgatct tcccagaaaa agaggcagaa gcagtagcag   4260
aacaggccac acaatcgcaa gtgattaacg tccacacagg tatagggttt ctggaccata   4320
```

```
tgatacatgc tctggccaag cattccggct ggtcgctaat cgttgagtgc attggtgact   4380
tacacataga cgaccatcac accactgaag actgcgggat tgctctcggt caagctttta   4440
aagaggccct actggcgcgt ggagtaaaaa ggtttggatc aggatttgcg cctttggatg   4500
aggcactttc cagagcggtg gtagatcttt cgaacaggcc gtacgcagtt gtcgaacttg   4560
gtttgcaaag ggagaaagta ggagatctct cttgcgagat gatcccgcat tttcttgaaa   4620
gctttgcaga ggctagcaga attaccctcc acgttgattg tctgcgaggc aagaatgatc   4680
atcaccgtag tgagagtgcg ttcaaggctc ttgcggttgc cataagagaa gccacctcgc   4740
ccaatggtac caacgatgtt ccctccacca aaggtgttct tatgtagtga caccgattat   4800
ttaaagctgc agcatacgat atatatacat gtgtatatat gtatacctat gaatgtcagt   4860
aagtatgtat acgaacagta tgatactgaa gatgacaagg taatgcatca ttctatacgt   4920
gtcattctga acgaggcgcg ctttcctttt ttcttttttgc tttttctttt tttttctctt   4980
gaactcgacg gatctatgcg gtgtgaaata ccgcacagat gcgtaaggag aaaataccgc   5040
atcaggaaat tgtaaacgtt aatattttgt taaaattcgc gttaaatttt tgttaaatca   5100
gctcattttt taaccaatag gccgaaatcg gcaaaatccc ttataaatca aaagaataga   5160
ccgagatagg gttgagtgtt gttccagttt ggaacaagag tccactatta aagaacgtgg   5220
actccaacgt caaagggcga aaaaccgtct atcagggcga tggcccacta cgtgaaccat   5280
caccctaatc aagttttttg gggtcgaggt gccgtaaagc actaaatcgg aaccctaaag   5340
ggagcccccg atttagagct tgacggggaa agccggcgaa cgtggcgaga aaggaaggga   5400
agaaagcgaa aggagcgggc gctagggcgc tggcaagtgt agcggtcacg ctgcgcgtaa   5460
ccaccacacc cgccgcgctt aatgcgccgc tacagggcgc gtcgcgccat tcgccattca   5520
ggctgcgcaa ctgttgggaa gggcgatcgg tgcgggcctc ttcgctatta cgccagctgg   5580
cgaaaggggg atgtgctgca aggcgattaa gttgggtaac gccagggttt tcccagtcac   5640
gacgttgtaa aacgacggcc agtgagcgcg cgtaatacga ctcactatag ggcgaattgg   5700
gtaccgggcc ccccctcgag gtcgacggta tcgataagct tgatatcgaa ttcctgcgcc   5760
cgggccacta gtcagatgcc gcgggcactt gagcacctca tgcacagcaa taacacaaca   5820
caatggttag tagcaacctg aattcggtca ttgatgcatg catgtgccgt gaagcgggac   5880
aaccagaaaa gtcgtctata aatgccggca cgtgcgatca tcgtggcggg gttttaagag   5940
tgcatatcac aaattgtcgc attaccgcgg aaccgccaga tattcattac ttgacgcaaa   6000
agcgtttgaa ataatgacga aaaagaagga agaaaaaaaa agaaaaatac cgcttctagg   6060
cgggttatct actgatccga gcttccacta ggatagcacc caaacacctg catatttgga   6120
cgacctttac ttacaccacc aaaaaccact ttcgcctctc ccgcccctga taacgtccac   6180
taattgagcg attacctgag cggtcctctt ttgtttgcag catgagactt gcatactgca   6240
aatcgtaagt agcaacgtct caaggtcaaa actgtatgga aaccttgtca cctcacttaa   6300
ttctagctag cctaccctgc aagtcaagag gtctccgtga ttcctagcca cctcaaggta   6360
tgcctctccc cggaaactgt ggccttttct ggcacacatg atctccacga tttcaacata   6420
taaatagctt ttgataatgg caatattaat caaatttatt ttacttcttt cttgtaacat   6480
ctctcttgta atcccttatt ccttctagct atttttcata aaaaaccaag caactgctta   6540
tcaacacaca aacactaaat caaagctgag gatggattta tttgagtcat tagcacaaaa   6600
aattactggt aaagatcaaa caattgtttt ccctgaagga actgaacccc gaattgtcgg   6660
tgcggcagcg cgattagctg cagacggctt ggttaagccg attgttttag gtgcaacgga   6720
```

```
caaagttcag gctgtggcta acgatttgaa tgcggattta acaggcgttc aagtccttga   6780
tcctgcgaca tacccggctg aagataagca agcaatgctt gatgccctcg ttgaacggcg   6840
gaaaggtaag aatacgccag aacaagcggc taaaatgctg gaagatgaaa actactttgg   6900
cacgatgctc gtttatatgg gcaaagcgga tgggatggtt tcaggtgcaa tccatccaac   6960
tggtgatacg gtacggccag cgttacaaat tattaagacc aagcccggtt cacaccgaat   7020
ctcgggtgca tttatcatgc aaaagggtga ggaacgctac gtctttgctg actgtgccat   7080
caatattgat cccgatgccg atacgttagc ggaaattgcc actcagagtg cggctactgc   7140
taaggtcttc gatattgacc cgaaagttgc gatgctcagc ttctcaacta agggttcggc   7200
taagggtgaa atggtcacta aagtgcaaga agcaacggcc aaggcgcaag ctgctgaacc   7260
ggaattggct atcgatggtg aacttcaatt tgacgcggcc ttcgttgaaa aagttggttt   7320
gcaaaaggct cctggttcca aagtagctgg tcatgccaat gtctttgtat ttccagagct   7380
tcagtctggt aatattggct ataagattgc gcaacgattt ggtcattttg aagcggtggg   7440
tcctgtcttg caaggcctga acaagccggt ctccgacttg tcacgtggat gcagtgaaga   7500
agacgtttat aaggttgcga ttattacagc agcccaagga ttagcttaat taattaagag   7560
taagcgaatt tcttatgatt tatgattttt attattaaat aagttataaa aaaaataagt   7620
gtatacaaat tttaaagtga ctcttaggtt ttaaaacgaa aattcttatt cttgagtaac   7680
tctttcctgt aggtcaggtt gctttctcag gtatagcatg aggtcgctct tattgaccac   7740
acctctaccg gcatgccgag caaatgcctg caaatcgctc cccatttcac ccaattgtag   7800
atatgctaac tccagcaatg agttgatgaa tctcggtgtg tattttatgt cctcagagga   7860
caacacctgt ggtactagtt ctagagcggc cgcccgcaaa ttaaagcctt cgagcgtccc   7920
aaaaccttct caagcaaggt tttcagtata atgttacatg cgtacacgcg tttgtacaga   7980
aaaaaaagaa aaatttgaaa tataaataac gttcttaata ctaacataac tattaaaaaa   8040
aataaatagg gacctagact tcaggttgtc taactccttc cttttcggtt agagcggatg   8100
tgggaggagg gcgtgaatgt aagcgtgaca taactaatta catgattaat taattatttt   8160
aaacccttcc attgccaatc attaacttct ggcaagtcag ttccggcatc ccggatatag   8220
gcattgtgtt tagcaagcat attatccatg gattgaacga aggccgcacc agtgttttcc   8280
attgctggtt gcgccgcaat tgccgactta gctaagtcga agcggtccat ctggttcatg   8340
acccgtacgt cgaatggtgt ggtaatatca ccattttcac ggtaaccgtg gacgtataag   8400
ttatggttgt gacgatcaaa gaagatgtca cgaactaagt cttcgtaacc gtggaaagca   8460
aagaccactg gtttgtcctt agtaaagtaa tggtcaaact cagcatctga caagccccgc   8520
ggatcctttt caggactacg taacttcaag atgtcgacca cgttcacgaa acgaatcttc   8580
atctctggga aactgtcgtg tagtaattgg atggcagcca acgtttcaag cgttggttcc   8640
gtcccagcag ctgcaaagac aatgtctggt tcgctacctt ggtccgtact tgcccaatca   8700
atgataccaa gaccattgtc aactaattgc ttagcttctt caatgctgaa ccattgttga   8760
cgtgggtgtt ttgacgtaac cacgtagttg atcttttctt ggctccggaa aatgacgtca   8820
ccgacagcta ataacgtgtt ggcatcggct ggtaaatatt cacgaatgta ttctggtttc   8880
ttttcggcca aatgagttaa tgcacctgga tcttggtggg tataaccatt atggtcttgt   8940
tggaatacag ttgaagccgc gataatgtta agtgatgggt actttttacg ccaatcaagt   9000
tcattggctt tacgtaacca cttgaagtgt tgcgtcaaca ttgagtccac aacgcgtagg   9060
```

```
aaggcttcat aactggcaaa taacccatga cgtccagtta agacgtaacc ttctaaccaa   9120

ccttcagctt ggtgttcaga taactgagca tctaagaccc ggccagctgg tgcttcatat   9180

tggtcactat ctggatgaat gtcttccatc cattgacgat tagtggtttc gaagacacca   9240

tataaacggt tagacatggt ttcatcaggt ccgaacaacc ggaagttatc aggatttttc   9300

ttgatgacat cccgcaaata gtctgaccaa acgatcatat cttgcttaac attcgcgcct   9360

tctttggacg tatcgaccgc ataatcacgg aagtttggta agttcaaggc tttcggatcg   9420

accccaccat tggtgattgg gttagcagcc atccgactgt ccccagtagg aataatttct   9480

ttaatatcat ccttcaaaga gccatcttca ttgaagagtt cttttggttg atatgattcg   9540

agccaatcaa ctaaagcatc cgcatgttcc atgtcatttt gatcaacagg aatcggaatt   9600

tgatgagcac ggaatgaacc ttcgatctta tcaccgtccc atgacttcgg accagtccag   9660

cccttaggtg cgcggaagac gatcattggc catactggca atgttgcatc gttattttcg   9720

cgagcatgct tctggattgc cttgatcttt tcaacggctt catccatggc cttagctaag   9780

gctgggtgaa ccttttcagg atcgtcacct tcaacgaaga ttggttccca attcatgctt   9840

tcgaagtatt ccttaatctt agcatcagaa gtccgaccaa aaatcgttgg attagaaatc   9900

ttaaaaccat ttaagttcaa gattggtaaa acagccccgt cgttgattgg gttaatgaac   9960

ttcgttgatt gccatgaagt tgctaatgga cccgtttcgg attccccatc accaacaaca  10020

accgcggcga tttcgtcagg attgtcaaga attgccccaa ccccgtgtga aattgagtaa  10080

ccaagttcgc caccttcgtg gattgaaccg ggtgtttcag gtgccgcatg ggaagcaacc  10140

ccacctggga atgagaattg cttgaagagc ttttgcatcc cttcaacatc ctgcgtaatt  10200

tctggataaa tatcggtgta agtaccgtca aggtaagagt ttgaaaccat cacttgacca  10260

ccatgacctg gaccttcaac gtagaacatc ttcaaaccgt acttgttgat gacccggtta  10320

agatgagcat agataaagtt ttgaccggca atcgtccccc agtgaccaat tggatgaacc  10380

ttaacgtcac tggccttcaa tggccgttgt aatagtggat tatcttttaa ataaagttga  10440

ccaactgata agtagttggc agcacgccag tacttatcaa ctttttgcaa atatgctggt  10500

gatgagtaat ctgttgtcat cctcagctgg aacttagatt agattgctat gctttctctc  10560

taacgagcaa gaagtaaaaa aagttgtaat agaacaagaa aaatgaaact gaagcttgag  10620

aaattgaaga ccgtttatta gcttaaatat caatgggagg tcatcgaaag agaaaaaaat  10680

caagaaagaa actctcaaga aaaagaaacg tgataaaaat ttttattgcc tctctcgacg  10740

aagagaaaga aacgaggcgg tcccttttt cttttccaaa cctttagtac gggtaattag  10800

cgacacccta gaggaagaaa gaggggaaat ttagtatgct gtgcttgggt gtcttgaagt  10860

ggtacggcga tgcgcggagt ccgagaaaat ctggaagagt aaaaaggggg tagaagcgtt  10920

ttgaagctat ccgc                                                     10934
```

<210> SEQ ID NO 171
<211> LENGTH: 80
<212> TYPE: DNA
<213> ORGANISM: Artificial Sequence
<220> FEATURE:
<223> OTHER INFORMATION: N1341

<400> SEQUENCE: 171

```
gttgcaagaa atgcattatg caattttttg attatgacaa tctctcgaaa atagcttcaa     60

aacgcttcta ccccctttt                                                 80
```

<210> SEQ ID NO 172
<211> LENGTH: 80
<212> TYPE: DNA
<213> ORGANISM: Artificial Sequence
<220> FEATURE:
<223> OTHER INFORMATION: N1338

<400> SEQUENCE: 172
catacattat acgaacggta ctgaacatta gaatacgtaa tccgcaatgc ccgcaaatta 60
aagccttcga gcgtcccaaa 80

<210> SEQ ID NO 173
<211> LENGTH: 30
<212> TYPE: DNA
<213> ORGANISM: Artificial Sequence
<220> FEATURE:
<223> OTHER INFORMATION: N1033c

<400> SEQUENCE: 173
gcattgcgga ttacgtattc taatgttcag 30

<210> SEQ ID NO 174
<211> LENGTH: 81
<212> TYPE: DNA
<213> ORGANISM: Artificial Sequence
<220> FEATURE:
<223> OTHER INFORMATION: N1342

<400> SEQUENCE: 174
acatatgtga aaaaaaatag ttgatatttt aaaccaaatc agaaatttat caccttggct 60
aactcgttgt atcatcactg g 81

<210> SEQ ID NO 175
<211> LENGTH: 30
<212> TYPE: DNA
<213> ORGANISM: Artificial Sequence
<220> FEATURE:
<223> OTHER INFORMATION: N1364

<400> SEQUENCE: 175
atgacaacag attactcatc accagcatat 30

<210> SEQ ID NO 176
<211> LENGTH: 604
<212> TYPE: DNA
<213> ORGANISM: Artificial Sequence
<220> FEATURE:
<223> OTHER INFORMATION: L8

<400> SEQUENCE: 176
gcctacttgg cttcacatac gttgcatacg acgatataga aaataatgat aatgacagca 60
ggattatcgt ataacgtaat agtcgaaaaa tctcaaaaat ctgtgggtca ttacgtaaat 120
aatgatagga atgtgattct tctatttttc ctttttccat tctggcagcc gtcgggaaaa 180
cgtggcttcc tctctttcgg gctctattgg agtaacgctg ccgtgagctt cctctctttc 240
catatctaac aactgagcac gtaaccaatg gtaaagcatg agcttagcgt tgctccaaag 300
aagtattgga aggttaatac catgtgtctg ttctcttctg actttgactc ctcaaataaa 360
aaaaaattct acaatcaaca gatcgcttca attacgctct cacaaaaact tttttccttc 420
ttcttcgccc acgttaaatt ttaaccctca tgctgtctaa cggatttctg cacttaattt 480
attataaaac gacaaagaca taatacttct ctatcaattt cagttattgt tcttcattgc 540
attactcttc tgttcttctt tttcatttgt catatacaac cataaccaaa taatacatat 600
tcaa 604

<210> SEQ ID NO 177
<211> LENGTH: 80
<212> TYPE: DNA
<213> ORGANISM: Artificial Sequence
<220> FEATURE:
<223> OTHER INFORMATION: N1366

<400> SEQUENCE: 177
gttgcaagaa atgcattatg caattttttg attatgacaa tctctcgaaa gcctacttgg 60
cttcacatac gttgcatacg 80

<210> SEQ ID NO 178
<211> LENGTH: 65
<212> TYPE: DNA
<213> ORGANISM: Artificial Sequence
<220> FEATURE:
<223> OTHER INFORMATION: N1368

<400> SEQUENCE: 178
atatgctggt gatgagtaat ctgttgtcat tttgaatatg tattatttgg ttatggttgt 60
atatg 65

<210> SEQ ID NO 179
<211> LENGTH: 80
<212> TYPE: DNA
<213> ORGANISM: Artificial Sequence
<220> FEATURE:
<223> OTHER INFORMATION: N1371

<400> SEQUENCE: 179
aaaaactaat acgtaaacct gcattaaggt aagattatat cagaaaatgt gttgcaagaa 60
atgcattatg caattttttg 80

<210> SEQ ID NO 180
<211> LENGTH: 85
<212> TYPE: DNA
<213> ORGANISM: Artificial Sequence
<220> FEATURE:
<223> OTHER INFORMATION: N1372

<400> SEQUENCE: 180
tagaagctaa tctttaacct ggaagacagg acagaaaagt aattacaaga acatatgtga 60
aaaaaaatag ttgatatttt aaacc 85

<210> SEQ ID NO 181
<211> LENGTH: 25
<212> TYPE: DNA
<213> ORGANISM: Artificial Sequence
<220> FEATURE:
<223> OTHER INFORMATION: BK93

<400> SEQUENCE: 181
aaaaattgat tctcatcgta aatgc 25

<210> SEQ ID NO 182
<211> LENGTH: 30
<212> TYPE: DNA
<213> ORGANISM: Artificial Sequence
<220> FEATURE:
<223> OTHER INFORMATION: N1114

<400> SEQUENCE: 182
atatgctggt gatgagtaat ctgttgtcat 30

<210> SEQ ID NO 183
<211> LENGTH: 6728
<212> TYPE: DNA
<213> ORGANISM: Artificial Sequence
<220> FEATURE:
<223> OTHER INFORMATION: pJT254

<400> SEQUENCE: 183
tcgcgcgttt cggtgatgac ggtgaaaacc tctgacacat gcagctcccg gagacggtca 60
cagcttgtct gtaagcggat gccgggagca gacaagcccg tcagggcgcg tcagcgcgtg 120
ttggcgggtg tcggggctgg cttaactatg cggcatcaga gcagattgta ctgagagtgc 180
accataaatt cccgttttaa gagcttggtg agcgctagga gtcactgcca ggtatcgttt 240
gaacacggca ttagtcaggg aagtcataac acagtccttt cccgcaattt tctttttcta 300
ttactcttgg cctcctctag tacactctat attttttat gcctcggtaa tgattttcat 360 ttttttttt cccctagcgg atgactcttt ttttttctta gcgattggca ttatcacata 420
atgaattata cattatataa agtaatgtga tttcttcgaa gaatatacta aaaaatgagc 480
aggcaagata aacgaaggca aagatgacag agcagaaagc cctagtaaag cgtattacaa 540
atgaaaccaa gattcagatt gcgatctctt taaagggtgg tcccctagcg atagagcact 600
cgatcttccc agaaaaagag gcagaagcag tagcagaaca ggccacacaa tcgcaagtga 660
ttaacgtcca cacaggtata gggtttctgg accatatgat acatgctctg gccaagcatt 720
ccggctggtc gctaatcgtt gagtgcattg gtgacttaca catagacgac catcacacca 780
ctgaagactg cgggattgct ctcggtcaag cttttaaaga ggccctactg gcgcgtggag 840
taaaaaggtt tggatcagga tttgcgcctt tggatgaggc actttccaga gcggtggtag 900
atctttcgaa caggccgtac gcagttgtcg aacttggttt gcaaagggag aaagtaggag 960
atctctcttg cgagatgatc ccgcattttc ttgaaagctt tgcagaggct agcagaatta 1020
ccctccacgt tgattgtctg cgaggcaaga atgatcatca ccgtagtgag agtgcgttca 1080
aggctcttgc ggttgccata agagaagcca cctcgcccaa tggtaccaac gatgttccct 1140
ccaccaaagg tgttcttatg tagtgacacc gattatttaa agctgcagca tacgatatat 1200
atacatgtgt atatatgtat acctatgaat gtcagtaagt atgtatacga acagtatgat 1260
actgaagatg acaaggtaat gcatcattct atacgtgtca ttctgaacga ggcgcgcttt 1320 cctttttct ttttgctttt tctttttttt tctcttgaac tcgacggatc tatgcggtgt 1380
gaaataccgc acagatgcgt aaggagaaaa taccgcatca ggaaattgta aacgttaata 1440
ttttgttaaa attcgcgtta aatttttgtt aaatcagctc atttttaac caataggccg 1500 aaatcggcaa aatcccttat aaatcaaaag aatagaccga gatagggttg agtgttgttc 1560
cagtttggaa caagagtcca ctattaaaga acgtggactc caacgtcaaa gggcgaaaaa 1620
ccgtctatca gggcgatggc ccactacgtg aaccatcacc ctaatcaagt tttttggggt 1680
cgaggtgccg taaagcacta aatcggaacc ctaaagggag cccccgattt agagcttgac 1740
ggggaaagcc ggcgaacgtg gcgagaaagg aagggaagaa agcgaaagga gcgggcgcta 1800
gggcgctggc aagtgtagcg gtcacgctgc gcgtaaccac cacacccgcc gcgcttaatg 1860
cgccgctaca gggcgcgtcg cgccattcgc cattcaggct gcgcaactgt tgggaagggc 1920

```
gatcggtgcg ggcctcttcg ctattacgcc agctggcgaa agggggatgt gctgcaaggc   1980
gattaagttg ggtaacgcca gggttttccc agtcacgacg ttgtaaaacg acggccagtg   2040
agcgcgcgta atacgactca ctatagggcg aattgggtac cgggcccccc ctcgaggtcg   2100
acggtatcga taagcttgat tagaagccgc cgagcgggcg acagccctcc gacggaagac   2160
tctcctccgt gcgtcctcgt cttcaccggt cgcgttcctg aaacgcagat gtgcctcgcg   2220
ccgcactgct ccgaacaata aagattctac aatactagct tttatggtta tgaagaggaa   2280
aaattggcag taacctggcc ccacaaacct tcaaattaac gaatcaaatt aacaaccata   2340
ggatgataat gcgattagtt ttttagcctt atttctgggg taattaatca gcgaagcgat   2400
gatttttgat ctattaacag atatataaat ggaaaagctg cataaccact ttaactaata   2460
ctttcaacat tttcagtttg tattacttct tattcaaatg tcataaaagt atcaacaaaa   2520
aattgttaat atacctctat actttaacgt caaggagaaa aatgtccaat ttactgcccg   2580
tacaccaaaa tttgcctgca ttaccggtcg atgcaacgag tgatgaggtt cgcaagaacc   2640
tgatggacat gttcagggat cgccaggcgt tttctgagca tacctggaaa atgcttctgt   2700
ccgtttgccg gtcgtgggcg gcatggtgca agttgaataa ccggaaatgg tttcccgcag   2760
aacctgaaga tgttcgcgat tatcttctat atcttcaggc gcgcggtctg gcagtaaaaa   2820
ctatccagca acatttgggc cagctaaaca tgcttcatcg tcggtccggg ctgccacgac   2880
caagtgacag caatgctgtt tcactggtta tgcggcggat ccgaaaagaa aacgttgatg   2940
ccggtgaacg tgcaaaacag gctctagcgt tcgaacgcac tgatttcgac caggttcgtt   3000
cactcatgga aaatagcgat cgctgccagg atatacgtaa tctggcattt ctggggattg   3060
cttataacac cctgttacgt atagccgaaa ttgccaggat cagggttaaa gatatctcac   3120
gtactgacgg tgggagaatg ttaatccata ttggcagaac gaaaacgctg gttagcaccg   3180
caggtgtaga gaaggcactt agcctggggg taactaaact ggtcgagcga tggatttccg   3240
tctctggtgt agctgatgat ccgaataact acctgttttg ccgggtcaga aaaaatggtg   3300
ttgccgcgcc atctgccacc agccagctat caactcgcgc cctggaaggg atttttgaag   3360
caactcatcg attgatttac ggcgctaagg atgactctgg tcagagatac ctggcctggt   3420
ctggacacag tgcccgtgtc ggagccgcgc gagatatggc ccgcgctgga gtttcaatac   3480
cggagatcat gcaagctggt ggctggacca atgtaaatat tgtcatgaac tatatccgta   3540
acctggatag tgaaacaggg gcaatggtgc gcctgctgga agatggcgat taggagtaag   3600
cgaatttctt atgatttatg atttttatta ttaaataagt tataaaaaaa ataagtgtat   3660
acaaatttta aagtgactct taggttttaa aacgaaaatt cttattcttg agtaactctt   3720
tcctgtaggt caggttgctt tctcaggtat agcatgaggt cgctcttatt gaccacacct   3780
ctaccggcat gccgagcaaa tgcctgcaaa tcgctcccca tttcacccaa ttgtagatat   3840
gctaactcca gcaatgagtt gatgaatctc ggtgtgtatt ttatgtcctc agaggacaac   3900
acctgtggtg ttctagagcg gccgccaccg cggtggagct ccagcttttg ttccctttag   3960
tgagggttaa ttgcgcgctt ggcgtaatca tggtcatagc tgtttcctgt gtgaaattgt   4020
tatccgctca caattccaca caacatagga gccggaagca taaagtgtaa agcctggggt   4080
gcctaatgag tgaggtaact cacattaatt gcgttgcgct cactgcccgc tttccagtcg   4140
ggaaacctgt cgtgccagct gcattaatga atcggccaac gcgcggggag aggcggtttg   4200
cgtattgggc gctcttccgc ttcctcgctc actgactcgc tgcgctcggt cgttcggctg   4260
cggcgagcgg tatcagctca ctcaaaggcg gtaatacggt tatccacaga atcaggggat   4320
```

```
aacgcaggaa agaacatgtg agcaaaaggc cagcaaaagg ccaggaaccg taaaaaggcc   4380
gcgttgctgg cgtttttcca taggctccgc ccccctgacg agcatcacaa aaatcgacgc   4440
tcaagtcaga ggtggcgaaa cccgacagga ctataaagat accaggcgtt tccccctgga   4500
agctccctcg tgcgctctcc tgttccgacc ctgccgctta ccggatacct gtccgccttt   4560
ctcccttcgg gaagcgtggc gctttctcat agctcacgct gtaggtatct cagttcggtg   4620
taggtcgttc gctccaagct gggctgtgtg cacgaacccc ccgttcagcc cgaccgctgc   4680
gccttatccg gtaactatcg tcttgagtcc aacccggtaa gacacgactt atcgccactg   4740
gcagcagcca ctggtaacag gattagcaga gcgaggtatg taggcggtgc tacagagttc   4800
ttgaagtggt ggcctaacta cggctacact agaaggacag tatttggtat ctgcgctctg   4860
ctgaagccag ttaccttcgg aaaaagagtt ggtagctctt gatccggcaa acaaaccacc   4920
gctggtagcg gtggtttttt tgtttgcaag cagcagatta cgcgcagaaa aaaaggatct   4980
caagaagatc ctttgatctt ttctacgggg tctgacgctc agtggaacga aaactcacgt   5040
taagggattt tggtcatgag attatcaaaa aggatcttca cctagatcct tttaaattaa   5100
aaatgaagtt ttaaatcaat ctaaagtata tatgagtaaa cttggtctga cagttaccaa   5160
tgcttaatca gtgaggcacc tatctcagcg atctgtctat ttcgttcatc catagttgcc   5220
tgactccccg tcgtgtagat aactacgata cgggagggct taccatctgg ccccagtgct   5280
gcaatgatac cgcgagaccc acgctcaccg gctccagatt tatcagcaat aaaccagcca   5340
gccggaaggg ccgagcgcag aagtggtcct gcaactttat ccgcctccat ccagtctatt   5400
aattgttgcc gggaagctag agtaagtagt tcgccagtta atagtttgcg caacgttgtt   5460
gccattgcta caggcatcgt ggtgtcacgc tcgtcgtttg gtatggcttc attcagctcc   5520
ggttcccaac gatcaaggcg agttacatga tcccccatgt tgtgcaaaaa agcggttagc   5580
tccttcggtc ctccgatcgt tgtcagaagt aagttggccg cagtgttatc actcatggtt   5640
atggcagcac tgcataattc tcttactgtc atgccatccg taagatgctt ttctgtgact   5700
ggtgagtact caaccaagtc attctgagaa tagtgtatgc ggcgaccgag ttgctcttgc   5760
ccggcgtcaa tacgggataa taccgcgcca catagcagaa ctttaaaagt gctcatcatt   5820
ggaaaacgtt cttcggggcg aaaactctca aggatcttac cgctgttgag atccagttcg   5880
atgtaaccca ctcgtgcacc caactgatct tcagcatctt ttactttcac cagcgtttct   5940
gggtgagcaa aaacaggaag gcaaaatgcc gcaaaaaagg gaataagggc gacacggaaa   6000
tgttgaatac tcatactctt cctttttcaa tattattgaa gcatttatca gggttattgt   6060
ctcatgagcg gatacatatt tgaatgtatt tagaaaaata aacaaatagg ggttccgcgc   6120
acatttcccc gaaaagtgcc acctgggtcc ttttcatcac gtgctataaa aataattata   6180
atttaaattt tttaatataa atatataaat taaaaataga aagtaaaaaa agaaattaaa   6240
gaaaaaatag tttttgtttt ccgaagatgt aaaagactct agggggatcg ccaacaaata   6300
ctacctttta tcttgctctt cctgctctca ggtattaatg ccgaattgtt tcatcttgtc   6360
tgtgtagaag accacacacg aaaatcctgt gattttacat tttacttatc gttaatcgaa   6420
tgtatatcta tttaatctgc ttttcttgtc taataaatat atatgtaaag tacgcttttt   6480
gttgaaattt tttaaacctt tgtttatttt tttttcttca ttccgtaact cttctacctt   6540
ctttatttac tttctaaaat ccaaatacaa aacataaaaa taaataaaca cagagtaaat   6600
tcccaaatta ttccatcatt aaaagatacg aggcgcgtgt aagttacagg caagcgatcc   6660
```

gtcctaagaa accattatta tcatgacatt aacctataaa aataggcgta tcacgaggcc 6720
ctttcgtc 6728

<210> SEQ ID NO 184
<211> LENGTH: 22
<212> TYPE: DNA
<213> ORGANISM: Artificial Sequence
<220> FEATURE:
<223> OTHER INFORMATION: N160Seq F5

<400> SEQUENCE: 184
cctgaagtct aggtccctat tt 22

<210> SEQ ID NO 185
<211> LENGTH: 1650
<212> TYPE: DNA
<213> ORGANISM: Artificial Sequence
<220> FEATURE:
<223> OTHER INFORMATION: Amn1

<400> SEQUENCE: 185
atgaagctgg agcgcgtgag ttctaacggg agctttaagc gtggccgtga catccaaagt 60
ttggagagtc cgtgtacccg cccattaaag aaaatgtcgc catcaccttc atttacgagc 120
ctgaagatgg aaaaaccgtt taaggacatt gttcgaaaat acgggggtca cctgcaccag 180
tcctcgtata acccaggttc ttcaaaagtt gaactcgtgc gtccggacct gagcttgaaa 240
acggaccaat catttttgca gagcagcgtg cagacaaccc cgaacaaaaa gagttgtaac 300
gagtatctgt ccacacccga agccactccc cttaagaaca cggccaccga gaatgcgtgg 360
gctacgtcaa gggtggtgag cgcatcaagc ctgtcaatcg tcacgccgac cgaaatcaaa 420
aatatactgg ttgacgagtt tagtgaacta aaacttggtc agcccttaac agcccagcac 480
caacggagcc atgcagtttt cgagatacct gagatcgtag agaacataat caagatgatc 540
gtttccctcg agagcgccaa tattccgaaa gaacgtccgt gcctgcgtcg caacccgcag 600
agttatgagc attcccttct gatgtataaa gacgaggaac gcgcgaagaa agcatggtcc 660
gcggctcaac aactgcgcga tccgccgctg gtgggtcata aggaaaaaaa acagggcgct 720
ctgtttagct gcatgatggt caaccgcctg tggttgaatg tcacgcgtcc gttcttattt 780
aagtctctgc atttcaaatc agtgcacaac ttcaaagaat ttctgcgcac aagtcaggaa 840
accacgcaag tgatgaggcc atcgcacttt atcctgcata aattgcacca ggtaacgcag 900
ccggatattg agagactgtc tagaatggaa tgccagaacc tcaagtggtt ggaattttat 960
gtatgtcccc gtattacacc tccactgtct tggttcgaca atttgcataa gttagaaaaa 1020
ttaatcatcc ccggaaacaa gaatatcgac gataatttcc tcttacggct gtctcagagt 1080
attcctaacc tgaaacacct cgtgcttcgt gcttgcgaca atgtttccga tagtggtgta 1140
gtttgtatcg ccctgaactg ccctaagctg aagacgttca acatcggacg tcatcgccgc 1200
ggcaatctga ttacatcagt tagcttggtt gccctgggta agtatacgca agttgagacc 1260
gttggttttg caggctgcga tgtggacgac gcaggcatat gggagttcgc gcgtttaaac 1320
gggaaaaacg tcgagcgcct gtcactcaac agttgccggc ttttaaccga ctatagcttg 1380
ccaatcctgt ttgcccttaa tagtttcccg aaccttgcgg tgttggaaat tcgaaacctc 1440
gataaaatta cagatgtccg ccattttgtg aaatataatc tgtggaagaa atcactggat 1500
gctcctatcc tgattgaggc gtgcgaacgc ataacaaagc tgattgatca ggaagagaac 1560
cgggtcaaac gcataaatag cctggtcgct ttaaaggata tgaccgcgtg ggtgaacgct 1620

```
gacgatgaaa ttgaaaacaa cgtcgattga                                  1650


<210> SEQ ID NO 186
<211> LENGTH: 549
<212> TYPE: PRT
<213> ORGANISM: Artificial Sequence
<220> FEATURE:
<223> OTHER INFORMATION: Amn1

<400> SEQUENCE: 186

Met Lys Leu Glu Arg Val Ser Ser Asn Gly Ser Phe Lys Arg Gly Arg
1               5                   10                  15

Asp Ile Gln Ser Leu Glu Ser Pro Cys Thr Arg Pro Leu Lys Lys Met
            20                  25                  30

Ser Pro Ser Pro Ser Phe Thr Ser Leu Lys Met Glu Lys Pro Phe Lys
        35                  40                  45

Asp Ile Val Arg Lys Tyr Gly Gly His Leu His Gln Ser Ser Tyr Asn
    50                  55                  60

Pro Gly Ser Ser Lys Val Glu Leu Val Arg Pro Asp Leu Ser Leu Lys
65                  70                  75                  80

Thr Asp Gln Ser Phe Leu Gln Ser Ser Val Gln Thr Thr Pro Asn Lys
                85                  90                  95

Lys Ser Cys Asn Glu Tyr Leu Ser Thr Pro Glu Ala Thr Pro Leu Lys
            100                 105                 110

Asn Thr Ala Thr Glu Asn Ala Trp Ala Thr Ser Arg Val Val Ser Ala
        115                 120                 125

Ser Ser Leu Ser Ile Val Thr Pro Thr Glu Ile Lys Asn Ile Leu Val
    130                 135                 140

Asp Glu Phe Ser Glu Leu Lys Leu Gly Gln Pro Leu Thr Ala Gln His
145                 150                 155                 160

Gln Arg Ser His Ala Val Phe Glu Ile Pro Glu Ile Val Glu Asn Ile
                165                 170                 175

Ile Lys Met Ile Val Ser Leu Glu Ser Ala Asn Ile Pro Lys Glu Arg
            180                 185                 190

Pro Cys Leu Arg Arg Asn Pro Gln Ser Tyr Glu His Ser Leu Leu Met
        195                 200                 205

Tyr Lys Asp Glu Glu Arg Ala Lys Lys Ala Trp Ser Ala Ala Gln Gln
    210                 215                 220

Leu Arg Asp Pro Pro Leu Val Gly His Lys Glu Lys Lys Gln Gly Ala
225                 230                 235                 240

Leu Phe Ser Cys Met Met Val Asn Arg Leu Trp Leu Asn Val Thr Arg
                245                 250                 255

Pro Phe Leu Phe Lys Ser Leu His Phe Lys Ser Val His Asn Phe Lys
            260                 265                 270

Glu Phe Leu Arg Thr Ser Gln Glu Thr Thr Gln Val Met Arg Pro Ser
        275                 280                 285

His Phe Ile Leu His Lys Leu His Gln Val Thr Gln Pro Asp Ile Glu
    290                 295                 300

Arg Leu Ser Arg Met Glu Cys Gln Asn Leu Lys Trp Leu Glu Phe Tyr
305                 310                 315                 320

Val Cys Pro Arg Ile Thr Pro Pro Leu Ser Trp Phe Asp Asn Leu His
                325                 330                 335

Lys Leu Glu Lys Leu Ile Ile Pro Gly Asn Lys Asn Ile Asp Asp Asn
            340                 345                 350
```

```
Phe Leu Leu Arg Leu Ser Gln Ser Ile Pro Asn Leu Lys His Leu Val
        355                 360                 365

Leu Arg Ala Cys Asp Asn Val Ser Asp Ser Gly Val Val Cys Ile Ala
    370                 375                 380

Leu Asn Cys Pro Lys Leu Lys Thr Phe Asn Ile Gly Arg His Arg Arg
385                 390                 395                 400

Gly Asn Leu Ile Thr Ser Val Ser Leu Val Ala Leu Gly Lys Tyr Thr
                405                 410                 415

Gln Val Glu Thr Val Gly Phe Ala Gly Cys Asp Val Asp Asp Ala Gly
            420                 425                 430

Ile Trp Glu Phe Ala Arg Leu Asn Gly Lys Asn Val Glu Arg Leu Ser
        435                 440                 445

Leu Asn Ser Cys Arg Leu Leu Thr Asp Tyr Ser Leu Pro Ile Leu Phe
    450                 455                 460

Ala Leu Asn Ser Phe Pro Asn Leu Ala Val Leu Glu Ile Arg Asn Leu
465                 470                 475                 480

Asp Lys Ile Thr Asp Val Arg His Phe Val Lys Tyr Asn Leu Trp Lys
                485                 490                 495

Lys Ser Leu Asp Ala Pro Ile Leu Ile Glu Ala Cys Glu Arg Ile Thr
            500                 505                 510

Lys Leu Ile Asp Gln Glu Glu Asn Arg Val Lys Arg Ile Asn Ser Leu
        515                 520                 525

Val Ala Leu Lys Asp Met Thr Ala Trp Val Asn Ala Asp Asp Glu Ile
    530                 535                 540

Glu Asn Asn Val Asp
545


<210> SEQ ID NO 187
<211> LENGTH: 6638
<212> TYPE: DNA
<213> ORGANISM: Artificial Sequence
<220> FEATURE:
<223> OTHER INFORMATION: pLA67

<400> SEQUENCE: 187

aaacgccagc aacgcggcct ttttacggtt cctggccttt tgctggcctt ttgctcacat      60

gttctttcct gcgttatccc ctgattctgt ggataaccgt attaccgcct ttgagtgagc     120

tgataccgct cgccgcagcc gaacgaccga gcgcagcgag tcagtgagcg aggaagcgga     180

agagcgccca atacgcaaac cgcctctccc cgcgcgttgg ccgattcatt aatgcagctg     240

gcacgacagg tttcccgact ggaaagcggg cagtgagcgc aacgcaatta atgtgagtta     300

gctcactcat taggcacccc aggctttaca ctttatgctt ccggctcgta tgttgtgtgg     360

aattgtgagc ggataacaat ttcacacagg aaacagctat gaccatgatt acgccaagct     420

tgcatgcctg caggtcgact ctagaggatc cgcattgcgg attacgtatt ctaatgttca     480

gtaccgttcg tataatgtat gctatacgaa gttatgcaga ttgtactgag agtgcaccat     540

accacagctt ttcaattcaa ttcatcattt ttttttatt ctttttttg atttcggttt     600

ctttgaaatt tttttgattc ggtaatctcc gaacagaagg aagaacgaag gaaggagcac     660

agacttagat tggtatatat acgcatatgt agtgttgaag aaacatgaaa ttgcccagta     720

ttcttaaccc aactgcacag aacaaaaacc tgcaggaaac gaagataaat catgtcgaaa     780

gctacatata aggaacgtgc tgctactcat cctagtcctg ttgctgccaa gctatttaat     840

atcatgcacg aaaagcaaac aaacttgtgt gcttcattgg atgttcgtac caccaaggaa     900
```

```
ttactggagt tagttgaagc attaggtccc aaaatttgtt tactaaaaac acatgtggat    960
atcttgactg atttttccat ggagggcaca gttaagccgc taaaggcatt atccgccaag   1020
tacaattttt tactcttcga agacagaaaa tttgctgaca ttggtaatac agtcaaattg   1080
cagtactctg cgggtgtata cagaatagca gaatgggcag acattacgaa tgcacacggt   1140
gtggtgggcc caggtattgt tagcggtttg aagcaggcgg cagaagaagt aacaaaggaa   1200
cctagaggcc ttttgatgtt agcagaattg tcatgcaagg gctccctatc tactggagaa   1260
tatactaagg gtactgttga cattgcgaag agcgacaaag attttgttat cggctttatt   1320
gctcaaagag acatgggtgg aagagatgaa ggttacgatt ggttgattat gacacccggt   1380
gtgggtttag atgacaaggg agacgcattg ggtcaacagt atagaaccgt ggatgatgtg   1440
gtctctacag gatctgacat tattattgtt ggaagaggac tatttgcaaa gggaagggat   1500
gctaaggtag agggtgaacg ttacagaaaa gcaggctggg aagcatattt gagaagatgc   1560
ggccagcaaa actaaaaaac tgtattataa gtaaatgcat gtatactaaa ctcacaaatt   1620
agagcttcaa tttaattata tcagttatta ccctatgcgg tgtgaaatac cgcacagatg   1680
cgtaaggaga aaataccgca tcaggaaatt gtaaacgtta atattttgtt aaaattcgcg   1740
ttaaattttt gttaaatcag ctcatttttt aaccaatagg ccgaaatcgg caaaatccct   1800
tataaatcaa aagaatagac cgagataggg ttgagtgttg ttccagtttg gaacaagagt   1860
ccactattaa agaacgtgga ctccaacgtc aaagggcgaa aaaccgtcta tcagggcgat   1920
ggcccactac gtgaaccatc accctaatca agataacttc gtataatgta tgctatacga   1980
acggtaccag tgatgataca acgagttagc caaggtgaat tcgacttagg atgtctcatc   2040
aatcatctta ttcctgctgg tgtttttgt atcgccttgc cttggagtgt ttatgcttgt   2100
cctttgttca gtaaccattc ttcaagtttg tttcaagtag taggatacct tcagatatac   2160
gaaagaaagg gagtatagtt gtggatatat atatatatag caacccttct ttataagggt   2220
cctatagact atactcttca cactttaaag tacggaatta aggcccaagg gaactaacaa   2280
aaacgttcaa aaagttttaa aactatatgt gttaactgta caaaaataac ttatttatca   2340
tatcattttt ttctctgttt atttcttcta gaacttatac ctgtcttttc cttttattct   2400
ttgaatttgk tttaatatcc ctttttgktt taatatccat ccattccttt cacttagaac   2460
taataattcc cttcgtttga taatttatca ttttcctttt ctgttagtaa agtacccatt   2520
aaatgaagct ggagcgcgtg agttctaacg ggagctttaa gcgtggccgt gacatccaaa   2580
gtttggagag tccgtgtacc cgcccattaa agaaaatgtc gccatcacct tcatttacga   2640
gcctgaagat ggaaaaaccg tttaaggaca ttgttcgaaa atacgggggt cacctgcacc   2700
agtcctcgta taacccaggt tcttcaaaag ttgaactcgt gcgtccggac ctgagcttga   2760
aaacggacca atcattttg cagagcagcg tgcagacaac cccgaacaaa aagagttgta   2820
acgagtatct gtccacaccc gaagccactc cccttaagaa cacggccacc gagaatgcgt   2880
gggctacgtc aagggtggtg agcgcatcaa gcctgtcaat cgtcacgccg accgaaatca   2940
aaaatatact ggttgacgag tttagtgaac taaaacttgg tcagccctta acagcccagc   3000
accaacggag ccatgcagtt ttcgagatac ctgagatcgt agagaacata atcaagatga   3060
tcgtttccct cgagagcgcc aatattccga aagaacgtcc gtgcctgcgt cgcaacccgc   3120
agagttatga gcattccctt ctgatgtata aagacgagga acgcgcgaag aaagcatggt   3180
ccgcggctca acaactgcgc gatccgccgc tggtgggtca taaggaaaaa aaacagggcg   3240
ctctgtttag ctgcatgatg gtcaaccgcc tgtggttgaa tgtcacgcgt ccgttcttat   3300
```

```
ttaagtctct gcatttcaaa tcagtgcaca acttcaaaga atttctgcgc acaagtcagg   3360
aaaccacgca agtgatgagg ccatcgcact ttatcctgca taaattgcac caggtaacgc   3420
agccggatat tgagagactg tctagaatgg aatgccagaa cctcaagtgg ttggaatttt   3480
atgtatgtcc ccgtattaca cctccactgt cttggttcga caatttgcat aagttagaaa   3540
aattaatcat ccccggaaac aagaatatcg acgataattt cctcttacgg ctgtctcaga   3600
gtattcctaa cctgaaacac ctcgtgcttc gtgcttgcga caatgtttcc gatagtggtg   3660
tagtttgtat cgccctgaac tgccctaagc tgaagacgtt caacatcgga cgtcatcgcc   3720
gcggcaatct gattacatca gttagcttgg ttgccctggg taagtatacg caagttgaga   3780
ccgttggttt tgcaggctgc gatgtggacg acgcaggcat atgggagttc gcgcgtttaa   3840
acgggaaaaa cgtcgagcgc ctgtcactca acagttgccg gcttttaacc gactatagct   3900
tgccaatcct gtttgccctt aatagtttcc cgaaccttgc ggtgttggaa attcgaaacc   3960
tcgataaaat tacagatgtc cgccattttg tgaaatataa tctgtggaag aaatcactgg   4020
atgctcctat cctgattgag gcgtgcgaac gcataacaaa gctgattgat caggaagaga   4080
accgggtcaa acgcataaat agcctggtcg ctttaaagga tatgaccgcg tgggtgaacg   4140
ctgacgatga aattgaaaac aacgtcgatt gagacgatga aattgaaaac aacgtcgatt   4200
gaggtaccat ggtttttgtg actttaccta taaatagtac acaacagacc accagtaatt   4260
ctacacactt cttaactgat aatattatta taattgtaac tttttagcag cactaaattt   4320
aatgaataca tagattttta actagcattt tactattctg tactttttac ttgaaattcc   4380
agaagggccg aagaaaccag aattccttca cagaaaacga attcactggc cgtcgtttta   4440
caacgtcgtg actgggaaaa ccctggcgtt acccaactta atcgccttgc agcacatccc   4500
cctttcgcca gctggcgtaa tagcgaagag gcccgcaccg atcgcccttc ccaacagttg   4560
cgcagcctga atggcgaatg gcgcctgatg cggtattttc tccttacgca tctgtgcggt   4620
atttcacacc gcatatggtg cactctcagt acaatctgct ctgatgccgc atagttaagc   4680
cagccccgac acccgccaac acccgctgac gcgccctgac gggcttgtct gctcccggca   4740
tccgcttaca gacaagctgt gaccgtctcc gggagctgca tgtgtcagag gttttcaccg   4800
tcatcaccga aacgcgcgag acgaaagggc ctcgtgatac gcctattttt ataggttaat   4860
gtcatgataa taatggtttc ttagacgtca ggtggcactt ttcggggaaa tgtgcgcgga   4920
acccctattt gtttattttt ctaaatacat tcaaatatgt atccgctcat gagacaataa   4980
ccctgataaa tgcttcaata atattgaaaa aggaagagta tgagtattca acatttccgt   5040
gtcgccctta ttcccttttt tgcggcattt tgccttcctg tttttgctca cccagaaacg   5100
ctggtgaaag taaaagatgc tgaagatcag ttgggtgcac gagtgggtta catcgaactg   5160
gatctcaaca gcggtaagat ccttgagagt tttcgccccg aagaacgttt tccaatgatg   5220
agcactttta aagttctgct atgtggcgcg gtattatccc gtattgacgc cgggcaagag   5280
caactcggtc gccgcataca ctattctcag aatgacttgg ttgagtactc accagtcaca   5340
gaaaagcatc ttacggatgg catgacagta agagaattat gcagtgctgc cataaccatg   5400
agtgataaca ctgcggccaa cttacttctg acaacgatcg gaggaccgaa ggagctaacc   5460
gcttttttgc acaacatggg ggatcatgta actcgccttg atcgttggga accggagctg   5520
aatgaagcca taccaaacga cgagcgtgac accacgatgc ctgtagcaat ggcaacaacg   5580
ttgcgcaaac tattaactgg cgaactactt actctagctt cccggcaaca attaatagac   5640
```

```
tggatggagg cggataaagt tgcaggacca cttctgcgct cggcccttcc ggctggctgg   5700

tttattgctg ataaatctgg agccggtgag cgtgggtctc gcggtatcat tgcagcactg   5760

gggccagatg gtaagccctc ccgtatcgta gttatctaca cgacggggag tcaggcaact   5820

atggatgaac gaaatagaca gatcgctgag ataggtgcct cactgattaa gcattggtaa   5880

ctgtcagacc aagtttactc atatatactt tagattgatt taaaacttca tttttaattt   5940

aaaaggatct aggtgaagat cctttttgat aatctcatga ccaaaatccc ttaacgtgag   6000

ttttcgttcc actgagcgtc agaccccgta gaaaagatca aaggatcttc ttgagatcct   6060

tttttctgc gcgtaatctg ctgcttgcaa acaaaaaaac caccgctacc agcggtggtt   6120

tgtttgccgg atcaagagct accaactctt tttccgaagg taactggctt cagcagagcg   6180

cagataccaa atactgtcct tctagtgtag ccgtagttag gccaccactt caagaactct   6240

gtagcaccgc ctacatacct cgctctgcta atcctgttac cagtggctgc tgccagtggc   6300

gataagtcgt gtcttaccgg gttggactca agacgatagt taccggataa ggcgcagcgg   6360

tcgggctgaa cggggggttc gtgcacacag cccagcttgg agcgaacgac ctacaccgaa   6420

ctgagatacc tacagcgtga gctatgagaa agcgccacgc ttcccgaagg gagaaaggcg   6480

gacaggtatc cggtaagcgg cagggtcgga acaggagagc gcacgaggga gcttccaggg   6540

ggaaacgcct ggtatcttta tagtcctgtc gggtttcgcc acctctgact tgagcgtcga   6600

tttttgtgat gctcgtcagg ggggcggagc ctatggaa                           6638
```

```
<210> SEQ ID NO 188
<211> LENGTH: 100
<212> TYPE: DNA
<213> ORGANISM: Artificial Sequence
<220> FEATURE:
<223> OTHER INFORMATION: LA712

<400> SEQUENCE: 188

cttaattgaa agaaagaatt tccttcaact tcggtttcct ggttccgcta tttctcgctt     60

gtttcttcta gcattgcgga ttacgtattc taatgttcag                          100


<210> SEQ ID NO 189
<211> LENGTH: 30
<212> TYPE: DNA
<213> ORGANISM: Artificial Sequence
<220> FEATURE:
<223> OTHER INFORMATION: LA746

<400> SEQUENCE: 189

gttttctgtg aaggaattct ggtttcttcg                                      30


<210> SEQ ID NO 190
<211> LENGTH: 66
<212> TYPE: PRT
<213> ORGANISM: Homo sapiens

<400> SEQUENCE: 190

Arg Val Thr Met Trp Val Phe Glu Glu Asp Ile Gly Gly Lys Lys Leu
1               5                   10                  15

Thr Glu Ile Ile Asn Thr Gln His Glu Asn Val Lys Tyr Leu Pro Gly
            20                  25                  30

His Lys Leu Pro Pro Asn Val Val Ala Val Pro Asp Val Val Gln Ala
        35                  40                  45

Ala Glu Asp Ala Asp Ile Leu Ile Phe Val Val Pro His Gln Phe Ile
    50                  55                  60
```

```
Gly Lys
65


<210> SEQ ID NO 191
<211> LENGTH: 66
<212> TYPE: PRT
<213> ORGANISM: Saccharomyces cerevisiae

<400> SEQUENCE: 191

Ile Val Gln Met Trp Val Phe Glu Glu Glu Ile Asn Gly Glu Lys Leu
1               5                   10                  15

Thr Glu Ile Ile Asn Thr Arg His Gln Asn Val Lys Tyr Leu Pro Gly
            20                  25                  30

Ile Thr Leu Pro Asp Asn Leu Val Ala Asn Pro Asp Leu Ile Asp Ser
        35                  40                  45

Val Lys Asp Val Asp Ile Ile Val Phe Asn Ile Pro His Gln Phe Leu
    50                  55                  60

Pro Arg
65


<210> SEQ ID NO 192
<211> LENGTH: 60
<212> TYPE: PRT
<213> ORGANISM: Rickettsia prowazekii

<400> SEQUENCE: 192

Asn Val Thr Leu Phe Leu Arg Asp Glu Ile Ile Leu Lys Glu Ile Leu
1               5                   10                  15

Tyr Lys Lys Thr Asn Ala Gln Tyr Leu Gly Asp Ile Glu Leu Pro Thr
            20                  25                  30

Asn Leu Gln Ala Thr Thr Asn Leu Ser Val Ile Lys Asp Phe Glu Leu
        35                  40                  45

Ile Ile Ile Ala Val Pro Ser Tyr Ala Phe Asp Asp
    50                  55                  60


<210> SEQ ID NO 193
<211> LENGTH: 61
<212> TYPE: PRT
<213> ORGANISM: Beggiatoa alba

<400> SEQUENCE: 193

Pro Ile Tyr Leu Trp Gly Lys Asp Pro Ala His Val His Thr Leu Gln
1               5                   10                  15

Ile Gln Arg Cys Asn Gln Arg Phe Leu Pro Asn Ala Val Phe Pro Asp
            20                  25                  30

Asn Leu Tyr Ala Ile Thr Asp Phe Val Thr Leu Met Pro Ile Val Glu
        35                  40                  45

Asp Ile Ile Ile Val Val Pro Ser His Gly Phe Arg Glu
    50                  55                  60


<210> SEQ ID NO 194
<211> LENGTH: 61
<212> TYPE: PRT
<213> ORGANISM: Kangiella koreensis

<400> SEQUENCE: 194

Ser Val Gln Leu Trp Ala Arg Asn Ser Gln His Val Val Glu Met Gln
1               5                   10                  15

Gln Ala Lys Gln Asn Thr Lys Tyr Leu Pro Asp Val Ala Phe Pro Asp
```

```
            20                  25                  30

Asn Leu Ser Val Thr Asp Gln Ile Asp Val Ala Leu Lys His His Pro
        35                  40                  45

Ile Ile Leu Val Ala Val Pro Ser His Ala Phe Arg Asp
    50                  55                  60


<210> SEQ ID NO 195
<211> LENGTH: 391
<212> TYPE: PRT
<213> ORGANISM: Saccharomyces cerevisiae

<400> SEQUENCE: 195

Met Ser Ala Ala Ala Asp Arg Leu Asn Leu Thr Ser Gly His Leu Asn
1               5                   10                  15

Ala Gly Arg Lys Arg Ser Ser Ser Ser Val Ser Leu Lys Ala Ala Glu
            20                  25                  30

Lys Pro Phe Lys Val Thr Val Ile Gly Ser Gly Asn Trp Gly Thr Thr
        35                  40                  45

Ile Ala Lys Val Val Ala Glu Asn Cys Lys Gly Tyr Pro Glu Val Phe
    50                  55                  60

Ala Pro Ile Val Gln Met Trp Val Phe Glu Glu Glu Ile Asn Gly Glu
65                  70                  75                  80

Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
        115                 120                 125

Phe Leu Pro Arg Ile Cys Ser Gln Leu Lys Gly His Val Asp Ser His
    130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
        195                 200                 205

Glu Gly Lys Asp Val Asp His Lys Val Leu Lys Ala Leu Phe His Arg
    210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
            260                 265                 270

Leu Gly Glu Ile Ile Arg Phe Gly Gln Met Phe Phe Pro Glu Ser Arg
        275                 280                 285

Glu Glu Thr Tyr Tyr Gln Glu Ser Ala Gly Val Ala Asp Leu Ile Thr
    290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
                325                 330                 335
```

```
Ser Ala Gln Gly Leu Ile Thr Cys Lys Glu Val His Glu Trp Leu Glu
            340                 345                 350

Thr Cys Gly Ser Val Glu Asp Phe Pro Leu Phe Glu Ala Val Tyr Gln
        355                 360                 365

Ile Val Tyr Asn Asn Tyr Pro Met Lys Asn Leu Pro Asp Met Ile Glu
    370                 375                 380

Glu Leu Asp Leu His Glu Asp
385                 390


<210> SEQ ID NO 196
<211> LENGTH: 391
<212> TYPE: PRT
<213> ORGANISM: Artificial Sequence
<220> FEATURE:
<223> OTHER INFORMATION: F73G

<400> SEQUENCE: 196

Met Ser Ala Ala Ala Asp Arg Leu Asn Leu Thr Ser Gly His Leu Asn
1               5                   10                  15

Ala Gly Arg Lys Arg Ser Ser Ser Ser Val Ser Leu Lys Ala Ala Glu
            20                  25                  30

Lys Pro Phe Lys Val Thr Val Ile Gly Ser Gly Asn Trp Gly Thr Thr
        35                  40                  45

Ile Ala Lys Val Val Ala Glu Asn Cys Lys Gly Tyr Pro Glu Val Phe
    50                  55                  60

Ala Pro Ile Val Gln Met Trp Val Gly Glu Glu Ile Asn Gly Glu
65                  70                  75                  80

Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
        115                 120                 125

Phe Leu Pro Arg Ile Cys Ser Gln Leu Lys Gly His Val Asp Ser His
    130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
        195                 200                 205

Glu Gly Lys Asp Val Asp His Lys Val Leu Lys Ala Leu Phe His Arg
    210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
            260                 265                 270

Leu Gly Glu Ile Ile Arg Phe Gly Gln Met Phe Phe Pro Glu Ser Arg
        275                 280                 285

Glu Glu Thr Tyr Tyr Gln Glu Ser Ala Gly Val Ala Asp Leu Ile Thr
    290                 295                 300
```

```
Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
                325                 330                 335

Ser Ala Gln Gly Leu Ile Thr Cys Lys Glu Val His Glu Trp Leu Glu
            340                 345                 350

Thr Cys Gly Ser Val Glu Asp Phe Pro Leu Phe Glu Ala Val Tyr Gln
        355                 360                 365

Ile Val Tyr Asn Asn Tyr Pro Met Lys Asn Leu Pro Asp Met Ile Glu
    370                 375                 380

Glu Leu Asp Leu His Glu Asp
385                 390


<210> SEQ ID NO 197
<211> LENGTH: 391
<212> TYPE: PRT
<213> ORGANISM: Artificial Sequence
<220> FEATURE:
<223> OTHER INFORMATION: F73A

<400> SEQUENCE: 197

Met Ser Ala Ala Ala Asp Arg Leu Asn Leu Thr Ser Gly His Leu Asn
1               5                   10                  15

Ala Gly Arg Lys Arg Ser Ser Ser Ser Val Ser Leu Lys Ala Ala Glu
            20                  25                  30

Lys Pro Phe Lys Val Thr Val Ile Gly Ser Gly Asn Trp Gly Thr Thr
        35                  40                  45

Ile Ala Lys Val Val Ala Glu Asn Cys Lys Gly Tyr Pro Glu Val Phe
    50                  55                  60

Ala Pro Ile Val Gln Met Trp Val Ala Glu Glu Glu Ile Asn Gly Glu
65                  70                  75                  80

Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
        115                 120                 125

Phe Leu Pro Arg Ile Cys Ser Gln Leu Lys Gly His Val Asp Ser His
    130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
        195                 200                 205

Glu Gly Lys Asp Val Asp His Lys Val Leu Lys Ala Leu Phe His Arg
    210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
            260                 265                 270
```

```
Leu Gly Glu Ile Ile Arg Phe Gly Gln Met Phe Phe Pro Glu Ser Arg
        275                 280                 285

Glu Glu Thr Tyr Tyr Gln Glu Ser Ala Gly Val Ala Asp Leu Ile Thr
    290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
                325                 330                 335

Ser Ala Gln Gly Leu Ile Thr Cys Lys Glu Val His Glu Trp Leu Glu
            340                 345                 350

Thr Cys Gly Ser Val Glu Asp Phe Pro Leu Phe Glu Ala Val Tyr Gln
        355                 360                 365

Ile Val Tyr Asn Asn Tyr Pro Met Lys Asn Leu Pro Asp Met Ile Glu
    370                 375                 380

Glu Leu Asp Leu His Glu Asp
385                 390
```

<210> SEQ ID NO 198
<211> LENGTH: 391
<212> TYPE: PRT
<213> ORGANISM: Artificial Sequence
<220> FEATURE:
<223> OTHER INFORMATION: F73R

<400> SEQUENCE: 198

```
Met Ser Ala Ala Ala Asp Arg Leu Asn Leu Thr Ser Gly His Leu Asn
1               5                   10                  15

Ala Gly Arg Lys Arg Ser Ser Ser Ser Val Ser Leu Lys Ala Ala Glu
            20                  25                  30

Lys Pro Phe Lys Val Thr Val Ile Gly Ser Gly Asn Trp Gly Thr Thr
        35                  40                  45

Ile Ala Lys Val Val Ala Glu Asn Cys Lys Gly Tyr Pro Glu Val Phe
    50                  55                  60

Ala Pro Ile Val Gln Met Trp Val Arg Glu Glu Glu Ile Asn Gly Glu
65                  70                  75                  80

Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
        115                 120                 125

Phe Leu Pro Arg Ile Cys Ser Gln Leu Lys Gly His Val Asp Ser His
    130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
        195                 200                 205

Glu Gly Lys Asp Val Asp His Lys Val Leu Lys Ala Leu Phe His Arg
    210                 215                 220

Pro Tyr Phe His Val Ser Val Ile Glu Asp Val Ala Gly Ile Ser Ile
225                 230                 235                 240
```

Cys Gly Ala Leu Lys Asn Val Val Ala Leu Gly Cys Gly Phe Val Glu
245 250 255

Gly Leu Gly Trp Gly Asn Asn Ala Ser Ala Ala Ile Gln Arg Val Gly
260 265 270

Leu Gly Glu Ile Ile Arg Phe Gly Gln Met Phe Phe Pro Glu Ser Arg
275 280 285

Glu Glu Thr Tyr Tyr Gln Glu Ser Ala Gly Val Ala Asp Leu Ile Thr
290 295 300

Thr Cys Ala Gly Gly Arg Asn Val Lys Val Ala Arg Leu Met Ala Thr
305 310 315 320

Ser Gly Lys Asp Ala Trp Glu Cys Glu Lys Glu Leu Leu Asn Gly Gln
325 330 335

Ser Ala Gln Gly Leu Ile Thr Cys Lys Glu Val His Glu Trp Leu Glu
340 345 350

Thr Cys Gly Ser Val Glu Asp Phe Pro Leu Phe Glu Ala Val Tyr Gln
355 360 365

Ile Val Tyr Asn Asn Tyr Pro Met Lys Asn Leu Pro Asp Met Ile Glu
370 375 380

Glu Leu Asp Leu His Glu Asp
385 390

<210> SEQ ID NO 199
<211> LENGTH: 391
<212> TYPE: PRT
<213> ORGANISM: Artificial Sequence
<220> FEATURE:
<223> OTHER INFORMATION: F73K

<400> SEQUENCE: 199

Met Ser Ala Ala Ala Asp Arg Leu Asn Leu Thr Ser Gly His Leu Asn
1 5 10 15

Ala Gly Arg Lys Arg Ser Ser Ser Ser Val Ser Leu Lys Ala Ala Glu
20 25 30

Lys Pro Phe Lys Val Thr Val Ile Gly Ser Gly Asn Trp Gly Thr Thr
35 40 45

Ile Ala Lys Val Val Ala Glu Asn Cys Lys Gly Tyr Pro Glu Val Phe
50 55 60

Ala Pro Ile Val Gln Met Trp Val Lys Glu Glu Glu Ile Asn Gly Glu
65 70 75 80

Lys Leu Thr Glu Ile Ile Asn Thr Arg His Gln Asn Val Lys Tyr Leu
85 90 95

Pro Gly Ile Thr Leu Pro Asp Asn Leu Val Ala Asn Pro Asp Leu Ile
100 105 110

Asp Ser Val Lys Asp Val Asp Ile Ile Val Phe Asn Ile Pro His Gln
115 120 125

Phe Leu Pro Arg Ile Cys Ser Gln Leu Lys Gly His Val Asp Ser His
130 135 140

Val Arg Ala Ile Ser Cys Leu Lys Gly Phe Glu Val Gly Ala Lys Gly
145 150 155 160

Val Gln Leu Leu Ser Ser Tyr Ile Thr Glu Glu Leu Gly Ile Gln Cys
165 170 175

Gly Ala Leu Ser Gly Ala Asn Ile Ala Thr Glu Val Ala Gln Glu His
180 185 190

Trp Ser Glu Thr Thr Val Ala Tyr His Ile Pro Lys Asp Phe Arg Gly
195 200 205

```
Glu Gly Lys Asp Val Asp His Lys Val Leu Lys Ala Leu Phe His Arg
    210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
            260                 265                 270

Leu Gly Glu Ile Ile Arg Phe Gly Gln Met Phe Phe Pro Glu Ser Arg
        275                 280                 285

Glu Glu Thr Tyr Tyr Gln Glu Ser Ala Gly Val Ala Asp Leu Ile Thr
    290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
                325                 330                 335

Ser Ala Gln Gly Leu Ile Thr Cys Lys Glu Val His Glu Trp Leu Glu
            340                 345                 350

Thr Cys Gly Ser Val Glu Asp Phe Pro Leu Phe Glu Ala Val Tyr Gln
        355                 360                 365

Ile Val Tyr Asn Asn Tyr Pro Met Lys Asn Leu Pro Asp Met Ile Glu
    370                 375                 380

Glu Leu Asp Leu His Glu Asp
385                 390


<210> SEQ ID NO 200
<211> LENGTH: 391
<212> TYPE: PRT
<213> ORGANISM: Artificial Sequence
<220> FEATURE:
<223> OTHER INFORMATION: F129G

<400> SEQUENCE: 200

Met Ser Ala Ala Ala Asp Arg Leu Asn Leu Thr Ser Gly His Leu Asn
1               5                   10                  15

Ala Gly Arg Lys Arg Ser Ser Ser Ser Val Ser Leu Lys Ala Ala Glu
            20                  25                  30

Lys Pro Phe Lys Val Thr Val Ile Gly Ser Gly Asn Trp Gly Thr Thr
        35                  40                  45

Ile Ala Lys Val Val Ala Glu Asn Cys Lys Gly Tyr Pro Glu Val Phe
    50                  55                  60

Ala Pro Ile Val Gln Met Trp Val Phe Glu Glu Glu Ile Asn Gly Glu
65                  70                  75                  80

Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
        115                 120                 125

Gly Leu Pro Arg Ile Cys Ser Gln Leu Lys Gly His Val Asp Ser His
    130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175
```

```
Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
        195                 200                 205

Glu Gly Lys Asp Val Asp His Lys Val Leu Lys Ala Leu Phe His Arg
    210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
            260                 265                 270

Leu Gly Glu Ile Ile Arg Phe Gly Gln Met Phe Phe Pro Glu Ser Arg
        275                 280                 285

Glu Glu Thr Tyr Tyr Gln Glu Ser Ala Gly Val Ala Asp Leu Ile Thr
    290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
                325                 330                 335

Ser Ala Gln Gly Leu Ile Thr Cys Lys Glu Val His Glu Trp Leu Glu
            340                 345                 350

Thr Cys Gly Ser Val Glu Asp Phe Pro Leu Phe Glu Ala Val Tyr Gln
        355                 360                 365

Ile Val Tyr Asn Asn Tyr Pro Met Lys Asn Leu Pro Asp Met Ile Glu
    370                 375                 380

Glu Leu Asp Leu His Glu Asp
385                 390


<210> SEQ ID NO 201
<211> LENGTH: 391
<212> TYPE: PRT
<213> ORGANISM: Artificial Sequence
<220> FEATURE:
<223> OTHER INFORMATION: F129A

<400> SEQUENCE: 201

Met Ser Ala Ala Ala Asp Arg Leu Asn Leu Thr Ser Gly His Leu Asn
1               5                   10                  15

Ala Gly Arg Lys Arg Ser Ser Ser Ser Val Ser Leu Lys Ala Ala Glu
            20                  25                  30

Lys Pro Phe Lys Val Thr Val Ile Gly Ser Gly Asn Trp Gly Thr Thr
        35                  40                  45

Ile Ala Lys Val Val Ala Glu Asn Cys Lys Gly Tyr Pro Glu Val Phe
    50                  55                  60

Ala Pro Ile Val Gln Met Trp Val Phe Glu Glu Glu Ile Asn Gly Glu
65                  70                  75                  80

Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
        115                 120                 125

Ala Leu Pro Arg Ile Cys Ser Gln Leu Lys Gly His Val Asp Ser His
    130                 135                 140
```

```
Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
        195                 200                 205

Glu Gly Lys Asp Val Asp His Lys Val Leu Lys Ala Leu Phe His Arg
    210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
            260                 265                 270

Leu Gly Glu Ile Ile Arg Phe Gly Gln Met Phe Phe Pro Glu Ser Arg
        275                 280                 285

Glu Glu Thr Tyr Tyr Gln Glu Ser Ala Gly Val Ala Asp Leu Ile Thr
    290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
                325                 330                 335

Ser Ala Gln Gly Leu Ile Thr Cys Lys Glu Val His Glu Trp Leu Glu
            340                 345                 350

Thr Cys Gly Ser Val Glu Asp Phe Pro Leu Phe Glu Ala Val Tyr Gln
        355                 360                 365

Ile Val Tyr Asn Asn Tyr Pro Met Lys Asn Leu Pro Asp Met Ile Glu
    370                 375                 380

Glu Leu Asp Leu His Glu Asp
385                 390
```

<210> SEQ ID NO 202
<211> LENGTH: 391
<212> TYPE: PRT
<213> ORGANISM: Artificial Sequence
<220> FEATURE:
<223> OTHER INFORMATION: F129R

<400> SEQUENCE: 202

```
Met Ser Ala Ala Ala Asp Arg Leu Asn Leu Thr Ser Gly His Leu Asn
1               5                   10                  15

Ala Gly Arg Lys Arg Ser Ser Ser Ser Val Ser Leu Lys Ala Ala Glu
            20                  25                  30

Lys Pro Phe Lys Val Thr Val Ile Gly Ser Gly Asn Trp Gly Thr Thr
        35                  40                  45

Ile Ala Lys Val Val Ala Glu Asn Cys Lys Gly Tyr Pro Glu Val Phe
    50                  55                  60

Ala Pro Ile Val Gln Met Trp Val Phe Glu Glu Glu Ile Asn Gly Glu
65                  70                  75                  80

Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
            100                 105                 110
```

```
Asp Ser Val Lys Asp Val Asp Ile Ile Val Phe Asn Ile Pro His Gln
        115                 120                 125

Arg Leu Pro Arg Ile Cys Ser Gln Leu Lys Gly His Val Asp Ser His
    130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
        195                 200                 205

Glu Gly Lys Asp Val Asp His Lys Val Leu Lys Ala Leu Phe His Arg
    210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
            260                 265                 270

Leu Gly Glu Ile Ile Arg Phe Gly Gln Met Phe Phe Pro Glu Ser Arg
        275                 280                 285

Glu Glu Thr Tyr Tyr Gln Glu Ser Ala Gly Val Ala Asp Leu Ile Thr
    290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
                325                 330                 335

Ser Ala Gln Gly Leu Ile Thr Cys Lys Glu Val His Glu Trp Leu Glu
            340                 345                 350

Thr Cys Gly Ser Val Glu Asp Phe Pro Leu Phe Glu Ala Val Tyr Gln
        355                 360                 365

Ile Val Tyr Asn Asn Tyr Pro Met Lys Asn Leu Pro Asp Met Ile Glu
    370                 375                 380

Glu Leu Asp Leu His Glu Asp
385                 390


<210> SEQ ID NO 203
<211> LENGTH: 391
<212> TYPE: PRT
<213> ORGANISM: Artificial Sequence
<220> FEATURE:
<223> OTHER INFORMATION: F129K

<400> SEQUENCE: 203

Met Ser Ala Ala Ala Asp Arg Leu Asn Leu Thr Ser Gly His Leu Asn
1               5                   10                  15

Ala Gly Arg Lys Arg Ser Ser Ser Ser Val Ser Leu Lys Ala Ala Glu
            20                  25                  30

Lys Pro Phe Lys Val Thr Val Ile Gly Ser Gly Asn Trp Gly Thr Thr
        35                  40                  45

Ile Ala Lys Val Val Ala Glu Asn Cys Lys Gly Tyr Pro Glu Val Phe
    50                  55                  60

Ala Pro Ile Val Gln Met Trp Val Phe Glu Glu Glu Ile Asn Gly Glu
65                  70                  75                  80
```

```
Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
        115                 120                 125

Lys Leu Pro Arg Ile Cys Ser Gln Leu Lys Gly His Val Asp Ser His
    130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
        195                 200                 205

Glu Gly Lys Asp Val Asp His Lys Val Leu Lys Ala Leu Phe His Arg
    210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
            260                 265                 270

Leu Gly Glu Ile Ile Arg Phe Gly Gln Met Phe Phe Pro Glu Ser Arg
        275                 280                 285

Glu Glu Thr Tyr Tyr Gln Glu Ser Ala Gly Val Ala Asp Leu Ile Thr
    290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
                325                 330                 335

Ser Ala Gln Gly Leu Ile Thr Cys Lys Glu Val His Glu Trp Leu Glu
            340                 345                 350

Thr Cys Gly Ser Val Glu Asp Phe Pro Leu Phe Glu Ala Val Tyr Gln
        355                 360                 365

Ile Val Tyr Asn Asn Tyr Pro Met Lys Asn Leu Pro Asp Met Ile Glu
    370                 375                 380

Glu Leu Asp Leu His Glu Asp
385                 390


<210> SEQ ID NO 204
<211> LENGTH: 391
<212> TYPE: PRT
<213> ORGANISM: Artificial Sequence
<220> FEATURE:
<223> OTHER INFORMATION: F73A F129G

<400> SEQUENCE: 204

Met Ser Ala Ala Ala Asp Arg Leu Asn Leu Thr Ser Gly His Leu Asn
1               5                   10                  15

Ala Gly Arg Lys Arg Ser Ser Ser Ser Val Ser Leu Lys Ala Ala Glu
            20                  25                  30

Lys Pro Phe Lys Val Thr Val Ile Gly Ser Gly Asn Trp Gly Thr Thr
        35                  40                  45
```

```
Ile Ala Lys Val Val Ala Glu Asn Cys Lys Gly Tyr Pro Glu Val Phe
    50                  55                  60

Ala Pro Ile Val Gln Met Trp Val Ala Glu Glu Glu Ile Asn Gly Glu
65                  70                  75                  80

Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
        115                 120                 125

Gly Leu Pro Arg Ile Cys Ser Gln Leu Lys Gly His Val Asp Ser His
    130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
        195                 200                 205

Glu Gly Lys Asp Val Asp His Lys Val Leu Lys Ala Leu Phe His Arg
    210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
            260                 265                 270

Leu Gly Glu Ile Ile Arg Phe Gly Gln Met Phe Phe Pro Glu Ser Arg
        275                 280                 285

Glu Glu Thr Tyr Tyr Gln Glu Ser Ala Gly Val Ala Asp Leu Ile Thr
    290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
                325                 330                 335

Ser Ala Gln Gly Leu Ile Thr Cys Lys Glu Val His Glu Trp Leu Glu
            340                 345                 350

Thr Cys Gly Ser Val Glu Asp Phe Pro Leu Phe Glu Ala Val Tyr Gln
        355                 360                 365

Ile Val Tyr Asn Asn Tyr Pro Met Lys Asn Leu Pro Asp Met Ile Glu
    370                 375                 380

Glu Leu Asp Leu His Glu Asp
385                 390
```

<210> SEQ ID NO 205
<211> LENGTH: 391
<212> TYPE: PRT
<213> ORGANISM: Artificial Sequence
<220> FEATURE:
<223> OTHER INFORMATION: F73A F129A

<400> SEQUENCE: 205

```
Met Ser Ala Ala Ala Asp Arg Leu Asn Leu Thr Ser Gly His Leu Asn
1               5                   10                  15
```

```
Ala Gly Arg Lys Arg Ser Ser Ser Ser Val Ser Leu Lys Ala Ala Glu
            20                  25                  30

Lys Pro Phe Lys Val Thr Val Ile Gly Ser Gly Asn Trp Gly Thr Thr
        35                  40                  45

Ile Ala Lys Val Val Ala Glu Asn Cys Lys Gly Tyr Pro Glu Val Phe
    50                  55                  60

Ala Pro Ile Val Gln Met Trp Val Ala Glu Glu Glu Ile Asn Gly Glu
65                  70                  75                  80

Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
        115                 120                 125

Ala Leu Pro Arg Ile Cys Ser Gln Leu Lys Gly His Val Asp Ser His
    130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
        195                 200                 205

Glu Gly Lys Asp Val Asp His Lys Val Leu Lys Ala Leu Phe His Arg
    210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
            260                 265                 270

Leu Gly Glu Ile Ile Arg Phe Gly Gln Met Phe Phe Pro Glu Ser Arg
        275                 280                 285

Glu Glu Thr Tyr Tyr Gln Glu Ser Ala Gly Val Ala Asp Leu Ile Thr
    290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
                325                 330                 335

Ser Ala Gln Gly Leu Ile Thr Cys Lys Glu Val His Glu Trp Leu Glu
            340                 345                 350

Thr Cys Gly Ser Val Glu Asp Phe Pro Leu Phe Glu Ala Val Tyr Gln
        355                 360                 365

Ile Val Tyr Asn Asn Tyr Pro Met Lys Asn Leu Pro Asp Met Ile Glu
    370                 375                 380

Glu Leu Asp Leu His Glu Asp
385                 390
```

```
<210> SEQ ID NO 206
<211> LENGTH: 391
<212> TYPE: PRT
<213> ORGANISM: Artificial Sequence
<220> FEATURE:
<223> OTHER INFORMATION: F73A F129R
```

<400> SEQUENCE: 206

```
Met Ser Ala Ala Ala Asp Arg Leu Asn Leu Thr Ser Gly His Leu Asn
1               5                   10                  15

Ala Gly Arg Lys Arg Ser Ser Ser Ser Val Ser Leu Lys Ala Ala Glu
            20                  25                  30

Lys Pro Phe Lys Val Thr Val Ile Gly Ser Gly Asn Trp Gly Thr Thr
        35                  40                  45

Ile Ala Lys Val Val Ala Glu Asn Cys Lys Gly Tyr Pro Glu Val Phe
    50                  55                  60

Ala Pro Ile Val Gln Met Trp Val Ala Glu Glu Glu Ile Asn Gly Glu
65                  70                  75                  80

Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
        115                 120                 125

Arg Leu Pro Arg Ile Cys Ser Gln Leu Lys Gly His Val Asp Ser His
    130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
        195                 200                 205

Glu Gly Lys Asp Val Asp His Lys Val Leu Lys Ala Leu Phe His Arg
    210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
            260                 265                 270

Leu Gly Glu Ile Ile Arg Phe Gly Gln Met Phe Phe Pro Glu Ser Arg
        275                 280                 285

Glu Glu Thr Tyr Tyr Gln Glu Ser Ala Gly Val Ala Asp Leu Ile Thr
    290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
                325                 330                 335

Ser Ala Gln Gly Leu Ile Thr Cys Lys Glu Val His Glu Trp Leu Glu
            340                 345                 350

Thr Cys Gly Ser Val Glu Asp Phe Pro Leu Phe Glu Ala Val Tyr Gln
        355                 360                 365

Ile Val Tyr Asn Asn Tyr Pro Met Lys Asn Leu Pro Asp Met Ile Glu
    370                 375                 380

Glu Leu Asp Leu His Glu Asp
385                 390
```

<210> SEQ ID NO 207
<211> LENGTH: 391
<212> TYPE: PRT
<213> ORGANISM: Artificial Sequence
<220> FEATURE:
<223> OTHER INFORMATION: F73A F129K

<400> SEQUENCE: 207

```
Met Ser Ala Ala Ala Asp Arg Leu Asn Leu Thr Ser Gly His Leu Asn
1               5                   10                  15

Ala Gly Arg Lys Arg Ser Ser Ser Ser Val Ser Leu Lys Ala Ala Glu
            20                  25                  30

Lys Pro Phe Lys Val Thr Val Ile Gly Ser Gly Asn Trp Gly Thr Thr
        35                  40                  45

Ile Ala Lys Val Val Ala Glu Asn Cys Lys Gly Tyr Pro Glu Val Phe
    50                  55                  60

Ala Pro Ile Val Gln Met Trp Val Ala Glu Glu Glu Ile Asn Gly Glu
65                  70                  75                  80

Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
        115                 120                 125

Lys Leu Pro Arg Ile Cys Ser Gln Leu Lys Gly His Val Asp Ser His
    130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
        195                 200                 205

Glu Gly Lys Asp Val Asp His Lys Val Leu Lys Ala Leu Phe His Arg
    210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
            260                 265                 270

Leu Gly Glu Ile Ile Arg Phe Gly Gln Met Phe Phe Pro Glu Ser Arg
        275                 280                 285

Glu Glu Thr Tyr Tyr Gln Glu Ser Ala Gly Val Ala Asp Leu Ile Thr
    290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
                325                 330                 335

Ser Ala Gln Gly Leu Ile Thr Cys Lys Glu Val His Glu Trp Leu Glu
            340                 345                 350

Thr Cys Gly Ser Val Glu Asp Phe Pro Leu Phe Glu Ala Val Tyr Gln
        355                 360                 365

Ile Val Tyr Asn Asn Tyr Pro Met Lys Asn Leu Pro Asp Met Ile Glu
```

```
    370                 375                 380

Glu Leu Asp Leu His Glu Asp
385                 390


<210> SEQ ID NO 208
<211> LENGTH: 391
<212> TYPE: PRT
<213> ORGANISM: Artificial Sequence
<220> FEATURE:
<223> OTHER INFORMATION: F73G F129G

<400> SEQUENCE: 208

Met Ser Ala Ala Ala Asp Arg Leu Asn Leu Thr Ser Gly His Leu Asn
1               5                   10                  15

Ala Gly Arg Lys Arg Ser Ser Ser Ser Val Ser Leu Lys Ala Ala Glu
            20                  25                  30

Lys Pro Phe Lys Val Thr Val Ile Gly Ser Gly Asn Trp Gly Thr Thr
        35                  40                  45

Ile Ala Lys Val Val Ala Glu Asn Cys Lys Gly Tyr Pro Glu Val Phe
    50                  55                  60

Ala Pro Ile Val Gln Met Trp Val Gly Glu Glu Glu Ile Asn Gly Glu
65                  70                  75                  80

Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
        115                 120                 125

Gly Leu Pro Arg Ile Cys Ser Gln Leu Lys Gly His Val Asp Ser His
    130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
        195                 200                 205

Glu Gly Lys Asp Val Asp His Lys Val Leu Lys Ala Leu Phe His Arg
    210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
            260                 265                 270

Leu Gly Glu Ile Ile Arg Phe Gly Gln Met Phe Phe Pro Glu Ser Arg
        275                 280                 285

Glu Glu Thr Tyr Tyr Gln Glu Ser Ala Gly Val Ala Asp Leu Ile Thr
    290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
                325                 330                 335

Ser Ala Gln Gly Leu Ile Thr Cys Lys Glu Val His Glu Trp Leu Glu
```

```
            340                 345                 350

Thr Cys Gly Ser Val Glu Asp Phe Pro Leu Phe Glu Ala Val Tyr Gln
        355                 360                 365

Ile Val Tyr Asn Asn Tyr Pro Met Lys Asn Leu Pro Asp Met Ile Glu
    370                 375                 380

Glu Leu Asp Leu His Glu Asp
385                 390


<210> SEQ ID NO 209
<211> LENGTH: 391
<212> TYPE: PRT
<213> ORGANISM: Artificial Sequence
<220> FEATURE:
<223> OTHER INFORMATION: F73G F129A

<400> SEQUENCE: 209

Met Ser Ala Ala Ala Asp Arg Leu Asn Leu Thr Ser Gly His Leu Asn
1               5                   10                  15

Ala Gly Arg Lys Arg Ser Ser Ser Ser Val Ser Leu Lys Ala Ala Glu
            20                  25                  30

Lys Pro Phe Lys Val Thr Val Ile Gly Ser Gly Asn Trp Gly Thr Thr
        35                  40                  45

Ile Ala Lys Val Val Ala Glu Asn Cys Lys Gly Tyr Pro Glu Val Phe
    50                  55                  60

Ala Pro Ile Val Gln Met Trp Val Gly Glu Glu Glu Ile Asn Gly Glu
65                  70                  75                  80

Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
        115                 120                 125

Ala Leu Pro Arg Ile Cys Ser Gln Leu Lys Gly His Val Asp Ser His
    130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
        195                 200                 205

Glu Gly Lys Asp Val Asp His Lys Val Leu Lys Ala Leu Phe His Arg
    210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
            260                 265                 270

Leu Gly Glu Ile Ile Arg Phe Gly Gln Met Phe Phe Pro Glu Ser Arg
        275                 280                 285

Glu Glu Thr Tyr Tyr Gln Glu Ser Ala Gly Val Ala Asp Leu Ile Thr
    290                 295                 300

Thr Cys Ala Gly Gly Arg Asn Val Lys Val Ala Arg Leu Met Ala Thr
```

```
305                 310                 315                 320

Ser Gly Lys Asp Ala Trp Glu Cys Glu Lys Glu Leu Leu Asn Gly Gln
                325                 330                 335

Ser Ala Gln Gly Leu Ile Thr Cys Lys Glu Val His Glu Trp Leu Glu
            340                 345                 350

Thr Cys Gly Ser Val Glu Asp Phe Pro Leu Phe Glu Ala Val Tyr Gln
        355                 360                 365

Ile Val Tyr Asn Asn Tyr Pro Met Lys Asn Leu Pro Asp Met Ile Glu
    370                 375                 380

Glu Leu Asp Leu His Glu Asp
385                 390


<210> SEQ ID NO 210
<211> LENGTH: 391
<212> TYPE: PRT
<213> ORGANISM: Artificial Sequence
<220> FEATURE:
<223> OTHER INFORMATION: F73G F129R

<400> SEQUENCE: 210

Met Ser Ala Ala Ala Asp Arg Leu Asn Leu Thr Ser Gly His Leu Asn
1               5                   10                  15

Ala Gly Arg Lys Arg Ser Ser Ser Ser Val Ser Leu Lys Ala Ala Glu
            20                  25                  30

Lys Pro Phe Lys Val Thr Val Ile Gly Ser Gly Asn Trp Gly Thr Thr
        35                  40                  45

Ile Ala Lys Val Val Ala Glu Asn Cys Lys Gly Tyr Pro Glu Val Phe
    50                  55                  60

Ala Pro Ile Val Gln Met Trp Val Gly Glu Glu Glu Ile Asn Gly Glu
65                  70                  75                  80

Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
        115                 120                 125

Arg Leu Pro Arg Ile Cys Ser Gln Leu Lys Gly His Val Asp Ser His
    130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
        195                 200                 205

Glu Gly Lys Asp Val Asp His Lys Val Leu Lys Ala Leu Phe His Arg
    210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
            260                 265                 270

Leu Gly Glu Ile Ile Arg Phe Gly Gln Met Phe Phe Pro Glu Ser Arg
```

```
        275                 280                 285

Glu Glu Thr Tyr Tyr Gln Glu Ser Ala Gly Val Ala Asp Leu Ile Thr
    290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
                325                 330                 335

Ser Ala Gln Gly Leu Ile Thr Cys Lys Glu Val His Glu Trp Leu Glu
            340                 345                 350

Thr Cys Gly Ser Val Glu Asp Phe Pro Leu Phe Glu Ala Val Tyr Gln
        355                 360                 365

Ile Val Tyr Asn Asn Tyr Pro Met Lys Asn Leu Pro Asp Met Ile Glu
    370                 375                 380

Glu Leu Asp Leu His Glu Asp
385                 390


<210> SEQ ID NO 211
<211> LENGTH: 390
<212> TYPE: PRT
<213> ORGANISM: Artificial Sequence
<220> FEATURE:
<223> OTHER INFORMATION: F73G F129K

<400> SEQUENCE: 211

Met Ser Ala Ala Ala Asp Arg Leu Asn Leu Thr Ser Gly His Leu Asn
1               5                   10                  15

Ala Gly Arg Lys Arg Ser Ser Ser Ser Val Ser Leu Lys Ala Ala Glu
            20                  25                  30

Lys Pro Phe Lys Val Thr Val Ile Gly Ser Gly Asn Trp Gly Thr Thr
        35                  40                  45

Ile Ala Lys Val Val Ala Glu Asn Cys Lys Gly Tyr Pro Glu Val Phe
    50                  55                  60

Ala Pro Ile Val Gln Met Trp Val Gly Glu Glu Glu Ile Asn Gly Glu
65                  70                  75                  80

Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
        115                 120                 125

Lys Leu Pro Arg Ile Cys Ser Gln Leu Lys Gly His Val Asp Ser His
    130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
        195                 200                 205

Glu Gly Lys Asp Val Asp His Lys Val Leu Lys Ala Leu Phe His Arg
    210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
```

```
                245                 250                 255

Gly Leu Gly Trp Gly Asn Asn Ala Ser Ala Ala Ile Gln Arg Val Gly
            260                 265                 270

Leu Gly Glu Ile Ile Arg Phe Gly Gln Met Phe Phe Pro Glu Ser Arg
        275                 280                 285

Glu Glu Thr Tyr Tyr Gln Glu Ser Ala Gly Val Ala Asp Leu Ile Thr
    290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
                325                 330                 335

Ser Ala Gln Gly Leu Ile Thr Cys Lys Glu Val His Glu Trp Leu Glu
            340                 345                 350

Thr Cys Gly Ser Val Glu Asp Phe Pro Leu Phe Glu Ala Val Tyr Gln
        355                 360                 365

Ile Val Tyr Asn Asn Tyr Pro Met Lys Asn Leu Pro Asp Met Ile Glu
    370                 375                 380

Glu Leu Asp Leu His Glu
385                 390


<210> SEQ ID NO 212
<211> LENGTH: 391
<212> TYPE: PRT
<213> ORGANISM: Artificial Sequence
<220> FEATURE:
<223> OTHER INFORMATION: N44A

<400> SEQUENCE: 212

Met Ser Ala Ala Ala Asp Arg Leu Asn Leu Thr Ser Gly His Leu Asn
1               5                   10                  15

Ala Gly Arg Lys Arg Ser Ser Ser Ser Val Ser Leu Lys Ala Ala Glu
            20                  25                  30

Lys Pro Phe Lys Val Thr Val Ile Gly Ser Gly Ala Trp Gly Thr Thr
        35                  40                  45

Ile Ala Lys Val Val Ala Glu Asn Cys Lys Gly Tyr Pro Glu Val Phe
    50                  55                  60

Ala Pro Ile Val Gln Met Trp Val Phe Glu Glu Glu Ile Asn Gly Glu
65                  70                  75                  80

Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
        115                 120                 125

Phe Leu Pro Arg Ile Cys Ser Gln Leu Lys Gly His Val Asp Ser His
    130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
        195                 200                 205

Glu Gly Lys Asp Val Asp His Lys Val Leu Lys Ala Leu Phe His Arg
```

```
    210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
            260                 265                 270

Leu Gly Glu Ile Ile Arg Phe Gly Gln Met Phe Phe Pro Glu Ser Arg
        275                 280                 285

Glu Glu Thr Tyr Tyr Gln Glu Ser Ala Gly Val Ala Asp Leu Ile Thr
    290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
                325                 330                 335

Ser Ala Gln Gly Leu Ile Thr Cys Lys Glu Val His Glu Trp Leu Glu
            340                 345                 350

Thr Cys Gly Ser Val Glu Asp Phe Pro Leu Phe Glu Ala Val Tyr Gln
        355                 360                 365

Ile Val Tyr Asn Asn Tyr Pro Met Lys Asn Leu Pro Asp Met Ile Glu
    370                 375                 380

Glu Leu Asp Leu His Glu Asp
385                 390


<210> SEQ ID NO 213
<211> LENGTH: 391
<212> TYPE: PRT
<213> ORGANISM: Artificial Sequence
<220> FEATURE:
<223> OTHER INFORMATION: N44C

<400> SEQUENCE: 213

Met Ser Ala Ala Ala Asp Arg Leu Asn Leu Thr Ser Gly His Leu Asn
1               5                   10                  15

Ala Gly Arg Lys Arg Ser Ser Ser Ser Val Ser Leu Lys Ala Ala Glu
            20                  25                  30

Lys Pro Phe Lys Val Thr Val Ile Gly Ser Gly Cys Trp Gly Thr Thr
        35                  40                  45

Ile Ala Lys Val Val Ala Glu Asn Cys Lys Gly Tyr Pro Glu Val Phe
    50                  55                  60

Ala Pro Ile Val Gln Met Trp Val Phe Glu Glu Glu Ile Asn Gly Glu
65                  70                  75                  80

Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
        115                 120                 125

Phe Leu Pro Arg Ile Cys Ser Gln Leu Lys Gly His Val Asp Ser His
    130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
```

```
            180                 185                 190

Trp Ser Glu Thr Thr Val Ala Tyr His Ile Pro Lys Asp Phe Arg Gly
        195                 200                 205

Glu Gly Lys Asp Val Asp His Lys Val Leu Lys Ala Leu Phe His Arg
    210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
            260                 265                 270

Leu Gly Glu Ile Ile Arg Phe Gly Gln Met Phe Phe Pro Glu Ser Arg
        275                 280                 285

Glu Glu Thr Tyr Tyr Gln Glu Ser Ala Gly Val Ala Asp Leu Ile Thr
    290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
                325                 330                 335

Ser Ala Gln Gly Leu Ile Thr Cys Lys Glu Val His Glu Trp Leu Glu
            340                 345                 350

Thr Cys Gly Ser Val Glu Asp Phe Pro Leu Phe Glu Ala Val Tyr Gln
        355                 360                 365

Ile Val Tyr Asn Asn Tyr Pro Met Lys Asn Leu Pro Asp Met Ile Glu
    370                 375                 380

Glu Leu Asp Leu His Glu Asp
385                 390


<210> SEQ ID NO 214
<211> LENGTH: 391
<212> TYPE: PRT
<213> ORGANISM: Artificial Sequence
<220> FEATURE:
<223> OTHER INFORMATION: N44G

<400> SEQUENCE: 214

Met Ser Ala Ala Ala Asp Arg Leu Asn Leu Thr Ser Gly His Leu Asn
1               5                   10                  15

Ala Gly Arg Lys Arg Ser Ser Ser Ser Val Ser Leu Lys Ala Ala Glu
            20                  25                  30

Lys Pro Phe Lys Val Thr Val Ile Gly Ser Gly Asn Trp Gly Thr Thr
        35                  40                  45

Ile Ala Lys Val Val Ala Glu Asn Cys Lys Gly Tyr Pro Glu Val Phe
    50                  55                  60

Ala Pro Ile Val Gln Met Trp Val Phe Glu Glu Glu Ile Asn Gly Glu
65                  70                  75                  80

Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
        115                 120                 125

Phe Leu Pro Arg Ile Cys Ser Gln Leu Lys Gly His Val Asp Ser His
    130                 135                 140

Val Arg Ala Ile Ser Cys Leu Lys Gly Phe Glu Val Gly Ala Lys Gly
```

```
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
        195                 200                 205

Glu Gly Lys Asp Val Asp His Lys Val Leu Lys Ala Leu Phe His Arg
    210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
            260                 265                 270

Leu Gly Glu Ile Ile Arg Phe Gly Gln Met Phe Phe Pro Glu Ser Arg
        275                 280                 285

Glu Glu Thr Tyr Tyr Gln Glu Ser Ala Gly Val Ala Asp Leu Ile Thr
    290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
                325                 330                 335

Ser Ala Gln Gly Leu Ile Thr Cys Lys Glu Val His Glu Trp Leu Glu
            340                 345                 350

Thr Cys Gly Ser Val Glu Asp Phe Pro Leu Phe Glu Ala Val Tyr Gln
        355                 360                 365

Ile Val Tyr Asn Asn Tyr Pro Met Lys Asn Leu Pro Asp Met Ile Glu
    370                 375                 380

Glu Leu Asp Leu His Glu Asp
385                 390


<210> SEQ ID NO 215
<211> LENGTH: 391
<212> TYPE: PRT
<213> ORGANISM: Artificial Sequence
<220> FEATURE:
<223> OTHER INFORMATION: N44I

<400> SEQUENCE: 215

Met Ser Ala Ala Ala Asp Arg Leu Asn Leu Thr Ser Gly His Leu Asn
1               5                   10                  15

Ala Gly Arg Lys Arg Ser Ser Ser Ser Val Ser Leu Lys Ala Ala Glu
            20                  25                  30

Lys Pro Phe Lys Val Thr Val Ile Gly Ser Gly Ile Trp Gly Thr Thr
        35                  40                  45

Ile Ala Lys Val Val Ala Glu Asn Cys Lys Gly Tyr Pro Glu Val Phe
    50                  55                  60

Ala Pro Ile Val Gln Met Trp Val Phe Glu Glu Glu Ile Asn Gly Glu
65                  70                  75                  80

Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
```

```
        115                 120                 125

Phe Leu Pro Arg Ile Cys Ser Gln Leu Lys Gly His Val Asp Ser His
    130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
        195                 200                 205

Glu Gly Lys Asp Val Asp His Lys Val Leu Lys Ala Leu Phe His Arg
    210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
            260                 265                 270

Leu Gly Glu Ile Ile Arg Phe Gly Gln Met Phe Phe Pro Glu Ser Arg
        275                 280                 285

Glu Glu Thr Tyr Tyr Gln Glu Ser Ala Gly Val Ala Asp Leu Ile Thr
    290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
                325                 330                 335

Ser Ala Gln Gly Leu Ile Thr Cys Lys Glu Val His Glu Trp Leu Glu
            340                 345                 350

Thr Cys Gly Ser Val Glu Asp Phe Pro Leu Phe Glu Ala Val Tyr Gln
        355                 360                 365

Ile Val Tyr Asn Asn Tyr Pro Met Lys Asn Leu Pro Asp Met Ile Glu
    370                 375                 380

Glu Leu Asp Leu His Glu Asp
385                 390
```

<210> SEQ ID NO 216
<211> LENGTH: 391
<212> TYPE: PRT
<213> ORGANISM: Artificial Sequence
<220> FEATURE:
<223> OTHER INFORMATION: N44L

<400> SEQUENCE: 216

```
Met Ser Ala Ala Ala Asp Arg Leu Asn Leu Thr Ser Gly His Leu Asn
1               5                   10                  15

Ala Gly Arg Lys Arg Ser Ser Ser Ser Val Ser Leu Lys Ala Ala Glu
            20                  25                  30

Lys Pro Phe Lys Val Thr Val Ile Gly Ser Gly Leu Trp Gly Thr Thr
        35                  40                  45

Ile Ala Lys Val Val Ala Glu Asn Cys Lys Gly Tyr Pro Glu Val Phe
    50                  55                  60

Ala Pro Ile Val Gln Met Trp Val Phe Glu Glu Glu Ile Asn Gly Glu
65                  70                  75                  80

Lys Leu Thr Glu Ile Ile Asn Thr Arg His Gln Asn Val Lys Tyr Leu
```

```
                85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
        115                 120                 125

Phe Leu Pro Arg Ile Cys Ser Gln Leu Lys Gly His Val Asp Ser His
    130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
        195                 200                 205

Glu Gly Lys Asp Val Asp His Lys Val Leu Lys Ala Leu Phe His Arg
    210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
            260                 265                 270

Leu Gly Glu Ile Ile Arg Phe Gly Gln Met Phe Phe Pro Glu Ser Arg
        275                 280                 285

Glu Glu Thr Tyr Tyr Gln Glu Ser Ala Gly Val Ala Asp Leu Ile Thr
    290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
                325                 330                 335

Ser Ala Gln Gly Leu Ile Thr Cys Lys Glu Val His Glu Trp Leu Glu
            340                 345                 350

Thr Cys Gly Ser Val Glu Asp Phe Pro Leu Phe Glu Ala Val Tyr Gln
        355                 360                 365

Ile Val Tyr Asn Asn Tyr Pro Met Lys Asn Leu Pro Asp Met Ile Glu
    370                 375                 380

Glu Leu Asp Leu His Glu Asp
385                 390
```

<210> SEQ ID NO 217
<211> LENGTH: 391
<212> TYPE: PRT
<213> ORGANISM: Artificial Sequence
<220> FEATURE:
<223> OTHER INFORMATION: N44M

<400> SEQUENCE: 217

```
Met Ser Ala Ala Ala Asp Arg Leu Asn Leu Thr Ser Gly His Leu Asn
1               5                   10                  15

Ala Gly Arg Lys Arg Ser Ser Ser Ser Val Ser Leu Lys Ala Ala Glu
            20                  25                  30

Lys Pro Phe Lys Val Thr Val Ile Gly Ser Gly Met Trp Gly Thr Thr
        35                  40                  45

Ile Ala Lys Val Val Ala Glu Asn Cys Lys Gly Tyr Pro Glu Val Phe
```

```
    50                  55                  60

Ala Pro Ile Val Gln Met Trp Val Phe Glu Glu Glu Ile Asn Gly Glu
65                  70                  75                  80

Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
        115                 120                 125

Phe Leu Pro Arg Ile Cys Ser Gln Leu Lys Gly His Val Asp Ser His
    130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
        195                 200                 205

Glu Gly Lys Asp Val Asp His Lys Val Leu Lys Ala Leu Phe His Arg
    210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
            260                 265                 270

Leu Gly Glu Ile Ile Arg Phe Gly Gln Met Phe Phe Pro Glu Ser Arg
        275                 280                 285

Glu Glu Thr Tyr Tyr Gln Glu Ser Ala Gly Val Ala Asp Leu Ile Thr
    290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
                325                 330                 335

Ser Ala Gln Gly Leu Ile Thr Cys Lys Glu Val His Glu Trp Leu Glu
            340                 345                 350

Thr Cys Gly Ser Val Glu Asp Phe Pro Leu Phe Glu Ala Val Tyr Gln
        355                 360                 365

Ile Val Tyr Asn Asn Tyr Pro Met Lys Asn Leu Pro Asp Met Ile Glu
    370                 375                 380

Glu Leu Asp Leu His Glu Asp
385                 390


<210> SEQ ID NO 218
<211> LENGTH: 391
<212> TYPE: PRT
<213> ORGANISM: Artificial Sequence
<220> FEATURE:
<223> OTHER INFORMATION: N44S

<400> SEQUENCE: 218

Met Ser Ala Ala Ala Asp Arg Leu Asn Leu Thr Ser Gly His Leu Asn
1               5                   10                  15

Ala Gly Arg Lys Arg Ser Ser Ser Ser Val Ser Leu Lys Ala Ala Glu
```

```
            20                  25                  30

Lys Pro Phe Lys Val Thr Val Ile Gly Ser Gly Ser Trp Gly Thr Thr
        35                  40                  45

Ile Ala Lys Val Val Ala Glu Asn Cys Lys Gly Tyr Pro Glu Val Phe
    50                  55                  60

Ala Pro Ile Val Gln Met Trp Val Phe Glu Glu Glu Ile Asn Gly Glu
65                  70                  75                  80

Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
        115                 120                 125

Phe Leu Pro Arg Ile Cys Ser Gln Leu Lys Gly His Val Asp Ser His
    130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
        195                 200                 205

Glu Gly Lys Asp Val Asp His Lys Val Leu Lys Ala Leu Phe His Arg
    210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
            260                 265                 270

Leu Gly Glu Ile Ile Arg Phe Gly Gln Met Phe Phe Pro Glu Ser Arg
        275                 280                 285

Glu Glu Thr Tyr Tyr Gln Glu Ser Ala Gly Val Ala Asp Leu Ile Thr
    290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
                325                 330                 335

Ser Ala Gln Gly Leu Ile Thr Cys Lys Glu Val His Glu Trp Leu Glu
            340                 345                 350

Thr Cys Gly Ser Val Glu Asp Phe Pro Leu Phe Glu Ala Val Tyr Gln
        355                 360                 365

Ile Val Tyr Asn Asn Tyr Pro Met Lys Asn Leu Pro Asp Met Ile Glu
    370                 375                 380

Glu Leu Asp Leu His Glu Asp
385                 390
```

<210> SEQ ID NO 219
<211> LENGTH: 391
<212> TYPE: PRT
<213> ORGANISM: Artificial Sequence
<220> FEATURE:
<223> OTHER INFORMATION: N44V

<400> SEQUENCE: 219

```
Met Ser Ala Ala Ala Asp Arg Leu Asn Leu Thr Ser Gly His Leu Asn
1               5                   10                  15

Ala Gly Arg Lys Arg Ser Ser Ser Ser Val Ser Leu Lys Ala Ala Glu
            20                  25                  30

Lys Pro Phe Lys Val Thr Val Ile Gly Ser Gly Val Trp Gly Thr Thr
        35                  40                  45

Ile Ala Lys Val Val Ala Glu Asn Cys Lys Gly Tyr Pro Glu Val Phe
    50                  55                  60

Ala Pro Ile Val Gln Met Trp Val Phe Glu Glu Glu Ile Asn Gly Glu
65                  70                  75                  80

Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
        115                 120                 125

Phe Leu Pro Arg Ile Cys Ser Gln Leu Lys Gly His Val Asp Ser His
    130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
        195                 200                 205

Glu Gly Lys Asp Val Asp His Lys Val Leu Lys Ala Leu Phe His Arg
    210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
            260                 265                 270

Leu Gly Glu Ile Ile Arg Phe Gly Gln Met Phe Phe Pro Glu Ser Arg
        275                 280                 285

Glu Glu Thr Tyr Tyr Gln Glu Ser Ala Gly Val Ala Asp Leu Ile Thr
    290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
                325                 330                 335

Ser Ala Gln Gly Leu Ile Thr Cys Lys Glu Val His Glu Trp Leu Glu
            340                 345                 350

Thr Cys Gly Ser Val Glu Asp Phe Pro Leu Phe Glu Ala Val Tyr Gln
        355                 360                 365

Ile Val Tyr Asn Asn Tyr Pro Met Lys Asn Leu Pro Asp Met Ile Glu
    370                 375                 380

Glu Leu Asp Leu His Glu Asp
385                 390
```

<210> SEQ ID NO 220

<211> LENGTH: 391
<212> TYPE: PRT
<213> ORGANISM: Artificial Sequence
<220> FEATURE:
<223> OTHER INFORMATION: W45A

<400> SEQUENCE: 220

```
Met Ser Ala Ala Ala Asp Arg Leu Asn Leu Thr Ser Gly His Leu Asn
1               5                   10                  15

Ala Gly Arg Lys Arg Ser Ser Ser Ser Val Ser Leu Lys Ala Ala Glu
            20                  25                  30

Lys Pro Phe Lys Val Thr Val Ile Gly Ser Gly Asn Ala Gly Thr Thr
        35                  40                  45

Ile Ala Lys Val Val Ala Glu Asn Cys Lys Gly Tyr Pro Glu Val Phe
    50                  55                  60

Ala Pro Ile Val Gln Met Trp Val Phe Glu Glu Glu Ile Asn Gly Glu
65                  70                  75                  80

Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
        115                 120                 125

Phe Leu Pro Arg Ile Cys Ser Gln Leu Lys Gly His Val Asp Ser His
    130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
        195                 200                 205

Glu Gly Lys Asp Val Asp His Lys Val Leu Lys Ala Leu Phe His Arg
    210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
            260                 265                 270

Leu Gly Glu Ile Ile Arg Phe Gly Gln Met Phe Phe Pro Glu Ser Arg
        275                 280                 285

Glu Glu Thr Tyr Tyr Gln Glu Ser Ala Gly Val Ala Asp Leu Ile Thr
    290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
                325                 330                 335

Ser Ala Gln Gly Leu Ile Thr Cys Lys Glu Val His Glu Trp Leu Glu
            340                 345                 350

Thr Cys Gly Ser Val Glu Asp Phe Pro Leu Phe Glu Ala Val Tyr Gln
        355                 360                 365

Ile Val Tyr Asn Asn Tyr Pro Met Lys Asn Leu Pro Asp Met Ile Glu
    370                 375                 380
```

```
Glu Leu Asp Leu His Glu Asp
385                 390


<210> SEQ ID NO 221
<211> LENGTH: 391
<212> TYPE: PRT
<213> ORGANISM: Artificial Sequence
<220> FEATURE:
<223> OTHER INFORMATION: W45C

<400> SEQUENCE: 221

Met Ser Ala Ala Ala Asp Arg Leu Asn Leu Thr Ser Gly His Leu Asn
1               5                   10                  15

Ala Gly Arg Lys Arg Ser Ser Ser Ser Val Ser Leu Lys Ala Ala Glu
            20                  25                  30

Lys Pro Phe Lys Val Thr Val Ile Gly Ser Gly Asn Cys Gly Thr Thr
        35                  40                  45

Ile Ala Lys Val Val Ala Glu Asn Cys Lys Gly Tyr Pro Glu Val Phe
    50                  55                  60

Ala Pro Ile Val Gln Met Trp Val Phe Glu Glu Glu Ile Asn Gly Glu
65                  70                  75                  80

Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
        115                 120                 125

Phe Leu Pro Arg Ile Cys Ser Gln Leu Lys Gly His Val Asp Ser His
    130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
        195                 200                 205

Glu Gly Lys Asp Val Asp His Lys Val Leu Lys Ala Leu Phe His Arg
    210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
            260                 265                 270

Leu Gly Glu Ile Ile Arg Phe Gly Gln Met Phe Phe Pro Glu Ser Arg
        275                 280                 285

Glu Glu Thr Tyr Tyr Gln Glu Ser Ala Gly Val Ala Asp Leu Ile Thr
    290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
                325                 330                 335

Ser Ala Gln Gly Leu Ile Thr Cys Lys Glu Val His Glu Trp Leu Glu
            340                 345                 350
```

```
Thr Cys Gly Ser Val Glu Asp Phe Pro Leu Phe Glu Ala Val Tyr Gln
        355                 360                 365

Ile Val Tyr Asn Asn Tyr Pro Met Lys Asn Leu Pro Asp Met Ile Glu
    370                 375                 380

Glu Leu Asp Leu His Glu Asp
385                 390


<210> SEQ ID NO 222
<211> LENGTH: 391
<212> TYPE: PRT
<213> ORGANISM: Artificial Sequence
<220> FEATURE:
<223> OTHER INFORMATION: W45G

<400> SEQUENCE: 222

Met Ser Ala Ala Ala Asp Arg Leu Asn Leu Thr Ser Gly His Leu Asn
1               5                   10                  15

Ala Gly Arg Lys Arg Ser Ser Ser Ser Val Ser Leu Lys Ala Ala Glu
            20                  25                  30

Lys Pro Phe Lys Val Thr Val Ile Gly Ser Gly Asn Gly Gly Thr Thr
        35                  40                  45

Ile Ala Lys Val Val Ala Glu Asn Cys Lys Gly Tyr Pro Glu Val Phe
    50                  55                  60

Ala Pro Ile Val Gln Met Trp Val Phe Glu Glu Glu Ile Asn Gly Glu
65                  70                  75                  80

Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
        115                 120                 125

Phe Leu Pro Arg Ile Cys Ser Gln Leu Lys Gly His Val Asp Ser His
    130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
        195                 200                 205

Glu Gly Lys Asp Val Asp His Lys Val Leu Lys Ala Leu Phe His Arg
    210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
            260                 265                 270

Leu Gly Glu Ile Ile Arg Phe Gly Gln Met Phe Phe Pro Glu Ser Arg
        275                 280                 285

Glu Glu Thr Tyr Tyr Gln Glu Ser Ala Gly Val Ala Asp Leu Ile Thr
    290                 295                 300

Thr Cys Ala Gly Gly Arg Asn Val Lys Val Ala Arg Leu Met Ala Thr
305                 310                 315                 320
```

```
Ser Gly Lys Asp Ala Trp Glu Cys Glu Lys Glu Leu Leu Asn Gly Gln
                325                 330                 335

Ser Ala Gln Gly Leu Ile Thr Cys Lys Glu Val His Glu Trp Leu Glu
            340                 345                 350

Thr Cys Gly Ser Val Glu Asp Phe Pro Leu Phe Glu Ala Val Tyr Gln
        355                 360                 365

Ile Val Tyr Asn Asn Tyr Pro Met Lys Asn Leu Pro Asp Met Ile Glu
    370                 375                 380

Glu Leu Asp Leu His Glu Asp
385                 390


<210> SEQ ID NO 223
<211> LENGTH: 391
<212> TYPE: PRT
<213> ORGANISM: Artificial Sequence
<220> FEATURE:
<223> OTHER INFORMATION: W45H

<400> SEQUENCE: 223

Met Ser Ala Ala Ala Asp Arg Leu Asn Leu Thr Ser Gly His Leu Asn
1               5                   10                  15

Ala Gly Arg Lys Arg Ser Ser Ser Ser Val Ser Leu Lys Ala Ala Glu
            20                  25                  30

Lys Pro Phe Lys Val Thr Val Ile Gly Ser Gly Asn His Gly Thr Thr
        35                  40                  45

Ile Ala Lys Val Val Ala Glu Asn Cys Lys Gly Tyr Pro Glu Val Phe
    50                  55                  60

Ala Pro Ile Val Gln Met Trp Val Phe Glu Glu Glu Ile Asn Gly Glu
65                  70                  75                  80

Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
        115                 120                 125

Phe Leu Pro Arg Ile Cys Ser Gln Leu Lys Gly His Val Asp Ser His
    130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
        195                 200                 205

Glu Gly Lys Asp Val Asp His Lys Val Leu Lys Ala Leu Phe His Arg
    210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
            260                 265                 270

Leu Gly Glu Ile Ile Arg Phe Gly Gln Met Phe Phe Pro Glu Ser Arg
        275                 280                 285
```

```
Glu Glu Thr Tyr Tyr Gln Glu Ser Ala Gly Val Ala Asp Leu Ile Thr
    290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
                325                 330                 335

Ser Ala Gln Gly Leu Ile Thr Cys Lys Glu Val His Glu Trp Leu Glu
            340                 345                 350

Thr Cys Gly Ser Val Glu Asp Phe Pro Leu Phe Glu Ala Val Tyr Gln
        355                 360                 365

Ile Val Tyr Asn Asn Tyr Pro Met Lys Asn Leu Pro Asp Met Ile Glu
    370                 375                 380

Glu Leu Asp Leu His Glu Asp
385                 390


<210> SEQ ID NO 224
<211> LENGTH: 391
<212> TYPE: PRT
<213> ORGANISM: Artificial Sequence
<220> FEATURE:
<223> OTHER INFORMATION: W45I

<400> SEQUENCE: 224

Met Ser Ala Ala Ala Asp Arg Leu Asn Leu Thr Ser Gly His Leu Asn
1               5                   10                  15

Ala Gly Arg Lys Arg Ser Ser Ser Ser Val Ser Leu Lys Ala Ala Glu
            20                  25                  30

Lys Pro Phe Lys Val Thr Val Ile Gly Ser Gly Asn Ile Gly Thr Thr
        35                  40                  45

Ile Ala Lys Val Val Ala Glu Asn Cys Lys Gly Tyr Pro Glu Val Phe
    50                  55                  60

Ala Pro Ile Val Gln Met Trp Val Phe Glu Glu Glu Ile Asn Gly Glu
65                  70                  75                  80

Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
        115                 120                 125

Phe Leu Pro Arg Ile Cys Ser Gln Leu Lys Gly His Val Asp Ser His
    130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
        195                 200                 205

Glu Gly Lys Asp Val Asp His Lys Val Leu Lys Ala Leu Phe His Arg
    210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255
```

```
Gly Leu Gly Trp Gly Asn Asn Ala Ser Ala Ala Ile Gln Arg Val Gly
            260                 265                 270

Leu Gly Glu Ile Ile Arg Phe Gly Gln Met Phe Phe Pro Glu Ser Arg
        275                 280                 285

Glu Glu Thr Tyr Tyr Gln Glu Ser Ala Gly Val Ala Asp Leu Ile Thr
    290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
                325                 330                 335

Ser Ala Gln Gly Leu Ile Thr Cys Lys Glu Val His Glu Trp Leu Glu
            340                 345                 350

Thr Cys Gly Ser Val Glu Asp Phe Pro Leu Phe Glu Ala Val Tyr Gln
        355                 360                 365

Ile Val Tyr Asn Asn Tyr Pro Met Lys Asn Leu Pro Asp Met Ile Glu
    370                 375                 380

Glu Leu Asp Leu His Glu Asp
385                 390


<210> SEQ ID NO 225
<211> LENGTH: 391
<212> TYPE: PRT
<213> ORGANISM: Artificial Sequence
<220> FEATURE:
<223> OTHER INFORMATION: W45K

<400> SEQUENCE: 225

Met Ser Ala Ala Ala Asp Arg Leu Asn Leu Thr Ser Gly His Leu Asn
1               5                   10                  15

Ala Gly Arg Lys Arg Ser Ser Ser Ser Val Ser Leu Lys Ala Ala Glu
            20                  25                  30

Lys Pro Phe Lys Val Thr Val Ile Gly Ser Gly Asn Lys Gly Thr Thr
        35                  40                  45

Ile Ala Lys Val Val Ala Glu Asn Cys Lys Gly Tyr Pro Glu Val Phe
    50                  55                  60

Ala Pro Ile Val Gln Met Trp Val Phe Glu Glu Glu Ile Asn Gly Glu
65                  70                  75                  80

Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
        115                 120                 125

Phe Leu Pro Arg Ile Cys Ser Gln Leu Lys Gly His Val Asp Ser His
    130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
        195                 200                 205

Glu Gly Lys Asp Val Asp His Lys Val Leu Lys Ala Leu Phe His Arg
    210                 215                 220
```

```
Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
            260                 265                 270

Leu Gly Glu Ile Ile Arg Phe Gly Gln Met Phe Phe Pro Glu Ser Arg
        275                 280                 285

Glu Glu Thr Tyr Tyr Gln Glu Ser Ala Gly Val Ala Asp Leu Ile Thr
    290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
                325                 330                 335

Ser Ala Gln Gly Leu Ile Thr Cys Lys Glu Val His Glu Trp Leu Glu
            340                 345                 350

Thr Cys Gly Ser Val Glu Asp Phe Pro Leu Phe Glu Ala Val Tyr Gln
        355                 360                 365

Ile Val Tyr Asn Asn Tyr Pro Met Lys Asn Leu Pro Asp Met Ile Glu
    370                 375                 380

Glu Leu Asp Leu His Glu Asp
385                 390


<210> SEQ ID NO 226
<211> LENGTH: 391
<212> TYPE: PRT
<213> ORGANISM: Artificial Sequence
<220> FEATURE:
<223> OTHER INFORMATION: W45L

<400> SEQUENCE: 226

Met Ser Ala Ala Ala Asp Arg Leu Asn Leu Thr Ser Gly His Leu Asn
1               5                   10                  15

Ala Gly Arg Lys Arg Ser Ser Ser Ser Val Ser Leu Lys Ala Ala Glu
            20                  25                  30

Lys Pro Phe Lys Val Thr Val Ile Gly Ser Gly Asn Leu Gly Thr Thr
        35                  40                  45

Ile Ala Lys Val Val Ala Glu Asn Cys Lys Gly Tyr Pro Glu Val Phe
    50                  55                  60

Ala Pro Ile Val Gln Met Trp Val Phe Glu Glu Glu Ile Asn Gly Glu
65                  70                  75                  80

Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
        115                 120                 125

Phe Leu Pro Arg Ile Cys Ser Gln Leu Lys Gly His Val Asp Ser His
    130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
            180                 185                 190
```

```
Trp Ser Glu Thr Thr Val Ala Tyr His Ile Pro Lys Asp Phe Arg Gly
        195                 200                 205

Glu Gly Lys Asp Val Asp His Lys Val Leu Lys Ala Leu Phe His Arg
    210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
            260                 265                 270

Leu Gly Glu Ile Ile Arg Phe Gly Gln Met Phe Phe Pro Glu Ser Arg
        275                 280                 285

Glu Glu Thr Tyr Tyr Gln Glu Ser Ala Gly Val Ala Asp Leu Ile Thr
    290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
                325                 330                 335

Ser Ala Gln Gly Leu Ile Thr Cys Lys Glu Val His Glu Trp Leu Glu
            340                 345                 350

Thr Cys Gly Ser Val Glu Asp Phe Pro Leu Phe Glu Ala Val Tyr Gln
        355                 360                 365

Ile Val Tyr Asn Asn Tyr Pro Met Lys Asn Leu Pro Asp Met Ile Glu
    370                 375                 380

Glu Leu Asp Leu His Glu Asp
385                 390


<210> SEQ ID NO 227
<211> LENGTH: 391
<212> TYPE: PRT
<213> ORGANISM: Artificial Sequence
<220> FEATURE:
<223> OTHER INFORMATION: W45M

<400> SEQUENCE: 227

Met Ser Ala Ala Ala Asp Arg Leu Asn Leu Thr Ser Gly His Leu Asn
1               5                   10                  15

Ala Gly Arg Lys Arg Ser Ser Ser Ser Val Ser Leu Lys Ala Ala Glu
            20                  25                  30

Lys Pro Phe Lys Val Thr Val Ile Gly Ser Gly Asn Met Gly Thr Thr
        35                  40                  45

Ile Ala Lys Val Val Ala Glu Asn Cys Lys Gly Tyr Pro Glu Val Phe
    50                  55                  60

Ala Pro Ile Val Gln Met Trp Val Phe Glu Glu Glu Ile Asn Gly Glu
65                  70                  75                  80

Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
        115                 120                 125

Phe Leu Pro Arg Ile Cys Ser Gln Leu Lys Gly His Val Asp Ser His
    130                 135                 140

Val Arg Ala Ile Ser Cys Leu Lys Gly Phe Glu Val Gly Ala Lys Gly
145                 150                 155                 160
```

```
Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
        195                 200                 205

Glu Gly Lys Asp Val Asp His Lys Val Leu Lys Ala Leu Phe His Arg
    210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
            260                 265                 270

Leu Gly Glu Ile Ile Arg Phe Gly Gln Met Phe Phe Pro Glu Ser Arg
        275                 280                 285

Glu Glu Thr Tyr Tyr Gln Glu Ser Ala Gly Val Ala Asp Leu Ile Thr
    290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
                325                 330                 335

Ser Ala Gln Gly Leu Ile Thr Cys Lys Glu Val His Glu Trp Leu Glu
            340                 345                 350

Thr Cys Gly Ser Val Glu Asp Phe Pro Leu Phe Glu Ala Val Tyr Gln
        355                 360                 365

Ile Val Tyr Asn Asn Tyr Pro Met Lys Asn Leu Pro Asp Met Ile Glu
    370                 375                 380

Glu Leu Asp Leu His Glu Asp
385                 390
```

<210> SEQ ID NO 228
<211> LENGTH: 391
<212> TYPE: PRT
<213> ORGANISM: Artificial Sequence
<220> FEATURE:
<223> OTHER INFORMATION: W45N

<400> SEQUENCE: 228

```
Met Ser Ala Ala Ala Asp Arg Leu Asn Leu Thr Ser Gly His Leu Asn
1               5                   10                  15

Ala Gly Arg Lys Arg Ser Ser Ser Ser Val Ser Leu Lys Ala Ala Glu
            20                  25                  30

Lys Pro Phe Lys Val Thr Val Ile Gly Ser Gly Asn Asn Gly Thr Thr
        35                  40                  45

Ile Ala Lys Val Val Ala Glu Asn Cys Lys Gly Tyr Pro Glu Val Phe
    50                  55                  60

Ala Pro Ile Val Gln Met Trp Val Phe Glu Glu Glu Ile Asn Gly Glu
65                  70                  75                  80

Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
        115                 120                 125
```

```
Phe Leu Pro Arg Ile Cys Ser Gln Leu Lys Gly His Val Asp Ser His
    130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
        195                 200                 205

Glu Gly Lys Asp Val Asp His Lys Val Leu Lys Ala Leu Phe His Arg
    210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
            260                 265                 270

Leu Gly Glu Ile Ile Arg Phe Gly Gln Met Phe Phe Pro Glu Ser Arg
        275                 280                 285

Glu Glu Thr Tyr Tyr Gln Glu Ser Ala Gly Val Ala Asp Leu Ile Thr
    290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
                325                 330                 335

Ser Ala Gln Gly Leu Ile Thr Cys Lys Glu Val His Glu Trp Leu Glu
            340                 345                 350

Thr Cys Gly Ser Val Glu Asp Phe Pro Leu Phe Glu Ala Val Tyr Gln
        355                 360                 365

Ile Val Tyr Asn Asn Tyr Pro Met Lys Asn Leu Pro Asp Met Ile Glu
    370                 375                 380

Glu Leu Asp Leu His Glu Asp
385                 390


<210> SEQ ID NO 229
<211> LENGTH: 391
<212> TYPE: PRT
<213> ORGANISM: Artificial Sequence
<220> FEATURE:
<223> OTHER INFORMATION: W45Q

<400> SEQUENCE: 229

Met Ser Ala Ala Ala Asp Arg Leu Asn Leu Thr Ser Gly His Leu Asn
1               5                   10                  15

Ala Gly Arg Lys Arg Ser Ser Ser Ser Val Ser Leu Lys Ala Ala Glu
            20                  25                  30

Lys Pro Phe Lys Val Thr Val Ile Gly Ser Gly Asn Gln Gly Thr Thr
        35                  40                  45

Ile Ala Lys Val Val Ala Glu Asn Cys Lys Gly Tyr Pro Glu Val Phe
    50                  55                  60

Ala Pro Ile Val Gln Met Trp Val Phe Glu Glu Glu Ile Asn Gly Glu
65                  70                  75                  80

Lys Leu Thr Glu Ile Ile Asn Thr Arg His Gln Asn Val Lys Tyr Leu
                85                  90                  95
```

```
Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
        115                 120                 125

Phe Leu Pro Arg Ile Cys Ser Gln Leu Lys Gly His Val Asp Ser His
    130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
        195                 200                 205

Glu Gly Lys Asp Val Asp His Lys Val Leu Lys Ala Leu Phe His Arg
    210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
            260                 265                 270

Leu Gly Glu Ile Ile Arg Phe Gly Gln Met Phe Phe Pro Glu Ser Arg
        275                 280                 285

Glu Glu Thr Tyr Tyr Gln Glu Ser Ala Gly Val Ala Asp Leu Ile Thr
    290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
                325                 330                 335

Ser Ala Gln Gly Leu Ile Thr Cys Lys Glu Val His Glu Trp Leu Glu
            340                 345                 350

Thr Cys Gly Ser Val Glu Asp Phe Pro Leu Phe Glu Ala Val Tyr Gln
        355                 360                 365

Ile Val Tyr Asn Asn Tyr Pro Met Lys Asn Leu Pro Asp Met Ile Glu
    370                 375                 380

Glu Leu Asp Leu His Glu Asp
385                 390


<210> SEQ ID NO 230
<211> LENGTH: 391
<212> TYPE: PRT
<213> ORGANISM: Artificial Sequence
<220> FEATURE:
<223> OTHER INFORMATION: W45R

<400> SEQUENCE: 230

Met Ser Ala Ala Ala Asp Arg Leu Asn Leu Thr Ser Gly His Leu Asn
1               5                   10                  15

Ala Gly Arg Lys Arg Ser Ser Ser Ser Val Ser Leu Lys Ala Ala Glu
            20                  25                  30

Lys Pro Phe Lys Val Thr Val Ile Gly Ser Gly Asn Arg Gly Thr Thr
        35                  40                  45

Ile Ala Lys Val Val Ala Glu Asn Cys Lys Gly Tyr Pro Glu Val Phe
    50                  55                  60
```

```
Ala Pro Ile Val Gln Met Trp Val Phe Glu Glu Glu Ile Asn Gly Glu
65                  70                  75                  80

Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
        115                 120                 125

Phe Leu Pro Arg Ile Cys Ser Gln Leu Lys Gly His Val Asp Ser His
    130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
        195                 200                 205

Glu Gly Lys Asp Val Asp His Lys Val Leu Lys Ala Leu Phe His Arg
    210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
            260                 265                 270

Leu Gly Glu Ile Ile Arg Phe Gly Gln Met Phe Phe Pro Glu Ser Arg
        275                 280                 285

Glu Glu Thr Tyr Tyr Gln Glu Ser Ala Gly Val Ala Asp Leu Ile Thr
    290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
                325                 330                 335

Ser Ala Gln Gly Leu Ile Thr Cys Lys Glu Val His Glu Trp Leu Glu
            340                 345                 350

Thr Cys Gly Ser Val Glu Asp Phe Pro Leu Phe Glu Ala Val Tyr Gln
        355                 360                 365

Ile Val Tyr Asn Asn Tyr Pro Met Lys Asn Leu Pro Asp Met Ile Glu
    370                 375                 380

Glu Leu Asp Leu His Glu Asp
385                 390
```

<210> SEQ ID NO 231
<211> LENGTH: 391
<212> TYPE: PRT
<213> ORGANISM: Artificial Sequence
<220> FEATURE:
<223> OTHER INFORMATION: W45S

<400> SEQUENCE: 231

```
Met Ser Ala Ala Ala Asp Arg Leu Asn Leu Thr Ser Gly His Leu Asn
1               5                   10                  15

Ala Gly Arg Lys Arg Ser Ser Ser Ser Val Ser Leu Lys Ala Ala Glu
            20                  25                  30
```

```
Lys Pro Phe Lys Val Thr Val Ile Gly Ser Gly Asn Ser Gly Thr Thr
        35                  40                  45

Ile Ala Lys Val Val Ala Glu Asn Cys Lys Gly Tyr Pro Glu Val Phe
    50                  55                  60

Ala Pro Ile Val Gln Met Trp Val Phe Glu Glu Glu Ile Asn Gly Glu
65                  70                  75                  80

Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
        115                 120                 125

Phe Leu Pro Arg Ile Cys Ser Gln Leu Lys Gly His Val Asp Ser His
    130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
        195                 200                 205

Glu Gly Lys Asp Val Asp His Lys Val Leu Lys Ala Leu Phe His Arg
    210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
            260                 265                 270

Leu Gly Glu Ile Ile Arg Phe Gly Gln Met Phe Phe Pro Glu Ser Arg
        275                 280                 285

Glu Glu Thr Tyr Tyr Gln Glu Ser Ala Gly Val Ala Asp Leu Ile Thr
    290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
                325                 330                 335

Ser Ala Gln Gly Leu Ile Thr Cys Lys Glu Val His Glu Trp Leu Glu
            340                 345                 350

Thr Cys Gly Ser Val Glu Asp Phe Pro Leu Phe Glu Ala Val Tyr Gln
        355                 360                 365

Ile Val Tyr Asn Asn Tyr Pro Met Lys Asn Leu Pro Asp Met Ile Glu
    370                 375                 380

Glu Leu Asp Leu His Glu Asp
385                 390
```

<210> SEQ ID NO 232
<211> LENGTH: 391
<212> TYPE: PRT
<213> ORGANISM: Artificial Sequence
<220> FEATURE:
<223> OTHER INFORMATION: W45T

<400> SEQUENCE: 232

```
Met Ser Ala Ala Ala Asp Arg Leu Asn Leu Thr Ser Gly His Leu Asn
1               5                   10                  15

Ala Gly Arg Lys Arg Ser Ser Ser Ser Val Ser Leu Lys Ala Ala Glu
            20                  25                  30

Lys Pro Phe Lys Val Thr Val Ile Gly Ser Gly Asn Thr Gly Thr Thr
        35                  40                  45

Ile Ala Lys Val Val Ala Glu Asn Cys Lys Gly Tyr Pro Glu Val Phe
    50                  55                  60

Ala Pro Ile Val Gln Met Trp Val Phe Glu Glu Glu Ile Asn Gly Glu
65                  70                  75                  80

Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
        115                 120                 125

Phe Leu Pro Arg Ile Cys Ser Gln Leu Lys Gly His Val Asp Ser His
    130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
        195                 200                 205

Glu Gly Lys Asp Val Asp His Lys Val Leu Lys Ala Leu Phe His Arg
    210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
            260                 265                 270

Leu Gly Glu Ile Ile Arg Phe Gly Gln Met Phe Phe Pro Glu Ser Arg
        275                 280                 285

Glu Glu Thr Tyr Tyr Gln Glu Ser Ala Gly Val Ala Asp Leu Ile Thr
    290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
                325                 330                 335

Ser Ala Gln Gly Leu Ile Thr Cys Lys Glu Val His Glu Trp Leu Glu
            340                 345                 350

Thr Cys Gly Ser Val Glu Asp Phe Pro Leu Phe Glu Ala Val Tyr Gln
        355                 360                 365

Ile Val Tyr Asn Asn Tyr Pro Met Lys Asn Leu Pro Asp Met Ile Glu
    370                 375                 380

Glu Leu Asp Leu His Glu Asp
385                 390
```

<210> SEQ ID NO 233
<211> LENGTH: 391

```
<212> TYPE: PRT
<213> ORGANISM: Artificial Sequence
<220> FEATURE:
<223> OTHER INFORMATION: W45V

<400> SEQUENCE: 233

Met Ser Ala Ala Ala Asp Arg Leu Asn Leu Thr Ser Gly His Leu Asn
1               5                   10                  15

Ala Gly Arg Lys Arg Ser Ser Ser Ser Val Ser Leu Lys Ala Ala Glu
            20                  25                  30

Lys Pro Phe Lys Val Thr Val Ile Gly Ser Gly Asn Val Gly Thr Thr
        35                  40                  45

Ile Ala Lys Val Val Ala Glu Asn Cys Lys Gly Tyr Pro Glu Val Phe
    50                  55                  60

Ala Pro Ile Val Gln Met Trp Val Phe Glu Glu Glu Ile Asn Gly Glu
65                  70                  75                  80

Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
        115                 120                 125

Phe Leu Pro Arg Ile Cys Ser Gln Leu Lys Gly His Val Asp Ser His
    130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
        195                 200                 205

Glu Gly Lys Asp Val Asp His Lys Val Leu Lys Ala Leu Phe His Arg
    210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
            260                 265                 270

Leu Gly Glu Ile Ile Arg Phe Gly Gln Met Phe Phe Pro Glu Ser Arg
        275                 280                 285

Glu Glu Thr Tyr Tyr Gln Glu Ser Ala Gly Val Ala Asp Leu Ile Thr
    290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
                325                 330                 335

Ser Ala Gln Gly Leu Ile Thr Cys Lys Glu Val His Glu Trp Leu Glu
            340                 345                 350

Thr Cys Gly Ser Val Glu Asp Phe Pro Leu Phe Glu Ala Val Tyr Gln
        355                 360                 365

Ile Val Tyr Asn Asn Tyr Pro Met Lys Asn Leu Pro Asp Met Ile Glu
    370                 375                 380
```

Glu Leu Asp Leu His Glu Asp
385 390

<210> SEQ ID NO 234
<211> LENGTH: 90
<212> TYPE: DNA
<213> ORGANISM: Artificial Sequence
<220> FEATURE:
<223> OTHER INFORMATION: F1

<400> SEQUENCE: 234
tcaagaaaca attgtatatt gtacaccccc cccctccaca aacacaaata ttgataatat 60
aaagatgaac caacgtaatg cttcaatgac 90

<210> SEQ ID NO 235
<211> LENGTH: 52
<212> TYPE: DNA
<213> ORGANISM: Artificial Sequence
<220> FEATURE:
<223> OTHER INFORMATION: R1

<400> SEQUENCE: 235
ctgaacatta gaatacgtaa tccgcaatgc ttagtggctg ctgcgctcgt cc 52

<210> SEQ ID NO 236
<211> LENGTH: 52
<212> TYPE: DNA
<213> ORGANISM: Artificial Sequence
<220> FEATURE:
<223> OTHER INFORMATION: F2

<400> SEQUENCE: 236
ggacgagcgc agcagccact aagcattgcg gattacgtat tctaatgttc ag 52

<210> SEQ ID NO 237
<211> LENGTH: 93
<212> TYPE: DNA
<213> ORGANISM: Artificial Sequence
<220> FEATURE:
<223> OTHER INFORMATION: R2

<400> SEQUENCE: 237
gatatagaag agcctcgaaa aaagtggggg aaagtatgat atgttatctt tctccaataa 60
atcaccttgg ctaactcgtt gtatcatcac tgg 93

<210> SEQ ID NO 238
<211> LENGTH: 42
<212> TYPE: DNA
<213> ORGANISM: Artificial Sequence
<220> FEATURE:
<223> OTHER INFORMATION: Ptrc-gpsA NcoI F

<400> SEQUENCE: 238
taaggaggaa taaaccatga accaacgtaa tgcttcaatg ac 42

<210> SEQ ID NO 239
<211> LENGTH: 36
<212> TYPE: DNA
<213> ORGANISM: Artificial Sequence
<220> FEATURE:
<223> OTHER INFORMATION: Ptrc-gpsA PstI R

<400> SEQUENCE: 239
atggtaccag ctgcattagt ggctgctgcg ctcgtc 36

<210> SEQ ID NO 240
<211> LENGTH: 11222
<212> TYPE: DNA
<213> ORGANISM: Artificial Sequence
<220> FEATURE:
<223> OTHER INFORMATION: pLMH11-JM44

<400> SEQUENCE: 240

```
tcccattacc gacatttggg cgctatacgt gcatatgttc atgtatgtat ctgtatttaa     60
aacacttttg tattattttt cctcatatat gtgtataggt ttatacggat gatttaatta    120
ttacttcacc accctttatt tcaggctgat atcttagcct tgttactaga ttaatcatgt    180
aattagttat gtcacgctta cattcacgcc ctccccccac atccgctcta accgaaaagg    240
aaggagttag acaacctgaa gtctaggtcc ctatttattt ttttatagtt atgttagtat    300
taagaacgtt atttatattt caaatttttc ttttttttct gtacagacgc gtgtacgcat    360
gtaacattat actgaaaacc ttgcttgaga aggttttggg acgctcgaag gctttaattt    420
gcgggcggcc gcacctggta aaacctctag tggagtagta gatgtaatca atgaagcgga    480
agccaaaaga ccagagtaga ggcctataga agaaactgcg ataccttttg tgatggctaa    540
acaaacagac atctttttat atgtttttac ttctgtatat cgtgaagtag taagtgataa    600
gcgaatttgg ctaagaacgt tgtaagtgaa caagggacct cttttgcctt tcaaaaaagg    660
attaaatgga gttaatcatt gagatttagt tttcgttaga ttctgtatcc ctaaataact    720
cccttacccg acgggaaggc acaaaagact tgaataatag caaacggcca gtagccaaga    780
ccaaataata ctagagttaa ctgatggtct taaacaggca ttacgtggtg aactccaaga    840
ccaatataca aaatatcgat aagttattct tgcccaccaa tttaaggagc ctacatcagg    900
acagtagtac cattcctcag agaagaggta tacataacaa gaaaatcgcg tgaacacctt    960
atataactta gcccgttatt gagctaaaaa accttgcaaa atttcctatg aataagaata   1020
cttcagacgt gataaaaatt tactttctaa ctcttctcac gctgccccta tctgttcttc   1080
cgctctaccg tgagaaataa agcatcgagt acggcagttc gctgtcactg aactaaaaca   1140
ataaggctag ttcgaatgat gaacttgctt gctgtcaaac ttctgagttg ccgctgatgt   1200
gacactgtga caataaattc aaaccggtta tagcggtctc ctccggtacc ggttctgcca   1260
cctccaatag agctcagtag gagtcagaac ctctgcggtg gctgtcagtg actcatccgc   1320
gtttcgtaag ttgtgcgcgt gcacatttcg cccgttcccg ctcatcttgc agcaggcgga   1380
aattttcatc acgctgtagg acgcaaaaaa aaaataatta atcgtacaag aatcttggaa   1440
aaaaaattga aaaattttgt ataaaaggga tgacctaact tgactcaatg gcttttacac   1500
ccagtatttt ccctttcctt gtttgttaca attatagaag caagacaaaa acatatagac   1560
aacctattcc taggagttat atttttttac cctaccagca atataagtaa aaaactgttt   1620
aaacagtatg gctaagattt actaccaaga agactgtaac ttgtccttgt tggatggtaa   1680
gactatcgcc gttatcggtt acggttctca aggtcacgct catgccctga atgctaagga   1740
atccggttgt aacgttatca ttggtttatt cgaaggtgcg gaggagtgga aaagagctga   1800
agaacaaggt ttcgaagtct acaccgctgc tgaagctgct aagaaggctg acatcattat   1860
gatcttgatc ccagatgaat accaggctgt catgtacaaa aacgacatcg aaccaaactt   1920
ggaagccggt aacatgttga tgttcgctca cggtttcaac atccatttcg gttgtattgt   1980
tccaccaaag gacgttgatg tcactatgat cgctccaaag ggtccaggtc acaccgttag   2040
atccgaatac gaagaaggta aaggtgtccc atgcttggtt gctgtcgaac aagacgctac   2100
```

```
tggcaaggct ttggatatgg ctttggccta cgctttagcc atcggtggtg ctagagccgg   2160
tgtcttggaa actaccttca gaaccgaaac tgaaaccgac ttgttcggtg aacaagctgt   2220
tttatgtggt ggtgtctgcg ctttgatgca ggccggtttt gaaaccttgg ttgaagccgg   2280
ttacgaccca agaaacgctt acttcgaatg tatccacgaa atgaagttga tcgttgactt   2340
gatctaccaa tctggtttct ccggtatgcg ttactctatc tccaacactg ctgaatacgg   2400
tgactacatt accggtccaa agatcattac tgaagatacc aagaaggcta tgaagaagat   2460
tttgtctgac attcaagatg gtacctttgc caaggacttc ttggttgaca tgtctgatgc   2520
tggttcccag gtccacttca aggctatgag aaagttggcc tccgaacacc cagctgaagt   2580
tgtcggtgaa gaaattagat ccttgtactc ctggtccgac gaagacaagt tgattaacaa   2640
ctgaggccct gcaggccaga ggaaaataat atcaagtgct ggaaactttt tctcttggaa   2700
tttttgcaac atcaagtcat agtcaattga attgacccaa tttcacattt aagatttttt   2760
ttttttcatc cgacatacat ctgtacacta ggaagccctg tttttctgaa gcagcttcaa   2820
atatatatat tttttacata tttattatga ttcaatgaac aatctaatta aatcgaaaac   2880
aagaaccgaa acgcgaataa ataatttatt tagatggtga caagtgtata agtcctcatc   2940
gggacagcta cgatttctct ttcggttttg gctgagctac tggttgctgt gacgcagcgg   3000
cattagcgcg gcgttatgag ctaccctcgt ggcctgaaag atggcgggaa taaagcggaa   3060
ctaaaaatta ctgactgagc catattgagg tcaatttgtc aactcgtcaa gtcacgtttg   3120
gtggacggcc cctttccaac gaatcgtata tactaacatg cgcgcgcttc ctatatacac   3180
atatacatat atatatatat atatatgtgt gcgtgtatgt gtacacctgt atttaatttc   3240
cttactcgcg ggtttttctt ttttctcaat tcttggcttc ctctttctcg agcggaccgg   3300
atcctcgcga actccaaaat gagctatcaa aaacgataga tcgattagga tgactttgaa   3360
atgactccgc agtggactgg ccgttaattt caagcgtgag taaaatagtg catgacaaaa   3420
gatgagctag gcttttgtaa aaatatctta cgttgtaaaa ttttagaaat cattatttcc   3480
ttcatatcat tttgtcattg accttcagaa gaaaagagcc gaccaataat ataaataaat   3540
aaataaaaat aatattccat tatttctaaa cagattcaat actcattaaa aaactatatc   3600
aattaatttg aattaacgcg gccgcttaac cacagcaacc aggacaacat tttttgccag   3660
tttcttcagg cttccaaaag tctgttacgg ctcccctaga agcagacgaa acgatgtgag   3720
catatttacc aaggataccg cgtgaataga gcggtggcaa ttcaatggtc tcttgacgat   3780
gttttaactc ttcatcggag atatcaaagt gtaattcctt agtgtcttgg tcaatagtga   3840
ctatgtctcc tgtttgcagg taggcgattg gaccgccatc ttgtgcttca ggagcgatat   3900
gacccacgac aagaccataa gtaccacctg agaagcggcc atctgtcaga agggcaactt   3960
tttcaccttg ccctttacca acaatcattg atgaaaggga aagcatttca ggcataccag   4020
gaccgccctt tggtcctaca aaacgtacga caacaacatc accatcaaca atatcatcat   4080
tcaagacagc ttcaatggct tcttcttcag aattaaagac cttagcagga ccgacatgac   4140
gacgcacttt tacaccagaa actttggcaa cggcaccgtc tggagccaag ttaccatgga   4200
gaataatgac cggaccatct tcacgtttag gattttcaag cggcataata accttttgac   4260
caggtgttaa atcatcaaaa gccttcaaat tttcagcgac tgttttgcca gtacaagtga   4320
tacggtcacc atgaaggaag ccatttttaa ggagatattt cataactgct ggtacccctc   4380
cgaccttgta aaggtcttgg aatacatatt gaccagaagg tttcaaatca gccaaatgag   4440
```

gaactttttc ttggaaagta ttgaaatcat caagtgtcaa ttccacatta gcagcatggg 4500
caatagctaa gaggtgaagg gttgagttgg ttgaacctcc cagagccata gttacagtaa 4560
tagcatcttc aaaagcttca cgcgttaaaa tgtcagaagg ttttaagccc atttcgagca 4620
ttttgacaac agcgcgacca gcttcttcaa tatctgcttt cttttctgcg gattcagccg 4680
ggtgagaaga tgaacccgga aggctaagtc ccaaaacttc aatagctgtc gccattgtgt 4740
tagcagtata cataccaccg cagcctccag gaccgggaca agcattacat tccaaagctt 4800
taacttcttc tttggtcata tcgccgtggt tccaatggcc gacaccttca aagacagaga 4860
ctaaatcgat atctttgccg tctaaattac caggtgcaat tgttccgccg taagcaaaaa 4920
tggctgggat atccatgtta gccatagcga taacagaacc gggcatgttt ttatcacaac 4980
cgccaatggc tacaaaagca tccgcattat gacctcccat ggctgcttca atagaatctg 5040
caataatatc acgagatgtc aaggagaaac gcattccttg ggttcccatg gcgattccat 5100
cagaaaccgt gattgttccg aactgaactg gccaagcacc agcttcctta acaccgactt 5160
tggctagttt accaaagtca tgtaagtgga tattacaagg tgtgttttca gcccaagttg 5220
aaatgacacc gacgataggt tttcaaagt cttcatcttg cataccagtt gcacgcaaca 5280
tagcacgatt aggtgattta accattgaat cgtaaacaga actacgattt cttaagtctt 5340
taagagtttt tttgtcagtc atactcacgt gaaacttaga ttagattgct atgctttctt 5400
tccaatgagc aagaagtaaa aaaagttgta atagaacagg aaaaatgaag ctgaaacttg 5460
agaaattgaa gaccgtttgt taactcaaat atcaatggga ggtcgtcgaa agagaacaaa 5520
atcgaaaaaa aagttttcaa gagaaagaaa cgtgataaaa atttttattg ccttctccga 5580
cgaagaaaaa gggacgaggc ggtctctttt tccttttcca aacctttagt acgggtaatt 5640
aacggcaccc tagaggaagg aggaggggga atttagtatg ctgtgcttgg gtgttttgaa 5700
gtggtacggc ggtgcgcgga gtccgagaaa atctggaaga gtaaaaaagg agtagagaca 5760
ttttgaagct atgccggcag atctatttaa atggcgcgcc gacgtcaggt ggcacttttc 5820
ggggaaatgt gcgcggaacc cctatttgtt tatttttcta aatacattca aatatgtatc 5880
cgctcatgag acaataaccc tgataaatgc ttcaataata ttgaaaaagg aagagtatga 5940
gtattcaaca tttccgtgtc gcccttattc ccttttttgc ggcattttgc cttcctgttt 6000
ttgctcaccc agaaacgctg gtgaaagtaa aagatgctga agatcagttg ggtgcacgag 6060
tgggttacat cgaactggat ctcaacagcg gtaagatcct tgagagtttt cgccccgaag 6120
aacgttttcc aatgatgagc acttttaaag ttctgctatg tggcgcggta ttatcccgta 6180
ttgacgccgg gcaagagcaa ctcggtcgcc gcatacacta ttctcagaat gacttggttg 6240
agtactcacc agtcacagaa aagcatctta cggatggcat gacagtaaga gaattatgca 6300
gtgctgccat aaccatgagt gataacactg cggccaactt acttctgaca acgatcggag 6360
gaccgaagga gctaaccgct tttttgcaca acatggggga tcatgtaact cgccttgatc 6420
gttgggaacc ggagctgaat gaagccatac caaacgacga gcgtgacacc acgatgcctg 6480
tagcaatggc aacaacgttg cgcaaactat taactggcga actacttact ctagcttccc 6540
ggcaacaatt aatagactgg atggaggcgg ataaagttgc aggaccactt ctgcgctcgg 6600
cccttccggc tggctggttt attgctgata aatctggagc cggtgagcgt gggtctcgcg 6660
gtatcattgc agcactgggg ccagatggta agccctcccg tatcgtagtt atctacacga 6720
cggggagtca ggcaactatg gatgaacgaa atagacagat cgctgagata ggtgcctcac 6780
tgattaagca ttggtaactg tcagaccaag tttactcata tatactttag attgatttaa 6840

```
aacttcattt ttaatttaaa aggatctagg tgaagatcct ttttgataat ctcatgacca   6900
aaatccctta acgtgagttt tcgttccact gagcgtcaga ccccgtagaa aagatcaaag   6960
gatcttcttg agatcctttt tttctgcgcg taatctgctg cttgcaaaca aaaaaaccac   7020
cgctaccagc ggtggtttgt ttgccggatc aagagctacc aactcttttt ccgaaggtaa   7080
ctggcttcag cagagcgcag ataccaaata ctgttcttct agtgtagccg tagttaggcc   7140
accacttcaa gaactctgta gcaccgccta catacctcgc tctgctaatc ctgttaccag   7200
tggctgctgc cagtggcgat aagtcgtgtc ttaccgggtt ggactcaaga cgatagttac   7260
cggataaggc gcagcggtcg ggctgaacgg ggggttcgtg cacacagccc agcttggagc   7320
gaacgaccta caccgaactg agatacctac agcgtgagct atgagaaagc gccacgcttc   7380
ccgaagggag aaaggcggac aggtatccgg taagcggcag ggtcggaaca ggagagcgca   7440
cgagggagct tccaggggga aacgcctggt atctttatag tcctgtcggg tttcgccacc   7500
tctgacttga gcgtcgattt ttgtgatgct cgtcaggggg gcggagccta tggaaaaacg   7560
ccagcaacgc ggccttttta cggttcctgg ccttttgctg gccttttgct cacatgttct   7620
ttcctgcgtt atcccctgat tctgtggata accgtattac cgcctttgag tgagctgata   7680
ccgctcgccg cagccgaacg accgagcgca gcgagtcagt gagcgaggaa gcggaagagc   7740
gcccaatacg caaaccgcct ctccccgcgc gttggccgat tcattaatgc agctggcacg   7800
acaggtttcc cgactggaaa gcgggcagtg agcgcaacgc aattaatgtg agttagctca   7860
ctcattaggc accccaggct ttacacttta tgcttccggc tcgtatgttg tgtggaattg   7920
tgagcggata acaatttcac acaggaaaca gctatgacca tgattacgcc aagctttttc   7980
tttccaattt tttttttttc gtcattataa aaatcattac gaccgagatt cccgggtaat   8040
aactgatata attaaattga agctctaatt tgtgagttta gtatacatgc atttacttat   8100
aatacagttt tttagttttg ctggccgcat cttctcaaat atgcttccca gcctgctttt   8160
ctgtaacgtt caccctctac cttagcatcc cttccctttg caaatagtcc tcttccaaca   8220
ataataatgt cagatcctgt agagaccaca tcatccacgg ttctatactg ttgacccaat   8280
gcgtctccct tgtcatctaa acccacaccg ggtgtcataa tcaaccaatc gtaaccttca   8340
tctcttccac ccatgtctct ttgagcaata aagccgataa caaaatcttt gtcgctcttc   8400
gcaatgtcaa cagtaccctt agtatattct ccagtagata gggagccctt gcatgacaat   8460
tctgctaaca tcaaaaggcc tctaggttcc tttgttactt cttctgccgc ctgcttcaaa   8520
ccgctaacaa tacctgggcc caccacaccg tgtgcattcg taatgtctgc ccattctgct   8580
attctgtata cacccgcaga gtactgcaat ttgactgtat taccaatgtc agcaaatttt   8640
ctgtcttcga agagtaaaaa attgtacttg gcggataatg cctttagcgg cttaactgtg   8700
ccctccatgg aaaaatcagt caagatatcc acatgtgttt ttagtaaaca aattttggga   8760
cctaatgctt caactaactc cagtaattcc ttggtggtac gaacatccaa tgaagcacac   8820
aagtttgttt gcttttcgtg catgatatta aatagcttgg cagcaacagg actaggatga   8880
gtagcagcac gttccttata tgtagctttc gacatgattt atcttcgttt cctgcaggtt   8940
tttgttctgt gcagttgggt taagaatact gggcaatttc atgtttcttc aacactacat   9000
atgcgtatat ataccaatct aagtctgtgc tccttccttc gttcttcctt ctgttcggag   9060
attaccgaat caaaaaaatt tcaaggaaac cgaaatcaaa aaaaagaata aaaaaaaaat   9120
gatgaattga aaagcttgca tgcctgcagg tcgactctag tatactccgt ctactgtacg   9180
```

```
atacacttcc gctcaggtcc ttgtccttta acgaggcctt accactcttt tgttactcta   9240
ttgatccagc tcagcaaagg cagtgtgatc taagattcta tcttcgcgat gtagtaaaac   9300
tagctagacc gagaaagaga ctagaaatgc aaaaggcact tctacaatgg ctgccatcat   9360
tattatccga tgtgacgctg catttttttt tttttttttt tttttttttt tttttttttt   9420
tttttttttt ttttgtacgt cacctggcaa aacgacgatc ttcttagggg cagacattac   9480
aatggtatat ccttgaaata tatataaaaa aaaaaaaaaa aaaaaaaaaa aaaaatgcag   9540
cttctcaatg atattcgaat acgctttgag gagatacagc ctaatatccg acaaactgtt   9600
ttacagattt acgatcgtac ttgttaccca tcattgaatt ttgaacatcc gaacctggga   9660
gttttccctg aaacagatag tatatttgaa cctgtataat aatatatagt ctagcgcttt   9720
acggaagaca atgtatgtat ttcggttcct ggagaaacta ttgcatctat tgcataggta   9780
atcttgcacg tcgcatcccc ggttcatttt ctgcgtttcc atcttgcact tcaatagcat   9840
atctttgtta acgaagcatc tgtgcttcat tttgtagaac aaaaatgcaa cgcgagagcg   9900
ctaatttttc aaacaaagaa tctgagctgc atttttacag aacagaaatg caacgcgaaa   9960
gcgctatttt accaacgaag aatctgtgct tcatttttgt aaaacaaaaa tgcaacgcga  10020
gagcgctaat ttttcaaaca aagaatctga gctgcatttt tacagaacag aaatgcaacg  10080
cgagagcgct attttaccaa caaagaatct atacttcttt tttgttctac aaaaatgcat  10140
cccgagagcg ctatttttct aacaaagcat cttagattac tttttttctc ctttgtgcgc  10200
tctataatgc agtctcttga taactttttg cactgtaggt ccgttaaggt tagaagaagg  10260
ctactttggt gtctattttc tcttccataa aaaaagcctg actccacttc ccgcgtttac  10320
tgattactag cgaagctgcg ggtgcatttt ttcaagataa aggcatcccc gattatattc  10380
tataccgatg tggattgcgc atactttgtg aacagaaagt gatagcgttg atgattcttc  10440
attggtcaga aaattatgaa cggtttcttc tattttgtct ctatatacta cgtataggaa  10500
atgtttacat tttcgtattg ttttcgattc actctatgaa tagttcttac tacaattttt  10560
ttgtctaaag agtaatacta gagataaaca taaaaaatgt agaggtcgag tttagatgca  10620
agttcaagga gcgaaaggtg gatgggtagg ttatataggg atatagcaca gagatatata  10680
gcaaagagat acttttgagc aatgtttgtg gaagcggtat tcgcaatatt ttagtagctc  10740
gttacagtcc ggtgcgtttt tggtttttttg aaagtgcgtc ttcagagcgc ttttggtttt  10800
caaaagcgct ctgaagttcc tatactttct agagaatagg aacttcggaa taggaacttc  10860
aaagcgtttc cgaaaacgag cgcttccgaa aatgcaacgc gagctgcgca catacagctc  10920
actgttcacg tcgcacctat atctgcgtgt tgcctgtata tatatataca tgagaagaac  10980
ggcatagtgc gtgtttatgc ttaaatgcgt acttatatgc gtctatttat gtaggatgaa  11040
aggtagtcta gtacctcctg tgatattatc ccattccatg cggggtatcg tatgcttcct  11100
tcagcactac cctttagctg ttctatatgc tgccactcct caattggatt agtctcatcc  11160
ttcaatgcta tcatttcctt tgatattgga tcatatgcat agtaccgaga aactagagga  11220
tc                                                                 11222
```

<210> SEQ ID NO 241
<211> LENGTH: 54
<212> TYPE: DNA
<213> ORGANISM: Artificial Sequence
<220> FEATURE:
<223> OTHER INFORMATION: oBP1350

<400> SEQUENCE: 241
gattgaggcg atcggctgcg gcggacatct ttatattatc aatatttgtg tttg 54

<210> SEQ ID NO 242
<211> LENGTH: 53
<212> TYPE: DNA
<213> ORGANISM: Artificial Sequence
<220> FEATURE:
<223> OTHER INFORMATION: oBP1351

<400> SEQUENCE: 242
aaacacaaat attgataata taaagatgtc cgccgcagcc gatcgcctca atc 53

<210> SEQ ID NO 243
<211> LENGTH: 40
<212> TYPE: DNA
<213> ORGANISM: Artificial Sequence
<220> FEATURE:
<223> OTHER INFORMATION: oBP1352

<400> SEQUENCE: 243
ttaagtttaa acttaatcct catgcagatc cagttcttcg 40

<210> SEQ ID NO 244
<211> LENGTH: 53
<212> TYPE: DNA
<213> ORGANISM: Artificial Sequence
<220> FEATURE:
<223> OTHER INFORMATION: oBP1353

<400> SEQUENCE: 244
gtttaatcta tcagcagcag cagacatctt tatattatca atatttgtgt ttg 53

<210> SEQ ID NO 245
<211> LENGTH: 52
<212> TYPE: DNA
<213> ORGANISM: Artificial Sequence
<220> FEATURE:
<223> OTHER INFORMATION: oBP1354

<400> SEQUENCE: 245
aaacacaaat attgataata taaagatgtc tgctgctgct gatagattaa ac 52

<210> SEQ ID NO 246
<211> LENGTH: 39
<212> TYPE: DNA
<213> ORGANISM: Artificial Sequence
<220> FEATURE:
<223> OTHER INFORMATION: oBP1355

<400> SEQUENCE: 246
ttaagtttaa acctaatctt catgtagatc taattcttc 39

<210> SEQ ID NO 247
<211> LENGTH: 27
<212> TYPE: DNA
<213> ORGANISM: Artificial Sequence
<220> FEATURE:
<223> OTHER INFORMATION: oBP1356

<400> SEQUENCE: 247
agaaacgtca aggttgctag gctaatg 27

<210> SEQ ID NO 248
<211> LENGTH: 26
<212> TYPE: DNA

<213> ORGANISM: Artificial Sequence
<220> FEATURE:
<223> OTHER INFORMATION: oBP1357

<400> SEQUENCE: 248
gtgaagaaac gtattatcag gagtcg 26

<210> SEQ ID NO 249
<211> LENGTH: 7063
<212> TYPE: DNA
<213> ORGANISM: Artificial Sequence
<220> FEATURE:
<223> OTHER INFORMATION: pBP3518GPD1_EcOpt

<400> SEQUENCE: 249
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcaggcgcc 240
attcgccatt caggctgcgc aactgttggg aagggcgatc ggtgcgggcc tcttcgctat 300
tacgccagct ggcgaaaggg ggatgtgctg caaggcgatt aagttgggta acgccagggt 360
tttcccagtc acgacgttgt aaaacgacgg ccagtgaatt cgagctcggt acccggggat 420
ccggcgcgcc gtgtagacgt agtataacag tatatctgac acgcacgtga tgaccacgta 480
atcgcatcgc ccctcacatc tcacctctca ccgctgactc agcttcacta aaaaggaaaa 540
tatatactct ttcccaggca aggtgacagc ggtccccgtc tcctccacaa aggcctctcc 600
tggggtttga gcaagtctaa gtttacgtag cataaaaatt ctcggattgc gtcaaataat 660
aaaaaaagta actccacttc tacttctaca tcggaaaaac attccattca catatcgtct 720
ttggcctatc ttgttttgtc cttggtagat caggtcagta caaacgcaac acgaaagaac 780
aaaaaaagaa gaaaacagaa ggccaagaca gggtcaatga gactgttgtc ctcctactgt 840
ccctatgtct ctggccgatc acgcgccatt gtccctcaga aacaaatcaa acacccacac 900
cccgggcacc caaagtcccc acccacacca ccaatacgta aacggggcgc cccctgcagg 960
ccctcctgcg cgcggcctcc cgccttgctt ctctcccctc ccttttcttt ttccagtttt 1020
ccctattttg tcccttttc cgcacaacaa gtatcagaat gggttcatca aatctatcca 1080
acctaattcg cacgtagact ggcttggtat tggcagtttc gcagttatat atatactacc 1140
atgagtgaaa ctgttacgtt accttaaatt ctttctccct ttaattttct tttatcttac 1200
tctcctacat aagacatcaa gaaacaattg tatattgtac accccccccc tccacaaaca 1260
caaatattga taatataaag atgtccgccg cagccgatcg cctcaatctc acgtccggtc 1320
atttgaacgc aggtcgtaaa cgcagcagca gctccgttag cttgaaagcg gcggagaagc 1380
cgtttaaagt gaccgtgatt ggtagcggta actggggcac caccattgcg aaagtggtcg 1440
cagagaactg taagggctac ccggaagtgt tcgctccgat tgttcagatg tgggtgtttg 1500
aagaagagat caatggtgaa aaactgacgg agatcatcaa cacccgccac caaaacgtca 1560
aatatctgcc tggcatcacc ttgccggaca atctggtggc gaatccggac ctgatcgatt 1620
ctgtcaaaga cgttgacatt attgttttca acatcccgca ccagtttctg ccgcgtattt 1680
gcagccagct gaagggtcac gtcgatagcc acgtccgcgc gattagctgc ctgaaaggct 1740
tcgaggtggg cgcgaagggt gttcaattgc tgtctagcta catcaccgaa gagctgggca 1800
ttcagtgcgg tgcgctgtcc ggtgctaata tcgctaccga agttgcacaa gagcattgga 1860

```
gcgagactac ggtcgcgtat cacattccga aggacttccg tggcgaaggc aaggatgtcg   1920
accataaagt tctgaaggcg ctgtttcacc gtccgtactt tcatgtcagc gtcatcgaag   1980
atgttgccgg tatcagcatt tgtggtgcgt tgaagaacgt tgttgcactg ggttgcggtt   2040
ttgttgaggg tctgggttgg ggtaacaacg cgtctgcggc aattcaacgt gtgggtctgg   2100
gcgagatcat ccgtttcggc cagatgttct tcccagagag ccgtgaagaa acgtattatc   2160
aggagtcggc cggtgtggcc gacctgatca ccacttgcgc tggtggccgc aatgttaagg   2220
tagcgcgtct gatggcgacc agcggcaagg acgcctggga gtgcgagaaa gagctgctga   2280
atggtcagag cgcacaaggt ctgattacct gtaaagaagt gcacgaatgg ctggaaacgt   2340
gtggcagcgt cgaggacttc ccgctgtttg aggcagtgta ccaaattgtg tacaacaatt   2400
acccgatgaa gaatctgccg gatatgatcg aagaactgga tctgcatgag gattaagttt   2460
aaactcatgt aattagttat gtcacgctta cattcacgcc ctcctcccac atccgctcta   2520
accgaaaagg aaggagttag acaacctgaa gtctaggtcc ctatttattt tttttaatag   2580
ttatgttagt attaagaacg ttatttatat ttcaaatttt tctttttttt ctgtacaaac   2640
gcgtgtacgc atgtaacatt atactgaaaa ccttgcttga gaaggttttg ggacgctcga   2700
aggctttaat ttgcggggcc ggccgcattg cggattacgt attctaatgt tcagtaccgt   2760
tcgtataatg tatgctatac gaagttatgc agattgtact gagagtgcac cataccacct   2820
tttcaattca tcattttttt tttattcttt tttttgattt cggtttcctt gaaatttttt   2880
tgattcggta atctccgaac agaaggaaga acgaaggaag gagcacagac ttagattggt   2940
atatatacgc atatgtagtg ttgaagaaac atgaaattgc ccagtattct taacccaact   3000
gcacagaaca aaaacctgca ggaaacgaag ataaatcatg tcgaaagcta catataagga   3060
acgtgctgct actcatccta gtcctgttgc tgccaagcta tttaatatca tgcacgaaaa   3120
gcaaacaaac ttgtgtgctt cattggatgt tcgtaccacc aaggaattac tggagttagt   3180
tgaagcatta ggtcccaaaa tttgtttact aaaaacacat gtggatatct tgactgattt   3240
ttccatggag ggcacagtta agccgctaaa ggcattatcc gccaagtaca attttttact   3300
cttcgaagac agaaaatttg ctgacattgg taatacagtc aaattgcagt actctgcggg   3360
tgtatacaga atagcagaat gggcagacat tacgaatgca cacggtgtgg tgggcccagg   3420
tattgttagc ggtttgaagc aggcggcaga agaagtaaca aaggaaccta gaggcctttt   3480
gatgttagca gaattgtcat gcaagggctc cctatctact ggagaatata ctaagggtac   3540
tgttgacatt gcgaagagcg acaaagattt tgttatcggc tttattgctc aaagagacat   3600
gggtggaaga gatgaaggtt acgattggtt gattatgaca cccggtgtgg gtttagatga   3660
caagggagac gcattgggtc aacagtatag aaccgtggat gatgtggtct ctacaggatc   3720
tgacattatt attgttggaa gaggactatt tgcaaaggga agggatgcta aggtagaggg   3780
tgaacgttac agaaaagcag gctgggaagc atatttgaga agatgcggcc agcaaaacta   3840
aaaaactgta ttataagtaa atgcatgtat actaaactca caaattagag cttcaattta   3900
attatatcag ttattaccct atgcggtgtg aaataccgca cagatgcgta aggagaaaat   3960
accgcatcag gaaattgtaa gcgttaatat tttgttaaaa ttcgcgttaa atttttgtta   4020
aatcagctca ttttttaacc aataggccga aatcggcaaa atcccttata aatcaaaaga   4080
atagaccgag atagggttga gtgttgttcc agtttggaac aagagtccac tattaaagaa   4140
cgtggactcc aacgtcaaag ggcgaaaaac cgtctatcag ggcgatggcc cactacgtga   4200
```

```
accatcaccc taatcaagat aacttcgtat aatgtatgct atacgaacgg taccagtgat   4260
gatacaacga gttagccaag gtggcggccg catttattgg agaaagataa catatcatac   4320
tttcccccac ttttttcgag gctcttctat atcatattca taaattagca ttatgtcatt   4380
tctcataact actttatcac gttagaaatt acttattatt attaaattaa tacaaaattt   4440
agtaaccaaa taaatataaa taaatatgca tatttaaatt ttaaaaaaaa aatcctatag   4500
agcaaaagga ttctccatta taatatgagc tatacacctc ttacgcattt tttgagggtg   4560
gttacaacac cactcattca gaggctgtcg gcacagttgc ttccagcatc tggcgtccgt   4620
atgtatgggt gtattttaaa taataaacaa agtgccacac cttcaccaat tatgtcttta   4680
agaaatggac aagttccaaa gagcttgccc aaggctcgac aaggatgtac tttagaatat   4740
ctatattcaa gtacgtggcg cgcatatgtt tgagtgtgca cacaataaag gttaattaat   4800
ctagagtcga cctgcaggca tgcaagcttg gcgtaatcat ggtcatagct gtttcctgtg   4860
tgaaattgtt atccgctcac aattccacac aacatacgag ccggaagcat aaagtgtaaa   4920
gcctggggtg cctaatgagt gagctaactc acattaattg cgttgcgctc actgcccgct   4980
ttccagtcgg gaaacctgtc gtgccagctg cattaatgaa tcggccaacg cgcggggaga   5040
ggcggtttgc gtattgggcg ctcttccgct tcctcgctca ctgactcgct gcgctcggtc   5100
gttcggctgc ggcgagcggt atcagctcac tcaaaggcgg taatacggtt atccacagaa   5160
tcaggggata acgcaggaaa gaacatgtga gcaaaaggcc agcaaaaggc caggaaccgt   5220
aaaaaggccg cgttgctggc gtttttccat aggctccgcc cccctgacga gcatcacaaa   5280
aatcgacgct caagtcagag gtggcgaaac ccgacaggac tataaagata ccaggcgttt   5340
ccccctggaa gctccctcgt gcgctctcct gttccgaccc tgccgcttac cggatacctg   5400
tccgcctttc tcccttcggg aagcgtggcg ctttctcata gctcacgctg taggtatctc   5460
agttcggtgt aggtcgttcg ctccaagctg ggctgtgtgc acgaaccccc cgttcagccc   5520
gaccgctgcg ccttatccgg taactatcgt cttgagtcca acccggtaag acacgactta   5580
tcgccactgg cagcagccac tggtaacagg attagcagag cgaggtatgt aggcggtgct   5640
acagagttct tgaagtggtg gcctaactac ggctacacta gaaggacagt atttggtatc   5700
tgcgctctgc tgaagccagt taccttcgga aaaagagttg gtagctcttg atccggcaaa   5760
caaaccaccg ctggtagcgg tggttttttt gtttgcaagc agcagattac gcgcagaaaa   5820
aaaggatctc aagaagatcc tttgatcttt tctacggggt ctgacgctca gtggaacgaa   5880
aactcacgtt aagggatttt ggtcatgaga ttatcaaaaa ggatcttcac ctagatcctt   5940
ttaaattaaa aatgaagttt taaatcaatc taaagtatat atgagtaaac ttggtctgac   6000
agttaccaat gcttaatcag tgaggcacct atctcagcga tctgtctatt tcgttcatcc   6060
atagttgcct gactccccgt cgtgtagata actacgatac gggagggctt accatctggc   6120
cccagtgctg caatgatacc gcgagaccca cgctcaccgg ctccagattt atcagcaata   6180
aaccagccag ccggaagggc cgagcgcaga agtggtcctg caactttatc cgcctccatc   6240
cagtctatta attgttgccg ggaagctaga gtaagtagtt cgccagttaa tagtttgcgc   6300
aacgttgttg ccattgctac aggcatcgtg gtgtcacgct cgtcgtttgg tatggcttca   6360
ttcagctccg gttcccaacg atcaaggcga gttacatgat cccccatgtt gtgcaaaaaa   6420
gcggttagct ccttcggtcc tccgatcgtt gtcagaagta agttggccgc agtgttatca   6480
ctcatggtta tggcagcact gcataattct cttactgtca tgccatccgt aagatgcttt   6540
tctgtgactg gtgagtactc aaccaagtca ttctgagaat agtgtatgcg gcgaccgagt   6600
```

```
tgctcttgcc cggcgtcaat acgggataat accgcgccac atagcagaac tttaaaagtg   6660

ctcatcattg gaaaacgttc ttcggggcga aaactctcaa ggatcttacc gctgttgaga   6720

tccagttcga tgtaacccac tcgtgcaccc aactgatctt cagcatcttt tactttcacc   6780

agcgtttctg ggtgagcaaa aacaggaagg caaaatgccg caaaaaaggg aataagggcg   6840

acacggaaat gttgaatact catactcttc ctttttcaat attattgaag catttatcag   6900

ggttattgtc tcatgagcgg atacatattt gaatgtattt agaaaaataa acaaataggg   6960

gttccgcgca catttccccg aaaagtgcca cctgacgtct aagaaaccat tattatcatg   7020

acattaacct ataaaaatag gcgtatcacg aggccctttc gtc                     7063
```

<210> SEQ ID NO 250
<211> LENGTH: 7063
<212> TYPE: DNA
<213> ORGANISM: Artificial Sequence
<220> FEATURE:
<223> OTHER INFORMATION: pBP3518GPD1_Native

<400> SEQUENCE: 250

```
tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accatatgcg gtgtgaaata ccgcacagat gcgtaaggag aaaataccgc atcaggcgcc    240

attcgccatt caggctgcgc aactgttggg aagggcgatc ggtgcgggcc tcttcgctat    300

tacgccagct ggcgaaaggg ggatgtgctg caaggcgatt aagttgggta acgccagggt    360

tttcccagtc acgacgttgt aaaacgacgg ccagtgaatt cgagctcggt acccggggat    420

ccggcgcgcc gtgtagacgt agtataacag tatatctgac acgcacgtga tgaccacgta    480

atcgcatcgc ccctcacatc tcacctctca ccgctgactc agcttcacta aaaaggaaaa    540

tatatactct ttcccaggca aggtgacagc ggtccccgtc tcctccacaa aggcctctcc    600

tggggtttga gcaagtctaa gtttacgtag cataaaaatt ctcggattgc gtcaaataat    660

aaaaaaagta actccacttc tacttctaca tcggaaaaac attccattca catatcgtct    720

ttggcctatc ttgttttgtc cttggtagat caggtcagta caaacgcaac acgaaagaac    780

aaaaaaagaa gaaaacagaa ggccaagaca gggtcaatga gactgttgtc ctcctactgt    840

ccctatgtct ctggccgatc acgcgccatt gtccctcaga aacaaatcaa acacccacac    900

cccgggcacc caaagtcccc acccacacca ccaatacgta aacggggcgc cccctgcagg    960

ccctcctgcg cgcggcctcc cgccttgctt ctctcccctc ccttttcttt ttccagtttt   1020

ccctattttg tccctttttc cgcacaacaa gtatcagaat gggttcatca aatctatcca   1080

acctaattcg cacgtagact ggcttggtat tggcagtttc gcagttatat atatactacc   1140

atgagtgaaa ctgttacgtt accttaaatt ctttctccct ttaattttct tttatcttac   1200

tctcctacat aagacatcaa gaaacaattg tatattgtac accccccccc tccacaaaca   1260

caaatattga taatataaag atgtctgctg ctgctgatag attaaactta acttccggcc   1320

acttgaatgc tggtagaaag agaagttcct cttctgtttc tttgaaggct gccgaaaagc   1380

ctttcaaggt tactgtgatt ggatctggta actggggtac tactattgcc aaggtggttg   1440

ccgaaaattg taagggatac ccagaagttt tcgctccaat agtacaaatg tgggtgttcg   1500

aagaagagat caatggtgaa aaattgactg aaatcataaa tactagacat caaaacgtga   1560
```

```
aatacttgcc tggcatcact ctacccgaca atttggttgc taatccagac ttgattgatt   1620
cagtcaagga tgtcgacatc atcgttttca acattccaca tcaatttttg ccccgtatct   1680
gtagccaatt gaaaggtcat gttgattcac acgtcagagc tatctcctgt ctaaagggtt   1740
ttgaagttgg tgctaaaggt gtccaattgc tatcctctta catcactgag gaactaggta   1800
ttcaatgtgg tgctctatct ggtgctaaca ttgccaccga agtcgctcaa gaacactggt   1860
ctgaaacaac agttgcttac cacattccaa aggatttcag aggcgagggc aaggacgtcg   1920
accataaggt tctaaaggcc ttgttccaca gaccttactt ccacgttagt gtcatcgaag   1980
atgttgctgg tatctccatc tgtggtgctt tgaagaacgt tgttgcctta ggttgtggtt   2040
tcgtcgaagg tctaggctgg ggtaacaacg cttctgctgc catccaaaga gtcggtttgg   2100
gtgagatcat cagattcggt caaatgtttt tcccagaatc tagagaagaa acatactacc   2160
aagagtctgc tggtgttgct gatttgatca ccacctgcgc tggtggtaga aacgtcaagg   2220
ttgctaggct aatggctact tctggtaagg acgcctggga atgtgaaaag gagttgttga   2280
atggccaatc cgctcaaggt ttaattacct gcaaagaagt tcacgaatgg ttggaaacat   2340
gtggctctgt cgaagacttc ccattatttg aagccgtata ccaaatcgtt tacaacaact   2400
acccaatgaa gaacctgccg gacatgattg aagaattaga tctacatgaa gattaggttt   2460
aaactcatgt aattagttat gtcacgctta cattcacgcc ctcctcccac atccgctcta   2520
accgaaaagg aaggagttag acaacctgaa gtctaggtcc ctatttattt tttttaatag   2580
ttatgttagt attaagaacg ttatttatat ttcaaatttt tctttttttt ctgtacaaac   2640
gcgtgtacgc atgtaacatt atactgaaaa ccttgcttga gaaggttttg ggacgctcga   2700
aggctttaat ttgcggggcc ggccgcattg cggattacgt attctaatgt tcagtaccgt   2760
tcgtataatg tatgctatac gaagttatgc agattgtact gagagtgcac cataccacct   2820
tttcaattca tcattttttt tttattcttt tttttgattt cggtttcctt gaaatttttt   2880
tgattcggta atctccgaac agaaggaaga acgaaggaag gagcacagac ttagattggt   2940
atatatacgc atatgtagtg ttgaagaaac atgaaattgc ccagtattct taacccaact   3000
gcacagaaca aaaacctgca ggaaacgaag ataaatcatg tcgaaagcta catataagga   3060
acgtgctgct actcatccta gtcctgttgc tgccaagcta tttaatatca tgcacgaaaa   3120
gcaaacaaac ttgtgtgctt cattggatgt tcgtaccacc aaggaattac tggagttagt   3180
tgaagcatta ggtcccaaaa tttgtttact aaaaacacat gtggatatct tgactgattt   3240
ttccatggag ggcacagtta agccgctaaa ggcattatcc gccaagtaca attttttact   3300
cttcgaagac agaaaatttg ctgacattgg taatacagtc aaattgcagt actctgcggg   3360
tgtatacaga atagcagaat gggcagacat tacgaatgca cacggtgtgg tgggcccagg   3420
tattgttagc ggtttgaagc aggcggcaga agaagtaaca aaggaaccta gaggcctttt   3480
gatgttagca gaattgtcat gcaagggctc cctatctact ggagaatata ctaagggtac   3540
tgttgacatt gcgaagagcg acaaagattt tgttatcggc tttattgctc aaagagacat   3600
gggtggaaga gatgaaggtt acgattggtt gattatgaca cccggtgtgg gtttagatga   3660
caagggagac gcattgggtc aacagtatag aaccgtggat gatgtggtct ctacaggatc   3720
tgacattatt attgttggaa gaggactatt tgcaaaggga agggatgcta aggtagaggg   3780
tgaacgttac agaaaagcag gctgggaagc atatttgaga agatgcggcc agcaaaacta   3840
aaaaactgta ttataagtaa atgcatgtat actaaactca caaattagag cttcaattta   3900
attatatcag ttattaccct atgcggtgtg aaataccgca cagatgcgta aggagaaaat   3960
```

```
accgcatcag gaaattgtaa gcgttaatat tttgttaaaa ttcgcgttaa atttttgtta   4020
aatcagctca ttttttaacc aataggccga aatcggcaaa atcccttata aatcaaaaga   4080
atagaccgag atagggttga gtgttgttcc agtttggaac aagagtccac tattaaagaa   4140
cgtggactcc aacgtcaaag ggcgaaaaac cgtctatcag ggcgatggcc cactacgtga   4200
accatcaccc taatcaagat aacttcgtat aatgtatgct atacgaacgg taccagtgat   4260
gatacaacga gttagccaag gtggcggccg catttattgg agaaagataa catatcatac   4320
tttcccccac tttttcgag gctcttctat atcatattca taaattagca ttatgtcatt   4380
tctcataact actttatcac gttagaaatt acttattatt attaaattaa tacaaaattt   4440
agtaaccaaa taaatataaa taaatatgca tatttaaatt ttaaaaaaaa aatcctatag   4500
agcaaaagga ttctccatta taatatgagc tatacacctc ttacgcattt tttgagggtg   4560
gttacaacac cactcattca gaggctgtcg gcacagttgc ttccagcatc tggcgtccgt   4620
atgtatgggt gtattttaaa taataaacaa agtgccacac cttcaccaat tatgtcttta   4680
agaaatggac aagttccaaa gagcttgccc aaggctcgac aaggatgtac tttagaatat   4740
ctatattcaa gtacgtggcg cgcatatgtt tgagtgtgca cacaataaag gttaattaat   4800
ctagagtcga cctgcaggca tgcaagcttg gcgtaatcat ggtcatagct gtttcctgtg   4860
tgaaattgtt atccgctcac aattccacac aacatacgag ccggaagcat aaagtgtaaa   4920
gcctggggtg cctaatgagt gagctaactc acattaattg cgttgcgctc actgcccgct   4980
ttccagtcgg gaaacctgtc gtgccagctg cattaatgaa tcggccaacg cgcggggaga   5040
ggcggtttgc gtattgggcg ctcttccgct tcctcgctca ctgactcgct gcgctcggtc   5100
gttcggctgc ggcgagcggt atcagctcac tcaaaggcgg taatacggtt atccacagaa   5160
tcaggggata acgcaggaaa gaacatgtga gcaaaaggcc agcaaaaggc caggaaccgt   5220
aaaaaggccg cgttgctggc gtttttccat aggctccgcc cccctgacga gcatcacaaa   5280
aatcgacgct caagtcagag gtggcgaaac ccgacaggac tataaagata ccaggcgttt   5340
ccccctggaa gctccctcgt gcgctctcct gttccgaccc tgccgcttac cggatacctg   5400
tccgcctttc tcccttcggg aagcgtggcg ctttctcata gctcacgctg taggtatctc   5460
agttcggtgt aggtcgttcg ctccaagctg ggctgtgtgc acgaaccccc cgttcagccc   5520
gaccgctgcg ccttatccgg taactatcgt cttgagtcca acccggtaag acacgactta   5580
tcgccactgg cagcagccac tggtaacagg attagcagag cgaggtatgt aggcggtgct   5640
acagagttct tgaagtggtg gcctaactac ggctacacta gaaggacagt atttggtatc   5700
tgcgctctgc tgaagccagt taccttcgga aaaagagttg gtagctcttg atccggcaaa   5760
caaaccaccg ctggtagcgg tggttttttt gtttgcaagc agcagattac gcgcagaaaa   5820
aaaggatctc aagaagatcc tttgatcttt tctacggggt ctgacgctca gtggaacgaa   5880
aactcacgtt aagggatttt ggtcatgaga ttatcaaaaa ggatcttcac ctagatcctt   5940
ttaaattaaa aatgaagttt taaatcaatc taaagtatat atgagtaaac ttggtctgac   6000
agttaccaat gcttaatcag tgaggcacct atctcagcga tctgtctatt tcgttcatcc   6060
atagttgcct gactccccgt cgtgtagata actacgatac gggagggctt accatctggc   6120
cccagtgctg caatgatacc gcgagaccca cgctcaccgg ctccagattt atcagcaata   6180
aaccagccag ccggaagggc cgagcgcaga agtggtcctg caactttatc cgcctccatc   6240
cagtctatta attgttgccg ggaagctaga gtaagtagtt cgccagttaa tagtttgcgc   6300
```

-continued

```
aacgttgttg ccattgctac aggcatcgtg gtgtcacgct cgtcgtttgg tatggcttca   6360

ttcagctccg gttcccaacg atcaaggcga gttacatgat cccccatgtt gtgcaaaaaa   6420

gcggttagct ccttcggtcc tccgatcgtt gtcagaagta agttggccgc agtgttatca   6480

ctcatggtta tggcagcact gcataattct cttactgtca tgccatccgt aagatgcttt   6540

tctgtgactg gtgagtactc aaccaagtca ttctgagaat agtgtatgcg gcgaccgagt   6600

tgctcttgcc cggcgtcaat acgggataat accgcgccac atagcagaac tttaaaagtg   6660

ctcatcattg gaaaacgttc ttcggggcga aaactctcaa ggatcttacc gctgttgaga   6720

tccagttcga tgtaacccac tcgtgcaccc aactgatctt cagcatcttt tactttcacc   6780

agcgtttctg ggtgagcaaa aacaggaagg caaaatgccg caaaaaaggg aataagggcg   6840

acacggaaat gttgaatact catactcttc ctttttcaat attattgaag catttatcag   6900

ggttattgtc tcatgagcgg atacatattt gaatgtattt agaaaaataa acaaataggg   6960

gttccgcgca catttccccg aaaagtgcca cctgacgtct aagaaaccat tattatcatg   7020

acattaacct ataaaaatag gcgtatcacg aggccctttc gtc                     7063
```